(12) United States Patent
Cooke et al.

(10) Patent No.: US 12,390,437 B2
(45) Date of Patent: Aug. 19, 2025

(54) ITACONIC ACID DERIVATIVES AND USES THEREOF INTREATING AN INFLAMMATORY DISEASE OR A DISEASE ASSOCIATED WITH AN UNDESIRABLE IMMUNE RESPONSE

(71) Applicant: Sitryx Therapeutics Limited, Oxford (GB)

(72) Inventors: Michael Liam Cooke, Nottingham (GB); David Cousin, Nottingham (GB); Matthew Colin Thor Fyfe, Oxfordshire (GB); Barry John Teobald, Oxfordshire (GB); Stephen Malcolm Thom, Nottingham (GB); Thomas Michael Waugh, Nottingham (GB)

(73) Assignee: Sitryx Therapeutics Limited, Oxford (GB)

( * ) Notice: Subject to any disclaimer, the term of this patent is extended or adjusted under 35 U.S.C. 154(b) by 846 days.

(21) Appl. No.: 17/606,884

(22) PCT Filed: Apr. 30, 2020

(86) PCT No.: PCT/GB2020/051060
§ 371 (c)(1),
(2) Date: Oct. 27, 2021

(87) PCT Pub. No.: WO2020/222011
PCT Pub. Date: Nov. 5, 2020

(65) Prior Publication Data
US 2022/0265595 A1  Aug. 25, 2022

(30) Foreign Application Priority Data

Apr. 30, 2019 (EP) ..................... 19172051
Aug. 2, 2019 (EP) ..................... 19189910
Dec. 19, 2019 (EP) ..................... 19217846
Mar. 11, 2020 (EP) ..................... 20162494

(51) Int. Cl.
*A61K 31/225* (2006.01)
*A61K 31/275* (2006.01)
(Continued)

(52) U.S. Cl.
CPC .......... *A61K 31/225* (2013.01); *A61K 31/275* (2013.01); *A61K 31/337* (2013.01);
(Continued)

(58) Field of Classification Search
CPC .. A61K 31/225; A61K 31/275; A61K 31/337; A61K 31/341; A61K 31/38; A61K 31/397; A61K 31/4015; A61K 31/41; A61K 31/445; A61K 31/46; A61K 31/495; A61K 31/5375; A61K 31/54; A61K 31/22; A61K 31/19; A61K 31/194; A61K 45/06; C07C 219/08; C07C 233/05; C07C 311/03; C07C 2601/18; C07C 51/418; C07C 69/734; C07C 2601/04; C07C 2601/14; C07C 2602/42; C07C 2602/46; C07C 2603/74; C07C 2603/94; C07C 69/65; C07C 235/06; C07C 255/46; C07C 311/04; C07C 63/26; C07C 67/30; C07C 69/736; C07C 69/75; C07C 219/10; C07C 233/18; C07C 311/26; C07C 317/22; C07C 2601/02; C07D 205/04; C07D 207/27; C07D 207/273; C07D 207/277; C07D 211/96; C07D 257/04; C07D 295/08; C07D 295/088;
(Continued)

(56) References Cited

U.S. PATENT DOCUMENTS

2011/0251119 A1 10/2011 Wabnitz et al.
2012/0270155 A1 10/2012 Komuro et al.
2017/0291906 A1 10/2017 Hoye et al.

FOREIGN PATENT DOCUMENTS

EP 2145920 A1 1/2010
EP 2423178 A1 2/2012
(Continued)

OTHER PUBLICATIONS

Punia, B., P. Yadav, G. Bumbrah, and R. Sharma, "Analysis of Illicit Liquor by Headspace Gas Chromatography-Mass Spectrometry (HS-GC-MS): A Preliminary Study", Journal of AOAC International (2017), 100 (1), pp. 109-125. (Year: 2017).*
Abramova, N., A. Bratov, A. Ipatov, S. Levichev, A. Aris, and E. Rodriguez, "New flow-through analytical system based on ion-selective field effect transistors with optimised calcium selective photocurable membrane for bovine serum analysis", Talanta (2013), 113, pp. 31-35. (Year: 2013).*
(Continued)

*Primary Examiner* — Joseph K Mckane
*Assistant Examiner* — Sagar Patel
(74) *Attorney, Agent, or Firm* — Faegre Drinker Biddle & Reath LLP

(57) ABSTRACT

The invention relates to compounds of formula (IW-1) and to their use in treating or preventing an inflammatory disease or a disease associated with an undesirable immune response: wherein $R^A$, $R^B$, $R^C$ and $R^D$ are as defined herein.

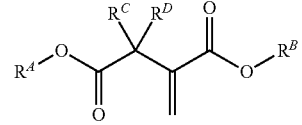

(IW-1)

11 Claims, No Drawings

(51) Int. Cl.

| | | |
|---|---|---|
| *A61K 31/337* | (2006.01) | |
| *A61K 31/341* | (2006.01) | |
| *A61K 31/351* | (2006.01) | |
| *A61K 31/38* | (2006.01) | |
| *A61K 31/397* | (2006.01) | |
| *A61K 31/4015* | (2006.01) | |
| *A61K 31/41* | (2006.01) | |
| *A61K 31/445* | (2006.01) | |
| *A61K 31/46* | (2006.01) | |
| *A61K 31/495* | (2006.01) | |
| *A61K 31/5375* | (2006.01) | |
| *A61K 31/54* | (2006.01) | |
| *C07C 69/593* | (2006.01) | |
| *C07C 219/08* | (2006.01) | |
| *C07C 233/05* | (2006.01) | |
| *C07C 255/14* | (2006.01) | |
| *C07C 311/03* | (2006.01) | |
| *C07C 317/18* | (2006.01) | |
| *C07D 205/04* | (2006.01) | |
| *C07D 207/27* | (2006.01) | |
| *C07D 207/273* | (2006.01) | |
| *C07D 207/277* | (2006.01) | |
| *C07D 211/96* | (2006.01) | |
| *C07D 257/04* | (2006.01) | |
| *C07D 295/08* | (2006.01) | |
| *C07D 295/088* | (2006.01) | |
| *C07D 305/08* | (2006.01) | |
| *C07D 307/20* | (2006.01) | |
| *C07D 309/12* | (2006.01) | |
| *C07D 331/04* | (2006.01) | |
| *C07D 451/10* | (2006.01) | |
| *C07D 519/00* | (2006.01) | |

(52) U.S. Cl.
CPC .......... *A61K 31/341* (2013.01); *A61K 31/351* (2013.01); *A61K 31/38* (2013.01); *A61K 31/397* (2013.01); *A61K 31/4015* (2013.01); *A61K 31/41* (2013.01); *A61K 31/445* (2013.01); *A61K 31/46* (2013.01); *A61K 31/495* (2013.01); *A61K 31/5375* (2013.01); *A61K 31/54* (2013.01); *C07C 69/593* (2013.01); *C07C 219/08* (2013.01); *C07C 233/05* (2013.01); *C07C 255/14* (2013.01); *C07C 311/03* (2013.01); *C07C 317/18* (2013.01); *C07D 205/04* (2013.01); *C07D 207/27* (2013.01); *C07D 207/273* (2013.01); *C07D 207/277* (2013.01); *C07D 211/96* (2013.01); *C07D 257/04* (2013.01); *C07D 295/08* (2013.01); *C07D 295/088* (2013.01); *C07D 305/08* (2013.01); *C07D 307/20* (2013.01); *C07D 309/12* (2013.01); *C07D 331/04* (2013.01); *C07D 451/10* (2013.01); *C07D 519/00* (2013.01); *C07C 2601/18* (2017.05); *C07C 2602/50* (2017.05)

(58) Field of Classification Search
CPC .. C07D 305/08; C07D 307/20; C07D 309/12; C07D 331/04; C07D 451/10; C07D 519/00; C07D 207/404; C07D 207/16; C07D 295/185; C07D 471/08; C07D 309/10; Y02A 50/30; A61P 29/00; A61P 1/00; A61P 1/16; A61P 3/10; A61P 7/00; A61P 9/04; A61P 9/10; A61P 11/00; A61P 11/06; A61P 13/12; A61P 15/00; A61P 17/00; A61P 17/06; A61P 17/14; A61P 19/00; A61P 19/02; A61P 25/00; A61P 27/12; A61P 27/16; A61P 35/00; A61P 37/00; A61P 37/02; A61P 37/06

See application file for complete search history.

(56) References Cited

FOREIGN PATENT DOCUMENTS

| WO | 2017142855 A1 | 8/2017 | |
|---|---|---|---|
| WO | WO-2019036509 A1 * | 2/2019 | ........... A61K 31/194 |
| WO | 2020006557 A1 | 1/2020 | |
| WO | 2021130492 A1 | 7/2021 | |

OTHER PUBLICATIONS

Bagavant G et al., "Studies on Anti-inflammatory and Analgesic Activities of Itaconic Acid Systems. Part 1: Itaconic Acids and Diesters," Indian J Pharm Sci, vol. 56, No. 3, pp. 80-85, 1994.

Brennan M. S. et al., "Dimethyl Fumarate and Monoethyl Fumarate Exhibit Differential Effects on KEAP1, NRF2 Activation, and Glutathione Depletion In Vitro, " PLOS ONE, vol. 10, No. 3, 2015, e0120254.

Fang et al., "The influence of monobutyl itaconate and [beta]-carboxyethyl acrylate on acrylic latex pressure sensitive adhesives", International Journal of Adhesion and Adhesives, 84, 387-393 (2018).

International Preliminary Report on Patentability received for PCT Patent Application No. PCT/GB2020/051060, mailed on Nov. 11, 2021, 11 pages.

Invitation to Pay Additional Fees received for PCT Patent Application No. PCT/GB2020/051060, mailed on Jul. 2, 2020, 10 pages.

Giacomelli R. et al. "IL-1β at the crossroad between rheumatoid arthritis and type 2 diabetes: may we kill two birds with one stone?", Expert Review of Clinical Immunology, 2016, vol. 12, No. 8, p. 849-p. 855.

Al-Hwas Z. S. et al. "A distinct inflammasome IL-1β gene expression profile in patients with psoriatic arthritis in Basra city", International Journal of Health Sciences, Mar. 27, 2022, vol. 6, p. 4570-p. 4577.

Sung S. J. et al. "Interactions among glomerulus infiltrating macrophages and intrinsic cells via cytokines in chronic lupus glomerulonephritis" Journal of Autoimmunity, 106 (2020) 102331, p. 1-p. 13.

Mendiola et al., "The IL-1b phenomena in neuroinflammatory diseases", A.E. J. Neural. Transm. 2018, 125, p. 781-p. 795.

Tsuji, G et al., "Metformin inhibits IL-1β secretion via impairment of NLRP3 inflammasome in keratinocytes: implications for preventing the development of psoriasis" Cell Death Discovery, 2020, 6:11, p. 1-p. 11.

Piotrowska M et al., "The Nrf2 in the pathophysiology of the intestine: Molecular mechanisms and therapeutic implications for inflammatory bowel diseases", Pharmacological Research 163 (2021) 105243, p. 1-p. 12.

Liso M. et al., "Interleukin 1b Blockade Reduces Intestinal Inflammation in a Murine Model of Tumor Necrosis Factor—Independent Ulcerative Colitis", Cellular Molecular Gastroenterology and Hepatology, 2022, vol. 14, No. 1, p. 151-p. 171.

Toplak N. et al., "The role of IL-1 inhibition in systemic juvenile idiopathic arthritis: current status and future perspectives" Drug Design, Development and Therapy, 2018, 12, p. 1633-p. 1643.

Fabiani C. et al., "Interleukin (IL)-1 inhibition with anakinra and canakinumab in Behçet's disease-related uveitis: a multicenter retrospective observational study", Clin. Rheumatology, (2017), 36, p. 191-p. 197.

Ferrandiz M. L. et al., "Nrf2 as a therapeutic target for rheumatic diseases", Biochemical Pharmacology, 152, 2018, p. 338-p. 346.

Italiani P. et al., "IL-1 family cytokines and soluble receptors in systemic lupus erythematosus", Arthritis Research & Therapy, (2018), 20;27, p. 1-p. 10.

Karpenko M. N. et al., "Interleukin-1β, interleukin-1 receptor antagonist, interleukin-6, interleukin- 10, and tumor necrosis fac-

(56) References Cited

OTHER PUBLICATIONS tor-α levels in CSF and serum in relation to the clinical diversity of Parkinson's disease", Cellular Immunology, 327, 2018, 7p. 7-p. 82.
Friedrich M. et al., "IL-1-driven stromal-neutrophil interactions define a subset of patients with inflammatory bowel disease that does not respond to therapies", Nature Medicine, vol. 27, Nov. 2021, p. 1970-p. 1981.
Nasserinejad M. et al., "The effects of IL-8, IL-6, and IL-1 on the risk of celiac disease: a Bayesian regression analysis", Gastroenterology and Hepatology From Bed to Bench, 2019, 12(S1), S117-S122.
Authier F. J. et al., "Interleukin-1 expression in inflammatory myopathies: evidence of marked immunoreactivity in sarcoid granulomas and muscle fibres showing ischaemic and regenerative changes", Neuropathology and Applied Neurobiology, 1997, 23(2), p. 132-p. 40.
Witte-Handel E. et al., "The IL-1 Pathway Is Hyperactive in Hidradenitis Suppurativa and Contributes to Skin Infiltration and Destruction", Journal of Investigative Dermatology, 2019, vol. 139, p. 1294-p. 1305.
Bårdsen K. et al., "Interleukin-1-related activity and hypocretin-1 in cerebrospinal fluid contribute to fatigue in primary Sjogren's syndrome", Journal of Neuroinflammation, 2019, 16, 102, p. 1-p. 9.
Ly Kim-Heang et al., "Interleukin-1 blockade in refractory giant cell arteritis", Joint Bone Spine, (2014), 81, p. 76-p. 78.
Migita K. et al., "Dysregulated mature IL-1b production in familial Mediterranean fever" Rheumatology, 2015, 54(4), p. 660-p. 665.
Dandekar P. et al., "Living with Tumour necrosis factor receptor-associated periodic fever syndrome (TRAPS)", Pediatric Rheumatology, 2015, 13(Suppl 1):P23.
Kaneko N. et al., "The role of interleukin-1 in general pathology", Inflammation and Regeneration, 2019, 39, 12, p. 1-p. 16.
Dhimolea Eugen, "Interleukin-1β inhibitors for the treatment of cryopyrin-associated periodic syndrome", The Application of Clinical Genetics, 2011, 4, p. 21-p. 27.
Takanohashi A. et al., "Elevation of proinflammatory cytokines in patients with Aicardi-Goutières syndrome", Neurology 2013, 80(11), p. 997-p. 1002.
H. Lindahl et al."Neuroinflammation Associated With Inborn Errors of Immunity", Frontiers in Immunology, Jan. 2022, vol. 12, Article 827815, p. 1-p. 21.
International Search Report and Written Opinion issued by the European Patent Office, dated Aug. 24, 2020, for International Application No. PCT/GB2020/051060; 15 pages.
Pan, Huai-Zhong et al., "Hydrogels Composed of Itaconates and Acrylates Having Pyrrolidinonyl With Other Functional Moieties and Novel Biomaterials Targeting to Foldable Intra Ocular Lens," American Chemical Society, Division of Polymer Chemistry, vol. 43, No. 2002, pp. 620-621.
Dominguez, Esther et al., "A Series of Mono and Diesters of Itaconic Acid: Synthesis and Structural Determination," Monatshefte Fur Chemie, vol. 120, pp. 743-748, (1989).
Katsikas, Lynee et al., "Improvement to the Flynn—Wall Method of Determining Apparent Activation Energies of the Thermal Degradation of Polymers,"Journal of Physical Chemistry, vol. 107, pp. 7522-7525(2003).
Chakraborty, Sanjiban, et al., "Suspension polymerization of itaconic acid diesters," Journal of Polymer Science, vol. 135, No. 26, p. 46417 (1)-46417 (5), (2018).
Wang, Runguo et al., "Design and Preparation of a Novel Cross-Linkable, High Molecular Weight, and Bio-Based Elastomer by Emulsion PolyMmerization," Macromolecules, vol. 45, No. 17, pp. 6830-6839( 2012).
Boschert, David et al,, "Synthesis and Bioactivity of Polymer-Based Synthetic Mimics of Antimicrobial Peptides (SMAMPs) Made from Asymmetrically Disubstituted Itaconates," Chemistry—A European Journal, vol. 24, No. 32, pp. 8217-8227(2018).
Padwa, Albert et al., "Cycloadittion—Rearrangement Sequence of 2-Amido Substituted Furans as a Method of Synthesizing Hexahydroindolinones," Journal of Organic Chemistry, vol. 64, No. 13(1999).
Kumazaki, Eri et al., "Steroselective catalytic hydrogenation and conjugate reduction of 4-methyl itaconate derivatives bearing a chiral auxiliary,"Tetrahedron, Elsevier Science Publishers, vol. 69, No. 16, pp. 3486-3494. (2013).
Matsumoto, Akikazu et al., "Synthesis and Radical Polymerization of Itaconates Containing an Adamantyl Ester Group," Bulletin of the Chemical Society of Japan, vol. 65, No. 3, (1992).
Funcke et al.; Arzneimittel Forschung Drug Research (in German), vol. 4, No. 8, pp. 492-492.494 (1954).

* cited by examiner

ITACONIC ACID DERIVATIVES AND USES THEREOF INTREATING AN INFLAMMATORY DISEASE OR A DISEASE ASSOCIATED WITH AN UNDESIRABLE IMMUNE RESPONSE

CROSS-REFERENCE TO RELATED APPLICATIONS

This application is a national phase application of International Application No. PCT/GB2020/051060, filed Apr. 30, 2020, which claims priority to EP19172051.5, filed Apr. 30, 2019, and EP19189910.3, filed Aug. 2, 2019, and EP19217846.5, filed Dec. 19, 2019, and EP20162494.7, filed Mar. 11, 2020: the entire disclosures of which are incorporated herein by reference.

FIELD OF THE INVENTION

The present invention relates to compounds and their use in treating or preventing inflammatory diseases or diseases associated with an undesirable immune response, and to related compositions, methods and intermediate compounds.

BACKGROUND OF THE INVENTION

Chronic inflammatory diseases such as rheumatoid arthritis, systemic lupus erythematosus (SLE), multiple sclerosis, psoriasis, Crohn's disease, ulcerative colitis, uveitis and chronic obstructive pulmonary disease (COPD) represent a significant burden to society because of life-long debilitating illness, increased mortality and high costs for therapy and care (Straub R. H. and Schradin C., 2016). Non-steroidal anti-inflammatory drugs (NSAIDs) are the most widespread medicines employed for treating inflammatory disorders, but these agents do not prevent the progression of the inflammation and only treat the accompanying symptoms. Glucocorticoids are powerful anti-inflammatory agents, making them emergency treatments for acute inflammatory flares, but given longer term these medicines give rise to a plethora of unwanted side-effects and may also be subject to resistance (Straub R. H. and Cutolo M., 2016). Thus, considerable unmet medical need still exists for the treatment of inflammatory disorders and extensive efforts to discover new medicines to alleviate the burden of these diseases is ongoing (Hanke T. et al., 2016).

Dimethyl fumarate (DMF), a diester of the citric acid cycle (CAC) intermediate fumaric acid, is utilised as an oral therapy for treating psoriasis (Brück J. et al., 2018) and multiple sclerosis (Mills E. A. et al., 2018). Importantly, following oral administration, none of this agent is detected in plasma (Dibbert S. et al., 2013), the only drug-related compounds observed being the hydrolysis product monomethyl fumarate (MMF) and glutathione (GSH) conjugates of both the parent (DMF) and metabolite (MMF). DMF's mechanism of action is complex and controversial. This compound's efficacy has been attributed to a multiplicity of different phenomena involving covalent modification of proteins and the conversion of "prodrug" DMF to MMF. In particular, the following pathways have been highlighted as being of relevance to DMF's anti-inflammatory effects: 1) activation of the anti-oxidant, anti-inflammatory, nuclear factor (erythroid-derived 2)-like 2 (NRF2) pathway as a consequence of reaction of the electrophilic α,β-unsaturated ester moiety with nucleophilic cysteine residues on kelch-like ECH-associated protein 1 (KEAP1) (Brennan M. S. et al., 2015); 2) induction of activating transcription factor 3 (ATF3), leading to suppression of pro-inflammatory cytokines interleukin (IL)-6 and IL-8 (Müller S. et al., 2017); 3) inactivation of the glycolytic enzyme glyceraldehyde 3-phosphate dehydrogenase (GAPDH) through succination of its catalytic cysteine residue with a Michael accepting unsaturated ester (Kornberg M. D. et al., 2018; Angiari S. and O'Neill L. A., 2018); 4) inhibition of nuclear factor-kappaB (NF-κB)-driven cytokine production (Gillard G. O. et al., 2015); 5) preventing the association of PKCθ with the costimulatory receptor CD28 to reduce the production of IL-2 and block T-cell activation (Blewett M. M. et al., 2016); 6) reaction of the electrophilic α,β-unsaturated ester with the nucleophilic thiol group of anti-oxidant GSH, impacting cellular responses to oxidative stress (Lehmann J. C. U. et al., 2007); 7) agonism of the hydroxycarboxylic acid receptor 2 (HCA2) by the MMF generated in vivo through DMF hydrolysis (von Glehn F. et al., 2018); 8) allosteric covalent inhibition of the p90 ribosomal S6 kinases (Andersen J. L. et al., 2018); 9) inhibition of the expression and function of hypoxia-inducible factor-1α (HIF-1α) and its target genes, such as IL-8 (Zhao G. et al., 2014); and 10) inhibition of Toll-like receptor (TLR)-induced M1 and K63 ubiquitin chain formation (McGuire V. A. et al., 2016). In general, with the exception of HCA2 agonism (Tang H. et al., 2008), membrane permeable diester DMF tends to exhibit much more profound biological effects in cells compared to its monoester counterpart MMF. However, the lack of systemic exposure of DMF in vivo has led some researchers to assert that MMF is, in fact, the principal active component following oral DMF administration (Mrowietz U. et al., 2018). As such, it is evident that some of the profound biology exerted by DMF in cells is lost because of hydrolysis in vivo to MMF.

Recently, it has been discovered that, during inflammatory macrophage activation, the CAC becomes anaplerotic and is diverted such that the unsaturated diacid itaconic acid, "itaconate", is generated (Murphy M. P. and O'Neill L. A. J., 2018; O'Neill L. A. J. and Artyomov M. N., 2019; Yu X.-H. et al., 2019). Instead of being hydrated to isocitrate by aconitate hydratase, the CAC intermediate aconitate is decarboxylated by the protein product of immune-responsive gene 1 (IRG1), one of the most highly upregulated genes in macrophages under proinflammatory conditions, subsequently named aconitate decarboxylase 1, to produce itaconic acid (Michelucci A. et al., 2013). This unsaturated diacid is an inhibitor of the bacterial enzyme isocitrate lyase and, as such, it exerts anti-bacterial activity. In addition, itaconic acid has been shown to inhibit the CAC enzyme succinate dehydrogenase (SDH) (Ackermann et al., 1949), leading accordingly to succinate accumulation (Cordes T. et al., 2016). By inhibiting SDH, an enzyme critical for the inflammatory response (E. L. Mills et al., 2016), itaconate ameliorates inflammation in vitro and in vivo during macrophage activation and ischemia-reperfusion injury (Lampropoulou V. et al., 2016).

Like fumaric acid, itaconic acid is an α,β-unsaturated carboxylic acid. As such, it is a Michael acceptor which induces a global electrophilic stress response. In this regard, the itaconic acid diesterdimethyl itaconate (DMI), like DMF, produces an anti-inflammatory response, reducing the expression levels of pro-inflammatory cytokines IL-1β, IL-6, IL-12 and IL-18 in lipopolysaccharide (LPS)-stimulated bone marrow-derived macrophages (WO2017/142855A1, incorporated herein by reference). This response appears to be mediated, in part, by NRF2 activation, via alkylation of KEAP1 cysteine residues by the electrophilic α,β-unsaturated ester moiety (Mills E. L. et al., 2018), which enhances the expression of downstream genes with antioxidant and anti-inflammatory capacities. Nevertheless, not all of the pronounced immunoregulatory effects engendered by DMI can be attributed to NRF2 activation. In particular, the modulation of IκBζ by DMI is independent of NRF2 and is mediated via upregulation of ATF3, a global negative regulator of immune activation that downregulates various cytokines, such as IL-6 (Bambouskova M. et al., 2018). Moreover, by inhibiting IκBζ protein production, DMI ameliorates IL-17-mediated pathologies, highlighting the therapeutic potential of this regulatory pathway (WO2019/036509A1, incorporated herein by reference). Further highlighting its pharmacologic potential, DMI has recently been reported to 1) demonstrate a protective effect on cerebral ischemia/reperfusion injury, thereby offering potential for the treatment of ischemic stroke (Zhang D. et al., 2019); 2) provide protection from the cardiotoxic effects of doxorubicin (Shan Q. et al., 2019); and 3) protect against lippolysaccharide-induced mastitis in mice by activating MAPKs and NRFrf2 while inhibiting NF-κB signaling pathways (Zhao C. et al., 2019). Furthermore, DMI is said to have utility in preventing and treating ulcerative colitis and canceration thereof (CN110731955, Sun Yat-sen University Cancer Center); and has been reported to protect against fungal keratitis by activating the NRF2/HO-1 signalling pathway (Gu L. et al., 2020). Nevertheless, it should be noted that DMI is not metabolised to itaconic acid intracellularly (ElAzzouny M. et al., 2017). Other α,β-unsaturated esters exhibit IL-1β-lowering effects in macrophages by inhibiting the NLRP3 inflammasome (Cocco M. et al., 2017 and 2014), and have been demonstrated to inhibit the TLR4 pathway, leading ultimately to suppression of LPS-induced stimulation of NF-κB, tumour necrosis factor (TNF)-α, IL-1β and nitric oxide release (Zhang S. et al., 2012).

Other itaconic acid derivatives have been demonstrated to elicit anti-inflammatory effects (Bagavant G. et al., 1994). A notable example is 4-octyl itaconic acid (4OI), an itaconate derivative with improved cellular uptake. Since the α,β-unsaturated carboxylic acid is not esterified in 4OI, this electrophile exhibits low reactivity with biological thiols (Schmidt T. J. et al., 2007), much like the situation encountered with itaconic acid itself. As a result of its low reactivity/electrophilicity, the NRF2-activating effects of 4OI are not attenuated by GSH, in contrast to the findings with the much more reactive DMI. In this latter case, the α,β-unsaturated carboxylic acid is esterified and, as a consequence, the IL-6-lowering and NRF2-activating effects of DMI are reversed by the thiols N-acetylcysteine and GSH, respectively. Through the reaction with KEAP1 and the resulting NRF2 activation, as well as GAPDH inhibition (Liao S.-T. et al., 2019), 4OI has been demonstrated to produce a wide range of interesting biological effects, including: 1) protection of neuronal cells from hydrogen peroxide (Liu H. et al., 2018); 2) inhibition of proinflammatory cytokine production in peripheral blood mononuclear cells of SLE patients (Tang C. et al., 2018); and 3) protection of human umbilical vein endothelial cells from high glucose (Tang C. et al., 2019); 4) inhibition of osteoclastogenesis by suppressing the E3 ubiquitin ligase Hrd1 and activating NRF2 signaling (Sun X. et al., 2019); 5) induction of repression of STING by NRF2 and type I IFN production in cells from patients with STING-dependent interferonopathies (Olagnier D. et al., 2018); 6) protection against renal fibrosis via inhibiting the TGF-beta/Smad pathway, autophagy and reducing generation of reactive oxygen species (Tian F. et al., 2020); 7) reduction of brain viral burden in mice intracranially injected with Zika virus (Daniels B. P. et al. 2019); and 8) protection against liver ischemia-reperfusion injury (Yi F. et al. 2020). Furthermore, itaconate has been reported to modulate tricarboxylic acid and redox metabolism to mitigate reperfusion injury (Cordes T. et al., 2020). In addition, raised plasma itaconate levels demonstrate a clear correlation with reduction in rheumatoid arthritis disease activity scores following commencement of therapy with conventional disease modifying anti-rheumatic drug (cDMARD) therapy (Daly R. et al. 2019).

Artyomov et al. (WO2017/142855; WO2019/036509) disclose the use of itaconate, malonate or a derivative thereof as an immunomodulatory agent.

In spite of the above findings, there remains a need to identify and develop new itaconate derivatives possessing enhanced properties compared to currently marketed anti-inflammatory agents, such as DMF. The present inventors have now discovered, surprisingly, that certain itaconate diesters are highly effective at reducing cytokine release in cells and/or in activating NRF2-driven effects. These properties, amongst others, make them potentially more effective than DMI and/or dimethyl fumarate. Such compounds therefore possess excellent anti-inflammatory properties.

SUMMARY OF THE INVENTION

In a first aspect, the present invention provides a compound of formula (IW-1):

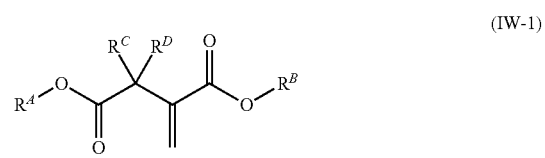

(IW-1)

wherein,
$R^A$ is selected from the group consisting of $C_{1-10}$ alkyl, $C_{2-10}$ alkenyl, $C_{3-10}$ cycloalkyl, $C_{5-10}$ spirocycloalkyl, 6-10 membered heterospirocyclyl and 4-10 membered heterocyclyl; wherein $R^A$ is optionally substituted by one or more substituents selected from the group consisting of oxo, $R^{1A}$, $OR^{2A}$, $NR^{2A}R^{3A}$, $SR^{2A}$, $SOR^{9A}$, $SO_2R^{9A}$, $SO_2NR^{2A}R^{3A}$, $C(O)R^{2A}$ and $CONR^{2A}R^{3A}$;
$R^{1A}$ is selected from the group consisting of fluoro, methyl, $CO_2H$, cyano, $SiR^{4A}R^{5A}R^{6A}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7A}$ and/or $R^{8A}$;
$R^{4A}$, $R^{5A}$ and $R^{6A}$ are independently selected from the group consisting of $C_{1-4}$ alkyl and phenyl; wherein phenyl is optionally substituted by one or more substituents selected from the group consisting of $C_{1-4}$ alkyl, $C_{1-4}$ alkoxy, hydroxy, $CO_2H$, cyano, methanesulfonyl and halo;
$R^{7A}$ and $R^{8A}$ are independently selected from the group consisting of oxo, $C_{1-4}$ alkyl, $C_{1-4}$ alkoxy, $C_{1-4}$ haloalkyl, $C_{1-4}$ haloalkoxy, hydroxy, $CO_2H$, cyano, methanesulfonyl and halo;
or, taken together, $R^{7A}$ and $R^{8A}$ form a $C_{3-8}$ cycloalkyl or 4-7 membered heterocyclic ring;
$R^{2A}$ and $R^{3A}$ are independently H, $C_{1-8}$ alkyl, $C_{3-8}$ cycloalkyl or phenyl; wherein $R^{2A}$ and $R^{3A}$ are independently optionally substituted by one or more substituents selected from the group consisting of $C_{1-8}$ alkyl, $C_{1-4}$ alkoxy, fluoro, hydroxy, oxo and —$(CH_2)_{qA}W^A$;

or, taken together, $R^{2A}$ and $R^{3A}$ form a 4-7 membered heterocyclic ring optionally independently substituted by one or more substituents selected from the group consisting of $C_{1-2}$ alkyl, hydroxy and oxo;

$R^{9A}$ is $C_{1-8}$ alkyl, $C_{3-8}$ cycloalkyl or phenyl; wherein $R^{9A}$ is optionally substituted by one or more substituents selected from the group consisting of $C_{1-8}$ alkyl, $C_{1-4}$ alkoxy, fluoro, hydroxy, oxo and —$(CH_2)_{qA}W^A$;

qA is 0 or 1;

$W^A$ is selected from the group consisting of $C_{3-8}$ cycloalkyl, phenyl and 5-6 membered heteroaryl; wherein $W^A$ is optionally substituted by one or more substituents selected from the group consisting of $C_{1-4}$ alkyl, $C_{1-4}$ alkoxy, hydroxy, $CO_2H$, cyano, methanesulfonyl and halo; wherein $R^B$ is selected from the group consisting of $C_{1-10}$ alkyl, $C_{2-10}$ alkenyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$;

$R^{1B}$ is selected from the group consisting of halo, trifluoromethyl, methyl, $CO_2H$, cyano, $SiR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$;

$R^{4B}$, $R^{5B}$ and $R^{6B}$ are independently selected from the group consisting of $C_{1-4}$ alkyl and phenyl; wherein phenyl is optionally substituted by one or more substituents selected from the group consisting of $C_{1-4}$ alkyl, $C_{1-4}$ alkoxy, hydroxy, $CO_2H$, cyano, methanesulfonyl and halo;

$R^{7B}$ and $R^{8B}$ are independently selected from the group consisting of oxo, $C_{1-4}$ alkyl, $C_{1-4}$ alkoxy, hydroxy, $CO_2H$, $CO_2(C_{1-6}$ alkyl), cyano, methanesulfonyl and halo;

or, taken together, $R^{7B}$ and $R^{8B}$ form a $C_{3-8}$ cycloalkyl or 4-7 membered heterocyclic ring;

$R^{2B}$ and $R^{3B}$ are independently H, $C_{1-8}$ alkyl, $C_{3-8}$ cycloalkyl or phenyl; wherein $R^{2B}$ and $R^{3B}$ are independently optionally substituted by one or more substituents selected from the group consisting of $C_{1-8}$ alkyl, $C_{1-4}$ alkoxy, fluoro, hydroxy, oxo and —$(CH_2)_{qB}W^B$;

or, taken together, $R^{2B}$ and $R^{3B}$ form a 4-7 membered heterocyclic ring optionally independently substituted by one or more substituents selected from the group consisting of $C_{1-2}$ alkyl, hydroxy and oxo;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, halo, $CO_2H$, hydroxy, oxo and —$(CH_2)_{qB}W^B$;

qB is 0 or 1;

$W^B$ is selected from the group consisting of $C_{3-8}$ cycloalkyl, phenyl and 5-6 membered heteroaryl; wherein $W^B$ is optionally substituted by one or more substituents selected from the group consisting of $C_{1-4}$ alkyl, $C_{1-4}$ alkoxy, hydroxy, $CO_2H$, cyano, methanesulfonyl and halo;

$R^C$ and $R^D$ are independently selected from the group consisting of H, $C_{1-2}$ alkyl, hydroxy, methoxy and fluoro;

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

The present invention provides a pharmaceutical composition comprising a compound of formula (IW-1) or a pharmaceutically acceptable salt and/or solvate thereof.

The present invention provides a compound of formula (IW-1) or a pharmaceutically acceptable salt and/or solvate thereof for use as a medicament.

The present invention provides a compound of formula (IW-1) or a pharmaceutically acceptable salt and/or solvate thereof for use in treating or preventing an inflammatory disease or a disease associated with an undesirable immune response.

The present invention provides the use of a compound of formula (IW-1) or a pharmaceutically acceptable salt and/or solvate thereof in the manufacture of a medicament for treating or preventing an inflammatory disease or a disease associated with an immune response.

The present invention provides a method of treating or preventing an inflammatory disease or a disease associated with an undesirable immune response, which comprises administering a compound of formula (IW-1) or a pharmaceutically acceptable salt and/or solvate thereof.

Also provided are intermediate compounds of use in the preparation of compounds of formula (IW-1).

DETAILED DESCRIPTION OF THE INVENTION

Compounds of Formula (IW-1)

Embodiments and preferences set out herein with respect to the compound of formula (IW-1) apply equally to the pharmaceutical composition, compound for use, use and method aspects of the invention.

The term "$C_{1-10}$ alkyl" refers to a straight or branched fully saturated hydrocarbon group having from 1 to 10 carbon atoms. The term encompasses methyl, ethyl, n-propyl, isopropyl, n-butyl, isobutyl, sec-butyl, tert-butyl, n-pentyl, n-heptyl, n-hexyl and n-octyl. Other branched variants such as heptyl-$CH(CH_3)$— and hexyl-$CH(CH_3)$— are also included. Further branched variants include n-pentyl-$CH(CH_2CH_3)$— and (n-Bu)$_2$CH—. Other branched variants include n-pentyl-$C(CH_3)_2$— or n-hexyl-$C(CH_3)_2$—. Another branched variant is —$CH(t-Bu)_2$. Other alkyl groups, for example $C_{1-9}$ alkyl, $C_{1-8}$ alkyl, $C_{1-7}$ alkyl, $C_{1-6}$ alkyl, $C_{1-5}$ alkyl, $C_{1-4}$alkyl, $C_{1-3}$ alkyl, $C_{1-2}$ alkyl, $C_{2-10}$ alkyl, $C_{2-9}$ alkyl, $C_{2-8}$ alkyl, $C_{2-7}$ alkyl, $C_{2-6}$ alkyl, $C_{2-5}$ alkyl, $C_{2-4}$ alkyl, $C_{2-3}$ alkyl, $C_{3-10}$ alkyl, $C_{3-9}$ alkyl, $C_{3-8}$ alkyl, $C_{3-7}$ alkyl, $C_{3-6}$ alkyl, $C_{3-5}$ alkyl, $C_{3-4}$alkyl, $C_{4-10}$ alkyl, $C_{4-9}$ alkyl, $C_{4-8}$ alkyl, $C_{4-7}$ alkyl, $C_{4-6}$ alkyl, $C_{4-5}$ alkyl, $C_{5-10}$ alkyl, $C_{5-9}$ alkyl, $C_{5-8}$ alkyl, $C_{5-7}$ alkyl, $C_{5-6}$ alkyl, $C_{6-10}$ alkyl, $C_{6-9}$ alkyl, $C_{6-8}$ alkyl, $C_{7-10}$ alkyl, $C_{7-9}$ alkyl, $C_{7-8}$ alkyl, $C_{8-10}$ alkyl, $C_{8-9}$ alkyl and $C_{9-10}$ alkyl are as defined above but contain different numbers of carbon atoms. The term "$C_{1-10}$ alkyl" also encompasses "$C_{1-10}$ alkylene" which is a bifunctional straight or branched fully saturated hydrocarbon group having from 1 to 10 carbon atoms. Example "$C_{1-10}$ alkylene" groups include methylene, ethylene, n-propylene, n-butylene, n-pentylene, n-heptylene, n-hexylene and n-octylene.

The term "$C_{2-10}$ alkenyl" refers to a straight or branched hydrocarbon group having from 2 to 10 carbon atoms and at least one carbon-carbon double bond. The term encompasses, $CH=CH_2$, $CH_2CH=CH_2$, $CH=CHCH_3$, $CH_2CH_2CH=CH_2$, $CH=CHCH_2CH_3$, $CH_2CH=CHCH_3$, $CH_2CH_2CH_2CH=CH_2$, $CH=CHCH_2CH_2CH_3$, $CH_2CH=CHCH_2CH_3$, $CH_2CH_2CH=CHCH_3$, $CH=CHCH=CHCH_3$ and $CH_2CH=CHCH=CH_2$. Branched variants such as $CH(CH_3)CH=CH_2$ and $CH=C(CH_3)CH_2$ are also included. Other alkenyl groups, for example $C_{2-9}$ alkenyl, $C_{2-8}$ alkenyl, $C_{2-7}$ alkenyl, $C_{2-6}$ alkenyl, $C_{2-5}$ alkenyl, $C_{2-4}$ alkenyl, $C_{2-3}$ alkenyl, $C_{3-10}$ alkenyl, $C_{3-9}$ alkenyl, $C_{3-8}$ alkenyl, $C_{3-7}$ alkenyl, $C_{3-6}$ alkenyl, $C_{3-5}$ alkenyl, $C_{3-4}$ alkenyl, $C_{4-10}$ alkenyl, $C_{4-9}$ alkenyl, $C_{4-8}$ alkenyl, $C_{4-7}$ alkenyl, $C_{4-6}$ alkenyl, $C_{4-5}$ alkenyl, $C_{5-10}$ alkenyl, $C_{5-9}$ alkenyl, $C_{5-8}$ alkenyl, $C_{5-7}$ alkenyl, $C_{5-6}$ alkenyl, $C_{6-10}$ alkenyl, $C_{6-9}$ alkenyl, $C_{6-8}$ alkenyl, $C_{7-10}$ alkenyl, $C_{7-9}$ alkenyl, $C_{7-8}$ alkenyl, $C_{3-10}$ alkenyl, $C_{8-9}$ alkenyl and $C_{9-10}$ alkenyl are as defined above but contain different numbers of carbon atoms.

The term "$C_{1-4}$ alkoxy" refers to a $C_{1-4}$ alkyl group (e.g. $C_{1-3}$ alkyl group, $C_{1-2}$ alkyl group or $C_1$ alkyl group) as defined above, singularly bonded to oxygen. The term encompasses methoxy, ethoxy, 1-propoxy and 2-propoxy, and is suitably methoxy.

The term "$C_{1-4}$ haloalkyl" (e.g. $C_{1-3}$ haloalkyl group, $C_{1-2}$ haloalkyl group or $C_1$ haloalkyl group) as used herein refers to a straight or a branched fully saturated hydrocarbon chain containing the specified number of carbon atoms and at least one halogen atom, such as fluoro or chloro, especially fluoro. An example of haloalkyl is $CF_3$. Further examples of haloalkyl are $CHF_2$ and $CH_2CF_3$.

The term "$C_{1-4}$ haloalkoxy" refers to a $C_{1-4}$ haloalkyl group (e.g. $C_{1-3}$ haloalkyl group, $C_{1-2}$ haloalkyl group or $C_1$ haloalkyl group) as defined above, singularly bonded to oxygen. Examples of $C_{1-4}$ haloalkoxy include $OCF_3$, $OCHF_2$ and $OCH_2CF_3$.

The term "$C_{3-10}$ cycloalkyl" refers to a fully saturated cyclic hydrocarbon group having from 3 to 10 carbon atoms. The term encompasses cyclopropyl, cyclobutyl, cyclopentyl, cyclohexyl, cycloheptyl, cyclooctyl, cyclononyl and cyclodecyl as well as bridged systems such as bicyclo[1.1.1]pentyl, bicyclo[2.2.1]heptyl, bicyclo[2.2.2]octyl and adamantyl. Other cycloalkyl groups, for example $C_{3-9}$ cycloalkyl, $C_{3-8}$ cycloalkyl, $C_{3-7}$ cycloalkyl, $C_{3-6}$ cycloalkyl, $C_{3-5}$ cycloalkyl, $C_{3-4}$ cycloalkyl, $C_{4-10}$ cycloalkyl, $C_{4-9}$ cycloalkyl, $C_{4-8}$ cycloalkyl, $C_{4-7}$ cycloalkyl, $C_{4-6}$ cycloalkyl, $C_{4-5}$ cycloalkyl, $C_{5-10}$ cycloalkyl, $C_{5-9}$ cycloalkyl, $C_{5-8}$ cycloalkyl, $C_{5-7}$ cycloalkyl, $C_{5-6}$ cycloalkyl, $C_{6-10}$ cycloalkyl, $C_{6-9}$ cycloalkyl, $C_{6-8}$ cycloalkyl, $C_{6-7}$ cycloalkyl, $C_{7-10}$ cycloalkyl, $C_{7-9}$ cycloalkyl, $C_{7-8}$ cycloalkyl, $C_{8-10}$ cycloalkyl, $C_{8-9}$ cycloalkyl and $C_{9-10}$ cycloalkyl are as defined above but contain different numbers of carbon atoms.

The term "$C_{5-10}$ spirocycloalkyl" refers to a bicyclic cycloalkyl group wherein the two rings are connected through just one atom. The rings can be different or identical. The term encompasses spiro[3.3]heptyl. Other spirocycloalkyl groups, for example $C_{5-9}$ spirocycloalkyl, $C_{5-8}$ spirocycloalkyl and $C_{5-7}$ spirocycloalkyl are as defined above but contain different numbers of carbon atoms.

The term "4-10 membered heterocyclyl" refers to a non-aromatic cyclic group having 4 to 10 ring atoms and at least one heteroatom selected from N, O, S and B. The term "heterocyclyl" is interchangeable with "heterocyclic ring".

The term encompasses oxetanyl, thietanyl, azetidinyl, pyrrolidinyl, tetrahydrofuranyl, tetrahydrothienyl, tetrahydropyranyl, piperidinyl, piperazinyl, morpholinyl, thiomorpholinyl and homomorpholinyl. Other heterocyclyl groups, for example, 4-9 membered heterocyclyl, 4-8 membered heterocyclyl, 4-7 membered heterocyclyl, 4-6 membered heterocyclyl and 4-5 membered heterocyclyl are as defined above but contain different numbers of ring atoms. 4-10 membered (e.g. 4-7 membered or 4-6 membered) heterocyclyl groups can typically be substituted by one or more oxo groups. Suitably, thietanyl is substituted by one or two oxo groups. Bicyclic heterocyclic compounds are also encompassed, such as the following:

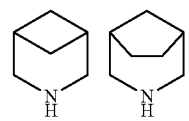

The term "6-10 membered heterospirocyclyl" refers to a bicyclic non aromatic group having 6-10 ring atoms and at least one heteroatom selected from N, O, S and B, wherein the two rings are connected through just one atom. The term encompasses the following group

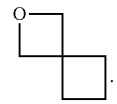

Other heterospirocyclyl groups, for example 6-9 membered heterospirocyclyl, 6-8 membered heterospirocyclyl, 7-10 membered heterospirocyclyl, 7-9 membered heterospirocyclyl and 7-8 membered heterospirocyclyl are as defined above but contain different numbers of ring atoms.

The term "hydroxy" (which may also be referred to as "hydroxyl") refers to an —OH group.

The term "oxo" refers to a =O substituent, whereby an oxygen atom is doubly bonded to carbon (e.g. C=O) or another element (e.g. S=O, S(=O)$_2$). The carbon or other element is suitably an atom of an alkyl, cycloalkyl, spirocycloalkyl or heterocyclyl group.

The term "5-6 membered heteroaryl" refers to a cyclic group with aromatic character having 5-6 ring atoms, at least one of which is a heteroatom independently selected from N, O and S. The term encompasses pyrrolyl, furanyl, thienyl, imidazolyl, pyrazolyl, thiazolyl, oxadiazolyl, thiadiazolyl, triazolyl, oxazolyl, tetrazolyl, pyridyl, pyrimidinyl, pyradizinyl and pyrazinyl.

The term "halo" as used herein, refers to fluorine, chlorine, bromine or iodine. Particular examples of halo are fluorine and chlorine, especially fluorine.

Where substituents are indicated as being optionally substituted in formulae (IW-1), (IW), (IW-a), (IW-b), (IW-c), (IW-d), (IW-e), (IY), (I), (IWA), (IYA), (IA), (IWB), (IYB), (IB), (IWC), (IC), (IWD-1), (IYD-1), (ID-1), (IWD-2), (IYD-2), (ID-2) and (IWE) in the embodiments and preferences set out below, said substituents are optionally substituted as specified in the given formula unless stated otherwise, even if the possible substitution is not explicitly listed in the embodiment.

In one embodiment, $R^4$ is selected from the group consisting of $C_{1-10}$ alkyl, $C_{2-10}$ alkenyl, $C_{3-10}$ cycloalkyl, $C_{5-10}$ spirocycloalkyl, 6-10 membered heterospirocyclyl and 4-10 membered heterocyclyl.

Suitably, $R^A$ is selected from the group consisting of $C_{1-8}$ alkyl, $C_{2-8}$ alkenyl, $C_{3-8}$ cycloalkyl, $C_{5-8}$ spirocycloalkyl, 6-9 membered heterospirocyclyl and 4-7 membered heterocyclyl. Suitably, $R^A$ is selected from the group consisting of $C_{1-8}$ alkyl, $C_{3-8}$ cycloalkyl and 4-7 membered heterocyclyl.

Suitably, $R^A$ is selected from the group consisting of $C_{1-10}$ alkyl, $C_{2-10}$ alkenyl, $C_{3-10}$ cycloalkyl and $C_{5-10}$ spirocycloalkyl. Suitably, $R^A$ is selected from the group consisting of $C_{6-10}$ alkyl, $C_{2-10}$ alkenyl, $C_{6-10}$ cycloalkyl and $C_{5-10}$ spirocycloalkyl, such as $R^A$ is selected from the group consisting of $C_{6-10}$ alkyl and $C_{6-10}$ cycloalkyl. Alternatively, $R^A$ is selected from the group consisting of methyl, ethyl, n-propyl, isopropyl, n-butyl, isobutyl, sec-butyl, tert-butyl, n-pentyl, n-hexyl, n-heptyl, n-octyl, heptyl-CH(CH$_3$)—, hexyl-CH(CH$_3$)— and $C_8$ cycloalkyl.

Suitably, $R^A$ is $C_{1-10}$ alkyl, in particular $C_{1-8}$ alkyl.

Suitably, $R^A$ is selected from the group consisting of methyl, ethyl, n-propyl, iso-propyl, n-butyl, n-pentyl, n-hexyl, n-heptyl and n-octyl, and in particular is selected from the group consisting of methyl, ethyl, n-propyl, iso-propyl, n-butyl, n-hexyl and n-octyl.

Suitably, $R^A$ is $C_{6-10}$ alkyl, in particular n-heptyl, n-octyl, heptyl-CH(CH$_3$)— and hexyl-CH(CH$_3$)—, such as hexyl-CH(CH$_3$)—.

Suitably, $R^A$ is n-pentyl-C(CH$_3$)$_2$— or n-hexyl-C(CH$_3$)$_2$—.

Suitably, $R^A$ is n-hexyl-CH(CH$_3$)—, n-pentyl-C(CH$_3$)$_2$— or n-hexyl-C(CH$_3$)$_2$—.

Most suitably, $R^A$ is hexyl-CH(CH$_3$)— and has the following structure:

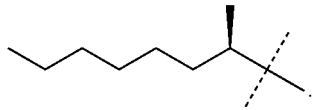

In one embodiment, $R^A$ is $C_{2-10}$ alkenyl, e.g. $C_{3-10}$ alkenyl, in particular CH$_2$CH=CH$_2$ or CH=CHCH$_3$. Alternatively, $R^A$ is $C_{2-8}$ alkenyl.

In one embodiment, $R^A$ is $C_{3-10}$ cycloalkyl, in particular $C_{3-8}$ cycloalkyl. Suitably, $R^A$ is $C_{6-10}$ cycloalkyl, in particular C cycloalkyl.

Suitably, $R^A$ is selected from the group consisting of cyclopropyl, cyclobutyl, cyclopentyl, cyclohexyl, cycloheptyl, cyclooctyl and bicyclo[2.2.1]heptyl; and in particular is cyclobutyl, cyclopentyl, cyclohexyl, cyclooctyl or bicyclo[2.2.1]heptyl. Alternatively, $R^A$ is selected from the group consisting of cyclopropyl, cyclobutyl, cyclopentyl, cyclohexyl, cycloheptyl and cyclooctyl, and in particular is cyclobutyl or cyclooctyl. Suitably, $R^A$ is cyclooctyl. Alternatively $R^A$ is cyclobutyl.

Suitably, $R^A$ is 1-adamantyl:

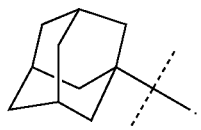

In one embodiment, $R^A$ is $C_{5-10}$ spirocycloalkyl, such as $C_{5-8}$ spirocycloalkyl, and in particular is spiro[3.3]heptyl.

In one embodiment, $R^A$ is 4-10 membered heterocyclyl, in particular 4-7 membered or 4-6 membered heterocyclyl, such as 4-7 membered heterocyclyl. Suitably, $R^A$ is 4-10 membered (e.g. 4-7 membered or 4-6 membered, such as 4-7 membered heterocyclyl) heterocyclyl containing one or two heteroatoms independently selected from N, O and S. Suitably, $R^A$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^A$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. Suitably, $R^A$ is 4 membered heterocyclyl e.g. selected from the group consisting of azetidinyl, oxetanyl and thietanyl. Suitably, thietanyl is substituted by one or two oxo groups.

In one embodiment, $R^A$ is 6-10 membered heterospirocyclyl, e.g. 7-10 membered heterospirocyclyl or 6-9 membered heterospirocyclyl, such as 6-9 membered heterospirocyclyl and in particular is:

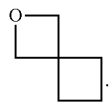

In one embodiment, $R^A$ e.g. as defined above, is not substituted. Suitably, $R^A$ is hexyl-CH(CH$_3$)— and is not substituted.

In another embodiment, $R^A$ e.g. as defined above, is substituted.

In one embodiment, $R^A$ is substituted by one or more substituents selected from the group consisting of oxo, $R^{1A}$, NR$^{2A}$R$^{3A}$, SR$^{2A}$, SOR$^{9A}$, SO$_2$R$^{9A}$, SO$_2$NR$^{2A}$R$^{3A}$, C(O)R$^{2A}$ and CONR$^{2A}$R$^{3A}$. Suitably, the one or more substituent is $R^{1A}$. Suitably, $R^A$ is substituted by one $R^{1A}$. Alternatively, $R^A$ is substituted by two $R^{1A}$. Alternatively, $R^A$ is substituted by three $R^{1A}$. In any one of the above embodiments, $R^{1A}$ may be the same or different.

When $R^A$ is substituted by at least one $R^{1A}$ group the substituent may replace any C—H bond present in $R^A$. When $R^A$ is substituted by at least two $R^{1A}$ groups, the $R^{1A}$ groups may be on the same carbon atom or different carbon atoms. When $R^A$ is a cyclic group, such as $C_{3-10}$ cycloalkyl, $C_{5-10}$ spirocycloalkyl, 6-10 membered heterospirocyclyl and 4-10 membered heterocyclyl, the group may be substituted at the point of attachment of $R^A$ to the oxygen atom such that the following structures form:

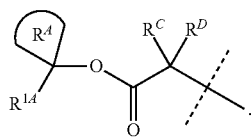

In one embodiment, $R^{1A}$ is selected from the group consisting of fluoro, methyl, CO$_2$H, cyano, SiR$^{4A}$R$^{5A}$R$^{6A}$, 4-7 membered heterocyclyl, phenyl and 5-6 membered heteroaryl; and in particular is selected from the group consisting of fluoro, methyl, cyano, SiR$^{4A}$R$^{5A}$R$^{6A}$ and phenyl. In a second embodiment, $R^{1A}$ is selected from the group consisting of methyl, cyano, SiR$^{4A}$R$^{5A}$R$^{6A}$, $C_{3-8}$ cycloalkyl, phenyl and 5-6 membered heteroaryl.

Suitably, $R^{1A}$ is fluoro. Alternatively, $R^{1A}$ is methyl. Alternatively, $R^{1A}$ is COOH. Alternatively, $R^{1A}$ is cyano. Alternatively, $R^{1A}$ is SiR$^{4A}$R$^{5A}$R$^{6A}$. Alternatively, $R^{1A}$ is $C_{3-8}$ cycloalkyl. Alternatively, $R^{1A}$ is 4-7 membered heterocyclyl. Alternatively, $R^{1A}$ is phenyl. Alternatively, $R^{1A}$ is 5-6 membered heteroaryl.

Most suitably, $R^{1A}$ is selected from fluoro, methyl, $C_{3-8}$ cycloalkyl and phenyl, such as fluoro and phenyl, especially fluoro.

In another embodiment, $R^A$ is substituted by one phenyl group. In another embodiment, $R^A$ is substituted by three fluoro groups. Suitably the three fluoro groups are attached to the same terminal carbon atom to form a $CF_3$ group.

In one embodiment, $R^{4A}$, $R^{5A}$ and $R^{6A}$ are independently selected from the group consisting of $C_{1-4}$ alkyl and phenyl. Suitably, $R^{4A}$, $R^{5A}$ and $R^{6A}$ are independently selected from the group consisting of methyl, ethyl, isopropyl, tert-butyl and phenyl. In one embodiment, the phenyl group is not substituted. In another embodiment the phenyl group is substituted by one or more substituents selected from the group consisting of $C_{1-4}$ alkyl, $C_{1-4}$ alkoxy, hydroxy, $CO_2H$, cyano, methanesulfonyl and halo. Suitably the substituent is $C_{1-4}$ alkyl. Alternatively, the substituent is $C_{1-4}$ alkoxy. Alternatively, the substituent is hydroxy. Alternatively, the substituent is $CO_2H$. Alternatively, the substituent is cyano. Alternatively, the substituent is methanesulfonyl. Alternatively, the substituent is halo. In one embodiment, the phenyl group is substituted by one substituent as defined above. In one embodiment, the phenyl group is substituted by two substituents as defined above. In one embodiment, the phenyl group is substituted by three substituents as defined above. In any one of the above embodiments, the substituents may be the same or different.

In one embodiment, $R^{1A}$ is substituted by $R^{7A}$ and/or $R^{8A}$ when $R^{1A}$ is methyl, $C_{3-8}$ cycloalkyl, 4-7 membered heterocyclyl, phenyl or 5-6 membered heteroaryl, such as methyl or phenyl. Suitably, $R^{1A}$ is substituted by $R^{7A}$ and $R^{8A}$. Alternatively, $R^{1A}$ is substituted by $R^{7A}$ or $R^{8A}$. In one embodiment, $R^{1A}$ is not substituted by $R^{7A}$ and/or $R^{8A}$ when $R^{1A}$ is methyl, $C_{3-8}$ cycloalkyl, 4-7 membered heterocyclyl, phenyl or 5-6 membered heteroaryl. In one embodiment $R^{1A}$ is substituted by $R^{7A}$ and $R^{8A}$ is absent.

In one embodiment, $R^{7A}$ and $R^{8A}$ are independently selected from the group consisting of oxo, $C_{1-4}$ alkyl, $C_{1-4}$ alkoxy, hydroxy, $CO_2H$, cyano, methanesulfonyl and halo; or, taken together, $R^{7A}$ and $R^{8A}$ form a $C_{3-8}$ cycloalkyl or 4-7 membered heterocyclic ring.

Suitably, $R^{7A}$ and $R^{8A}$ are independently selected from the group consisting of oxo, methyl, ethyl, methoxy, hydroxy, $CO_2H$, cyano, methanesulfonyl and halo (e.g. fluoro) such as oxo, methyl, ethyl, methoxy, hydroxy, cyano, methanesulfonyl and halo (e.g. fluoro); or, taken together, $R^{7A}$ and $R^{8A}$ form a $C_{3-8}$ cycloalkyl or 4-7 membered heterocyclic ring. In one embodiment, $R^{7A}$ and $R^{8A}$ are fluoro. In one embodiment, $R^{7A}$ and $R^{8A}$ are chloro. In one embodiment, $R^{7A}$ and $R^{8A}$ are independently selected from the group consisting of oxo, $C_{1-4}$ alkyl, $C_{1-4}$ alkoxy, hydroxy, cyano, methanesulfonyl and halo.

Suitably, $R^{7A}$ is oxo. Alternatively, $R^{7A}$ is $C_{1-4}$ alkyl, such as methyl. Alternatively, $R^{7A}$ is $C_{1-4}$ alkoxy such as methoxy. Alternatively, $R^{7A}$ is $C_{1-4}$ haloalkyl such as $CF_3$. Alternatively, $R^{7A}$ is $C_{1-4}$ haloalkoxy such as $OCF_3$. Alternatively, $R^{7A}$ is hydroxy. Alternatively, $R^{7A}$ is $CO_2H$. Alternatively, $R^{7A}$ is cyano. Alternatively, $R^{7A}$ is methanesulfonyl. Alternatively, $R^{7A}$ is halo such as chloro or fluoro, e.g., chloro. In any one of the above embodiments, suitably $R^{8A}$ is absent. Most suitably, $R^{7A}$ is halo such as chloro or fluoro, e.g., chloro, or $C_{1-4}$ haloalkyl such as $CF_3$ and $R^{8A}$ is absent.

Suitably, $R^{8A}$ is oxo. Alternatively, $R^{8A}$ is $C_{1-4}$ alkyl, such as methyl. Alternatively, $R^{8A}$ is $C_{1-4}$ alkoxy such as methoxy. Alternatively, $R^{8A}$ is $C_{1-4}$ haloalkyl such as $CF_3$. Alternatively, $R^{8A}$ is $C_{1-4}$ haloalkoxy such as $OCF_3$. Alternatively, $R^{8A}$ is hydroxy. Alternatively, $R^{8A}$ is $CO_2H$. Alternatively, $R^{8A}$ is cyano. Alternatively, $R^{8A}$ is methanesulfonyl. Alternatively, $R^{8A}$ is halo such as chloro or fluoro, e.g., chloro. In any one of the above embodiments, suitably $R^{7A}$ is absent.

In another embodiment, taken together, $R^{7A}$ and $R^{8A}$ form a $C_{3-8}$ cycloalkyl or 4-7 membered heterocyclic ring. Suitably, $R^{7A}$ and $R^{8A}$ form a $C_{3-3}$ cycloalkyl ring such as a $C_{3-6}$ cycloalkyl ring. Suitably, $R^{7A}$ and $R^{8A}$ form a 4-7 membered heterocyclic ring such as a 4-6 membered heterocyclic ring.

In one embodiment, $R^{2A}$ and $R^{3A}$ are independently H, $C_{1-8}$ alkyl, $C_{3-8}$ cycloalkyl or phenyl. Suitably, $R^{2A}$ and $R^{3A}$ are independently H, $C_{1-4}$ alkyl, $C_{3-8}$ cycloalkyl or phenyl.

Suitably, $R^{2A}$ is H. Alternatively, $R^{2A}$ is $C_{1-8}$ alkyl, such as $C_{1-4}$ alkyl e.g. methyl. Alternatively, $R^{2A}$ is $C_{3-8}$ cycloalkyl such as $C_{3-6}$ cycloalkyl. Alternatively, $R^{2A}$ is phenyl.

In one embodiment, $R^{2A}$ is methyl or phenyl, in particular phenyl.

Suitably, $R^{3A}$ is H. Alternatively, $R^{3A}$ is $C_{1-8}$ alkyl, such as $C_{1-4}$ alkyl e.g. methyl. Alternatively, $R^{3A}$ is $C_{3-8}$ cycloalkyl, such as $C_{3-6}$ cycloalkyl. Alternatively, $R^{3A}$ is phenyl.

In one embodiment, $R^{3A}$ is methyl.

In one embodiment, $R^{2A}$ and $R^{3A}$ are not substituted. In another embodiment, $R^{2A}$ and $R^{3A}$ are substituted by one or more substituents selected from the group consisting of $C_{1-8}$ alkyl, $C_{1-4}$ alkoxy, fluoro, hydroxy, oxo and $—(CH_2)_{qA}W^A$. In one embodiment, $R^{2A}$ is substituted as described herein and $R^{3A}$ is not substituted. In one embodiment, $R^{2A}$ is not substituted and $R^{3A}$ is substituted as described herein. Suitably, the substituent is $C_{1-8}$ alkyl such as methyl or ethyl. Alternatively, the substituent is $C_{1-4}$ alkoxy such as methoxy. Alternatively, the substituent is fluoro. Alternatively, the substituent is hydroxy. Alternatively, the substituent is oxo. Alternatively, the substituent is $—(CH_2)_{qA}W^A$. Suitably, $R^{2A}$ and/or $R^{3A}$ are substituted by one substituent. Alternatively, $R^{2A}$ and/or $R^{3A}$ are substituted by two substituents. Alternatively, $R^{2A}$ and/or $R^{3A}$ are substituted by three substituents. In any one of the above embodiments, the substituents may be the same or different.

In one embodiment, $R^{2A}$ and $R^{3A}$ form a 4-7 membered heterocyclic ring optionally independently substituted by one or more substituents selected from the group consisting of $C_{1-2}$ alkyl, hydroxy and oxo. Suitably, the 4-7 membered heterocyclic ring is not substituted. Alternatively, the 4-7 membered heterocyclic ring is substituted by one or more substituents selected from the group consisting of $C_{1-2}$ alkyl, hydroxy and oxo. Suitably the substituent is $C_{1-2}$ alkyl such as methyl. Alternatively, the substituent is hydroxy. Alternatively, the substituent is oxo. Suitably, the 4-7 membered heterocyclic ring is substituted by one substituent. Alternatively, the 4-7 membered heterocyclic ring is substituted by two substituents. Alternatively, the 4-7 membered heterocyclic ring is substituted by three substituents. In any one of the above embodiments, the substituents may be the same or different.

In one embodiment, $R^{9A}$ is $C_{1-8}$ alkyl, $C_{3-8}$ cycloalkyl or phenyl. Suitably, $R^{9A}$ is $C_{1-4}$ alkyl, $C_{3-8}$ cycloalkyl or phenyl. Suitably, $R^{9A}$ is $C_{1-4}$ alkyl such as methyl. Alternatively, $R^{9A}$ is $C_{3-8}$ cycloalkyl such as $C_{3-5}$ cycloalkyl. Alternatively, $R^{9A}$ is phenyl.

In one embodiment, $R^{9A}$ is methyl or phenyl, in particular phenyl.

In one embodiment, $R^{9A}$ is not substituted. In another embodiment, $R^{9A}$ is substituted by $C_{1-8}$ alkyl, $C_{1-4}$ alkoxy, fluoro, hydroxy, oxo and $—(CH_2)_{qA}W^A$. Suitably, the substituent is $C_{1-8}$ alkyl such as methyl or ethyl. Alternatively, the substituent is $C_{1-4}$ alkoxy such as methoxy. Alternatively, the substituent is fluoro. Alternatively, the substituent is hydroxy. Alternatively, the substituent is oxo. Alternatively, the substituent is —$(CH_2)_{qA}W^A$. Suitably, $R^{9A}$ is substituted by one substituent. Alternatively, $R^{9A}$ is substituted by two substituents. Suitably, $R^{9A}$ is substituted by three substituents. In any one of the above embodiments, the substituents may be the same or different.

In one embodiment, $W^A$ is selected from the group consisting of $C_{3-8}$ cycloalkyl, phenyl and 5-6 membered heteroaryl. Suitably, $W^A$ is selected from the group consisting of $C_{3-8}$ cycloalkyl and phenyl. In one embodiment, $W^A$ is not substituted. In another embodiment, $W^A$ is substituted by one or more substituents selected from the group consisting of $C_{1-4}$ alkyl, $C_{1-4}$ alkoxy, hydroxy, $CO_2H$, cyano, methanesulfonyl and halo. Suitably, the substituent is $C_{1-4}$ alkyl such as methyl or ethyl. Alternatively, the substituent is $C_{1-4}$ alkoxy such as methoxy. Alternatively, the substituent is hydroxy. Alternatively, the substituent is $CO_2H$. Alternatively, the substituent is cyano. Alternatively, the substituent is methanesulfonyl. Alternatively, the substituent is halo such as fluoro. Suitably, $W^A$ is substituted by one substituent. Alternatively, $W^A$ is substituted by two substituents. Suitably, $W^A$ is substituted by three substituents. In any one of the above embodiments, the substituents may be the same or different.

In one embodiment, qA is 0. In one embodiment, qA is 1.

In one embodiment, $R^A$ contains 6 or more carbon atoms, such as 6, 7, 8, 9 or 10 carbon atoms, such as 8, 9 or 10 carbon atoms. Suitably, $R^A$ contains 6 carbon atoms. Alternatively, $R^A$ contains 7 carbon atoms. Alternatively, $R^A$ contains 8 carbon atoms. Alternatively, $R^A$ contains 9 carbon atoms. Alternatively, $R^A$ contains 10 carbon atoms.

In one embodiment, $R^B$ is selected from the group consisting of $C_{1-10}$ alkyl, $C_{2-10}$ alkenyl, 3-10 cycloalkyl, $C_{5-10}$ spirocycloalkyl and 4-10 membered heterocyclyl. Suitably, $R^B$ is selected from the group consisting of $C_{1-8}$ alkyl, $C_{2-8}$ alkenyl, $C_{3-8}$ cycloalkyl and 4-7 membered heterocyclyl. Suitably, $R^B$ is selected from the group consisting of $C_{1-8}$ alkyl, $C_{3-8}$ cycloalkyl and 4-7 membered heterocyclyl. Alternatively, $R^B$ is selected from the group consisting of $C_{1-10}$ alkyl, $C_{2-10}$ alkenyl, $C_{3-6}$ cycloalkyl, $C_{5-10}$ spirocycloalkyl and 4-10 membered heterocyclyl. Alternatively, $R^B$ is selected from the group consisting of $C_{1-10}$ alkyl, $C_{2-10}$ alkenyl, $C_{5-10}$ spirocycloalkyl and 4-10 membered heterocyclyl.

In one embodiment, $R^B$ is $C_{1-10}$ alkyl, in particular $C_{1-8}$ alkyl, $C_{1-4}$ alkyl, $C_{1-3}$ alkyl or $C_{1-2}$ alkyl. In one embodiment, $R^B$ is $C_{1-2}$ alkyl. Suitably, $R^B$ is $C_{1-10}$ alkyl, such as $C_{1-2}$ alkyl substituted by $R^{1B}$. When $R^B$ is $C_{1-10}$ alkyl, in particular $C_{1-8}$ alkyl such as $C_{1-4}$ alkyl e.g. $C_{1-3}$ alkyl e.g. $C_{1-2}$ alkyl, suitably the alkyl group is n-alkyl.

Suitably, $R^B$ is selected from the group consisting of methyl, ethyl, n-propyl, iso-propyl, n-butyl, tert-butyl, n-pentyl, n-hexyl, n-heptyl and n-octyl, and in particular is selected from the group consisting of methyl, ethyl, n-propyl, iso-propyl, n-butyl and tert-butyl, such as methyl and ethyl.

In one embodiment, $R^B$ is $C_{2-10}$ alkenyl e.g. $C_{3-10}$ alkenyl, in particular $CH_2CH=CH_2$ or $CH=CHCH_3$. Alternatively, $R^B$ is $C_{2-8}$ alkenyl.

In one embodiment, $R^B$ is $C_{3-10}$ cycloalkyl, in particular $C_{3-8}$ cycloalkyl such as $C_{3-6}$ cycloalkyl.

Suitably, $R^B$ is selected from the group consisting of cyclopropyl, cyclobutyl, cyclopentyl, cyclohexyl, cycloheptyl, cyclooctyl and bicyclo[2.2.1]heptyl; and in particular is cyclobutyl, cyclopentyl, cyclohexyl, cyclooctyl or bicyclo[2.2.1]heptyl. In another embodiment, $R^B$ is selected from the group consisting of cyclopropyl, cyclobutyl, cyclopentyl, cyclohexyl, cycloheptyl and cyclooctyl, and in particular is cyclobutyl. In another embodiment, $R^B$ is selected from the group consisting of cyclobutyl and cyclohexyl.

In one embodiment, $R^B$ is $C_{5-10}$ spirocycloalkyl, such as $C_{5-8}$ spirocycloalkyl, and in particular is spiro[3.3]heptyl.

In one embodiment, $R^B$ is 4-10 membered heterocyclyl, in particular 4-7 membered or 4-6 membered heterocyclyl, such as 4-7 membered heterocyclyl. Suitably, $R^B$ is 4-10 membered (e.g. 4-7 membered or 4-6 membered) heterocyclyl containing one or two heteroatoms independently selected from N, O and S. Alternatively, $R^B$ is 4-10 membered (e.g. 4-7 membered or 4-6 membered) heterocyclyl containing one N atom. Alternatively, $R^B$ is 4-10 membered (e.g. 4-7 membered or 4-6 membered) heterocyclyl containing one O atom. In one embodiment, $R^B$ is 4-10 membered (e.g. 4-7 membered or 4-6 membered) heterocyclyl containing one S atom. Suitably, $R^B$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. Suitably, $R^B$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. Suitably, $R^B$ is selected from the group consisting of oxetanyl, thietanyl, azetidinyl, tetrahydrofuranyl, pyrrolidinyl, tetrahydropyranyl, piperidinyl and morpholinyl. Suitably, $R^B$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. Suitably, $R^B$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or $S(=O)_2$ functionality).

In one embodiment, $R^B$ is not substituted. In another embodiment, $R^B$ is substituted. Suitably, $R^B$ is substituted by $SO_2R^{9B}$. Alternatively, $R^B$ is substituted by $R^{1B}$. Suitably, $R^B$ is substituted by one $R^{1B}$. Alternatively, $R^B$ is substituted by two $R^{1B}$. Alternatively, $R^B$ is substituted by three $R^B$. In any one of the above embodiments, $R^{1B}$ may be the same or different.

When $R^B$ is substituted by at least one $R^{1B}$ group the substituent may replace any C—H bond present in $R^B$. When $R^B$ is substituted by at least two $R^{1B}$ groups, the $R^{1B}$ groups may be on the same carbon atom or different carbon atoms. When $R^B$ is a cyclic group, such as $C_{3-10}$ cycloalkyl, $C_{5-10}$ spirocycloalkyl and 4-10 membered heterocyclyl, the group may be substituted at the point of attachment of $R^B$ to the oxygen atom such that the following structures form:

When $R^B$ is n-$C_{1-10}$ alkyl, in particular n-$C_{1-8}$ alkyl such as n-$C_{1-4}$ alkyl e.g. n-$C_{1-3}$ alkyl e.g. n-$C_{1-2}$ alkyl, and is substituted by at least one (such as one) $R^{1B}$, suitably at least one (such as one) $R^{1B}$ is attached to the terminal carbon i.e. such that the following moiety forms:

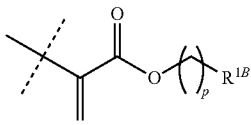

wherein p is 1 to 10 in particular 1 to 8 such as 1 to 4 e.g. 1 to 3 e.g. 1 to 2.

When $R^B$ is $C_{1-10}$ alkyl, in particular $C_{1-8}$ alkyl such as $C_{1-4}$ alkyl e.g. $C_{1-3}$ alkyl e.g. $C_{1-2}$ alkyl, and is substituted by at least one (such as one) $R^{1B}$, suitably the carbon atom of $R^B$ adjacent to the ester oxygen atom is also attached to at least one (such as one) hydrogen atom i.e. such that the following moiety forms:

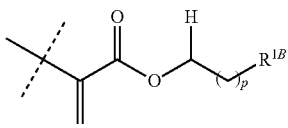

wherein p is 0 to 9 in particular 0 to 7 such as 0 to 3 e.g. 0 to 2 e.g. 0 to 1.

In one embodiment, $R^{1B}$ is selected from the group consisting of halo, trifluoromethyl, methyl, $CO_2H$, cyano, $SiR^{4B}R^{5B}R^{6B}$, $C_{3-8}$ cycloalkyl, 4-7 membered heterocyclyl, phenyl and 5-6 membered heteroaryl. Suitably, $R^{1B}$ is selected from the group consisting of trifluoromethyl, methyl $CO_2H$, cyano, $C_{3-8}$ cycloalkyl, 4-7 membered heterocyclyl, phenyl and 5-6 membered heteroaryl; and in particular is selected from the group consisting of trifluoromethyl, methyl, $CO_2H$, cyano, $C_{3-4}$ cycloalkyl and phenyl, and is suitably trifluoromethyl, $CO_2H$, cyano or cyclopropyl.

Suitably, $R^{1B}$ is halo e.g. fluoro. Alternatively, $R^{1B}$ is trifluoromethyl. Alternatively, $R^{1B}$ is methyl. Alternatively, $R^{1B}$ is $CO_2H$. Alternatively, $R^{1B}$ is cyano. Alternatively, $R^{1B}$ is $SiR^{4B}R^{5B}R^{6B}$. Alternatively, $R^{1B}$ is $C_{3-8}$ cycloalkyl such as $C_{3-5}$ cycloalkyl. Alternatively, $R^{1B}$ is 4-7 membered heterocyclyl such as a 6 membered heterocyclyl e.g. a piperidinyl. Alternatively, $R^{1B}$ is phenyl. Alternatively, $R^{1B}$ is 5-6 membered heteroaryl, in particular tetrazolyl, e.g., 5-tetrazolyl.

Most suitably, $R^{1B}$ is $CO_2H$. In one embodiment, $R^B$ is $C_1$ alkyl and $R^B$ is $CO_2H$. Suitably, $R^B$ is $C_1$ alkyl, $R^{1B}$ is $CO_2H$ and the carbon atom of the $C_1$ alkyl adjacent to the ester oxygen atom is also attached to at least one (such as one) hydrogen atom. In another embodiment, $R^B$ is $C_2$ alkyl and $R^{1B}$ is $CO_2H$. Suitably, $R^B$ is $C_2$ alkyl and $R^{1B}$ is $C_2H$ and the carbon atom of $R^B$ adjacent to the ester oxygen atom is also attached to at least one (such as one) hydrogen atom. In any one of these embodiments, suitably $R^B$ is not further substituted.

In one embodiment, $R^B$ (in particular when $R^B$ is $C_{1-10}$ alkyl, in particular $C_{1-8}$ alkyl, $C_{1-4}$ alkyl, $C_{1-3}$ alkyl or $C_{1-2}$ alkyl e.g $C_{1-2}$ alkyl) is substituted by $CO_2H$. Suitably, $R^B$ (in particular when $R^B$ is $C_{1-10}$ alkyl, in particular $C_{1-8}$ alkyl, $C_{1-4}$ alkyl, $C_{1-3}$ alkyl or $C_{1-2}$ alkyl e.g $C_{1-2}$ alkyl) is substituted by $CO_2H$ and at least one other substituent selected from the group consisting of halo, trifluoromethyl, methyl, cyano, $SiR^{4B}R^{5B}R^{6B}$, $C_{3-8}$ cycloalkyl, 4-7 membered heterocyclyl, phenyl and 5-6 membered heteroaryl, such as halo, trifluoromethyl and methyl. Suitably, $R^B$ is substituted by $CO_2H$ and one further substituent selected from the group consisting of halo, e.g., fluoro, trifluoromethyl, methyl, cyano, $SiR^{4B}R^{5B}R^{6B}$, $C_{3-8}$ cycloalkyl, 4-7 membered heterocyclyl, phenyl and 5-6 membered heteroaryl, such as halo e.g. fluoro, trifluoromethyl and methyl, such as methyl and trifluoromethyl e.g. trifluoromethyl. Suitably the $CO_2H$ is attached to the terminal carbon of the alkyl group and the one further substituent is attached to the carbon atom of $R^B$ adjacent to the ester oxygen atom. Suitably, $R^B$ is substituted by $CO_2H$ and two further substituents selected from the group consisting of halo e.g. fluoro, trifluoromethyl, cyano, $SiR^{4B}R^{5B}R^{6B}$, $C_{3-8}$ cycloalkyl, 4-7 membered heterocyclyl, phenyl and 5-6 membered heteroaryl, such as halo, e.g., fluoro and trifluoromethyl. Suitably the $CO_2H$ is attached to the terminal carbon of the alkyl group and one of the two further substituents is attached to the carbon atom of $R^B$ adjacent to the ester oxygen atom.

By the term "one further substituent is attached to the carbon atom of $R^B$ adjacent to the ester oxygen atom" it is meant that the following moiety forms:

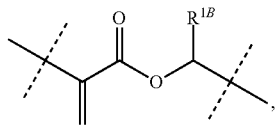

such as

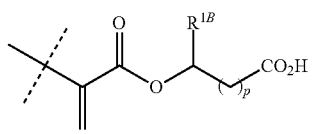

wherein p is 0 to 9 in particular 0 to 7 such as 0 to 3 e.g. 0 to 2 e.g. 0 to 1.

In one embodiment, $R^{4B}$, $R^{5B}$ and $R^{6B}$ are independently selected from the group consisting of $C_{1-4}$ alkyl and phenyl. Suitably $R^{4B}$, $R^{5B}$ and $R^{6B}$ are independently selected from the group consisting of methyl, ethyl, iso-propyl, tert-butyl and phenyl. In one embodiment, the phenyl group is not substituted. In another embodiment the phenyl group is substituted by one or more substituents selected from the group consisting of $C_{1-4}$ alkyl, $C_{1-4}$ alkoxy, hydroxy, $CO_2H$, cyano, methanesulfonyl and halo. Suitably the substituent is $C_{1-4}$ alkyl. Alternatively, the substituent is $C_{1-4}$ alkoxy. Alternatively, the substituent is hydroxy. Alternatively, the substituent is $CO_2H$. Alternatively, the substituent is cyano. Alternatively, the substituent is methanesulfonyl. Alternatively, the substituent is halo. In one embodiment, the phenyl group is substituted by one substituent as defined above. In one embodiment, the phenyl group is substituted by two substituents as defined above. In one embodiment, the phenyl group is substituted by three substituents as defined above. In any one of the above embodiments, the substituents may be the same or different.

In one embodiment, $R^{1B}$ is substituted by $R^{7B}$ and/or $R^{8B}$ when $R^{1B}$ is methyl, $C_{3-8}$ cycloalkyl, 4-7 membered heterocyclyl, phenyl and 5-6 membered heteroaryl. Suitably, $R^{1B}$ is substituted by $R^{7B}$ and $R^{8B}$. Alternatively, $R^{1B}$ is substituted by $R^{7B}$ or $R^{8B}$. In one embodiment, $R^{1B}$ is not substituted by $R^{7B}$ and/or $R^{8B}$ when $R^{1B}$ is methyl, $C_{3-8}$ cycloalkyl, 4-7 membered heterocyclyl, phenyl and 5-6 membered heteroaryl. In one embodiment, $R^{1B}$ is substituted by $R^{7B}$ and $R^{8B}$ is absent.

In one embodiment, $R^{7B}$ and $R^{8B}$ are independently selected from the group consisting of oxo, $C_{1-4}$ alkyl, $C_{1-4}$ alkoxy, hydroxy, $CO_2H$, $CO_2(C_{1-6}$ alkyl), cyano, methanesulfonyl and halo. Suitably, $R^{7B}$ and $R^{8B}$ are independently selected from the group consisting of oxo, methyl, ethyl, methoxy, hydroxy, $CO_2H$, $CO_2(C_{1-2}$ alkyl), cyano, methanesulfonyl and halo (e.g. fluoro); or, taken together, $R^{7B}$ and $R^{8B}$ form a $C_{3-8}$ cycloalkyl or 4-7 membered heterocyclic ring.

In one embodiment, $R^{7B}$ and $R^{8B}$ are independently selected from the group consisting of oxo, methyl, ethyl, methoxy, hydroxy, $CO_2H$, cyano, methanesulfonyl and halo (e.g. fluoro); or, taken together, $R^{7B}$ and $R^{8B}$ form a $C_{3-8}$ cycloalkyl or 4-7 membered heterocyclic ring. In one embodiment, $R^{7B}$ and $R^{8B}$ are cyano or fluoro e.g. fluoro.

Suitably, $R^{7B}$ is oxo. Alternatively, $R^{7B}$ is $C_4$ alkyl such as methyl and ethyl. Alternatively, $R^{7B}$ is $C_{1-4}$ alkoxy such as methoxy. Alternatively, $R^{7B}$ is hydroxy. Alternatively, $R^{7B}$ is $CO_2H$. Alternatively, $R^{7B}$ is $CO_2(C_{1-6}$ alkyl) such as $CO_2(C_{1-2}$ alkyl). Alternatively, $R^7B$is cyano. Alternatively, $R^{7B}$ is methanesulfonyl. Alternatively, $R^{7B}$ is halo such as fluoro. In any one of the above embodiments, suitably $R^{8B}$ is absent.

Suitably, $R^{8B}$ is oxo. Alternatively, $R^{8B}$ is $C_{1-4}$ alkyl such as methyl and ethyl. Alternatively, $R^{8B}$ is $C_{1-4}$ alkoxy such as methoxy. Alternatively, $R^{8B}$ is hydroxy. Alternatively, $R^{8B}$ is $CO_2H$. Alternatively, $R^{8B}$ is $CO_2(C_{1-6}$ alkyl) such as $CO_2(C_{1-2}$ alkyl). Alternatively, $R^8B$is cyano. Alternatively, $R^{8B}$ is methanesulfonyl. Alternatively, $R^{8B}$ is halo such as fluoro. In any one of the above embodiments, suitably $R^{7B}$ is absent.

In another embodiment, taken together, $R^{7B}$ and $R^{8B}$ form a $C_{3-8}$ cycloalkyl or 4-7 membered heterocyclic ring. Suitably, $R^{7B}$ and $R^{8B}$ form a $C_{3-8}$ cycloalkyl ring such as a $C_{3-5}$cycloalkyl ring. Suitably, $R^{7B}$ and $R^{8B}$ form a 4-7 membered heterocyclic ring such as a 4-6 membered heterocyclic ring.

In one embodiment, $R^{2B}$ and $R^{3B}$ are independently H, $C_{1-8}$ alkyl, $C_{3-8}$ cycloalkyl or phenyl. Suitably, $R^{2B}$ and $R^{3B}$ are independently H, $C_{1-4}$ alkyl, $C_{3-8}$ cycloalkyl or phenyl.

In one embodiment, $R^{2B}$ and/or $R^{36}$ are/is independently methyl, ethyl, tert-butyl or phenyl.

In one embodiment, $R^{2B}$ and/or $R^{3B}$ are/is optionally independently substituted by one or more substituents selected from the group consisting of $C_{1-4}$ alkyl, $C_{1-4}$ alkoxy, fluoro and oxo; and particular are/is optionally substituted by one or more substituents selected from the group consisting of methyl, fluoro and oxo e.g. selected from the group consisting of methyl and fluoro.

Suitably, $R^{2B}$ is H. Alternatively, $R^{2B}$ is $C_{1-8}$ alkyl, such as $C_{1-4}$ alkyl, e.g., methyl. Alternatively, $R^{2B}$ is $C_{3-8}$ cycloalkyl such as $C_{3-6}$ cycloalkyl. Alternatively, $R^{2B}$ is phenyl.

In one embodiment, $R^B$ is substituted by $OR^{2B}$, wherein $R^{2B}$ is acetyl.

In one embodiment, $R^{2B}$ is methyl or phenyl.

Suitably, $R^{3B}$ is H. Alternatively, $R^{3B}$ is $C_{1-8}$ alkyl, such as $C_{1-4}$ alkyl, e.g., methyl. Alternatively, $R^{3B}$ is $C_{3-8}$ cycloalkyl, such as $C_{3-6}$ cycloalkyl. Alternatively, $R^{3B}$ is phenyl.

In one embodiment, $R^{3B}$ is methyl.

In one embodiment, $R^{2B}$ and $R^{3B}$ are not substituted. In another embodiment, $R^{2B}$ and $R^{3B}$ are substituted by one or more substituents selected from the group consisting of $C_{1-8}$ alkyl, $C_{1-4}$ alkoxy, fluoro, hydroxy, oxo and $—(CH_2)_{qB}W^B$. In one embodiment, $R^{2B}$ is substituted as described herein and $R^{3B}$ is not substituted. In one embodiment, $R^{2B}$ is not substituted and $R^{3B}$ is substituted as described herein. Suitably, the substituent is $C_{1-8}$ alkyl such as methyl or ethyl.

Alternatively, the substituent is $C_{1-4}$ alkoxy such as methoxy. Alternatively, the substituent is fluoro.

Alternatively, the substituent is hydroxy. Alternatively, the substituent is oxo. Alternatively, the substituent is $—(CH_2)_{qB}W^B$. Suitably, $R^{2B}$ and/or $R^{3B}$ are substituted by one substituent. Alternatively, $R^{2B}$ and/or $R^{3B}$ are substituted by two substituents. Alternatively, $R^{2B}$ and/or $R^{3B}$ are substituted by three substituents. In any one of the above embodiments, the substituents may be the same or different.

In one embodiment, taken together, $R^{2B}$ and $R^{3B}$ form a 4-7 membered heterocyclic ring.

In one embodiment, taken together, $R^{2B}$ and $R^{3B}$ form a 5 membered heterocyclic ring; for example, taken together, $R^{2B}$ and $R^{3B}$ form pyrrolidine. In one embodiment, taken together, $R^{2B}$ and $R^{3B}$ form a 6 membered heterocyclic ring, for example morpholine.

In one embodiment, $R^{2B}$ and $R^{3B}$ form a 4-7 membered heterocyclic ring optionally independently substituted by one or more substituents selected from the group consisting of $C_{1-2}$ alkyl, hydroxy and oxo. Suitably, the 4-7 membered heterocyclic ring is not substituted. Alternatively, the 4-7 membered heterocyclic ring is substituted by one or more substituents selected from the group consisting of $C_{1-2}$ alkyl, hydroxy and oxo. Suitably the substituent is $C_{1-2}$ alkyl such as methyl.

Alternatively, the substituent is hydroxy. Alternatively, the substituent is oxo. Suitably, the 4-7 membered heterocyclic ring is substituted by one substituent. Alternatively, the 4-7 membered heterocyclic ring is substituted by two substituents. Alternatively, the 4-7 membered heterocyclic ring is substituted by three substituents. In any one of the above embodiments, the substituents may be the same or different.

In one embodiment, $R^{9B}$ is $C_{1-8}$ alkyl, $C_{3-8}$ cycloalkyl or phenyl. Suitably, $R^{9B}$ is $C_{1-4}$ alkyl or phenyl e.g. is methyl or phenyl. Suitably, $R^{9B}$ is $C_{1-4}$ alkyl such as methyl. Alternatively, $R^{9B}$ is $C_{3-8}$ cycloalkyl such as $C_{3-5}$ cycloalkyl. Alternatively, $R^{9B}$ is phenyl.

In one embodiment, $R^{9B}$ is optionally substituted by one or more substituents selected from the group consisting of $C_{1-8}$ alkyl, $C_{1-4}$ alkoxy, fluoro, hydroxy, oxo and $—(CH_2)_{qB}W^B$. $R^{9B}$ is optionally substituted by one or more substituents selected from the group consisting of $C_{1-4}$ alkyl, $C_{1-4}$ alkoxy, fluoro, chloro, $CO_2H$ and oxo. In another embodiment, $R^{9B}$ is optionally substituted by one or more substituents selected from the group consisting of $C_{1-4}$ alkyl, $C_{1-4}$ alkoxy, fluoro and oxo; and particular is optionally substituted by one or more substituents selected from the group consisting of methyl, fluoro and oxo e.g. selected from the group consisting of methyl and fluoro.

In one embodiment, $R^{9B}$ is not substituted. In another embodiment, $R^{9B}$ is substituted by $C_{1-8}$ alkyl, $C_{1-4}$ alkoxy, fluoro, hydroxy, oxo and $—(CH_2)_{qB}W^B$. Suitably, the substituent is $C_{1-8}$ alkyl such as methyl or ethyl. Alternatively, the substituent is $C_{1-4}$ alkoxy such as methoxy. Alternatively, the substituent is fluoro. Alternatively, the substituent is hydroxy. Alternatively, the substituent is oxo.

Alternatively, the substituent is $—(CH_2)_{qB}W^B$. Suitably, $R^{9B}$ is substituted by one substituent.

Alternatively, $R^{9B}$ is substituted by two substituents. Suitably, $R^{9B}$ is substituted by three substituents. In any one of the above embodiments, the substituents may be the same or different.

In one embodiment, W is selected from the group consisting of $C_{3-8}$ cycloalkyl, phenyl and 5-6 membered heteroaryl. Suitably, $W^B$ is selected from the group consisting of $C_{3-8}$ cycloalkyl and phenyl. In one embodiment, $W^B$ is not substituted. In another embodiment, W is substituted by one or more substituents selected from the group consisting of $C_{1-4}$ alkyl, $C_{1-4}$ alkoxy, hydroxy, $CO_2H$, cyano, methanesulfonyl and halo. Suitably, the substituent is $C_{1-4}$ alkyl such as methyl or ethyl. Alternatively, the substituent is $C_{1-4}$ alkoxy such as methoxy. Alternatively, the substituent is hydroxy. Alternatively, the substituent is $CO_2H$. Alternatively, the substituent is cyano.

Alternatively, the substituent is methanesulfonyl. Alternatively, the substituent is halo such as fluoro. Suitably, $W^B$ is substituted by one substituent. Alternatively, W is substituted by two substituents. Suitably, $W^B$ is substituted by three substituents. In any one of the above embodiments, the substituents may be the same or different.

In one embodiment, qB is 0. In one embodiment, qB is 1.

For a compound of formula (IW-1), or any other embodiment described herein, when neither $R^A$ nor $R^B$ contain heteroatoms, the total number of carbon atoms in groups $R^A$ and $R^B$ taken together is at least 6. According to the present invention, heteroatoms include O, N, S, F, Cl, Br, I, P, B and Si. Carbon and hydrogen atoms are not heteroatoms.

In one embodiment, one of $R^A$ and $R^B$ contains a heteroatom, for example selected from the group consisting of O, N, S, F, Cl, P and Si e.g. selected from the group consisting of O, N, S and F.

In one embodiment, when neither $R^A$ nor $R^B$ contain heteroatoms, the total number of carbon atoms in groups $R^A$ and $R^B$ taken together is at least 7 such as 7. In one embodiment, when neither $R^A$ nor $R^B$ contain heteroatoms, the total number of carbon atoms in groups $R^A$ and $R^B$ taken together is at least 8 such as 8. In one embodiment, when neither $R^A$ nor $R^B$ contain heteroatoms, the total number of carbon atoms in groups $R^A$ and $R^B$ taken together is at least 9 such as 9.

In one embodiment, $R^A$ is $C_{6-10}$ alkyl or $C_{6-10}$ cycloalkyl and $R^B$ is $C_{1-4}$ alkyl substituted by at least one $R^B$ group. Suitably, $R^A$ is $C_{6-10}$ alkyl such as $C_8$ alkyl. Alternatively, $R^A$ is $C_{6-10}$ cycloalkyl such as cyclooctyl. Suitably, $R^B$ is $C_{1-2}$ alkyl substituted by at least one $R^{1B}$ group, such as one $R^{1B}$ group. Suitably, the at least one (e.g. one) $R^{1B}$ group is COOH. $R^B$ may be further substituted by an additional $R^{1B}$ group e.g. trifluoromethyl.

In one embodiment, $R^C$ and $R^D$ are independently selected from the group consisting of H, $C_{1-2}$ alkyl, hydroxy, methoxy and fluoro. Suitably, $R^C$ and $R^D$ are independently selected from the group consisting of H, $C_{1-2}$ alkyl, hydroxy and fluoro. In one embodiment, $R^C$ and $R^D$ are independently selected from the group consisting of H, methoxy and fluoro.

In one embodiment, $R^C$ is H. In one embodiment, $R^C$ is $C_{1-2}$ alkyl, in particular methyl. In one embodiment, $R^C$ is hydroxy. In one embodiment, $R^C$ is fluoro. In one embodiment, $R^C$ is methoxy.

In one embodiment, $R^D$ is H. In one embodiment, $R^D$ is $C_{1-2}$ alkyl, in particular methyl. In one embodiment, $R^D$ is hydroxy. In one embodiment, $R^D$ is fluoro. In one embodiment, $R^D$ is methoxy.

In one embodiment, $R^C$ is H, $C_{1-2}$ alkyl (in particular methyl), hydroxy or fluoro; and $R^D$ is H, $C_{1-2}$ alkyl (in particular methyl), or fluoro. In one embodiment, $R^C$ is H, $C_{1-2}$ alkyl (in particular methyl), hydroxy or fluoro; and $R^D$ is H, $C_{1-2}$ alkyl (in particular methyl) or fluoro. In one embodiment, $R^C$ is H, $C_{1-2}$ alkyl (in particular methyl), hydroxy or fluoro; and $R^D$ is H or $C_{1-2}$ alkyl (in particular methyl).

In one embodiment, $R^C$ is H, $C_{1-2}$ alkyl (in particular methyl), hydroxy or fluoro; and $R^D$ is H or fluoro. In one embodiment, $R^C$ is H, $C_{1-2}$ alkyl (in particular methyl), hydroxy or fluoro; and $R^D$ is H. In one embodiment, $R^C$ is H and $R^D$ is H or $C_{1-2}$ alkyl (in particular methyl). In one embodiment, $R^C$ is H and $R^D$ is H or fluoro. In one embodiment, $R^C$ is H or $C_{1-2}$ alkyl (in particular methyl); and $R^D$ is H, $C_{1-2}$ alkyl (in particular methyl), or fluoro. In one embodiment, $R^C$ is H or $C_{1-2}$ alkyl (in particular methyl); and $R^D$ is H or $C_{1-2}$ alkyl (in particular methyl). In one embodiment, $R^C$ is H or $C_{1-2}$ alkyl (in particular methyl); and $R^D$ is H. In one embodiment, $R^C$ is H and $R^D$ is H. In one embodiment, both of $R^C$ and $R^D$ are not hydroxy. In one embodiment, $R^C$ is methoxy and $R^D$ is H.

In one embodiment, when $R^B$ contains 2 or more carbon atoms and 4 or more heteroatoms, then $R^A$ must contain 6 or more carbon atoms, and the number of carbon atoms in $R^A$ must exceed the number of heteroatoms in $R^A$ by at least 3 atoms.

In one embodiment, the molecular weight of the compound of formula (IW) is 150 Da-450 Da.

Suitably, there is provided a compound of formula (IW):

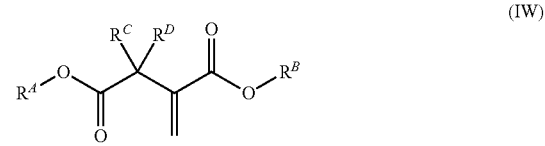

(IW)

wherein, $R^A$, $R^{1A}$, $R^{2A}$, $R^{3A}$, $R^{4A}$, $R^{5A}$, $R^{6A}$, $R^{9A}$, qA and $W^A$ are as defined for compounds of formula (IW-1); $R^{7A}$ and $R^{8A}$ are independently selected from the group consisting of oxo, $C_{1-4}$ alkyl, $C_{1-4}$ alkoxy, hydroxy, $CO_2H$, cyano, methanesulfonyl and halo; or, taken together, $R^{7A}$ and $R^{8A}$ form a $C_{3-8}$ cycloalkyl or 4-7 membered heterocyclic ring;

wherein $R^B$, $R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW-1);

$R^{1B}$ is selected from the group consisting of trifluoromethyl, methyl, $CO_2H$, cyano, $SiR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$;

$R^C$ and $R^D$ are as defined for compounds of formula (IW-1);

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW-1) apply equally to formula (IW).

Suitably, the present invention provides a compound of formula (IW-a):

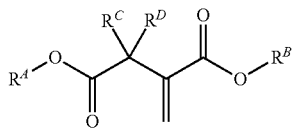

(IW-a)

wherein,
$R^A$ is selected from the group consisting of $C_{1-10}$ alkyl, $C_{2-10}$ alkenyl, $C_{3-10}$ cycloalkyl, $C_{5-10}$ spirocycloalkyl; wherein $R^A$ is optionally substituted by one or more substituents selected from the group consisting of oxo, $R^{1A}$, $NR^{2A}R^{3A}$, $SR^{2A}$, $SOR^{9A}$, $SO_2R^{9A}$, $SO_2NR^{2A}R^{3A}$, $C(O)R^{2A}$ and $CONR^{2A}R^{3A}$.

$R^{1A}$ is selected from the group consisting of methyl, cyano, $SiR^{4A}R^{5A}R^{8A}$, $C_{3-8}$ cycloalkyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7A}$ and/or $R^{8A}$;

$R^{4A}$, $R^{5A}$ and $R^{6A}$ are as defined for the compound of formula (IW-1);

$R^{7A}$ and $R^{8A}$ are independently selected from the group consisting of oxo, $C_{1-4}$ alkyl, $C_{1-4}$ alkoxy, hydroxy, cyano, methanesulfonyl and halo; or, taken together, $R^{7A}$ and $R^{8A}$ form a $C_{3-8}$ cycloalkyl or 4-7 membered heterocyclic ring;

$R^{2A}$ and $R^{3A}$ are as defined for the compound of formula (IW-1);

$R^{9A}$ is as defined for the compound of formula (IW-1);
qA is 0 or 1;
$W^A$ is as defined for the compound of formula (IW-1);
wherein $R^A$ contains 6 or more carbon atoms;
wherein
$R^B$ is selected from the group consisting of $C_{1-10}$ alkyl, $C_{2-10}$ alkenyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$;

$R^{1B}$ is selected from the group consisting of trifluoromethyl, methyl, $CO_2H$, cyano, $SiR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$;

$R^{4B}$, $R^{5B}$ and $R^{6B}$ are as defined for the compound of formula (IW-1);

$R^{7B}$ and $R^{8B}$ are as defined for the compound of formula (IW-1);

$R^{2B}$ and $R^{3B}$ are as defined for the compound of formula (IW-1);

$R^{9B}$ is as defined for the compound of formula (IW-1);
qB is 0 or 1;
$W^B$ is as defined for the compound of formula (IW-1);

$R^C$ and $R^D$ are independently selected from the group consisting of H, methoxy and fluoro; and wherein,
when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW-1) apply equally to formula (IW-a).

Suitably, the present invention provides a compound of formula (IW-b):

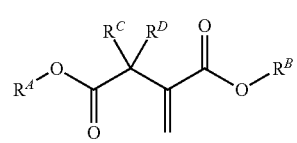

(IW-b)

wherein,
$R^A$ is selected from the group consisting of $C_{1-10}$ alkyl, $C_{2-10}$ alkenyl, $C_{3-10}$ cycloalkyl, $C_{5-10}$ spirocycloalkyl; wherein $R^A$ is optionally substituted by one or more substituents selected from the group consisting of oxo, $R^{1A}$, $NR^{2A}R^{3A}$, $SR^{2A}$, $SOR^{9A}$, $SO_2R^{9A}$, $SO_2NR^{2A}R^{3A}$, $C(O)R^{2A}$ and $CONR^{2A}R^{3A}$.

$R^{1A}$ is selected from the group consisting of methyl, cyano, $SiR^{4A}R^{5A}R^{6A}$, $C_{3-8}$ cycloalkyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7A}$ and/or $R^{8A}$;

$R^{4A}$, $R^{5A}$ and $R^{6A}$ are as defined for the compound of formula (IW-1);

$R^{7A}$ and $R^{8A}$ are independently selected from the group consisting of oxo, $C_{1-4}$ alkyl, $C_{1-4}$ alkoxy, hydroxy, cyano, methanesulfonyl and halo; or, taken together, $R^{7A}$ and $R^{8A}$ form a $C_{3-8}$ cycloalkyl or 4-7 membered heterocyclic ring;

$R^{2A}$ and $R^{3A}$ are as defined for the compound of formula (IW-1);

$R^{9A}$ is as defined for the compound of formula (IW-1);
qA is 0 or 1;
$W^A$ is as defined for the compound of formula (IW-1);
wherein
$R^B$ is selected from the group consisting of $C_{1-10}$ alkyl, $C_{2-10}$ alkenyl, $C_{3-6}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$.

$R^{1B}$ is selected from the group consisting of trifluoromethyl, methyl, $CO_2H$, cyano, $SiR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$;

$R^{4B}$, $R^{5B}$ and $R^{6B}$ are as defined for the compound of formula (IW-1);

$R^{7B}$ and $R^{8B}$ are as defined for the compound of formula (IW-1);

$R^{2B}$ and $R^{3B}$ are as defined for the compound of formula (IW-1);

$R^{9B}$ is as defined for the compound of formula (IW-1);

qB is 0 or 1;

$W^B$ is as defined for the compound of formula (IW-1);

$R^C$ and $R^D$ are independently selected from the group consisting of H, methoxy and fluoro;

and wherein, when neither $R^A$ nor $R^B$ contain heteroatoms, the total number of carbon atoms in groups $R^A$ and $R^B$ taken together is at least 6; and when $R^B$ contains 2 or more carbon atoms and 4 or more heteroatoms, then $R^A$ must contain 6 or more carbon atoms, and the number of carbon atoms in $R^A$ must exceed the number of heteroatoms in $R^A$ by at least 3 atoms;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW-1) apply equally to formula (IW-b).

Suitably, the present invention provides a compound of formula (IW-c):

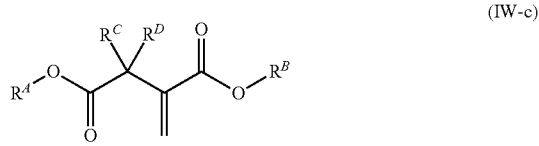

(IW-c)

wherein:

$R^A$ is selected from the group consisting of $C_{6-10}$ alkyl and $C_{6-10}$ cycloalkyl;

$R^B$ is $C_{1-10}$ alkyl substituted by $R^{1B}$;

$R^{1B}$ is selected from the group consisting of $CO_2H$ and 5-6 membered heteroaryl;

$R^C$ and $R^D$ are H;

or a pharmaceutically acceptable salt and/or solvate thereof.

Embodiments and preferences regarding groups $R^A$, $R^B$ and $R^{1B}$ described above with respect to formula (IW-1) apply equally to formula (IW-c).

Suitably, the present invention provides a compound of formula (IW-d):

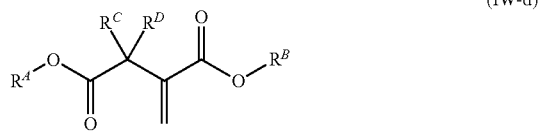

(IW-d)

wherein:

$R^A$ is selected from the group consisting of methyl, ethyl, n-propyl, isopropyl, n-butyl, isobutyl, sec-butyl, tert-butyl, n-pentyl, n-hexyl, n-heptyl, n-octyl, heptyl-CH($CH_3$)—, hexyl-CH($CH_3$)— and $C_8$ cycloalkyl;

$R^B$ is $C_{1-10}$ alkyl substituted by $R^{1B}$;

$R^{1B}$ is selected from the group consisting of trifluoromethyl, methyl, $CO_2H$, cyano, $C_{3-8}$ cycloalkyl, 4-7 membered heterocyclyl, phenyl and 5-6 membered heteroaryl;

$R^C$ and $R^D$ are H;

or a pharmaceutically acceptable salt and/or solvate thereof.

Embodiments and preferences regarding groups $R^A$, $R^B$ and $R^{1B}$ described above with respect to formula (IW-1) apply equally to formula (IW-d).

Suitably, the present invention provides a compound of formula (IW-e):

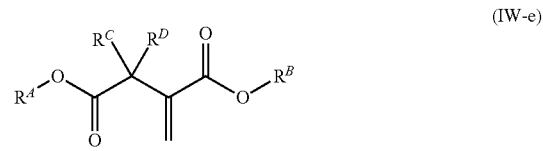

(IW-e)

wherein, $R^A$ is selected from the group consisting of $C_{1-10}$ alkyl, $C_{3-10}$ cycloalkyl and $C_510$ spirocycloalkyl; wherein $R^A$ is not substituted or is substituted by one or more substituents selected from the group consisting of oxo, $R^{1A}$, $OR^{2A}$, $NR^{2A}R^{3A}$, $SR^{2A}$, $SOR^{9A}$, $SO_2R^{9A}$, $SO_2NR^{2A}R^{3A}$, $C(O)R^{2A}$ and $CONR^{2A}R^{3A}$;

$R^{1A}$ is selected from the group consisting of fluoro, methyl, cyano, $SiR^{4A}R^{5A}R^{6A}$, $C_{3-8}$ cycloalkyl and phenyl; wherein methyl, $C_{3-8}$ cycloalkyl and phenyl are not substituted or are substituted by $R^{7A}$ and/or $R^{8A}$;

$R^{4A}$, $R^{5A}$ and $R^{6A}$ are independently selected from the group consisting of $C_{1-4}$ alkyl and phenyl;

$R^{7A}$ and $R^{8A}$ are independently selected from the group consisting of oxo, $C_{1-4}$ alkyl, $C_{1-4}$ alkoxy, $C_{1-4}$ haloalkyl, $C_{1-4}$ haloalkoxy, hydroxy, $CO_2H$, cyano, methanesulfonyl and halo;

or, taken together, $R^{7A}$ and $R^{8A}$ form a $C_{3-8}$ cycloalkyl or 4-7 membered heterocyclic ring;

$R^{2A}$ and $R^{3A}$ are independently H, $C_{1-8}$ alkyl, $C_{3-8}$ cycloalkyl or phenyl;

or, taken together, $R^{2A}$ and $R^{3A}$ form a 4-7 membered heterocyclic ring;

$R^{9A}$ is $C_{1-8}$ alkyl, $C_{3-8}$ cycloalkyl or phenyl; and $R^B$ is $C_{1-2}$ alkyl substituted by $CO_2H$ and is optionally further substituted by trifluoromethyl or methyl;

$R^C$ and $R^D$ are independently selected from the group consisting of H, $C_{1-2}$ alkyl, hydroxy, methoxy and fluoro;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$ and $R^B$ described above with respect to formula (IW-1) apply equally to formula (IW-e).

In one embodiment, the compound of formula (IW) is a compound of formula (IY):

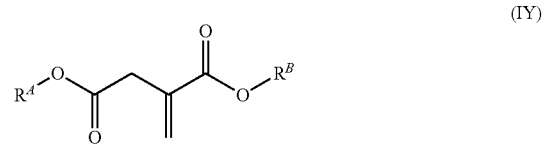

(IY)

wherein, $R^A$ is selected from the group consisting of $C_{1-10}$ alkyl, $C_{3-10}$ cycloalkyl, $C_{5-10}$ spirocycloalkyl and 4-10 membered heterocyclyl; wherein $R^A$ is optionally substituted as defined for compounds of formula (IW);
$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);
wherein
$R^B$, $R^{1B}$, $R^{4B}$, $R^{5B}$ and $R^{6B}$ are as defined for compounds of formula (IW);
$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;
or, taken together, $R^{7B}$ and $R^{8B}$ form a $C_{3-8}$ cycloalkyl or 4-7 membered heterocyclic ring;
$R^{2B}$, $R^{3B}$, qB and $W^B$ are as defined for compounds of formula (IW);
$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and —$(CH_2)_{qB}W^B$;
and wherein,
when neither $R^A$ nor $R^B$ contain heteroatoms, the total number of carbon atoms in groups $R^A$ and $R^B$ taken together is at least 6;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IY).

In one embodiment, the compound of formula (IW) is a compound of formula (I):

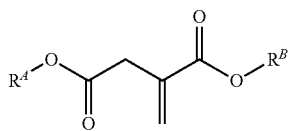

(I)

wherein,
$R^A$, $R^{1A}$, $R^{2A}$, $R^{3A}$, $R^{4A}$, $R^{5A}$, $R^{6A}$, $R^{7A}$, $R^{8A}$, $R^{9A}$, qA, $W^A$ are as defined for compounds of formula (IW);
wherein
$R^B$ is selected from the group consisting of $C_{1-10}$ alkyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$.
$R^{1B}$, $R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW);
and wherein,
when neither $R^A$ nor $R^B$ contain heteroatoms, the total number of carbon atoms in groups $R^A$ and $R^B$ taken together is at least 6;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (I).

In one embodiment, the compound of formula (IW) is a compound of formula (IWA),

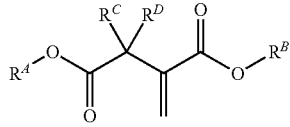

(IWA)

wherein,
$R^A$, $R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);
$R^B$ is $C_{1-2}$ alkyl, which is substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$; or
$R^B$ is 4-7 membered heterocyclyl, which is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$.
$R^{1B}$, $R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW);
$R^C$ and $R^D$ are as defined for compounds of formula (IW);
and wherein,
when neither $R^A$ nor $R^B$ contain heteroatoms, the total number of carbon atoms in groups $R^A$ and $R^B$ taken together is at least 6;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}R^{6B}$, $R^{7B}$, $R^{8B}$, $R^{9B}$, $W^B$, qB, $R^C$ and $R^D$ described above with respect to formula (IW) apply equally to formula (IWA).

In one embodiment, $R^B$ is methyl. In one embodiment, $R^B$ is ethyl.

In one embodiment, $R^B$ is a 4-7 membered (e.g. 4-6 membered) heterocyclyl containing one or two heteroatoms independently selected from N, O and S. In one embodiment, $R^B$ is a 4-7 membered (e.g. 4-6 membered) heterocyclyl containing one N atom. In one embodiment, $R^B$ is a 4-7 membered (e.g. 4-6 membered) heterocyclyl containing one O atom. In one embodiment, $R^B$ is a 4-7 membered (e.g. 4-6 membered) heterocyclyl containing one S atom. In one embodiment, $R^B$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^B$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^B$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or S(=O)$_2$ functionality).

In one embodiment, the compound of formula (IW) is a compound of formula (IYA), $$R^A\text{—O}\diagdown\diagup\diagdown\diagup\text{O—}R^B \quad \text{(IYA)}$$

wherein, $R^A$ is selected from the group consisting of $C_{1-10}$ alkyl, $C_{3-10}$ cycloalkyl, $C_5$10 spirocycloalkyl and 4-10 membered heterocyclyl; wherein $R^A$ is optionally substituted as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW); wherein $R^B$ is $C_{1-2}$ alkyl, which is substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$ and $CONR^{2B}R^{3B}$ or $R^B$ is 4-7 membered heterocyclyl, which is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$ and $CONR^{2B}R^{3B}$.

$R^{1B}$, $R^{2B}$, $R^{3B}$, $R^{4B}$, $R^{5B}$, $R^{6B}$, qB and $W^B$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and —(CH$_2$)$_{qB}$W$^B$;

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$$R^{6B}$, $R^{7B}$, $R^{8B}$, $R^{9B}$, $W^B$ and qB described above with respect to formula (IW) apply equally to formula (IYA).

In one embodiment, $R^B$ is methyl. In one embodiment, $R^B$ is ethyl.

In one embodiment, $R^B$ is 4-7 membered (e.g. 4-6 membered) heterocyclyl containing one or two heteroatoms independently selected from N, O and S. In one embodiment, $R^B$ is 4-7 membered (e.g. 4-6 membered) heterocyclyl containing one N atom. In one embodiment, $R^B$ is 4-7 membered (e.g. 4-6 membered) heterocyclyl containing one O atom. In one embodiment, $R^B$ is 4-7 membered (e.g. 4-6 membered) heterocyclyl containing one S atom. In one embodiment, $R^B$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^B$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^B$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or S(=O)$_2$ functionality).

In one embodiment, the compound of formula (IW) is a compound of formula (IA), $$R^A\text{—O}\diagdown\diagup\diagdown\diagup\text{O—}R^B \quad \text{(IA)}$$

wherein, $R^A$ is selected from the group consisting of $C_{1-10}$ alkyl, $C_{3-10}$ cycloalkyl, $C_{5-10}$ spirocycloalkyl and 4-10 membered heterocyclyl; wherein $R^A$ is optionally substituted as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA, $W^A$ are as defined for compounds of formula (IW);

wherein $R^B$ is $C_{1-2}$ alkyl, which is substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$; or $R^B$ is 4-7 membered heterocyclyl, which is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$.

$R^{1B}$, $R^{2B}$, $R^{3B}$, $R^{4B}$, $R^{5B}$, $R^{6B}$, qB and $W^B$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and —(CH$_2$)$_{qB}$W$^B$;

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$ $R^{6B}$, $R^{7B}$, $R^{8B}$, $R^{9B}$, $W^B$ and qB described above with respect to formula (IW) apply equally to formula (IA).

In one embodiment, $R^B$ is methyl. In one embodiment, $R^B$ is ethyl.

In one embodiment, $R^B$ is 4-7 membered (e.g. 4-6 membered) heterocyclyl containing one or two heteroatoms independently selected from N, O and S. In one embodiment, $R^B$ is 4-7 membered (e.g. 4-6 membered) heterocyclyl containing one N atom. In one embodiment, $R^B$ is 4-7 membered (e.g. 4-6 membered) heterocyclyl containing one O atom. In one embodiment, $R^B$ is 4-7 membered (e.g. 4-6 membered) heterocyclyl containing one S atom. In one embodiment, $R^B$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^B$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl. In one embodiment, $R^B$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^B$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or S(=O)$_2$ functionality).

In one embodiment, the compound of formula (IW) is a compound of formula (IWB), (IWB)

wherein,
$R^A$, $R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);
$R^W$ is selected from the group consisting of $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$; or
$R^W$ is a 4-7 membered heterocyclyl which is optionally substituted by $R^{7B}$ and/or $R^{8B}$.
$R^{1B}$, $R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW);
$R^C$ and $R^D$ are as defined for compounds of formula (IW); and wherein,
when neither $R^A$, $R^Q$ nor $R^W$ contain heteroatoms, the total number of carbon atoms in groups $R^A$, $R^Q$ and $R^W$ taken together is at least 4;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^{1B}$, $R^{2B}$, $R^{3B}$, $R^{4B}$, $R^{5B}$, $R^{6B}$, $R^{7B}$, $R^{8B}$, $R^{9B}$, $W^B$, qB, $R^C$ and $R^D$ described above with respect to formula (IW) apply equally to formula (IWB).

In one embodiment, $R^Q$ is H or methyl, in particular H.

In one embodiment, $R^W$ is selected from the group consisting of $R^{1B}$, $OR^{2B}$, $NR^{2B}R^{3B}$, $SO_2R^{9B}$, $SO_2NR^{2B}R^{3B}$, $NR^{2B}SO_2R^{9B}$, $C(O)R^{2B}$, $CONR^{2B}R^{3B}$, $C(O)NHSO_2R^{9B}$ and $C(O)NHSO_2NR^{2B}R^{3B}$; or $R^W$ is a 4-7 membered heterocyclyl.

In one embodiment, $R^W$ is a 4-7 membered (e.g. 4-6 membered) heterocyclyl. In one embodiment, $R^W$ is a 4-7 membered (e.g. 4-6 membered) heterocyclyl containing one or two heteroatoms independently selected from N, O and S. In one embodiment, $R^W$ is a 4-7 membered (e.g. 4-6 membered) heterocyclyl containing one N atom. In one embodiment, $R^W$ is a 4-7 membered (e.g. 4-6 membered) heterocyclyl containing one O atom. In one embodiment, $R^W$ is a 4-7 membered (e.g. 4-6 membered) heterocyclyl containing one S atom. In one embodiment, $R^W$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^W$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^W$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or S(=O)$_2$ functionality).

In one embodiment, the compound of formula (IW) is a compound of formula (IYB), (IYB)

wherein,
$R^A$ is selected from the group consisting of $C_{1-10}$ alkyl, $C_{3-10}$ cycloalkyl, $C_{5-10}$ spirocycloalkyl and 4-10 membered heterocyclyl; wherein $R^A$ is optionally substituted as defined for compounds of formula (IW);
$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);

wherein
$R^Q$ is H or $C_{1-2}$ alkyl;
$R^W$ is selected from the group consisting of $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$ and $CONR^{2B}R^{3B}$; or
$R^W$ is 4-7 membered heterocyclyl which is optionally substituted by $R^{7B}$ and/or $R^{8B}$;
$R^{1B}$, $R^{2B}$, $R^{3B}$, $R^{4B}$, $R^{5B}$, $R^{6B}$, qB and $W^B$ are as defined for compounds of formula (IW);
$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;
or, taken together, $R^{7B}$ and $R^{8B}$ form a $C_{3-8}$ cycloalkyl or 4-7 membered heterocyclic ring;
$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $-(CH_2)_{qB}W^B$;
and wherein,
when neither $R^A$, $R^Q$ nor $R^W$ contain heteroatoms, the total number of carbon atoms in groups $R^A$, $R^Q$ and $R^W$ taken together is at least 4;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IYB).

In one embodiment, $R^Q$ is H or methyl, in particular H.

In one embodiment, $R^W$ is selected from the group consisting of $R^{1B}$, $OR^{2B}$, $NR^{2B}R^{3B}$, $SO_2R^{9B}$, $SO_2NR^{2B}R^{3B}$, $NR^{2B}SO_2R^{9B}$, $C(O)R^{2B}$ and $CONR^{2B}R^{3B}$; or $R^W$ is 4-7 membered heterocyclyl.

In one embodiment, $R^W$ is 4-7 membered (e.g. 4-6 membered) heterocyclyl. In one embodiment, $R^W$ is 4-7 membered (e.g. 4-6 membered) heterocyclyl containing one or two heteroatoms independently selected from N, O and S. In one embodiment, $R^W$ is 4-7 membered (e.g. 4-6 membered) heterocyclyl containing one N atom. In one embodiment, $R^W$ is 4-7 membered (e.g. 4-6 membered) heterocyclyl containing one O atom. In one embodiment, $R^W$ is 4-7 membered (e.g. 4-6 membered) heterocyclyl containing one S atom. In one embodiment, $R^W$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^W$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^W$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or S(=O)$_2$ functionality).

In one embodiment, the compound of formula (IW) is a compound of formula (IB), (IB)

wherein,
$R^A$ is selected from the group consisting of $C_{1-10}$ alkyl, $C_{3-10}$ cycloalkyl, $C_{5-10}$ spirocycloalkyl and 4-10 membered heterocyclyl; wherein $R^A$ is optionally substituted as defined for compounds of formula (IW);
$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);
wherein
$R^Q$ is H or $C_{1-2}$ alkyl;
$R^W$ is selected from the group consisting of $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$ or
$R^W$ is 4-7 membered heterocyclyl which is optionally substituted by $R^{7B}$ and/or $R^{8B}$;
$R^{1B}$, $R^{2B}$, $R^{3B}$, $R^{4B}$, $R^{5B}$, $R^{6B}$, qB and $W^B$ are as defined for compounds of formula (IW);
$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;
or, taken together, $R^{7B}$ and $R^{8B}$ form a $C_{3-8}$ cycloalkyl or 4-7 membered heterocyclic ring;
$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $-(CH_2)_{qB}W^B$;
and wherein,
when neither $R^A$, $R^Q$ nor $R^W$ contain heteroatoms, the total number of carbon atoms in groups $R^A$, $R^Q$ and $R^W$ taken together is at least 4;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IB).

In one embodiment, $R^Q$ is H or methyl, in particular H.

In one embodiment, $R^W$ is selected from the group consisting of $R^{1B}$, $OR^{2B}$, $NR^{2B}R^{3B}$, $SO_2R^{9B}$, $SO_2NR^{2B}R^{3B}$, $C(O)R^{2B}$ and $CONR^{2B}R^{3B}$; or $R^W$ is 4-7 membered heterocyclyl.

In one embodiment, $R^W$ is 4-7 membered (e.g. 4-6 membered) heterocyclyl. In one embodiment, $R^W$ is 4-7 membered (e.g. 4-6 membered) heterocyclyl containing one or two heteroatoms independently selected from N, O and S. In one embodiment, $R^W$ is 4-7 membered (e.g. 4-6 membered) heterocyclyl containing one N atom. In one embodiment, $R^W$ is 4-7 membered (e.g. 4-6 membered) heterocyclyl containing one O atom. In one embodiment, $R^W$ is 4-7 membered (e.g. 4-6 membered) heterocyclyl containing one S atom. In one embodiment, $R^W$ is selected from the group consisting of oxetanyl, thietanyl, azetidinyl, tetrahydrofuranyl, pyrrolidinyl, tetrahydropyranyl, piperidinyl, piperazinyl, thiomorpholinyl and morpholinyl. In one embodiment, $R^W$ is selected from the group consisting of oxetanyl, thietanyl, azetidinyl, tetrahydrofuranyl, pyrrolidinyl, tetrahydropyranyl, piperazinyl, piperidinyl, thiomorpholinyl and morpholinyl, all of which are optionally substituted by one or more oxo groups. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl. In one embodiment, $R^W$ is selected from the group consisting of oxetanyl, thietanyl, azetidinyl, tetrahydrofuranyl, pyrrolidinyl, tetrahydropyranyl, piperidinyl and morpholinyl, all of which are optionally substituted by one or more oxo groups. In one embodiment, $R^W$ is selected from the group consisting of oxetanyl, thietanyl optionally substituted by one or more oxo groups, azetidinyl, tetrahydrofuranyl, pyrrolidinyl optionally substituted by one or more oxo groups, tetrahydropyranyl, piperidinyl and morpholinyl. Suitably, thietanyl is substituted by one or two oxo groups (e.g. to form a ring containing S=O or $S(=O)_2$ functionality).

In one embodiment, the compound of formula (IW) is a compound of formula (IWC),

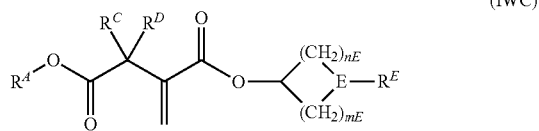

(IWC)

$R^A$, $R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW); wherein E is selected from the group consisting of N, O, S, S=O and $S(=O)_2$;

$R^E$ is absent, or is selected from the group consisting of H, $R^{1B}$, $SO_2R^{9B}$, $SO_2NR^{2B}R^{3B}$, $C(O)R^{2B}$ and $CONR^{2B}R^{3B}$.

$R^{1B}$ is selected from the group consisting of methyl, cyano, $SR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$.

$R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW);

nE and mE are independently 1 or 2;

$R^C$ and $R^D$ are as defined for compounds of formula (IW);

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{2B}$, $R^{3B}$, $R^{4B}$, $R^{5B}R^{6B}$, $R^{7B}$, $R^{8B}$, $R^{9B}$, $W^B$, qB, $R^C$ and $R^D$ described above with respect to formula (IW) apply equally to formula (IWC).

In one embodiment, E is selected from the group consisting of N, O and $S(=O)_2$. In one embodiment, E is N. In one embodiment, E is O. In one embodiment, E is S, S=O or $S(=O)_2$. In one embodiment, E is S. In one embodiment, E is S=O. In one embodiment, E is $S(=O)_2$.

In one embodiment, E is O or S and $R^E$ is absent.

In one embodiment, nE is 1 and mE is 1. In one embodiment, nE is 2 and mE is 1. In one embodiment, nE is 1 and mE is 2. In one embodiment, one of nE and mE is 2 and the other is 1. In one embodiment, nE is 2 and mE is 2.

In one embodiment, the compound of formula (IW) is a compound of formula (IC),

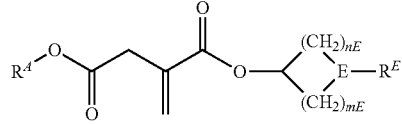

(IC)

$R^A$ is selected from the group consisting of $C_{1-10}$ alkyl, $C_{3-10}$ cycloalkyl, $C_{5-10}$ spirocycloalkyl and 4-10 membered heterocyclyl; wherein $R^A$ is optionally substituted as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW); wherein E is selected from the group consisting of N, O, S, S=O and $S(=O)_2$;

$R^E$ is absent, or is selected from the group consisting of H, $R^{1B}$, $SO_2R^{9B}$, $SO_2NR^{2B}R^{3B}$, $C(O)R^{2B}$ and $CONR^{2B}R^{3B}$ $R^{1B}$ is selected from the group consisting of methyl, cyano, $SR^{4B}R^{5B}R^{6B}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7B}$ and/or $R^{8B}$ $R^{4B}$, $R^{5B}$ and $R^{6B}$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{2B}$ and $R^{3B}$ are as defined for compounds of formula (IW);

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $-(CH_2)_{qB}W^B$;

qB and $W^B$ are as defined for compounds of formula (IW);

nE and mE are independently 1 or 2;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IC).

In one embodiment, E is selected from the group consisting of N, O and $S(=O)_2$. In one embodiment, E is N. In one embodiment, E is O. In one embodiment, E is S, S=O or $S(=O)_2$. In one embodiment, E is S. In one embodiment, E is S=O. In one embodiment, E is $S(=O)_2$.

In one embodiment, E is O or S and $R^E$ is absent.

In one embodiment, nE is 1 and mE is 1. In one embodiment, nE is 2 and mE is 1. In one embodiment, nE is 1 and mE is 2. In one embodiment, one of nE and mE is 2 and the other is 1. In one embodiment, nE is 2 and mE is 2.

In one embodiment, the compound of formula (IW) is a compound of formula (IWD-1):

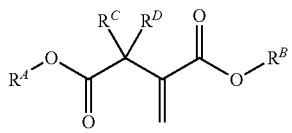

(IWD-1)

wherein,
$R^A$ is selected from the group consisting of $C_{1-10}$ alkyl and $C_{2-10}$ alkenyl; wherein $R^A$ is substituted by one or more substituents selected from the group consisting of oxo, $R^{1A}$, $OR^{2A}$, $SR^{2A}$, $SOR^{9A}$, $SO_2R^{9A}$, $SO_2NR^{2A}R^{3A}$, $C(O)R^{2A}$ and $CONR^{2A}R^{3A}$;
  $R^{1A}$ is selected from the group consisting of fluoro, cyano and $SiR^{4A}R^{5A}R^{6A}$;
    $R^{4A}$, $R^{5A}$ and $R^{6A}$ are as defined for compounds of formula (IW);
  $R^{2A}$ and $R^{3A}$ are independently $C_{1-8}$ alkyl, $C_{3-8}$ cycloalkyl or phenyl; wherein $R^{2A}$ and $R^{3A}$ are independently optionally substituted as defined for compounds of formula (IW);
  or, taken together, $R^{2A}$ and $R^{3A}$ form a 4-7 membered heterocyclic ring optionally independently substituted by one or more substituents selected from the group consisting of $C_{1-2}$ alkyl, hydroxy and oxo;
  $R^{9A}$, qA and $W^A$ are as defined for compounds of formula (IW);
wherein
  $R^B$, $R^{1B}$, $R^{2B}$, $R^{3B}$, $R^{4B}$, $R^{5B}$, $R^{6B}$, $R^{7B}$, $R^{8B}$, $R^{9B}$, qB and $W^B$ are as defined for compounds of formula (IW);
$R^C$ and $R^D$ are as defined for compounds of formula (IW);
and wherein,
when neither $R^A$ nor $R^B$ contain heteroatoms, the total number of carbon atoms in groups $R^A$ and $R^B$ taken together is at least 6;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{9A}$, $W^A$, qA, $R^B$, $R^{1B}$, $R^{2B}$, $R^{3B}$, $R^{4B}$, $R^{5B}R^{6B}$, $R^{7B}$, $R^{8B}$, $R^{9B}$, $W^B$, qB, $R^C$ and $R^D$ described above with respect to formula (IW) apply equally to formula (IWD-1).

In one embodiment, the compound of formula (IW) is a compound of formula (IYD-1):

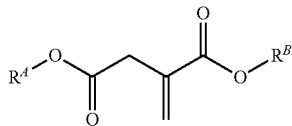

(IYD-1)

wherein,
$R^A$ is $C_{1-10}$ alkyl; wherein $R^A$ is substituted by one or more substituents selected from the group consisting of oxo, $R^{1A}$, $OR^{2A}$, $SR^{2A}$, $SOR^{9A}$, $SO_2R^{9A}$, $SO_2NR^{2A}R^{3A}$, $C(O)R^{2A}$ and $CONR^{2A}R^{3A}$;
  $R^{1A}$ is selected from the group consisting of fluoro, cyano and $SiR^{4A}R^{5A}R^{6A}$;
    $R^{4A}$, $R^{5A}$ and $R^{6A}$ are as defined for compounds of formula (IW);
  $R^{2A}$ and $R^{3A}$ are independently $C_{1-8}$ alkyl, $C_{3-8}$ cycloalkyl or phenyl; wherein $R^{2A}$ and $R^{3A}$ are independently optionally substituted as defined for compounds of formula (IW);
  or, taken together, $R^{2A}$ and $R^{3A}$ form a 4-7 membered heterocyclic ring optionally independently substituted by one or more substituents selected from the group consisting of $C_{1-2}$ alkyl, hydroxy and oxo;
  $R^{9A}$, qA and $W^A$ are as defined for compounds of formula (IW;
wherein
$R^B$ is selected from the group consisting of $C_{1-10}$ alkyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$ and $CONR^{2B}R^{3B}$.
  $R^{1B}$, $R^{2B}$, $R^{3B}$, $R^{4B}$, $R^{5B}$, $R^{6B}$ are as defined for compounds of formula (IW);
    $R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;
    or, taken together, $R^{7B}$ and $R^{8B}$ form a $C_{3-8}$ cycloalkyl or 4-7 membered heterocyclic ring;
  $R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $—(CH_2)_{qB}W^B$;
    qB and $W^B$ are as defined for compounds of formula (IW);
and wherein,
when neither $R^A$ nor $R^B$ contain heteroatoms, the total number of carbon atoms in groups $R^A$ and $R^B$ taken together is at least 6;
or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IYD-1).

In one embodiment, the compound of formula (IW) is a compound of formula (ID-1):

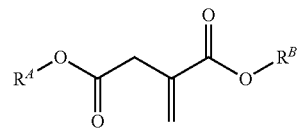

(ID-1)

wherein,
$R^A$ is $C_{1-10}$ alkyl; wherein $R^A$ is substituted by one or more substituents selected from the group consisting of oxo, $R^{1A}$, $OR^{2A}$, $SR^{2A}$, $SOR^{9A}$, $SO_2R^{9A}$, $SO_2NR^{2A}R^{3A}$, $C(O)R^{2A}$ and $CONR^{2A}R^{3A}$;
  $R^{1A}$ is selected from the group consisting of fluoro, cyano and $SiR^{4A}R^{5A}R^{6A}$;
    $R^{4A}$, $R^{5A}$ and $R^{6A}$ are as defined for compounds of formula (IW);
  $R^{2A}$ and $R^{3A}$ are independently $C_{1-8}$ alkyl, $C_{3-8}$ cycloalkyl or phenyl; wherein $R^{2A}$ and $R^{3A}$ are independently optionally substituted as defined for compounds of formula (IW);
  or, taken together, $R^{2A}$ and $R^{3A}$ form a 4-7 membered heterocyclic ring optionally independently substituted by one or more substituents selected from the group consisting of $C_{1-2}$ alkyl, hydroxy and oxo;

$R^{9A}$, qA and $W^A$ are as defined for compounds of formula (IW);

wherein $R^B$ is selected from the group consisting of $C_{1-10}$ alkyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$.

$R^{1B}$, $R^{2B}$, $R^{3B}$, $R^{4B}$, $R^{5B}$, $R^{6B}$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $-(CH_2)_{qB}W^B$;

qB and $W^B$ are as defined for compounds of formula (IW);

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (ID-1).

In one embodiment, the compound of formula (IW) is a compound of formula (IWD-2):

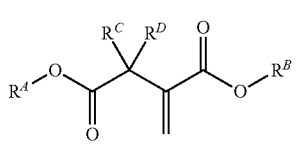

(IWD-2)

wherein, $R^A$ is selected from the group consisting of $C_{3-10}$ cycloalkyl, $C_{5-10}$ spirocycloalkyl, 6-10 membered heterospirocyclyl and 4-10 membered heterocyclyl; wherein $R^A$ is optionally substituted are as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);

wherein $R^B$, $R^{1B}$, $R^{2B}$, $R^{3B}$, $R^{4B}$, $R^{5B}$, $R^{6B}$, $R^{7B}$, $R^{8B}$, $R^{9B}$, qB, $W^B$ are as defined for compounds of formula (IW);

$R^C$ and $R^D$ are as defined for compounds of formula (IW);

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}R^{6B}$, $R^{7B}$, $R^{8B}$, $R^{9B}$, $W^B$, qB, $R^C$ and $R^D$ described above with respect to formula (IW) apply equally to formula (IWD-2).

In one embodiment, the compound of formula (IW) is a compound of formula (IYD-2):

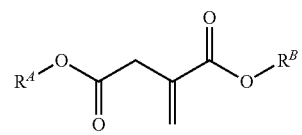

(IYD-2)

wherein, $R^A$ is selected from the group consisting of $C_{3-10}$ cycloalkyl, $C_{5-10}$ spirocycloalkyl and 4-10 membered heterocyclyl; wherein $R^A$ is optionally substituted as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);

wherein $R^B$ is selected from the group consisting of $C_{1-10}$ alkyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $NR^{2B}SO_2R^{9B}$, $C(O)R^{2B}$ and $CONR^{2B}R^{3B}$.

$R^{1B}$, $R^{2B}$, $R^{3B}$, $R^{4B}$, $R^{5B}$, $R^{6B}$, qB and $W^B$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $-(CH_2)_{qB}W^B$;

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (IYD-2).

In one embodiment, the compound of formula (IW) is a compound of formula (ID-2):

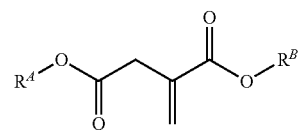

(ID-2)

wherein, $R^A$ is selected from the group consisting of $C_{3-10}$ cycloalkyl, $C_{5-10}$ spirocycloalkyl and 4-10 membered heterocyclyl; wherein $R^A$ is optionally substituted as defined for compounds of formula (IW);

$R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);

wherein $R^B$ is selected from the group consisting of $C_{1-10}$ alkyl, $C_{3-10}$ cycloalkyl, $C_{5-10}$ spirocycloalkyl and 4-10 membered heterocyclyl; wherein $R^B$ is optionally substituted by one or more substituents selected from the group consisting of oxo, $R^{1B}$, $OR^{2B}$, $NR^{2B}R^{3B}$, $SR^{2B}$, $SOR^{9B}$, $SO_2R^{9B}$, $SO_2NR^{2B}R^{3B}$, $C(O)R^{2B}$ and $CONR^{2B}R^{3B}$.

$R^{1B}$, $R^{2B}$, $R^{3B}$, $R^{4B}$, $R^{5B}$ and $R^{6B}$ are as defined for compounds of formula (IW);

$R^{7B}$ and $R^{8B}$ are independently selected from the group consisting of oxo, $C_{1-4}$ alkyl, $C_{1-4}$ alkoxy, hydroxy, $CO_2H$, cyano, methanesulfonyl and halo;

or, taken together, $R^{7B}$ and $R^{8B}$ form a $C_{3-8}$ cycloalkyl or 4-7 membered heterocyclic ring;

$R^{9B}$ is $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, fluoro, hydroxy, oxo and $—(CH_2)_{qB}W^B$;

qB and $W^B$ are as defined for compounds of formula (IW);

and wherein, when neither $R^A$ nor $R^B$ contain heteroatoms, the total number of carbon atoms in groups $R^A$ and $R^B$ taken together is at least 6;

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$ and qB described above with respect to formula (IW) apply equally to formula (ID-2).

In one embodiment, the compound of formula (IW) is a compound of formula (IWE):

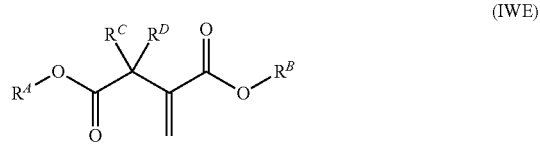

(IWE)

wherein, $R^A$, $R^{1A}$, $R^{2A}$, $R^{3A}$, $R^{4A}$, $R^{5A}$, $R^{6A}$, $R^{7A}$, $R^{8A}$, $R^{9A}$, qA and $W^A$ are as defined for compounds of formula (IW);

wherein $R^B$ is selected from the group consisting of $C_{1-10}$ alkyl, $C_{2-10}$ alkenyl, $C_{3-10}$ cycloalkyl or $C_{5-10}$ spirocycloalkyl; wherein $C_{1-10}$ alkyl, $C_{2-10}$ alkenyl, $C_{3-10}$ cycloalkyl or $C_{5-10}$ spirocycloalkyl are substituted by $SO_2R^{9B}$, $CO_2H$ or tetrazolyl; or $R^B$ is 4-10 membered heterocyclyl which is substituted by $SO_2R^{9B}$ or $CO_2H$;

wherein $R^B$ is optionally substituted by one or more $R^{1B}$ wherein $R^{1B}$, $R^{4B}$, $R^{5B}$, $R^{6B}$, $R^{7B}$, $R^{8B}$, qB and $W^B$ are as defined for compounds of formula (IW);

$R^{9B}$ is a $C_{1-8}$ alkyl, $C_{3-8}$ cycloalkyl or phenyl; wherein $R^{9B}$ is optionally substituted by one or more substituents selected from the group consisting of $C_{1-8}$ alkyl, $C_{1-4}$ alkoxy, halo, $CO_2H$, fluoro, hydroxy, oxo and $—(CH_2)_{qB}W^B$;

$R^C$ and $R^D$ are as defined for compounds of formula (IW);

or a pharmaceutically acceptable salt and/or solvate thereof.

Embodiments and preferences regarding groups $R^A$, $R^{1A}$, $R^{2A}$, $R^{3A}$, $R^{4A}$, $R^{5A}$, $R^{6A}$, $R^{7A}$, $R^{8A}$, $R^{9A}$, $W^A$, qA, $R^B$, $R^{1B}$, $R^{2B}$, $R^{3B}$, $R^{4B}$, $R^{5B}$, $R^{6B}$, $R^{7B}$, $R^{8B}$, $R^{9B}$, $W^B$, qB, $R^C$ and $R^D$ described above with respect to formula (IW) apply equally to formula (IWE).

In one embodiment, $R^A$ is a $C_{5-10}$ spirocycloalkyl, in particular spiro[3.3]heptyl.

In one embodiment, $R^B$ is a $C_{1-10}$ alkyl which is substituted by $SO_2R^{9B}$, $CO_2H$ or tetrazolyl, or a 4-10 membered heterocyclyl which is substituted by $SO_2R^{9B}$ or $CO_2H$.

In one embodiment, $R^B$ is a $C_{1-5}$ alkyl which is substituted by $SO_2R^{9B}$, $CO_2H$ or tetrazolyl. Suitably, $R^B$ is $C_{1-2}$ alkyl which is substituted by $SO_2R^{9B}$, $CO_2H$ or tetrazolyl, for example $R^B$ is methyl or ethyl which are substituted by $SO_2R^{9B}$, $CO_2H$ or tetrazolyl.

Suitably, the tetrazolyl is 5-tetrazolyl:

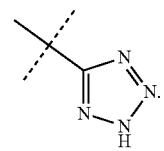

In one embodiment, $R^B$ is a 4-10 membered heterocyclyl which is substituted by $SO_2R^{9B}$ or $CO_2H$, wherein $R^{9B}$ is defined elsewhere herein. Suitably, $R^B$ is a 5-6 membered heterocyclyl which is substituted by $SO_2R^{9B}$ or $CO_2H$, wherein $R^{9B}$ is defined elsewhere herein.

In one embodiment, $R^B$ is a $C_{1-10}$ alkyl which is substituted by $SO_2R^{9B}$ wherein $R^{9B}$ is defined elsewhere herein. In another embodiment, $R^B$ is a $C_{1-10}$ alkyl which is substituted by $CO_2H$. In another embodiment, $R^B$ is a $C_{1-10}$ alkyl which is substituted by tetrazolyl. In each embodiment, suitably $C_{1-10}$ alkyl is $C_{1-2}$ alkyl.

In any one of the above embodiments, suitably when $R^B$ is:

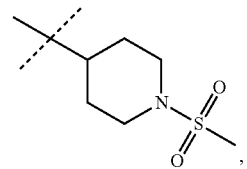

$R^{1A}$ is selected from the group consisting of fluoro, methyl, cyano, $SiR^{4A}R^{5A}R^{6A}$, $C_{3-8}$ cycloalkyl, 4-7 membered heterocyclyl, phenyl and 5-6 membered heteroaryl; wherein methyl, $C_{3-8}$ cycloalkyl, 4-7 membered heterocyclyl, phenyl and 5-6 membered heteroaryl are optionally substituted by $R^{7A}$ and/or $R^{8A}$ wherein $R^{4A}$, $R^{5A}$, $R^{6A}$, $R^{7A}$ and $R^{8A}$ are as defined elsewhere herein.

In any one of the above embodiments, suitably when $R^B$ is:

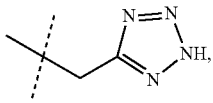

$R^A$ is selected from the group consisting of $C_{1-10}$ alkyl, $C_{2-10}$ alkenyl, $C_{3-10}$ cycloalkyl, and $C_{5-10}$ spirocycloalkyl; $R^A$ is optionally substituted by one or more substituents selected from the group consisting of oxo, $R^{7A}$, $NR^{2A}R^{3A}$, $SR^{2A}$, $SOR^{9A}$, $SO_2R^{9A}$, $SO_2NR^{2A}R^{3A}$, $C(O)R^{2A}$ and $CONR^{2A}R^{3A}$; and $R^{1A}$ is selected from the group consisting of $CO_2H$, cyano, $SiR^{4A}R^{5A}R^{6A}$, $C_{3-8}$ cycloalkyl, phenyl and 5-6 membered heteroaryl; wherein $C_{3-8}$ cycloalkyl, 4-7 membered heterocyclyl, phenyl and 5-6 membered heteroaryl are optionally substituted by $R^{7A}$ and/or $R^{8A}$; and the total number of carbon atoms in $R^A$ is at least 6, wherein $R^{2A}$, $R^{3A}$, $R^{4A}$, $R^{5A}$, $R^{6A}$, $R^{7A}$, $R^{8A}$, $R^{9A}$ are as defined elsewhere herein.

In any one of the above embodiments, suitably when $R^A$ is

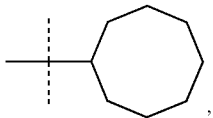

$R^A$ is unsubstituted.

In any one of the above embodiments, suitably when $R^B$ is:

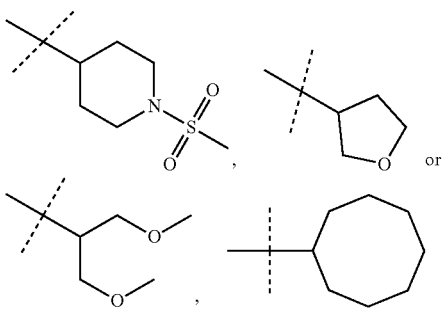

$R^A$ is not the same as $R^B$.

In one embodiment there is provided a compound of formula (IW-1), selected from the group consisting of:
1-(2-cyanoethyl) 4-octyl 2-methylenesuccinate;
1-(2-(methylsulfonyl)ethyl) 4-octyl 2-methylenesuccinate;
4-octyl 1-(3,3,3-trifluoropropyl) 2-methylenesuccinate;
4-octyl 1-(oxetan-3-yl) 2-methylenesuccinate;
4-octyl 1-(2-(2-oxopyrrolidin-1-yl)ethyl) 2-methylenesuccinate;
1-(3-(dimethylamino)-3-oxopropyl) 4-octyl 2-methylenesuccinate;
4-butyl 1-(2-(methylsulfonyl)ethyl) 2-methylenesuccinate;
1-(2-cyanoethyl) 4-butyl 2-methylenesuccinate;
1-(2-(2,5-dioxopyrrolidin-1-yl)ethyl) 4-octyl 2-methylenesuccinate;
1-(2-cyanoethyl) 4-methyl 2-methylenesuccinate;
1-(2-cyanoethyl) 4-hexyl 2-methylenesuccinate;
4-methyl 1-(2-(methylsulfonyl)ethyl) 2-methylenesuccinate;
4-octyl 1-(2-(trifluoromethoxy)ethyl) 2-methylenesuccinate;
4-hexyl 1-(2-(methylsulfonyl)ethyl) 2-methylenesuccinate;
4-methyl 1-(oxetan-3-yl) 2-methylenesuccinate;
1-(2-(N,N-dimethylsulfamoyl)ethyl) 4-octyl 2-methylenesuccinate;
1-(2-(dimethylamino)ethyl) 4-octyl 2-methylenesuccinate;
1-(3-(methylsulfonyl)propyl) 4-octyl 2-methylenesuccinate;
1-(1-(methylsulfonyl)propan-2-yl) 4-octyl 2-methylenesuccinate;
1-(2-(methylsulfonyl)ethyl) 4-(3-phenoxypropyl) 2-methylenesuccinate;
1-(2-(dimethylamino)-2-oxoethyl) 4-octyl 2-methylenesuccinate;
4-isopropyl 1-(2-(methylsulfonyl)ethyl) 2-methylenesuccinate;
(S)-4-octyl 1-(tetrahydrofuran-3-yl) 2-methylenesuccinate;
(R)-4-octyl 1-(tetrahydrofuran-3-yl) 2-methylenesuccinate;
4-cyclooctyl 1-(2-(methylsulfonyl)ethyl) 2-methylenesuccinate;
4-octyl 1-(tetrahydro-2H-pyran-4-yl) 2-methylenesuccinate;
1-(1-cyanopropan-2-yl) 4-octyl 2-methylenesuccinate;
1-(1-(methylsulfonyl)piperidin-4-yl) 4-octyl 2-methylenesuccinate;
1-(2-methoxyethyl) 4-octyl 2-methylenesuccinate;
1-(2-cyano-2-methylpropyl) 4-octyl 2-methylenesuccinate;
1-(1-methoxypropan-2-yl) 4-octyl 2-methylenesuccinate;
1-((1-cyanocyclopropyl)methyl) 4-octyl 2-methylenesuccinate;
1-(2-methoxypropyl) 4-octyl 2-methylenesuccinate;
1-(2-methoxy-2-methylpropyl) 4-octyl 2-methylenesuccinate;
1-(2-morpholinoethyl) 4-octyl 2-methylenesuccinate;
4-(2-(2-ethoxyethoxy)ethyl) 1-(2-(methylsulfonyl)ethyl) 2-methylenesuccinate;
4-butyl 1-(oxetan-3-yl) 2-methylenesuccinate;
4-hexyl 1-(oxetan-3-yl) 2-methylenesuccinate;
4-butyl 1-(2-tosylethyl) 2-methylenesuccinate;
4-octyl 1-(2-tosylethyl) 2-methylenesuccinate;
4-cyclooctyl 1-methyl 2-methylenesuccinate;
1-methyl 4-octyl 2-methylenesuccinate;
dicyclobutyl 2-methylenesuccinate;
di(oxetan-3-yl) 2-methylenesuccinate;
1-cyclobutyl 4-octyl 2-methylenesuccinate;
1-(1-acetoxyethyl) 4-octyl 2-methylenesuccinate;
1-(1,1-dioxidothietan-3-yl) 4-octyl 2-methylenesuccinate;
1-(2-(tert-butoxy)-2-oxoethyl) 4-octyl 2-methylenesuccinate;
2-((2-methylene-4-(octyloxy)-4-oxobutanoyl)oxy)acetic acid;
1-(1-acetylazetidin-3-yl) 4-octyl 2-methylenesuccinate;
1-(2-(4-methylpiperazin-1-yl)ethyl) 4-octyl 2-methylenesuccinate;
1-(2-(1,1-dioxidothiomorpholino)ethyl) 4-octyl 2-methylenesuccinate;
1-(2-(methylsulfonamido)ethyl) 4-octyl 2-methylenesuccinate;
4-cyclooctyl 1-(1,1-dioxidothietan-3-yl) 2-methylenesuccinate;
(R)-1-(2-(methylsulfonyl)ethyl) 4-(octan-2-yl) 2-methylenesuccinate;
1-(1-(methylsulfonyl)propan-2-yl) 4-((R)-octan-2-yl) 2-methylenesuccinate;
(R)-1-(1,1-dioxidothietan-3-yl) 4-(octan-2-yl) 2-methylenesuccinate;
(R)-1-(1-acetylazetidin-3-yl) 4-(octan-2-yl) 2-methylenesuccinate;
4-cyclohexyl 1-(1-(methylsulfonyl)propan-2-yl) 2-methylenesuccinate;

4-cyclohexyl 1-(1,1-dioxidothietan-3-yl) 2-methylenesuccinate;

4-cyclohexyl 1-(2-(methylsulfonyl)ethyl) 2-methylenesuccinate;

4-cyclooctyl 1-(1-(methylsulfonyl)propan-2-yl) 2-methylenesuccinate;

1-(1-acetylazetidin-3-yl) 4-cyclooctyl 2-methylenesuccinate;

4-cyclohexyl 1-(tetrahydro-2H-pyran-4-yl) 2-methylenesuccinate;

4-cyclohexyl 1-(2-(2-oxopyrrolidin-1-yl)ethyl) 2-methylenesuccinate;

(S)-1-(1-acetylazetidin-3-yl) 4-(octan-2-yl) 2-methylenesuccinate;

(S)-1-(1,1-dioxidothietan-3-yl) 4-(octan-2-yl) 2-methylenesuccinate;

1-(3-methyloxetan-3-yl) 4-octyl 2-methylenesuccinate;

4-cyclooctyl 1-(1-(methylsulfonyl)piperidin-4-yl) 2-methylenesuccinate;

4-cyclooctyl 1-(tetrahydro-2H-pyran-4-yl) 2-methylenesuccinate;

4-cyclooctyl 1-(2-(2-oxopyrrolidin-1-yl)ethyl) 2-methylenesuccinate;

(R)-4-(octan-2-yl) 1-(2-(2-oxopyrrolidin-1-yl)ethyl) 2-methylenesuccinate;

(R)-4-(octan-2-yl) 1-(tetrahydro-2H-pyran-4-yl) 2-methylenesuccinate;

1-(1-acetylazetidin-3-yl) 4-cyclohexyl 2-methylenesuccinate;

4-cyclohexyl 1-(1-(methylsulfonyl)piperidin-4-yl) 2-methylenesuccinate;

4-hexyl 1-(1-(methylsulfonyl)piperidin-4-yl) 2-methylenesuccinate;

4-hexyl 1-(2-(2-oxopyrrolidin-1-yl)ethyl) 2-methylenesuccinate;

1-(2-(1H-tetrazol-5-yl)ethyl) 4-hexyl 2-methylenesuccinate;

2-((2-methylene-4-(octyloxy)-4-oxobutanoyl)oxy)propanoic acid;

3-((2-methylene-4-(octyloxy)-4-oxobutanoyl)oxy)propanoic acid;

3-((4-((4-fluorobenzyl)oxy)-2-methylene-4-oxobutanoyl)oxy)propanoic acid;

3-((4-(cyclooctyloxy)-2-methylene-4-oxobutanoyl)oxy)propanoic acid;

3-((2-methylene-4-(neopentyloxy)-4-oxobutanoyl)oxy)propanoic acid;

(S)-3-((2-methylene-4-(octan-2-yloxy)-4-oxobutanoyl)oxy)propanoic acid;

3-((4-(hexyloxy)-2-methylene-4-oxobutanoyl)oxy)propanoic acid;

3-((2-methylene-4-oxo-4-(3-phenoxypropoxy)butanoyl)oxy)propanoic acid;

3-((4-(cyclohexyloxy)-2-methylene-4-oxobutanoyl)oxy)propanoic acid;

(R)-3-((2-methylene-4-(octan-2-yloxy)-4-oxobutanoyl)oxy)propanoic acid;

(S)-2-((2-methylene-4-(octan-2-yloxy)-4-oxobutanoyl)oxy)acetic acid;

2-((4-(cyclooctyloxy)-2-methylene-4-oxobutanoyl)oxy)acetic acid;

2-((4-(cyclohexyloxy)-2-methylene-4-oxobutanoyl)oxy)acetic acid;

2-((2-methylene-4-(neopentyloxy)-4-oxobutanoyl)oxy)acetic acid;

2-((4-((4-fluorobenzyl)oxy)-2-methylene-4-oxobutanoyl)oxy)acetic acid;

2-((4-(hexyloxy)-2-methylene-4-oxobutanoyl)oxy)acetic acid;

2-((2-methylene-4-oxo-4-(3-phenoxypropoxy)butanoyl)oxy)acetic acid;

2-((2-methylene-4-oxo-4-(spiro[3.3]heptan-2-yloxy)butanoyl)oxy)acetic acid;

2-((2-methylene-4-oxo-4-(2-tosylethoxy)butanoyl)oxy)acetic acid:

2-(N-methyl-2-((2-methylene-4-(octyloxy)-4-oxobutanoyl)oxy)acetamido)acetic acid;

(2-((2-methylene-4-(octyloxy)-4-oxobutanoyl)oxy)acetyl)-L-proline;

N-methyl-N-(2-((2-methylene-4-(octyloxy)-4-oxobutanoyl)oxy)propanoyl)glycine;

(2-((2-methylene-4-(octyloxy)-4-oxobutanoyl)oxy)propanoyl)-L-proline;

(2-((2-methylene-4-(octyloxy)-4-oxobutanoyl)oxy)propanoyl)glycine;

N-(2-((4-(cyclooctyloxy)-2-methylene-4-oxobutanoyl)oxy)acetyl)-N-methylglycine;

(2-((4-(cyclooctyloxy)-2-methylene-4-oxobutanoyl)oxy)acetyl)-L-proline;

(S)—N-methyl-N-(2-((2-methylene-4-(octan-2-yloxy)-4-oxobutanoyl)oxy)acetyl)glycine;

(S)-(2-((2-methylene-4-(octan-2-yloxy)-4-oxobutanoyl)oxy)acetyl)glycine;

1-(2-(4-methylpiperazin-1-yl)-2-oxoethyl) 4-octyl 2-methylenesuccinate;

1-(3-morpholino-3-oxopropyl) 4-octyl 2-methylenesuccinate;

1-(3-(diethylamino)-3-oxopropyl) 4-octyl 2-methylenesuccinate;

1-(3-(methylamino)-3-oxopropyl) 4-octyl 2-methylenesuccinate;

2-((4-(cyclohexyloxy)-2-methylene-4-oxobutanoyl)oxy)propanoic acid;

(R)-2-((2-methylene-4-(octan-2-yloxy)-4-oxobutanoyl)oxy)acetic acid;

2-((4-((4,4-difluorocyclohexyl)methoxy)-2-methylene-4-oxobutanoyl)oxy)acetic acid;

2-((4-(3-ethoxypropoxy)-2-methylene-4-oxobutanoyl)oxy)acetic acid;

2-((4-(bicyclo[2.2.1]heptan-2-yloxy)-2-methylene-4-oxobutanoyl)oxy)acetic acid;

2-((4-cyclobutoxy-2-methylene-4-oxobutanoyl)oxy)acetic acid;

3-((4-(cyclohexyloxy)-2-methylene-4-oxobutanoyl)oxy)-2,2-dimethylpropanoic acid;

1-(2-((N,N-dimethylsulfamoyl)amino)-2-oxoethyl) 4-hexyl 2-methylenesuccinate;

4-hexyl 1-(2-(methylsulfonamido)-2-oxoethyl) 2-methylenesuccinate;

4-hexyl 1-(3-(methylsulfonamido)-2-oxoethyl) 2-methylenesuccinate;

2-((4-(cyclohexyloxy)-2-methylene-4-oxobutanoyl)oxy)-3,3,3-trifluoropropanoic acid;

2-((4-(cyclooctyloxy)-2-methylene-4-oxobutanoyl)oxy)-3,3,3-trifluoropropanoic acid;

(E)-4-((4-(cyclohexyloxy)-2-methylene-4-oxobutanoyl)oxy)but-2-enoic acid;

3-((2-((4-(cyclohexyloxy)-2-methylene-4-oxobutanoyl)oxy)ethyl)sulfonyl)propanoic acid;

1-((2H-tetrazol-5-yl)methyl) 4-cyclohexyl 2-methylenesuccinate;

2-((3-((2-((3-chlorophenyl)sulfonyl)ethoxy)carbonyl)but-3-enoyl)oxy)acetic acid;

(R)-2-((4-(cyclohexyloxy)-2-methylene-4-oxobutanoyl)oxy)-2-phenylacetic acid;
1-(2-(1H-tetrazol-5-yl)ethyl) 4-cyclohexyl 2-methylenesuccinate;
(S)-1-(2-(1H-tetrazol-5-yl)ethyl) 4-octan-2-yl 2-methylenesuccinate;
1-(2-(1H-tetrazol-5-yl)ethyl) 4-cyclooctyl 2-methylenesuccinate;
1-(2-((3-chlorophenyl)sulfonyl)-2-methylpropyl) 4-cyclooctyl 2-methylenesuccinate;
4-cyclooctyl 1-(2-methyl-2-(methylsulfonyl)propyl) 2-methylenesuccinate;
1-(1-(1H-tetrazol-5-yl)ethyl) 4-cyclooctyl 2-methylenesuccinate;
1-((1H-tetrazol-5-yl)methyl) 4-cyclooctyl 2-methylenesuccinate;
(R)-1-(2-(1H-tetrazol-5-yl)ethyl) 4-octan-2-yl 2-methylenesuccinate;
(2R,3S)-2-acetamido-3-((4-(cyclooctyloxy)-2-methylene-4-oxobutanoyl)oxy)butanoic acid;
4-cyclooctyl 1-(3-(2-ethoxy-2-oxoethyl)oxetan-3-yl) 2-methylenesuccinate;
4-(2-(methylsulfonyl)ethyl) 1-octyl 2-methyl-3-methylenesuccinate;
1-octyl 4-((S)-tetrahydrofuran-3-yl) 2-methyl-3-methylenesuccinate;
1-(1-(1H-tetrazol-5-yl)propan-2-yl) 4-((R)-octan-2-yl) 2-methylenesuccinate;
1-(1-(1H-tetrazol-5-yl)propan-2-yl) 4-((S)-octan-2-yl) 2-methylenesuccinate;
4-cyclohexyl 1-((2-methyl-2H-tetrazol-5-yl)methyl) 2-methylenesuccinate;
4-cyclohexyl 1-((1-methyl-1H-tetrazol-5-yl)methyl) 2-methylenesuccinate;
3-((4-(cyclooctyloxy)-2-methylene-4-oxobutanoyl)oxy)-4,4,4-trifluorobutanoic acid;
2-(4-(cycloheptyloxy)-2-methylene-4-oxobutanoyloxy)acetic acid;
2-(2-methylene-4-(octan-3-yloxy)-4-oxobutanoyloxy)acetic acid;
2-(2-methylene-4-(octan-4-yloxy)-4-oxobutanoyloxy)acetic acid;
2-((4-(heptan-4-yloxy)-2-methylene-4-oxobutanoyl)oxy) acetic acid;
2-((4-((adamantan-2-yl)oxy)-2-methylene-4-oxobutanoyl)oxy)acetic acid;
2-((4-(1-cyclohexylethoxy)-2-methylene-4-oxobutanoyl)oxy) acetic acid;
2-((4-(1-cycloheptylethoxy)-2-methylene-4-oxobutanoyl)oxy)acetic acid;
2-(2-methylene-4-oxo-4-(spiro[3.4]octan-2-yloxy) butanoyloxy)acetic acid;
2-(2-methylene-4-oxo-4-(spiro[3.5]nonan-2-yloxy)butanoyloxy)acetic acid;
2-(2-methylene-4-oxo-4-(spiro[3.5]nonan-7-yloxy)butanoyloxy)acetic acid;
2-((4-((2,2-dimethylcyclohexyl)oxy)-2-methylene-4-oxobutanoyl)oxy)acetic acid;
bis((endo)-3-(methylsulfonyl)-3-azabicyclo[3.2.1]octan-8-yl) 2-methylenesuccinate;
1-((endo)-3-(methylsulfonyl)-3-azabicyclo[3.2.1]octan-8-yl) 4-(2-oxaspiro[3.3]heptan-6-yl) 2-methylenesuccinate;
1-((endo)-3-(methylsulfonyl)-3-azabicyclo[3.2.1]octan-8-yl) 4-(oxepan-4-yl) 2-methylenesuccinate;
4-(1-butoxypropan-2-yl) 1-((endo)-3-(methylsulfonyl)-3-azabicyclo[3.2.1]octan-8-yl) 2-methylenesuccinate;
4-spiro[3.3]heptan-2-yl 1-(3,3,3-trifluoro-2,2-dihydroxypropyl) 2-methylenesuccinate hydrate;
(R)-1-((2H-tetrazol-5-yl)methyl) 4-(octan-2-yl) 2-methylenesuccinate;
1-(2H-tetrazol-5-yl)methyl 4-cycloheptyl 2-methylenesuccinate;
1-(2H-tetrazol-5-yl)methyl 4-spiro[3.3]heptan-2-yl 2-methylenesuccinate;
(S)-1-(2H-tetrazol-5-yl)methyl 4-octan-2-yl 2-methylenesuccinate;
1-(1-(1H-tetrazol-5-yl)ethyl) 4-((S)-octan-2-yl) 2-methylenesuccinate;
1-(cyclopropyl(1H-tetrazol-5-yl)methyl) 4-((S)-octan-2-yl) 2-methylenesuccinate; dicyclohexyl 2-methylenesuccinate;
2-((4-(cyclooctyloxy)-3-methyl-2-methylene-4-oxobutanoyl)oxy)acetic acid;
2-((2-methylene-4-oxo-4-(2,2,4,4-tetramethylcyclobutoxy)butanoyl)oxy) acetic acid;
(S)-2-(2-methylene-4-(octan-3-yloxy)-4-oxobutanoyloxy) acetic acid;
2-((4-(cyclooctyloxy)-3-methoxy-2-methylene-4-oxobutanoyl)oxy)acetic acid; and
2-((4-((-adamantan-1-yl)oxy)-2-methylene-4-oxobutanoyl)oxy)acetic acid;
(R)-2-((4-(heptan-2-yloxy)-2-methylene-4-oxobutanoyl)oxy)acetic acid;
2-((2-methylene-4-(nonan-2-yloxy)-4-oxobutanoyl)oxy) acetic acid;
2-((2-methylene-4-(nonan-5-yloxy)-4-oxobutanoyl)oxy) acetic acid;
2-((4-(1-(3,5-dichlorophenyl)ethoxy)-2-methylene-4-oxobutanoyl)oxy)acetic acid;
2-((4-((1-(3,5-dichlorophenyl)propan-2-yl)oxy)-2-methylene-4-oxobutanoyl)oxy)acetic acid;
(R)-2-(2-methylene-4-(octan-3-yloxy)-4-oxobutanoyloxy) acetic acid;
2-((2-methylene-4-oxo-4-(((1R,2S,4R)-1,7,7-trimethylbicyclo[2.2.1]heptan-2-yl)oxy)butanoyl)oxy)acetic acid;
2-((4-(1-cyclohexyl-2,2,2-trifluoroethoxy)-2-methylene-4-oxobutanoyl)oxy)acetic acid;
2-((4-(bicyclo[3.3.1]nonan-9-yloxy)-2-methylene-4-oxobutanoyl)oxy)acetic acid;
(S)-2-((2-methylene-4-oxo-4-((1,1,1-trifluorooctan-2-yl)oxy)butanoyl)oxy)acetic acid;
(R)-2-((2-methylene-4-(nonan-2-yloxy)-4-oxobutanoyl)oxy)acetic acid;
(R)-2-((4-(1-cyclohexylethoxy)-2-methylene-4-oxobutanoyl)oxy)acetic acid;
1-(3,3-difluorocyclobutyl) 4-octyl 2-methylenesuccinate;
1-((endo)-3-(methylsulfonyl)-3-azabicyclo[3.2.1]octan-8-yl) 4-((R)-octan-2-yl) 2-methylenesuccinate;
(R)-4-(octan-2-yl) 1-((3-oxo-2,3-dihydroisoxazol-5-yl)methyl) 2-methylenesuccinate;
(R)-4,4,4-trifluoro-3-((2-methylene-4-(((R)-octan-2-yl)oxy)-4-oxobutanoyl)oxy)butanoic acid;
2-((4-(cyclooctyloxy)-3-hydroxy-2-methylene-4-oxobutanoyl)oxy)acetic acid;
2-(3-methylene-5-(4-methylheptan-4-yloxy)-5-oxopent-1-en-2-yloxy)acetic acid;
2-((4-(1-cyclohexylcyclobutoxy)-2-methylene-4-oxobutanoyl)oxy)acetic acid;
2-((2-methylene-4-((2-methyloctan-2-yl)oxy)-4-oxobutanoyl)oxy)acetic acid;
2-((2-methylene-4-((2-methylheptan-2-yl)oxy)-4-oxobutanoyl)oxy)acetic acid;

2-((2-methylene-4-oxo-4-(1-pentylcyclobutoxy)butanoyl) oxy) acetic acid;
2-((2-methylene-4-((2-methylspiro[3.5]nonan-2-yl)oxy)-4-oxobutanoyl)oxy)acetic acid;
2-((2-methylene-4-oxo-4-(((exo)-1,7,7-trimethylbicyclo[2.2.1]heptan-2-yl)oxy)butanoyl)oxy)acetic acid;
2-((2-methylene-4-oxo-4-((2,2,6,6-tetramethylcyclohexyl)oxy) butanoyl)oxy)acetic acid;
2-((4-(1-(3,5-dichlorophenyl)ethoxy)-2-methylene-4-oxobutanoyl)oxy)acetic acid (Isomer 1);
2-((4-(1-(3,5-dichlorophenyl)ethoxy)-2-methylene-4-oxobutanoyl)oxy)acetic acid (Isomer 2);
(R)-2-((2-methylene-4-oxo-4-(1-(4-(trifluoromethyl)phenyl)ethoxy)butanoyl) oxy) acetic acid);
(S)-2-((2-methylene-4-oxo-4-(1-(4-(trifluoromethyl)phenyl)ethoxy)butanoyl) oxy) acetic acid);
2-((4-(1-cyclohexylcyclopropoxy)-2-methylene-4-oxobutanoyl)oxy)acetic acid;
(S)-2-((4-(1-cyclohexylethoxy)-2-methylene-4-oxobutanoyl)oxy)acetic acid;
2-((2-methylene-4-oxo-4-((2,2,4,4-tetramethylpentan-3-yl)oxy)butanoyl) oxy)acetic acid;
(S)-4,4,4-trifluoro-3-((2-methylene-4-(((R)-octan-2-yl)oxy)-4-oxobutanoyl)oxy)butanoic acid;
2-((2-methylene-4-oxo-4-(1-pentylcyclopropoxy)butanoyl) oxy) acetic acid; and
3-((2-methylene-4-oxo-4-(2,2,4,4-tetramethylcyclobutoxy) butanoyl)oxy)propanoic acid; or a pharmaceutically acceptable salt and/or solvate of any one thereof.
Suitably, the compound is selected from the group consisting of:
(R)-2-((2-methylene-4-(octan-2-yloxy)-4-oxobutanoyl)oxy) acetic acid;
(R)-3-((2-methylene-4-(octan-2-yloxy)-4-oxobutanoyl)oxy) propanoic acid; and
2-((4-(cyclooctyloxy)-2-methylene-4-oxobutanoyl)oxy)acetic acid;
or a pharmaceutically acceptable salt and/or solvate of any one thereof.
Suitably, the compound is selected from the group consisting of:
(R)-2-((2-methylene-4-(octan-2-yloxy)-4-oxobutanoyl)oxy) acetic acid;
(R)-3-((2-methylene-4-(octan-2-yloxy)-4-oxobutanoyl)oxy) propanoic acid;
(S)-2-((2-methylene-4-oxo-4-((1,1,1-trifluorooctan-2-yl) oxy)butanoyl)oxy)acetic acid; and
2-((2-methylene-4-((2-methyloctan-2-yl)oxy)-4-oxobutanoyl)oxy)acetic acid;
or a pharmaceutically acceptable salt and/or solvate of any one thereof.
Suitably, the compound is selected from the group consisting of:
(R)-4,4,4-trifluoro-3-((2-methylene-4-(((R)-octan-2-yl)oxy)-4-oxobutanoyl)oxy)butanoic acid; and
(S)-4,4,4-trifluoro-3-((2-methylene-4-(((R)-octan-2-yl)oxy)-4-oxobutanoyl)oxy)butanoic acid;
or a pharmaceutically acceptable salt and/or solvate of any one thereof.

Compounds of formula (IW-1) such as (IW) may be prepared as set out in the Examples, e.g. as set out in General Procedures 1-4.

For example, compounds of formula (IW-1) such as (IW) may prepared using the following route:

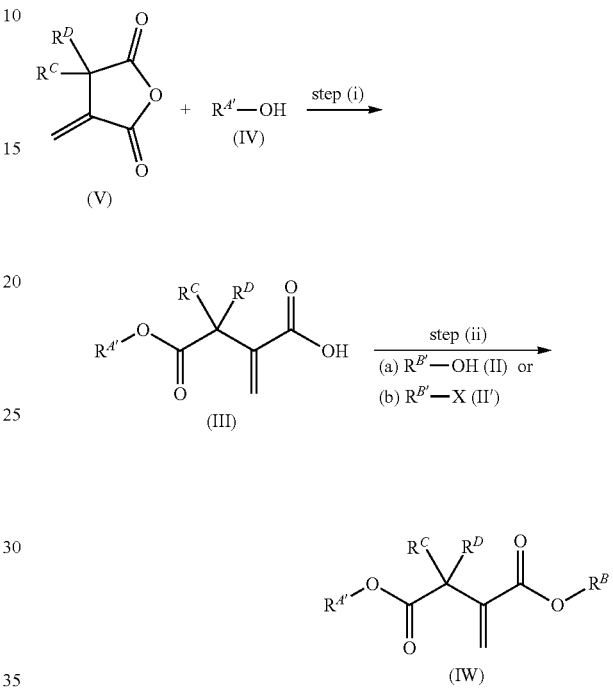

$R^A$, $R^B$, $R^C$ and $R^D$ are as defined elsewhere herein.

Step (i): itaconate anhydride (V) can be reacted with alcohol (IV), wherein $R^{A'}$ represents $R^A$ or a protected derivative thereof, in the presence of a catalyst such as p-TsOH·H$_2$O in a solvent such as toluene to give monoester (III).

Step (ii): Monoester (III) and alcohol (II), where $R^{B'}$ represents $R^B$ or a protected derivative thereof, can be condensed under standard coupling conditions as shown in the General Procedures 2 and 3 to give compounds of formula (IW) following any optional deprotection steps. Alternatively, monoester (III) can be reacted with compound (II'), wherein $R^{B'}$ represents $R^B$ or a protected derivative thereof and X represents a leaving group such as chloro, bromo, iodo, alkanesulfonate or arenesulfonate, in the presence of a base such as potassium carbonate to give compounds of formula (IW) after any requisite deprotection steps.

Compounds of formula (IW-1) such as (IW) may also be prepared by the following route:

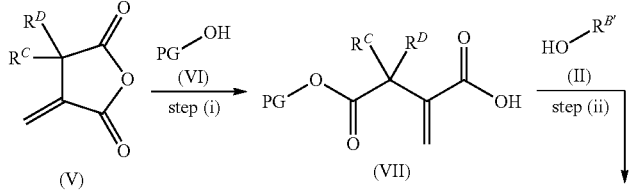

-continued

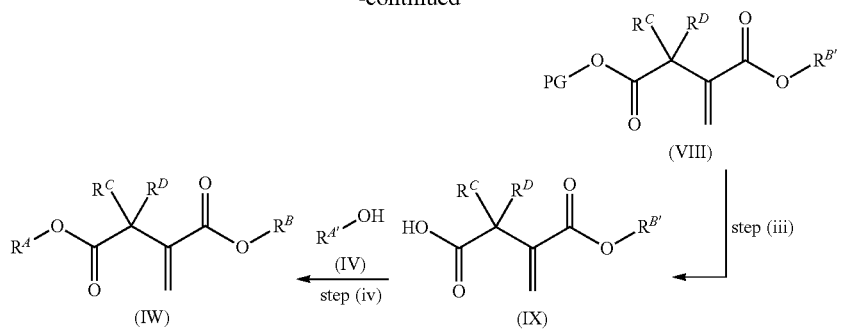

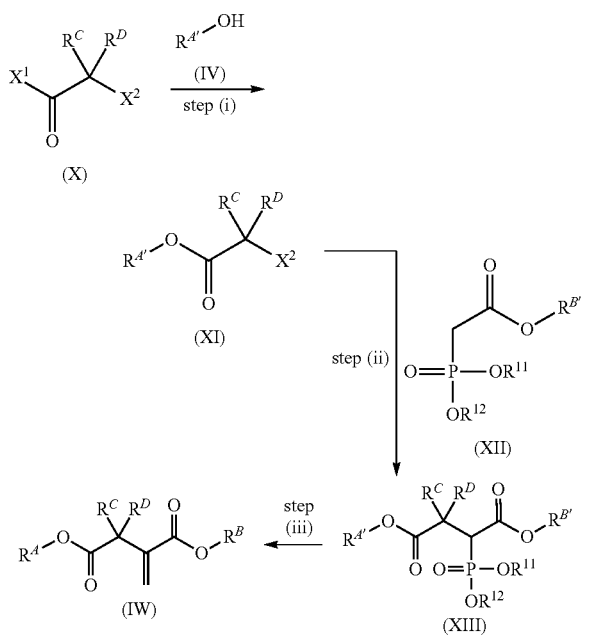

$R^A$, $R^B$, $R^C$ and $R^D$ are as defined elsewhere herein.

Step (i): itaconate anhydride (V) can be reacted with alcohol (VI), wherein PG represents a protecting group orthogonal to any protecting group present in $R^{B'}$, in the presence of a catalyst such as p-TsOH·H$_2$O in a solvent such as toluene to give monoester (VII).

Step (ii): Monoester (VII) and alcohol (II), wherein $R^{B'}$ represents $R^B$ or a protected derivative thereof, can be condensed under standard coupling conditions to give diesters of formula (VIII).

Step (iii): The orthogonal protecting group PG is removed using conditions known to the person skilled in the art to give itaconate (IX) possessing a free carboxyl group at the 4-position.

Step (iv): Itaconate (IX) is coupled with alcohol (IV), wherein $R^{A'}$ represents $R^A$ or a protected derivative thereof, under standard coupling conditions to give monoester (IW) following any deprotection steps required.

Compounds of formula (IW-1) such as (IW) may additionally be made by the following route:

$R^A$, $R^B$, $R^C$ and $R^D$ are as defined elsewhere herein.

Step (i): Alcohol (IV) is condensed with compound (X), wherein $X^1$ and $X^2$ represent leaving groups, such as halo e.g., chloro, bromo or iodo, and $R^{A'}$ represents $R^A$ or a protected derivative thereof, to give monoester (XI).

Step (ii): Monoester (XI) is reacted with a trialkylphosphonoacetate of formula (XII), wherein $R^{11}$ and $R^{12}$ independently represent $C_{1-4}$ alkyl optionally substituted with halo and $R^{B'}$ represents $R^B$ or a protected derivative thereof, to provide a compound of formula (XIII).

Step (iii): Condensation of a compound of formula (XIII) with formaldehyde or a formaldehyde equivalent thereof e.g., paraformaldehyde, and after any optional deprotection steps, provides the compound of formula (IW-a) such as (IW).

The skilled person will appreciate that protecting groups may be used throughout the synthetic schemes described herein to give protected derivatives of any of the above compounds or generic formulae. Protective groups and the means for their removal are described in "*Protective Groups in Organic Synthesis*", by Theodora W. Greene and Peter G. M. Wuts, published by John Wiley & Sons Inc; 4th Rev Ed., 2006, ISBN-10: 0471697540. Examples of nitrogen protecting groups include trityl (Tr), tert-butyloxycarbonyl (BOC), 9-fluorenylmethyloxycarbonyl (Fmoc), acetyl (Ac), benzyl (Bn) and para-methoxy benzyl (PMB). Examples of oxygen protecting groups include acetyl (Ac), methoxymethyl (MOM), para-methoxybenzyl (PMB), benzyl, tert-butyl, methyl, ethyl, tetrahydropyranyl (THP), and silyl ethers and esters (such as trimethylsilyl (TMS), tert-butyldimethylsilyl (TBDMS), tri-iso-propylsilyloxymethyl (TOM), and triisopropylsilyl (TIPS) ethers and esters). Specific examples of carboxylic acid protecting groups include alkyl esters (such as $C_{1-6}$ alkyl e.g. $C_{1-4}$ alkyl esters), benzyl esters and silyl esters.

Thus, in one embodiment there is provided a process for preparing a compound of formula (IW-1) such as (IW) or a salt such as a pharmaceutically acceptable salt thereof, which comprises reacting a compound of formula (III):

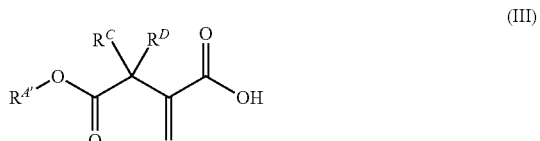

wherein $R^{A'}$, $R^C$ and $R^D$ are defined elsewhere herein, or a salt thereof;
with a compound of formula (II):

wherein $R^{B'}$ is defined elsewhere herein,
or a salt thereof.

In one embodiment there is provided a process for preparing a compound of formula (IW-1), such as (IW) or a salt such as a pharmaceutically acceptable salt thereof, which comprises reacting a compound of formula (III):

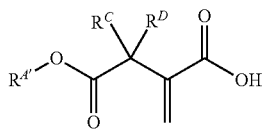
(III)

wherein $R^{A'}$ $R^C$ and $R^D$ are defined elsewhere herein, or a salt thereof;
with a compound of formula (II'):

$$R^{B'}—X \qquad (II')$$

wherein $R^{B'}$ and X are defined elsewhere herein, or a salt thereof.

There is also provided a process for preparing a compound of formula (III) or a salt thereof, which comprises reacting a compound of formula (V):

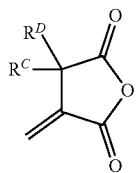
(V)

or a salt thereof;
with a compound of formula (IV):

$$R^{A'}—OH \qquad (IV)$$

wherein $R^{A'}$ is defined elsewhere herein, or a salt thereof.

There is also provided a process for preparing a compound of formula (IW-1), such as (IW) or a salt such as a pharmaceutically acceptable salt thereof, which comprises reacting a compound of formula (IX):

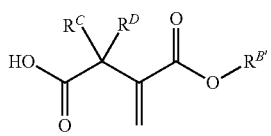
(IX)

wherein $R^{B'}$ $R^C$ and $R^D$ are defined elsewhere herein, or a salt thereof;
with a compound of formula (IV)

$$R^{A'}—OH \qquad (IV)$$

wherein $R^{A'}$ is defined elsewhere herein, or a salt thereof.

In one embodiment there is provided a process for preparing a compound of formula (VIII) or a salt thereof, which comprises reacting a compound of formula (VII):

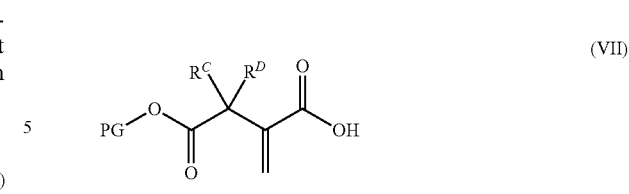
(VII)

wherein PG, $R^C$ and $R^D$ are defined elsewhere herein, or a salt thereof;
with a compound of formula (II):

$$R^{B'}—OH \qquad (II)$$

wherein $R^{B'}$ is defined elsewhere herein, or a salt thereof.

In one embodiment there is provided a process for preparing a compound of formula (IW-1), such as (IW) or a salt such as a pharmaceutically acceptable salt thereof, which comprises reacting a compound of formula (XIII):

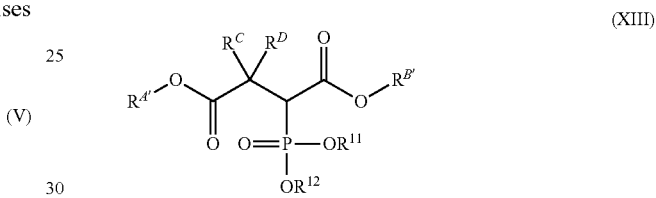
(XIII)

or a salt thereof,
with formaldehyde or an equivalent thereof;
wherein $R^{A'}$, $R^{B'}$, $R^C$, $R^D$, $R^{11}$ and $R^{12}$ are defined elsewhere herein.

In one embodiment there is provided a process for preparing a compound of formula (XIII) or a salt thereof, which comprises reacting a compound of formula (XI):

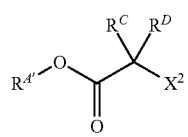
(XI)

wherein $R^{A'}$, $R^C$, $R^D$ and $X^2$ are defined elsewhere herein, or a salt thereof;
with a compound of formula (XII):

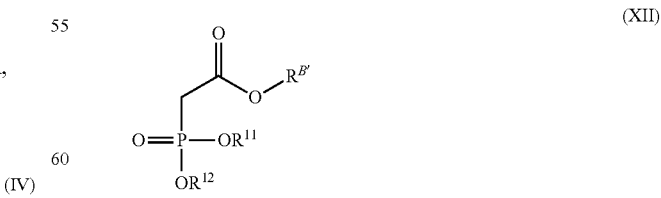
(XII)

wherein $R^{B'}$, $R^{11}$ and $R^{12}$ are defined elsewhere herein, or a salt thereof.

In one embodiment, there is provided a compound of formula (III):

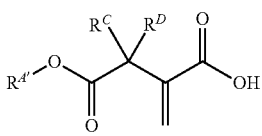

(III)

or a salt thereof, wherein $R^{A'}$, $R^C$ and $R^D$ are defined elsewhere herein.

In one embodiment, there is provided a compound of formula (IX):

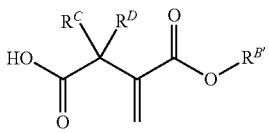

(IX)

or a salt thereof, wherein $R^{B'}$, $R^C$ and $R^D$ are defined elsewhere herein. Suitably, $R^{B'}$ represents $C_{1-2}$ alkyl substituted by $CO_2H$ and further substituted by trifluoromethyl or methyl and e.g. represents the group $CH(CF_3)CH_2CO_2H$ or $CH(CH_3)CH_2CO_2H$, or a corresponding group in which the carboxylic acid is protected.

In one embodiment, there is provided a compound of formula (VIII):

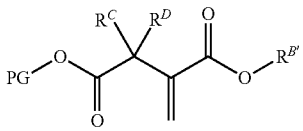

(VIII)

or a salt thereof, wherein PG, $R^{B'}$, $R^C$ and $R^D$ are defined elsewhere herein. Suitably, $R^{B'}$ represents $C_{1-2}$ alkyl substituted by $CO_2H$ and further substituted by trifluoromethyl or methyl and e.g. represents the group $CH(CF_3)CH_2CO_2H$ or $CH(CH_3)CH_2CO_2H$, or a corresponding group in which the carboxylic acid is protected.

In one embodiment, there is provided a compound of formula (XIII):

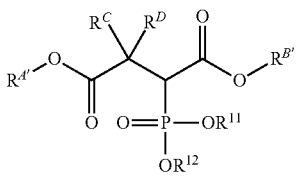

(XIII)

or a salt thereof, wherein $R^{A'}$, $R^{B'}$, $R^C$, $R^D$, $R^{11}$ and $R^{12}$ are defined elsewhere herein.

In one embodiment, there is provided a compound of formula (XI):

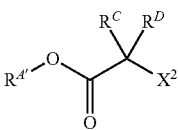

(XI)

or a salt thereof, wherein $R^{A'}$, $R^C$, $R^D$ and $X^2$ are defined elsewhere herein.

Certain intermediates are novel and are claimed as an aspect of the invention:
4-(cyclooctyloxy)-2-methylene-4-oxobutanoic acid;
2-methylene-4-oxo-4-(3-phenoxypropoxy)butanoic acid;
4-(2-(2-ethoxyethoxy)ethoxy)-2-methylene-4-oxobutanoic acid;
4-((4-fluorobenzyl)oxy)-2-methylene-4-oxobutanoic acid;
(R)-2-methylene-4-(octan-2-yloxy)-4-oxobutanoic acid;
(S)-2-methylene-4-(octan-2-yloxy)-4-oxobutanoic acid;
2-methylene-4-(neopentyloxy)-4-oxobutanoic acid;
3-((2-(tert-butoxy)-2-oxoethoxy)carbonyl)but-3-enoic acid; and
3-methyl-2-methylene-4-(octyloxy)-4-oxobutanoic acid
or salts thereof.

Reference hereinbelow to compounds of formula (IW-1) is taken to include reference to all formulae disclosed herein: compounds of formula (IW), (IW-a), (IW-b), (IW-c), (IW-d), (IW-e), (IY), (I), (IWA), (IYA), (IA), (IWB), (IYB), (IB), (IWC), (IC), (IWD-1), (IYD-1), (ID-1), (IWD-2), (IYD-2), (ID-2) and (IWE).

It will be appreciated that for use in therapy the salts of the compounds of formula (IW-1) should be pharmaceutically acceptable. Suitable pharmaceutically acceptable salts will be apparent to those skilled in the art. Pharmaceutically acceptable salts include acid addition salts formed with inorganic acids e.g. hydrochloric acid, hydrobromic acid, sulfuric acid, nitric acid or phosphoric acid. Also included are salts formed with organic acids e.g. succinic acid, maleic acid, acetic acid, fumaric acid, citric acid, tartaric acid, benzoic acid, p-toluenesulfonic acid, methanesulfonic acid, naphthalenesulfonic acid and 1,5-naphthalenedisulfonic acid. Other salts e.g. oxalates or formates, may be used, for example in the isolation of compounds of formula (IW-1) and are included within the scope of this invention, as are basic addition salts such as sodium, potassium, calcium, aluminium, zinc, magnesium and other metal salts.

Pharmaceutically acceptable salts may also be formed with organic bases such as basic amines e.g. with ammonia, meglumine, tromethamine, piperazine, arginine, choline, diethylamine, benzathine or lysine. Thus, in one embodiment there is provided a compound of formula (IW-1) in the form of a pharmaceutically acceptable salt. Alternatively, there is provided a compound of formula (IW-1) in the form of a free acid. When the compound contains a basic group as well as the free acid it may be Zwitterionic.

Suitably, the compound of formula (IW-1) is not a salt e.g. is not a pharmaceutically acceptable salt.

For compounds of formula (IW-1) which contain a carboxylic acid group, suitably, the pharmaceutically acceptable salt is a basic addition salt such as a carboxylate salt formed with a group 1 metal (e.g. a sodium or potassium salt), a group 2 metal (e.g. a magnesium or calcium salt) or an ammonium salt of a basic amine (e.g. an $NH_4^+$ salt), such as a sodium salt.

The compounds of formula (IW-1) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water). Suitably, the compound of formula (IW-1) is not a solvate.

The invention extends to a pharmaceutically acceptable derivative thereof, such as a pharmaceutically acceptable prodrug of compounds of formula (IW-1). Typical prodrugs of compounds of formula (IW-1) which comprise a carboxylic acid include ester (e.g. $C_{1-6}$ alkyl e.g. $C_{1-4}$ alkyl ester) derivatives thereof. Thus, in one embodiment, the compound of formula (IW-1) is provided as a pharmaceutically acceptable prodrug. In another embodiment, the compound of formula (IW-1) is not provided as a pharmaceutically acceptable prodrug.

Certain compounds of formula (IW-1) may metabolise under certain conditions such as by hydrolysis of the $R^B$ ester group. Certain metabolites of compounds of formula (IW-1) have activity, as described in Biological Example 8. Without wishing to be bound by theory, formation of an active metabolite (such as in vivo) of a compound of formula (IW-1) may be beneficial by contributing to the biological activity observed of the compound of formula (IW-1). Thus, in one embodiment, there is provided an active metabolite of the compound of formula (IW-1) and its use as a pharmaceutical e.g. for the treatment or prevention of the diseases mentioned herein.

It is to be understood that the present invention encompasses all isomers of compounds of formula (IW-1) (and compounds of formula (IW), (IW-a), (IW-b), (IW-c), (IW-d), (IY), (I), (IWA), (IYA), (IA), (IWB), (IYB), (IB), (IWC), (IC), (IWD-1), (IYD-1), (ID-1), (IWD-2), (IYD-2), (ID-2) and (IWE)) including all geometric, tautomeric and optical forms, and mixtures thereof (e.g. racemic mixtures). Where additional chiral centres are present in compounds of formula (IW-1), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present invention also includes all isotopic forms of the compounds provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Unnatural variant isotopic forms which incorporate deuterium i.e. $^2H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in positron emission topography (PET) studies for examining substrate receptor occupancy.

In one embodiment, the compounds of formula (IW-1) are provided in a natural isotopic form. In one embodiment, the compounds of formula (IW-1) are provided in an unnatural variant isotopic form. In a specific embodiment, the unnatural variant isotopic form is a form in which deuterium (i.e. $^2H$ or D) is incorporated where hydrogen is specified in the chemical structure in one or more atoms of a compound of formula (IW-1). In one embodiment, the atoms of the compounds of formula (IW-1) are in an isotopic form which is not radioactive. In one embodiment, one or more atoms of the compounds of formula (IW-1) are in an isotopic form which is radioactive. Suitably radioactive isotopes are stable isotopes. Suitably the unnatural variant isotopic form is a pharmaceutically acceptable form.

In one embodiment, a compound of formula (IW-1) is provided whereby a single atom of the compound exists in an unnatural variant isotopic form. In another embodiment, a compound of formula (IW-1) is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (IW-1) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Therapeutic Indications Compounds of formula (IW-1) are of use in therapy, particularly for treating or preventing an inflammatory disease or a disease associated with an undesirable immune response. As shown in Biological Example 1 below, example compounds of formula (IW-1) reduced cytokine release more effectively than dimethyl itaconate, as demonstrated by lower $IC_{50}$ values. Cytokines are important mediators of inflammation and immune-mediated disease as evidenced by the therapeutic benefit delivered by antibodies targeting them. As shown in Biological Example 2, example compounds of formula (IW-1) also exhibited a lower $EC_{50}$ and/or a higher $E_{max}$ compared with dimethyl itaconate in an NQO1 enzyme activation assay. NQO1 is an anti-oxidant target gene upregulated by increased NRF2 activity. Induction of this gene is concomitant with the inhibition of proinflammatory cytokine transcription and suppression of the inflammatory response (Kobayashi E. H. et al., 2016).

Thus, in a first aspect, the present invention provides a compound of formula (IW-1) or a pharmaceutically acceptable salt and/or solvate thereof as defined herein, for use as a medicament. Also provided is a pharmaceutical composition comprising a compound of formula (IW-1) or a pharmaceutically acceptable salt and/or solvate thereof as defined herein. Such a pharmaceutical composition contains the compound of formula (IW-1) and a pharmaceutically acceptable carrier or excipient.

In a further aspect, the present invention provides a compound of formula (IW-1) or a pharmaceutically acceptable salt and/or solvate thereof as defined herein, for use in treating or preventing an inflammatory disease or a disease associated with an undesirable immune response. In a further aspect, the present invention provides the use of a compound of formula (IW-1) or a pharmaceutically acceptable salt and/or solvate thereof as defined herein, in the manufacture of a medicament for treating or preventing an inflammatory disease or a disease associated with an undesirable immune response. In a further aspect, the present invention provides a method of treating or preventing an inflammatory disease or a disease associated with an undesirable immune response, which comprises administering a compound of formula (IW-1) or a pharmaceutically acceptable salt and/or solvate thereof as defined herein.

For all aspects of the invention, suitably the compound is administered to a subject in need thereof, wherein the subject is suitably a human subject.

In one embodiment is provided a compound of formula (IW-1) or a pharmaceutically acceptable salt and/or solvate thereof as defined herein, for use in treating an inflammatory disease or disease associated with an undesirable immune response. In one embodiment of the invention is provided the use of a compound of formula (IW-1) or a pharmaceutically acceptable salt and/or solvate thereof as defined herein, in the manufacture of a medicament for treating an inflammatory disease or a disease associated with an undesirable immune response. In one embodiment of the invention is provided a method of treating an inflammatory disease or a disease associated with an undesirable immune response, which comprises administering a compound of formula (IW-1) or a pharmaceutically acceptable salt and/or solvate thereof as defined herein.

In one embodiment is provided a compound of formula (IW-1) or a pharmaceutically acceptable salt and/or solvate thereof as defined herein, for use in preventing an inflammatory disease or a disease associated with an undesirable immune response. In one embodiment of the invention is provided the use of a compound of formula (IW-1) or a pharmaceutically acceptable salt and/or solvate thereof as defined herein, in the manufacture of a medicament for preventing an inflammatory disease or a disease associated with an undesirable immune response. In one embodiment of the invention is provided a method of preventing an inflammatory disease or a disease associated with an undesirable immune response, which comprises administering a compound of formula (IW-1) or a pharmaceutically acceptable salt and/or solvate thereof as defined herein.

In one embodiment is provided a compound of formula (IW-1) or a pharmaceutically acceptable salt and/or solvate thereof as defined herein, for use in treating or preventing an inflammatory disease. In one embodiment of the invention is provided the use of a compound of formula (IW-1) or a pharmaceutically acceptable salt and/or solvate thereof as defined herein, in the manufacture of a medicament for treating or preventing an inflammatory disease. In one embodiment of the invention is provided a method of treating or preventing an inflammatory disease, which comprises administering a compound of formula (IW-1) or a pharmaceutically acceptable salt and/or solvate thereof as defined herein.

In one embodiment is provided a compound of formula (IW-1) or a pharmaceutically acceptable salt and/or solvate thereof as defined herein, for use in treating or preventing a disease associated with an undesirable immune response. In one embodiment of the invention is provided the use of a compound of formula (IW-1) or a pharmaceutically acceptable salt and/or solvate thereof as defined herein, in the manufacture of a medicament for treating or preventing a disease associated with an undesirable immune response. In one embodiment of the invention is provided a method of treating or preventing a disease associated with an undesirable immune response, which comprises administering a compound of formula (IW-1) or a pharmaceutically acceptable salt and/or solvate thereof as defined herein.

An undesirable immune response will typically be an immune response which gives rise to a pathology i.e. is a pathological immune response or reaction.

In one embodiment, the inflammatory disease or disease associated with an undesirable immune response is an auto-immune disease.

In one embodiment, the inflammatory disease or disease associated with an undesirable immune response is, or is associated with, a disease selected from the group consisting of: psoriasis (including chronic plaque, erythrodermic, pustular, guttate, inverse and nail variants), asthma, chronic obstructive pulmonary disease (COPD, including chronic bronchitis and emphysema), heart failure (including left ventricular failure), myocardial infarction, angina pectoris, other atherosclerosis and/or atherothrombosis-related disorders (including peripheral vascular disease and ischaemic stroke), a mitochondrial and neurodegenerative disease (such as Parkinson's disease, Alzheimer's disease, Huntington's disease, amyotrophic lateral sclerosis, retinitis pigmentosa or mitochondrial encephalomyopathy), autoimmune paraneoplastic retinopathy, transplantation rejection (including antibody-mediated and T cell-mediated forms), multiple sclerosis, transverse myelitis, ischaemia-reperfusion injury (e.g. during elective surgery such as cardiopulmonary bypass for coronary artery bypass grafting or other cardiac surgery, following percutaneous coronary intervention, following treatment of acute ST-elevation myocardial infarction or ischaemic stroke, organ transplantation, or acute compartment syndrome), AGE-induced genome damage, an inflammatory bowel disease (e.g. Crohn's disease or ulcerative colitis), primary sclerosing cholangitis (PSC), PSC-autoimmune hepatitis overlap syndrome, non-alcoholic fatty liver disease (non-alcoholic steatohepatitis), rheumatica, granuloma annulare, cutaneous lupus erythematosus (CLE), systemic lupus erythematosus (SLE), lupus nephritis, drug-induced lupus, autoimmune myocarditis or myopericarditis, Dressler's syndrome, giant cell myocarditis, post-pericardiotomy syndrome, drug-induced hypersensitivity syndromes (including hypersensitivity myocarditis), eczema, sarcoidosis, erythema nodosum, acute disseminated encephalomyelitis (ADEM), neuromyelitis optica spectrum disorders, MOG (myelin oligodendrocyte glycoprotein) antibody-associated disorders (including MOG-EM), optic neuritis, CLIPPERS (chronic lymphocytic inflammation with pontine perivascular enhancement responsive to steroids), diffuse myelinoclastic sclerosis, Addison's disease, alopecia areata, ankylosing spondylitis, other spondyloarthritides (including peripheral spondyloarthritis, that is associated with psoriasis, inflammatory bowel disease, reactive arthritis or juvenile onset forms), antiphospholipid antibody syndrome, autoimmune hemolytic anaemia, autoimmune hepatitis, autoimmune inner ear disease, pemphigoid (including bullous pemphigoid, mucous membrane pemphigoid, cicatricial pemphigoid, herpes gestationis or pemphigoid gestationis, ocular cicatricial pemphigoid), linear IgA disease, Behget's disease, celiac disease, Chagas disease, dermatomyositis, diabetes mellitus type I, endometriosis, Goodpasture's syndrome, Graves' disease, Guillain-Barre syndrome and its subtypes (including acute inflammatory demyelinating polyneuropathy, AIDP, acute motor axonal neuropathy (AMAN), acute motor and sensory axonal neuropathy (AMSAN), pharyngeal-cervical-brachial variant, Miller-Fisher variant and Bickerstaff's brainstem encephalitis), progressive inflammatory neuropathy, Hashimoto's disease, hidradenitis suppurativa, inclusion body myositis, necrotising myopathy, Kawasaki disease, IgA nephropathy, Henoch-Schonlein purpura, idiopathic thrombocytopenic purpura, thrombotic thrombocytopenic purpura (TTP), Evans' syndrome, interstitial cystitis, mixed connective tissue disease, undifferentiated connective tissue disease, morphea, myasthenia gravis (including MuSK antibody positive and seronegative variants), narcolepsy, neuromyotonia, pemphigus vulgaris, pernicious anaemia, psoriatic arthritis, polymyositis, primary biliary cholangitis (also known as primary biliary cirrhosis), rheumatoid arthritis, palindromic rheumatism, schizophrenia, autoimmune (meningo-)encephalitis syndromes, scleroderma, Sjogren's syndrome, stiff person syndrome, polymylagia rheumatica, giant cell arteritis (temporal arteritis), Takayasu arteritis, polyarteritis nodosa, Kawasaki disease, granulomatosis with polyangitis (GPA; formerly known as Wegener's granulomatosis), eosinophilic granulomatosis with polyangiitis (EGPA; formerly known as Churg-Strauss syndrome), microscopic polyarteritis/polyangiitis, hypocomplementaemic urticarial vasculitis, hypersensitivity vasculitis, cryoglobulinemia, thromboangiitis obliterans (Buerger's disease), vasculitis, leukocytoclastic vasculitis, vitiligo, acute disseminated encephalomyelitis, adrenoleukodystrophy, Alexander's disease, Alper's disease, balo concentric sclerosis or Marburg disease, cryptogenic organising pneumonia (formerly known as bronchiolitis obliterans organizing pneumonia), Canavan disease, central nervous system vasculitic syndrome, Charcot-Marie-Tooth disease, childhood ataxia with central nervous system hypomyelination, chronic inflammatory demyelinating polyneuropathy (CIDP), diabetic retinopathy, globoid cell leukodystrophy (Krabbe disease), graft-versus-host disease (GVHD) (including acute and chronic forms, as well as intestinal GVHD), hepatitis C (HCV) infection or complication, herpes simplex viral infection or complication, human immunodeficiency virus (HIV) infection or complication, lichen planus, monomelic amyotrophy, cystic fibrosis, pulmonary arterial hypertension (PAH, including idiopathic PAH), lung sarcoidosis, idiopathic pulmonary fibrosis, paediatric asthma, atopic dermatitis, allergic dermatitis, contact dermatitis, allergic rhinitis, rhinitis, sinusitis, conjunctivitis, allergic conjunctivitis, keratoconjunctivitis sicca, dry eye, xerophthalmia, glaucoma, macular oedema, diabetic macular oedema, central retinal vein occlusion (CRVO), macular degeneration (including dry and/or wet age related macular degeneration, AMD), post-operative cataract inflammation, uveitis (including posterior, anterior, intermediate and pan uveitis), iridocyclitis, scleritis, corneal graft and limbal cell transplant rejection, gluten sensitive enteropathy (coeliac disease), dermatitis herpetiformis, eosinophilic esophagitis, achalasia, autoimmune dysautonomia, autoimmune encephalomyelitis, autoimmune oophoritis, autoimmune orchitis, autoimmune pancreatitis, aortitis and periaortitis, autoimmune retinopathy, autoimmune urticaria, Behcet's disease, (idiopathic) Castleman's disease, Cogan's syndrome, IgG4-related disease, retroperitoneal fibrosis, juvenile idiopathic arthritis including systemic juvenile idiopathic arthritis (Still's disease), adult-onset Still's disease, ligneous conjunctivitis, Mooren's ulcer, *Pityriasis lichenoides* et varioliformis acuta (PLEVA, also known as Mucha-Habermann disease), multifocal motor neuropathy (MMN), paediatric acute-onset neuropsychiatric syndrome (PANS) (including paediatric autoimmune neuropsychiatric disorders associated with streptococcal infections (PANDAS)), paraneoplastic syndromes (including paraneoplastic cerebellar degeneration, Lambert-Eaton myaesthenic syndrome, limbic encephalitis, brainstem encephalitis, opsoclonus myoclonus ataxia syndrome, anti-NMDA receptor encephalitis, thymoma-associated multiorgan autoimmunity), perivenous encephalomyelitis, reflex sympathetic dystrophy, relapsing polychondritis, sperm & testicular autoimmunity, Susac's syndrome, Tolosa-Hunt syndrome, Vogt-Koyanagi-Harada Disease, anti-synthetase syndrome, autoimmune enteropathy, immune dysregulation polyendocrinopathy enteropathy X-linked (IPEX), microscopic colitis, autoimmune lymphoproliferative syndrome (ALPS), autoimmune polyendocrinopathy-candidiasis-ectodermal dystrophy syndrome (APEX), gout, pseudogout, amyloid (including AA or secondary amyloidosis), eosinophilic fasciitis (Shulman syndrome) progesterone hypersensitivity (including progesterone dermatitis), familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutieres syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria), Schnitzler syndrome; familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation).

In one embodiment, the inflammatory disease or disease associated with an undesirable immune response is, or is associated with, a disease selected from the following autoinflammatory diseases: familial Mediterranean fever (FMF), tumour necrosis factor (TNF) receptor-associated periodic fever syndrome (TRAPS), hyperimmunoglobulinaemia D with periodic fever syndrome (HIDS), PAPA (pyogenic arthritis, pyoderma gangrenosum, and severe cystic acne) syndrome, deficiency of interleukin-1 receptor antagonist (DIRA), deficiency of the interleukin-36-receptor antagonist (DITRA), cryopyrin-associated periodic syndromes (CAPS) (including familial cold autoinflammatory syndrome [FCAS], Muckle-Wells syndrome, and neonatal onset multisystem inflammatory disease [NOMID]), NLRP12-associated autoinflammatory disorders (NLRP12AD), periodic fever aphthous stomatitis (PFAPA), chronic atypical neutrophilic dermatosis with lipodystrophy and elevated temperature (CANDLE), Majeed syndrome, Blau syndrome (also known as juvenile systemic granulomatosis), macrophage activation syndrome, chronic recurrent multifocal osteomyelitis (CRMO), familial cold autoinflammatory syndrome, mutant adenosine deaminase 2 and monogenic interferonopathies (including Aicardi-Goutieres syndrome, retinal vasculopathy with cerebral leukodystrophy, spondyloenchondrodysplasia, STING [stimulator of interferon genes]-associated vasculopathy with onset in infancy, proteasome associated autoinflammatory syndromes, familial chilblain lupus, dyschromatosis symmetrica hereditaria) and Schnitzler syndrome.

In one embodiment, the inflammatory disease or disease associated with an undesirable immune response is, or is associated with, a disease selected from the following diseases mediated by excess NF-κB or gain of function in the NF-κB signalling pathway or in which there is a major contribution to the abnormal pathogenesis therefrom (including non-canonical NF-κB signalling): familial cylindromatosis, congenital B cell lymphocytosis, OTULIN-related autoinflammatory syndrome, type 2 diabetes mellitus, insulin resistance and the metabolic syndrome (including obesity-associated inflammation), atherosclerotic disorders (e.g. myocardial infarction, angina, ischaemic heart failure, ischaemic nephropathy, ischaemic stroke, peripheral vascular disease, aortic aneurysm), renal inflammatory disorders (e.g. diabetic nephropathy, membranous nephropathy, minimal change disease, crescentic glomerulonephritis, acute kidney injury, renal transplantation), asthma, COPD, type 1 diabetes mellitus, rheumatoid arthritis, multiple sclerosis, inflammatory bowel disease (including ulcerative colitis and Crohn's disease), and SLE.

In one embodiment, the disease is selected from the group consisting of rheumatoid arthritis, psoriatic arthritis, ankylosing spondylitis, systemic lupus erythematosus, multiple sclerosis, psoriasis, Crohn's disease, ulcerative colitis, uveitis, cryopyrin-associated periodic syndromes, Muckle-Wells syndrome, juvenile idiopathic arthritis and chronic obstructive pulmonary disease.

In one embodiment, the disease is multiple sclerosis.

In one embodiment, the disease is psoriasis.

In one embodiment, the compound of formula (IW-1) exhibits a lower $IC_{50}$ compared with dimethyl itaconate when tested in a cytokine assay e.g. as described in Biological Example 1. In one embodiment, the compound of formula (IW-1) exhibits a lower $IC_{50}$ compared with dimethyl fumarate when tested in a cytokine assay e.g. as described in Biological Example 1.

In one embodiment, the compound of formula (IW-1) exhibits a lower $EC_{50}$ compared with dimethyl itaconate when tested in an NQO1 assay e.g. as described in Biological Example 2. In one embodiment, the compound of formula (IW-1) exhibits a higher $E_{max}$ compared with dimethyl itaconate when tested in an NQO1 assay e.g. as described in Biological Example 2. In one embodiment, the compound of formula (IW-1) exhibits a lower $EC_{50}$ and/or higher $E_{max}$ compared with dimethyl itaconate when tested in an NQO1 assay e.g. as described in Biological Example 2. In one embodiment, the compound of formula (IW-1) exhibits a lower $EC_{50}$ and higher $E_{max}$ compared with dimethyl itaconate when tested in an NQO1 assay e.g. as described in Biological Example 2. In one embodiment, the compound of formula (IW-1) exhibits a lower $EC_{50}$ compared with dimethyl fumarate when tested in an NQO1 assay e.g. as described in Biological Example 2. In one embodiment, the compound of formula (IW-1) exhibits a higher $E_{max}$ compared with dimethyl fumarate when tested in an NQO1 assay, e.g., as described in Biological Example 2. In one embodiment, the compound of formula (IW-1) exhibits a lower $EC_{50}$ and/or higher $E_{max}$ compared with dimethyl fumarate when tested in an NQO1 assay e.g. as described in Biological Example 2. In one embodiment, the compound of formula (IW-1) exhibits a lower $EC_{50}$ and higher $E_{max}$ compared with dimethyl fumarate when tested in an NQO1 assay, e.g., as described in Biological Example 2.

In one embodiment, the compound of formula (IW-1) exhibits a lower $EC_{50}$ compared with dimethyl itaconate when tested in an NRF2 assay e.g. as described in Biological Example 5. In one embodiment, the compound of formula (IW-1) exhibits a higher $E_{max}$ compared with dimethyl itaconate when tested in an NRF2 assay e.g. as described in Biological Example 5. In one embodiment, the compound of formula (IW-1) exhibits a lower $EC_{50}$ and/or higher $E_{max}$ compared with dimethyl itaconate when tested in an NRF2 assay e.g. as described in Biological Example 5. In one embodiment, the compound of formula (IW-1) exhibits a lower $EC_{50}$ and higher $E_{max}$ compared with dimethyl itaconate when tested in an NRF2 assay e.g. as described in Biological Example 5.

In one embodiment, the compound of formula (I) exhibits improved oral systemic bioavailability compared with dimethyl itaconate e.g. as described in Biological Example 6. In one embodiment, the compound of formula (I) exhibits reduced plasma clearance following intravenous dosing compared with dimethyl itaconate e.g. as described in Biological Example 6.

In one embodiment, the compound of formula (IW-1) exhibits lower intrinsic clearance ($Cl_{int}$) compared with 4-octyl itaconate when tested in a hepatocyte stability assay, e.g., as described in Biological Example 7. In one embodiment, the compound of formula (IW-1) exhibits a longer half-life (T½) compared with 4-octyl itaconate when tested in a hepatocyte stability assay, e.g. as described in Biological Example 7.

Administration

The compound of formula (IW-1) is usually administered as a pharmaceutical composition. Thus, in one embodiment, is provided a pharmaceutical composition comprising a compound of formula (IW-1) and one or more pharmaceutically acceptable diluents or carriers.

The compound of formula (IW-1) may be administered by any convenient method, e.g. by oral, parenteral, buccal, sublingual, nasal, rectal, intrathecal or transdermal administration, and the pharmaceutical compositions adapted accordingly.

The compound of formula (IW-1) may be administered topically to the target organ e.g. topically to the eye, lung, nose or skin. Hence the invention provides a pharmaceutical composition comprising a compound of formula (IW-1) optionally in combination with one or more topically acceptable diluents or carriers.

A compound of formula (IW-1) which is active when given orally can be formulated as a liquid or solid, e.g. as a syrup, suspension, emulsion, tablet, capsule or lozenge.

A liquid formulation will generally consist of a suspension or solution of the compound of formula (IW-1) in a suitable liquid carrier(s). Suitably the carrier is non-aqueous e.g. polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatine capsule; alternatively, a dispersion or suspension can be prepared using any suitable pharmaceutical carrier(s), e.g. aqueous gums, celluloses, silicates or oils and the dispersion or suspension then filled into a soft gelatine capsule.

Typical parenteral compositions consist of a solution or suspension of the compound of formula (IW-1) in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the compound of formula (IW-1) in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a chlorofluorocarbon (CFC) or a hydrofluorocarbon (HFC). Aerosol dosage forms can also take the form of pump-atomisers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC).

Topical administration to the lung may also be achieved by use of a non-pressurised formulation such as an aqueous solution or suspension. These may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents.

Topical administration to the lung may also be achieved by use of a dry-powder formulation. The formulation will typically contain a topically acceptable diluent such as lactose, glucose or mannitol (preferably lactose).

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Compositions suitable for buccal or sublingual administration include tablets, lozenges and pastilles where the compound of formula (IW-1) is formulated with a carrier such as sugar and acacia, tragacanth, or gelatine and glycerine.

Compositions suitable for transdermal administration include ointments, gels and patches.

The composition may contain from 0.1% to 100% by weight, for example from 10 to 60% by weight, of the compound of formula (IW-1), depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, such as from 1.0 mg to 50 mg, e.g. about 10 mg of the compound of formula (IW-1), depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, such as from 1.0 mg to 50 mg, e.g. about 10 mg and such unit doses may be administered more than once a day, for example two or three times a day. Such therapy may extend for a number of weeks or months.

In one embodiment of the invention, the compound of formula (IW-1) is used in combination with a further therapeutic agent or agents. When the compound of formula (IW-1) is used in combination with other therapeutic agents, the compounds may be administered either sequentially or simultaneously by any convenient route. Alternatively, the compounds may be administered separately.

Therapeutic agents which may be used in combination with the present invention include: corticosteroids (glucocorticoids), retinoids (e.g. acitretin, isotretinoin, tazarotene), anthralin, vitamin D analogues (e.g. cacitriol, calcipotriol), calcineurin inhibitors (e.g. tacrolimus, pimecrolimus), phototherapy or photochemotherapy (e.g. psoralen ultraviolet irradiation, PUVA) or other form of ultraviolet light irradiation therapy, ciclosporine, thiopurines (e.g. azathioprine, 6-mercaptopurine), methotrexate, anti-TNFα agents (e.g. infliximab, etanercept, adalimumab, certolizumab, golimumab and biosimilars), phosphodiesterase-4 (PDE4) inhibition (e.g. apremilast, crisaborole), anti-IL-17 agents (e.g. brodalumab, ixekizumab, secukinumab), anti-IL12/IL-23 agents (e.g. ustekinumab, briakinumab), anti-IL-23 agents (e.g. guselkumab, tildrakizumab), JAK (Janus Kinase) inhibitors (e.g. tofacitinib, ruxolitinib, baricitinib, filgotinib, upadacitinib), plasma exchange, intravenous immune globulin (IVIG), cyclophosphamide, anti-CD20 B cell depleting agents (e.g. rituximab, ocrelizumab, ofatumumab, obinutuzumab), anthracycline analogues (e.g. mitoxantrone), cladribine, sphingosine 1-phosphate receptor modulators or sphingosine analogues (e.g. fingolimod, siponimod, ozanimod, etrasimod), interferon beta preparations (including interferon beta 1b/1a), glatiramer, anti-CD3 therapy (e.g. OKT3), anti-CD52 targeting agents (e.g. alemtuzumab), leflunomide, teriflunomide, gold compounds, laquinimod, potassium channel blockers (e.g. dalfampridine/4-aminopyridine), mycophenolic acid, mycophenolate mofetil, purine analogues (e.g. pentostatin), mTOR (mechanistic target of rapamycin) pathway inhibitors (e.g. sirolimus, everolimus), anti-thymocyte globulin (ATG), IL-2 receptor (CD25) inhibitors (e.g. basiliximab, daclizumab), anti-IL-6 receptor or anti-IL-6 agents (e.g. tocilizumab, siltuximab), Bruton's tyrosine kinase (BTK) inhibitors (e.g. ibrutinib), tyrosine kinase inhibitors (e.g. imatinib), ursodeoxycholic acid, hydroxychloroquine, chloroquine, B cell activating factor (BAFF, also known as BLyS, B lymphocyte stimulator) inhibitors (e.g. belimumab, blisibimod), other B cell targeted therapy including fusion proteins targeting both APRIL (A PRoliferation-Inducing Ligand) and BLyS (e.g. atacicept), PI3K inhibitors including pan-inhibitors or those targeting the p110δ and/or p110γ containing isoforms (e.g. idelalisib, copanlisib, duvelisib), interferon α receptor inhibitors (e.g. anifrolumab, sifalimumab), T cell co-stimulation blockers (e.g. abatacept, belatacept), thalidomide and its derivatives (e.g. lenalidomide), dapsone, clofazimine, leukotriene antagonists (e.g. montelukast), theophylline, anti-IgE therapy (e.g. omalizumab), anti-IL-5 agents (e.g. mepolizumab, reslizumab), long-acting muscarinic agents (e.g. tiotropium, aclidinium, umeclidinium), PDE4 inhibitors (e.g. roflumilast), riluzole, free radical scavengers (e.g. edaravone), proteasome inhibitors (e.g. bortezomib), complement cascade inhibitors including those directed against C5 (e.g. eculizumab), immunoadsor, antithymocyte globulin, 5-aminosalicylates and their derivatives (e.g. sulfasalazine, balsalazide, mesalamine), anti-integrin agents including those targeting α4β1 and/or α4β7 integrins (e.g. natalizumab, vedolizumab), anti-CD11-α agents (e.g. efalizumab), non-steroidal anti-inflammatory drugs (NSAIDs) including the salicylates (e.g. aspirin), propionic acids (e.g. ibuprofen, naproxen), acetic acids (e.g. indomethacin, diclofenac, etodolac), oxicams (e.g. meloxicam) and fenamates (e.g. mefenamic acid), selective or relatively selective COX-2 inhibitors (e.g. celecoxib, etroxicoxib, valdecoxib and etodolac, meloxicam, nabumetone), colchicine, IL-4 receptor inhibitors (e.g. dupilumab), topical/contact immunotherapy (e.g. diphenylcyclopropenone, squaric acid dibutyl ester), anti-IL-1 receptor therapy (e.g. anakinra), IL-1β inhibitor (e.g. canakinumab), IL-1 neutralising therapy (e.g. rilonacept), chlorambucil, specific antibiotics with immunomodulatory properties and/or ability to modulate NRF2 (e.g. tetracyclines including minocycline, clindamycin, macrolide antibiotics), anti-androgenic therapy (e.g. cyproterone, spironolactone, finasteride), pentoxifylline, ursodeoxycholic acid, obeticholic acid, fibrate, cystic fibrosis transmembrane conductance regulator (CFTR) modulators, VEGF (vascular endothelial growth factor) inhibitors (e.g. bevacizumab, ranibizumab, pegaptanib, aflibercept), pirfenidone, and mizoribine.

Compounds of formula (IW-1) may display one or more of the following desirable properties:
- low $IC_{50}$ values for inhibiting release of cytokines e.g. IL-1β and/or IL-6, from cells;
- low $EC_{50}$ and/or high $E_{max}$ values for activating the enzyme NQO1 or the NRF2 pathway;
- enhanced efficacy through improved hydrolytic stability of carboxylic acid esters and/or augmented maximum response;
- reduced dose and dosing frequency through improved pharmacokinetics;
- improved oral systemic bioavailability;
- reduced plasma clearance following intravenous dosing;
- improved metabolic stability e.g. as demonstrated by improved stability in plasma and/or hepatocytes;
- augmented cell permeability;
- enhanced aqueous solubility;
- good tolerability, for example, by limiting the flushing and/or gastrointestinal side effects provoked by oral DMF (Hunt T. et al., 2015; WO2014/152494A1, incorporated herein by reference), possibly by reducing or eliminating HCA2 activity;
- low toxicity at the relevant therapeutic dose;
- distinct anti-inflammatory profiles resulting from varied electrophilicities, leading to differential targeting of the cysteine proteome (van der Reest J. et al., 2018) and, therefore, modified effects on gene activation;
- glutathione-sparing actions;
- avoiding the oncometabolite fumaric acid (Kulkarni R. A. et al., 2019).

Abbreviations

Ac₂O acetic anhydride
ADEM acute disseminated encephalomyelitis
AIDP acute inflammatory demyelinating polyneuropathy
ALPS autoimmune lymphoproliferative syndrome
AMAN acute motor axonal neuropathy
AMD age related macular degeneration
AMSAN acute motor and sensory axonal neuropathy
APEX autoimmune polyendocrinopathy-candidiasis-ectodermal dystrophy syndrome
APRIL A PRoliferation-Inducing Ligand
aq. aqueous
ATF3 activating transcription factor 3
ATG anti-thymocyte
BAFF B cell activating factor
BBFO broadband fluorine observe
BEH ethylene bridged hybrid
Boc tertiary-butoxycarbonyl
BSA bovine serum albumin
BTK Bruton's tyrosine kinase
CAC citric acid cycle
CANDLE chronic atypical neutrophilic dermatosis with lipodystrophy and elevated temperature
CAPS cryopyrin-associated periodic syndromes
CFC chlorofluorocarbon
CFTR cystic fibrosis transmembrane conductance regulator
CIOP chronic inflammatory demyelinating polyneuropathy
CLE cutaneous lupus erythematosus
CLIPPERS chronic lymphocytic inflammation with pontine perivascular enhancement responsive to steroids
CLL chronic lymphocytic leukaemia
COPD chronic obstructive pulmonary disease
CRMO chronic recurrent multifocal osteomyelitis
CRVO central retinal vein occlusion
CSH charged surface hybrid
DABCO 1,4-diazabicyclo[2.2.2]octane
DAD diode array detector
DBU 1,8-diazabicyclo(5.4.0)undec-7-ene
DCC N,N'-dicyclohexylcarbodiimide
DCM dichloromethane
DIPEA N,N-diisopropylethylamine
DIRA deficiency of interleukin-1 receptor antagonist
DITRA deficiency of the interleukin-36-receptor antagonist
DLBCL diffuse large B cell lymphoma
DMAP 4-dimethylaminopyridine
DMF dimethyl fumarate
DMI dimethyl itaconate
DMP Dess-Martin periodinane
DMSO dimethyl sulfoxide
EDC 1-ethyl-3-(3-dimethylaminopropyl)carbodiimide
EDTA ethylenediaminetetraacetic acid
EGPA eosinophilic granulomatosis with polyangiitis
EtOAc ethyl acetate
FBS fetal bovine serum
FCAS familial cold autoinflammatory syndrome
FMF familial Mediterranean fever
GAPDH glyceraldehyde 3-phosphate dehydrogenase
GPA granulomatosis with polyangiitis
GSH glutathione
GVHD graft versus host disease
HATU 1-[bis(dimethylamino)methylene]-1H-1,2,3-triazolo[4,5-b]pyridinium 3-oxid hexafluorophosphate
HCA2 hydroxycarboxylic acid receptor 2
HCV hepatitis C
HFC hydrofluorocarbon
HIF-1α hypoxia-inducible factor-1α
HIV human immunodeficiency virus
HMDMs human monocyte derived macrophages
HOBt 1-hydroxybenzotriazole
IL interleukin
IPEX immune dysregulation polyendocrinopathy enteropathy X-linked
IRG1 immune-responsive gene 1
IVIG intravenous immune globulin
JAK Janus kinase
KEAP1 kelch-like ECH-associated protein 1
LCMS liquid chromatography-mass spectrometry
LDA lithium diisopropylamide
LPS lipopolysaccharide
MALT mucosa-associated lymphoid tissue
mCPBA meta-chloroperoxybenzoic acid M-CSF macrophage-colony stimulating factor
MMF monomethyl fumarate
MMN multifocal motor neuropathy
MOG myelin oligodendrocyte glycoprotein
MS mass spectrometry
MSD mass selective detector
MTBE methyl tertiary-butyl ether
NLRP12AD NLRP12-associated autoinflammatory disorders
NMM N-methylmorpholine
NMR nuclear magnetic resonance
NOMID neonatal onset multisystem inflammatory disease
NQO1 NAD(P)H dehydrogenase [quinone] 1
NRF2 nuclear factor (erythroid-derived 2)-like 2
NSAIDs non-steroidal anti-inflammatory drugs
O/N overnight
PAH pulmonary arterial hypertension
PANDAS paediatric autoimmune neuropsychiatric disorders associated with streptococcal infections
PANS paediatric acute-onset neuropsychiatric syndrome
PAPA pyogenic arthritis, pyoderma gangrenosum, severe cystic acne
PMB 4-methoxybenzyl
PBMCs primary peripheral blood mononuclear cells
PBS phosphate buffered saline
PDA photodiode array
PDE4 phosphodiesterase-4
PET positron emission topography
PFAPA periodic fever aphthous stomatitis
PLEVA *Pityriasis lichenoides* et varioliformis acuta
PMA phorbol 12-myristate 13-acetate
PSC primary sclerosing cholangitis
PUVA psoralen ultraviolet irradiation
p-TsOH p-toluenesulfonic acid
4OI 4-octyl itaconic acid
RT room temperature
sat. saturated
SDH succinate dehydrogenase
SFC supercritical fluid chromatography
SLE systemic lupus erythematosus
STING stimulator of interferon genes
TFA trifluoroacetic acid
TLR Toll-like receptor
TNF tumour necrosis factor
TRAPS tumour necrosis factor receptor-associated periodic fever
Trt trityl, triphenylmethyl
TTP thrombotic thrombocytopenic purpura
UPLC ultra performance liquid chromatography
VEGF vascular endothelial growth factor
VWD variable wavelength detector
wt. weight

EXAMPLES

Analytical Equipment

NMR spectra were recorded using a Bruker 400 MHz Avance III spectrometer fitted with a BBFO 5 mm probe, or a Bruker 500 MHz Avance III HD spectrometer equipped with a Bruker 5 mm SmartProbe™. Spectra were measured at 298 K, unless indicated otherwise, and were referenced relative to the solvent resonance. The chemical shifts are reported in parts per million. Data were acquired using Bruker TopSpin software.

UPLC/MS analysis was carried out on a Waters Acquity UPLC system using either a Waters Acquity CSH C18 or BEH C18 column (2.1×30 mm) maintained at a temperature of 40° C. and eluted with a linear acetonitrile gradient appropriate for the lipophilicity of the compound over 3 or 10 minutes at a constant flow rate of 0.77 mL/min. The aqueous portion of the mobile phase was either 0.1% Formic Acid (CSH C18 column) or 10 mM Ammonium Bicarbonate (BEH C18 column). LC-UV chromatograms were recorded using a Waters Acquity PDA detector between 210 and 400 nm. Mass spectra were recorded using a Waters Acquity Qda detector with electrospray ionisation switching between positive and negative ion mode. Sample concentration was adjusted to give adequate UV response.

LCMS analysis was carried out on a Agilent LCMS system using either a Waters Acquity CSH C18 or BEH C18 column (4.6×30 mm) maintained at a temperature of 40° C. and eluted with a linear acetonitrile gradient appropriate for the lipophilicity of the compound over 4 or 15 minutes at a constant flow rate of 2.5 mL/min. The aqueous portion of the mobile phase was either 0.1% Formic Acid (CSH C18 column) or 10 mM Ammonium Bicarbonate (BEH C18 column). LC-UV chromatograms were recorded using an Agilent VWD or DAD detector at 254 nm. Mass spectra were recorded using an Agilent MSD detector with electrospray ionisation switching between positive and negative ion mode. Sample concentration was adjusted to give adequate UV response.

Alternatively, the following analytical LCMS equipment and methods were also used:

| LCMS/HPLC Instrument Details | | | | |
|---|---|---|---|---|
| System | Instrument Name | LC Detector | ELS detector | Mass detector |
| 1 | Agilent LCMS 1200 | G1315D DAD | 380 ELSD | Agilent G6120B |
| 2 | Agilent LCMS 1200 | G1315C DAD | 380 ELSD | Agilent G6110A |

| LCMS/HPLC Method Details | | | | | | | |
|---|---|---|---|---|---|---|---|
| Method Name | Solvent System | Column | Gradient | UV range | Mass Range | Column Temp. ° C. | Flow Rate ml/min |
| A | A) water + 10 mM NH₄HCO₃ B) acetonitrile | Waters X-Bridge C18 (50 mm × 4.6 mm × 3.5 μm) | From 95:5 to 0:100 in 1.6 min, 0:100 for 1.4 min, from 0:100 to 95:5 in 0.1 min, 95:5 for 0.7 min | 190-400 nm | 100-1800 amu | 40 | 2.0 |

| | | | | | | | |
|---|---|---|---|---|---|---|---|
| B | A) water + 0.05% TFA B) acetonitrile + 0.05% TFA | Waters X-Bridge C18 (50 mm × 4.6 mm × 3.5 μm) | From 95:5 to 0:100 in 1.6 min, 0:100 for 1.4 min, from 0:100 to 95:5 in 0.05 min, 95:5 for 0.7 min | 190-400 nm | 100-1100 amu | 40 | 2.0 |
| C | A) water + 0.05% TFA | Halo C18 (30 mm × 4.6 mm × 2.7 μm) | From 95:5 to 0:100 in 0.8 min, 0:100 for 0.4 min, from 0:100 to 95:5 in 0.01 min, 95:5 for 0.2 min | 190-400 nm | 100-1100 amu | 40 | 3.0 |

Commercial Materials

Dimethyl itaconate was purchased from Sigma-Aldrich (product number: 109533); 4-octyl itaconate was purchased from BOO biosciences (product number: B0001-007866); 4-methyl itaconate was purchased from Apollo Scientific (product number: OR10969); 4-butyl itaconate was purchased from Combi-Blocks (product number: QV-5962).

General Methods

Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

General Procedure 1—Synthesis of Monoesters

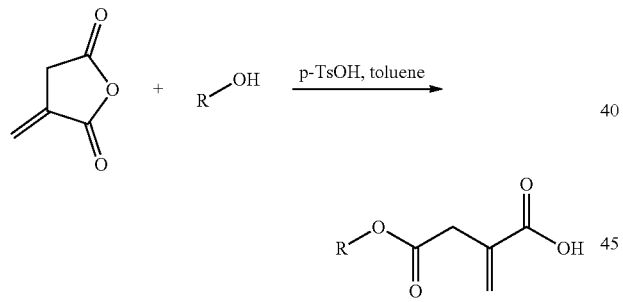

A suspension of itaconic anhydride (1 eq.) in toluene was treated with p-TsOH·H$_2$O (10 mol %) followed by the appropriate alcohol (R—OH, 1 eq.) which is defined where relevant below. The resultant yellow solution was stirred at 80-110° C. The reaction mixture was concentrated onto silica gel and the crude product was purified by chromatography on silica gel (0-5% MeOH/DCM) to afford the desired monoester.

General Procedure 2—Synthesis of Diesters

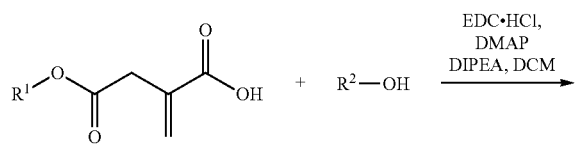

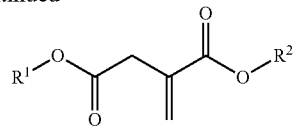

A solution of the appropriate itaconic acid monoester (1 eq.) which is defined where relevant below, EDC.HCl (1.5 eq.) and DMAP (5-200 mol %) in DCM was treated with DIPEA (3 eq.) and the appropriate alcohol (R$^2$—OH, 1.1 eq.) which is defined where relevant below. The resulting solution was stirred at RT for 20 h. The reaction mixture was concentrated onto silica and the crude product purified by chromatography on silica gel (0-5% MeOH/DCM) to afford the desired diester.

General Procedure 3—Synthesis of Diesters

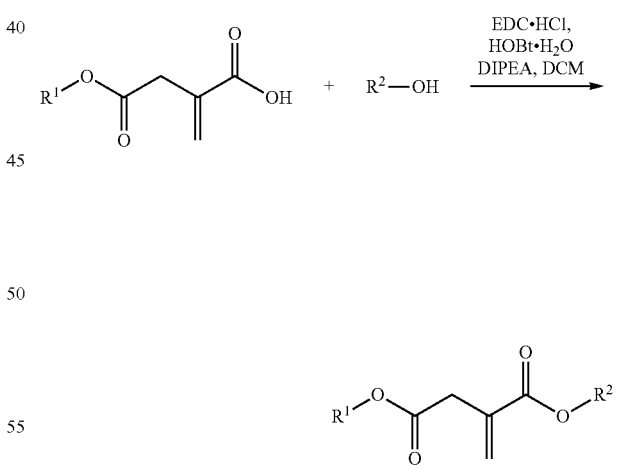

A solution of the appropriate alcohol (R$^2$—OH, 1 eq.) which is defined where relevant below, HOBt.H$_2$O hydrate (2 eq.) and EDC.HCl (2 eq.) in DCM was treated with the appropriate itaconic acid monoester (1 eq.) which is defined where relevant below, followed by dropwise addition of DIPEA (3 eq.) at RT. The resulting mixture was stirred at RT for 16 h. The reaction mixture was concentrated in vacuo and purified by column chromatography on silica gel (DCM/EtOAc 1:1) to provide the desired diester.

General Procedure 4—Synthesis of Diesters

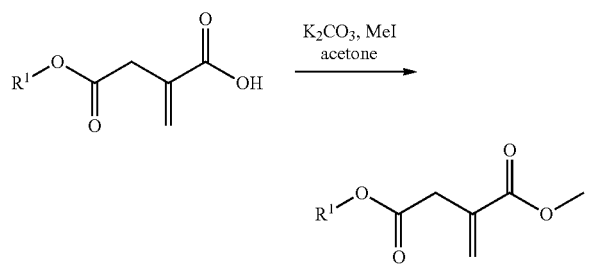

A mixture of the appropriate itaconic acid monoester (1 eq.) which is defined where relevant below, potassium carbonate (1.2 eq.) and iodomethane (1.2 eq.) in acetone was stirred for 18 h at RT. The mixture was filtered and the filtrate was concentrated onto silica gel. The crude product was purified by chromatography on silica gel (0-20% EtOAc/isohexane) to afford the desired diester.

In any one of the above General Procedures, suitably $R^1$ is $R^{A'}$ which is defined elsewhere herein.

Intermediate 1—4-(cyclooctyloxy)-2-methylene-4-oxobutanoic Acid

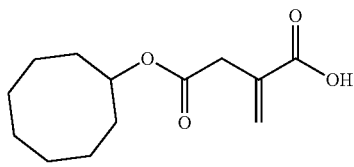 [SMILES: C=C(CC(=O)OC1CCCCCCC1)C(=O)O]

Intermediate 1 was prepared according to General Procedure 1, using cyclooctanol as R—OH. $^1$H NMR (500 MHz, DMSO-d6) δ 12.59 (br. s, 1H), 6.13 (d, J=1.6 Hz, 1H), 5.75-5.72 (m, 1H), 4.82 (tt, J=8.2, 3.9 Hz, 1H), 3.25 (s, 2H), 1.76-1.40 (m, 14H). LCMS m/z 263.2 (M+Na)$^+$ (ES$^+$); 239.2 (M–H)$^−$ (ES$^−$).

Intermediate 2—2-methylene-4-oxo-4-(3-phenoxypropoxy)butanoic Acid

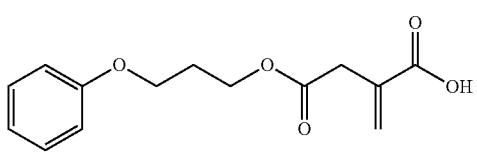 [SMILES: C=C(CC(=O)OCCCOc1ccccc1)C(=O)O]

Intermediate 2 was prepared according to General Procedure 1, using 3-phenoxypropan-1-ol as R—OH. $^1$H NMR (500 MHz, DMSO-d6) δ 12.65 (br. s, 1H), 7.32-7.26 (m, 2H), 6.95-6.91 (m, 3H), 6.15 (d, J=1.6 Hz, 1H), 5.76 (br. s, 2H), 4.18 (t, J=6.4 Hz, 2H), 4.02 (t, J=6.3 Hz, 2H), 3.33 (br. s, 4H), 2.01 (qu, J=6.3 Hz, 2H). LCMS m/z 287.1 (M+Na)$^+$ (ES$^+$); 263.1 (M–H)$^−$ (ES$^−$).

Intermediate 3—4-(hexyloxy)-2-methylene-4-oxobutanoic Acid

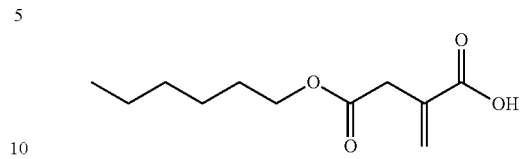

Intermediate 3 was prepared according to General Procedure 1, using hexan-1-ol as R—OH. $^1$H NMR (500 MHz, DMSO-d6) δ 12.57 (br. s, 1H), 6.15 (d, J=1.6 Hz, 1H), 5.78-5.74 (m, 1H), 4.01 (t, J=6.6 Hz, 2H), 3.30 (s, 2H), 1.58-1.51 (m, 2H), 1.35-1.21 (m, 6H), 0.87 (t, J=6.8 Hz, 3H). LCMS m/z 237.2 (M+H)+ (ES$^+$); 213.2 (M–H)$^−$ (ES$^−$).

Intermediate 4—4-isopropoxy-2-methylene-4-oxobutanoic Acid

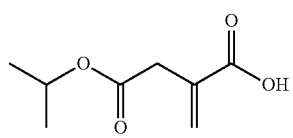

Intermediate 4 was prepared according to General Procedure 1, using propan-2-ol as R—OH. $^1$H NMR (500 MHz, CDCl$_3$) δ 6.47 (d, J=0.9 Hz, 1H), 5.84 (q, J=1.1 Hz, 1H), 5.05 (hept, J=6.3 Hz, 1H), 3.33 (s, 2H), 1.26 (d, J=6.3 Hz, 6H). LCMS m/z 171.1 (M–H)$^−$ (ES$^−$).

Intermediate 5—4-(2-(2-ethoxyethoxy)ethoxy)-2-methylene-4-oxobutanoic Acid

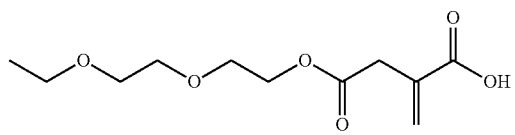 [SMILES: C=C(CC(=O)OCCOCCOCC)C(=O)O]

Intermediate 5 was prepared according to General Procedure 1, using 2-(2-ethoxyethoxy)ethan-1-ol as R—OH. $^1$H NMR (500 MHz, DMSO-d6) δ 12.62 (s, 1H), 6.17 (d, J=1.6 Hz, 1H), 5.78 (q, J=1.3 Hz, 1H), 4.15-4.11 (m, 2H), 3.61-3.58 (m, 2H), 3.54-3.51 (m, 2H), 3.49-3.46 (m, 2H), 3.43 (q, J=7.0 Hz, 2H), 3.33 (s, 2H), 1.10 (t, J=7.0 Hz, 3H). LCMS m/z 269.1 (M+Na)$^+$ (ES$^+$).

Intermediate 6—4-(cyclohexyloxy)-2-methylene-4-oxobutanoic Acid

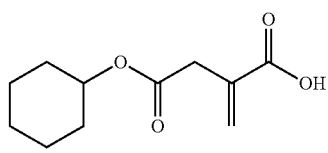

Intermediate 6 was prepared according to General Procedure 1, using cyclohexanol as R—OH. ¹H NMR (500 MHz, CDCl₃) δ 6.44 (d, J=0.9 Hz, 1H), 5.81 (d, J=1.2 Hz, 1H), 4.90-4.69 (m, 1H), 3.32 (s, 2H), 1.83-1.64 (m, 4H), 1.55-1.16 (m, 6H). ¹H NMR (500 MHz, DMSO-d6) δ 12.62 (s, 1H), 6.17 (d, J=1.6 Hz, 1H), 5.78 (q, J=1.3 Hz, 1H), 4.15-4.11 (m, 2H), 3.61-3.58 (m, 2H), 3.54-3.51 (m, 2H), 3.49-3.46 (m, 2H), 3.43 (q, J=7.0 Hz, 2H), 3.33 (s, 2H), 1.10 (t, J=7.0 Hz, 3H). LCMS m/z 210.7 (M–H)⁻ (ES⁻).

Intermediate 7—4-((4-fluorobenzyl)oxy)-2-methylene-4-oxobutanoic Acid

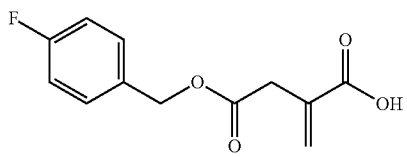 [SMILES: C=C(CC(=O)OCc1ccc(F)cc1)C(=O)O]

Intermediate 7 was prepared according to General Procedure 1, using (4-fluorophenyl)methanol as R—OH. ¹H NMR (500 MHz, DMSO-d6) δ 12.67 (s, 1H), 7.44-7.38 (m, 2H), 7.23-7.16 (m, 2H), 6.17 (d, J=1.6 Hz, 1H), 5.81-5.77 (m, 1H), 5.09 (s, 2H), 3.38 (s, 2H). LCMS m/z 237.3 (M–H)⁻ (ES⁻).

Intermediate 8—(R)-2-methylene-4-(octan-2-yloxy)-4-oxobutanoic Acid

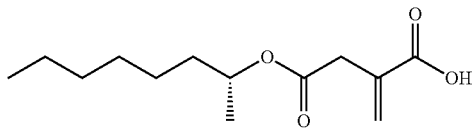 [SMILES: C=C(CC(=O)O[C@H](C)CCCCCC)C(=O)O]

Intermediate 8 was prepared according to General Procedure 1, using (R)-octan-2-ol as R—OH. ¹H NMR (500 MHz, CDCl₃) δ 12.58 (s, 1H), 6.13 (d, J=1.6 Hz, 1H), 5.74 (d, J=1.6 Hz, 1H), 4.88-4.58 (m, 1H), 3.26 (s, 2H), 1.54-1.38 (m, 2H), 1.30-1.20 (m, 8H), 1.13 (d, J=6.2 Hz, 3H), 0.85 (t, J=6.7 Hz, 3H). LCMS m/z 241.2 (M–H)⁻ (ES⁻).

Intermediate 9—(S)-2-methylene-4-(octan-2-yloxy)-4-oxobutanoic Acid

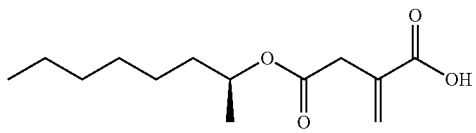 [SMILES: C=C(CC(=O)O[C@@H](C)CCCCCC)C(=O)O]

Intermediate 9 was prepared according to General Procedure 1, using (S)-octan-2-ol as R—OH. ¹H NMR (500 MHz, DMSO-d6) δ 12.58 (s, 1H), 6.14 (d, J=1.6 Hz, 1H), 5.75 (d, J=1.6 Hz, 1H), 4.84-4.74 (m, 1H), 3.26 (s, 2H), 1.56-1.40 (m, 2H), 1.33-1.20 (m, 8H), 1.14 (d, J=6.2 Hz, 3H), 0.86 (t, J=6.8 Hz, 3H). LCMS m/z 241.0 (M–H)⁻ (ES⁻).

Intermediate 10—2-methylene-4-(neopentyloxy)-4-oxobutanoic Acid

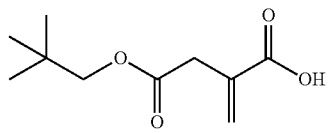

Intermediate 10 was prepared according to General Procedure 1, using 2,2-dimethylpropan-1-ol as R—OH. ¹H NMR (500 MHz, DMSO-d6) δ 12.63 (s, 1H), 6.16 (d, J=1.6 Hz, 1H), 5.77 (d, J=1.4 Hz, 1H), 3.72 (s, 2H), 3.34 (s, 2H), 0.88 (s, 9H). LCMS m/z 198.9 (M–H)⁻ (ES⁻).

Intermediate 11—3-((2-(tert-butoxy)-2-oxoethoxy)carbonyl)but-3-enoic Acid

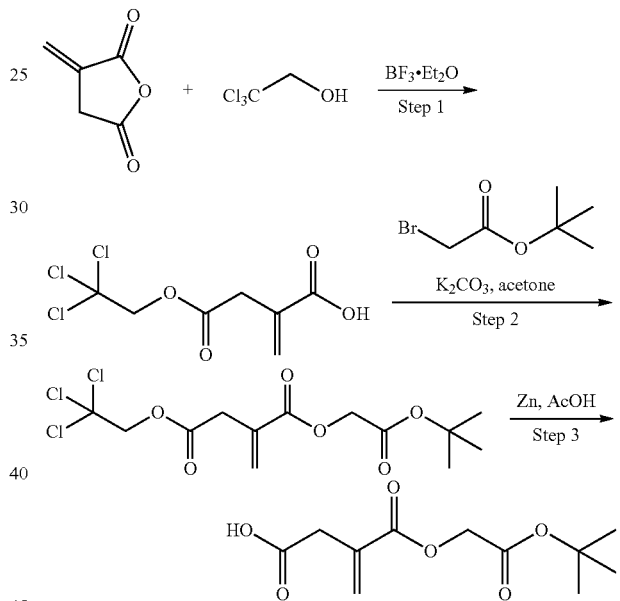

Step 1

Boron trifluoride diethyl etherate (1.43 mL, 11.6 mmol) was added to a mixture of itaconic anhydride (10 g, 89 mmol) and 2,2,2-trichloroethanol (15.4 mL, 161 mmol) under nitrogen at RT. The reaction mixture was heated to 95° C. for 30 mins, then cooled to RT. The residue was treated with sat. aq. NaHCO₃ (400 mL) and washed with EtOAc (3×100 mL). The aqueous phase was acidified to pH=2 with concentrated HCl and extracted with EtOAc (3×120 mL). The combined organic layers were dried (MgSO₄) and concentrated. The residue was recrystallised from a mixture of toluene and iso-hexane (1:1) (300 mL). The resulting solid was filtered, washed with iso-hexane and dried in vacuo to afford 2-methylene-4-oxo-4-(2,2,2-trichloroethoxy)butanoic acid (13.7 g, 51.3 mmol) as a white crystalline solid. ¹H NMR (400 MHz, DMSO-d6) δ 12.70 (s, 1H), 6.21 (d, J=1.5 Hz, 1H), 5.86 (d, J=1.3 Hz, 1H), 4.88 (s, 2H), 3.49 (s, 2H).

Step 2

Potassium carbonate (4.16 g, 30.1 mmol) was added portionwise to a solution of 2-methylene-4-oxo-4-(2,2,2- trichloroethoxy)butanoic acid (7.50 g, 28.7 mmol) in acetone (140 mL) at RT. After 5 min tert-butyl bromoacetate (4.45 mL, 30.1 mmol) was added dropwise. The reaction mixture was stirred at RT for 16 h, then diluted with EtOAc (150 mL) and filtered. The filtrate was concentrated to afford 1-(2-(tert-butoxy)-2-oxoethyl) 4-(2,2,2-trichloroethyl) 2-methylenesuccinate (10.7 g, 28.5 mmol) as a white solid. $^1$H NMR (400 MHz, DMSO-d6) δ 6.36 (d, J=1.2 Hz, 1H), 6.03 (q, J=1.1 Hz, 1H), 4.89 (s, 2H), 4.62 (s, 2H), 3.58 (d, J=1.0 Hz, 2H), 1.42 (s, 9H).

Step 3

Zinc (11.2 g, 171 mmol) was added portionwise over 5 min to a solution of 1-(2-(tert-butoxy)-2-oxoethyl) 4-(2,2,2-trichloroethyl) 2-methylenesuccinate (10.7 g, 28.5 mmol) in acetic acid (160 mL). The reaction mixture was stirred at RT for 18 h then diluted with water (100 mL) and EtOAc (300 mL). The mixture was carefully decanted and the phases were separated. The aqueous phase was extracted with EtOAc (3×200 mL). The combined organic extracts were washed with brine (3×150 mL), dried (Na$_2$SO$_4$) and concentrated to afford the title compound as a colourless solid (6.07 g). An analytically pure sample was obtained by recrystallisation of a small sample (300 mg) from toluene and isohexane (1:1). $^1$H NMR (400 MHz, DMSO-d6) δ 12.35 (s, 1H), 6.26 (d, J=1.3 Hz, 1H), 5.91-5.85 (m, 1H), 4.62 (s, 2H), 3.32 (s, 2H), 1.42 (s, 9H). LCMS m/z 267.1 (M+Na)$^+$ (ES$^+$).

Intermediate 12—3-methyl-2-methylene-4-(octyloxy)-4-oxobutanoic Acid

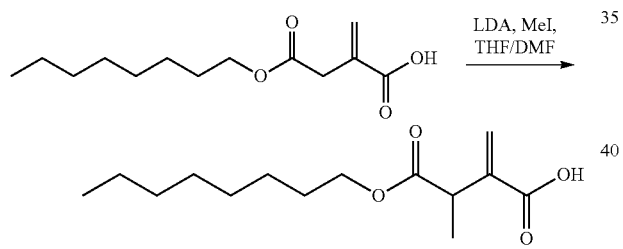

A solution of lithium diisopropylamide (2 M in THF, 4.3 mL, 8.6 mmol) was added dropwise to a solution of 4-octyl itaconate (1.00 g, 4.13 mmol) in THF (10 mL) at −78° C. The reaction mixture was stirred for 2 h at −78° C., before a solution of iodomethane (0.31 mL, 4.9 mmol) in DMF (5 mL) was added dropwise. The reaction mixture was stirred for 2 h at −78° C., then quenched with a 10% aq. citric acid solution (20 mL). The mixture was extracted with DCM (3×20 mL). The combined organic phases were passed through a hydrophobic phase separator and concentrated. The crude product was purified by chromatography on silica gel (0-50% EtOAc/isohexane) to afford 3-methyl-2-methylene-4-(octyloxy)-4-oxobutanoic acid (611 mg, 2.34 mmol) as a light yellow oil. $^1$H NMR (500 MHz, DMSO-d6) δ 12.63 (s, 1H), 6.17 (d, J=1.0 Hz, 1H), 5.70 (d, J=1.2 Hz, 1H), 4.06-3.84 (m, 2H), 3.57-3.42 (m, 1H), 1.60-1.39 (m, 2H), 1.39-1.01 (m, 13H), 0.86 (t, J=6.6 Hz, 3H). LCMS m/z 255.1 (M−H)$^−$ (ES$^−$).

Example 1—1-(2-cyanoethyl) 4-octyl 2-methylenesuccinate

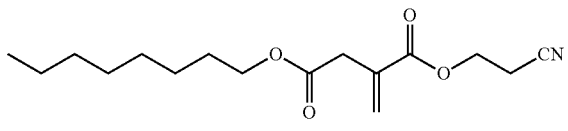 [SMILES: C=C(CC(=O)OCCCCCCCC)C(=O)OCCC#N]

Example 1 was prepared according to General Procedure 2, using 4-octyl itaconate as itaconic acid monoester and 3-hydroxypropanenitrile as R$^2$—OH. $^1$H NMR (500 MHz, DMSO-d6) δ 6.25 (d, J=1.2 Hz, 1H), 5.90 (d, J=1.3 Hz, 1H), 4.27 (t, J=6.0 Hz, 2H), 4.02 (t, J=6.6 Hz, 2H), 3.39 (s, 2H), 2.92 (t, J=6.0 Hz, 2H), 1.58-1.51 (m, 2H), 1.35-1.21 (m, 10H), 0.89-0.84 (m, 3H). LCMS m/z 318.2 (M+Na)$^+$ (ES$^+$).

Example 2—1-(2-(methylsulfonyl)ethyl) 4-octyl 2-methylenesuccinate

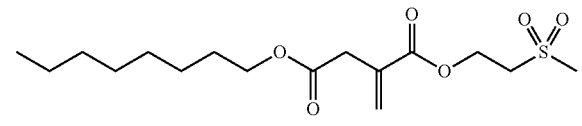 [SMILES: C=C(CC(=O)OCCCCCCCC)C(=O)OCCS(C)(=O)=O]

Example 2 was prepared according to General Procedure 2, using 4-octyl itaconate as itaconic acid monoester and 2-(methylsulfonyl)ethan-1-ol as R$^2$—OH. $^1$H NMR (500 MHz, DMSO-d6) δ 6.25 (d, J=1.2 Hz, 1H), 5.89 (d, J=1.3 Hz, 1H), 4.45 (t, J=5.8 Hz, 2H), 4.01 (t, J=6.6 Hz, 2H), 3.54 (t, J=5.8 Hz, 2H), 3.38 (s, 2H), 3.03 (s, 3H), 1.59-1.51 (m, 2H), 1.32-1.21 (m, 10H), 0.89-0.84 (m, 3H). LCMS m/z 371.2 (M+Na)$^+$ (ES$^+$).

Example 3—4-octyl 1-(3,3,3-trifluoropropyl) 2-methylenesuccinate

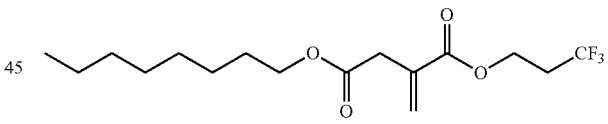

Example 3 was prepared according to General Procedure 2, using 4-octyl itaconate as itaconic acid monoester and 3,3,3-trifluoropropan-1-ol as R$^2$—OH. $^1$H NMR (500 MHz, DMSO-d6) δ 6.22 (d, J=1.3 Hz, 1H), 5.87 (q, J=1.2 Hz, 1H), 4.32-4.29 (m, 2H), 4.00 (t, J=6.6 Hz, 2H), 3.37 (d, J=1.0 Hz, 2H), 2.75-2.64 (m, 2H), 1.57-1.50 (m, 2H), 1.34-1.20 (m, 10H), 0.89-0.83 (m, 3H). LCMS m/z 361.3 (M+Na)$^+$ (ES$^+$).

Example 4—4-octyl 1-(oxetan-3-yl) 2-methylenesuccinate

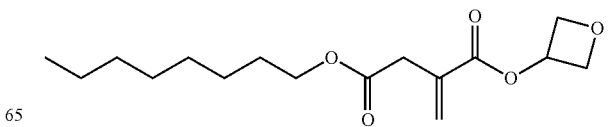

Example 4 was prepared according to General Procedure 2, using 4-octyl itaconate as itaconic acid monoester and oxetan-3-ol as R²—OH. ¹H NMR (500 MHz, DMSO-d6) δ 6.29 (d, J=1.2 Hz, 1H), 5.92 (d, J=1.3 Hz, 1H), 5.46-5.40 (m, 1H), 4.84-4.80 (m, 2H), 4.49 (dd, J=7.6, 5.0 Hz, 2H), 4.02 (t, J=6.6 Hz, 2H), 3.40 (s, 2H), 1.58-1.51 (m, 2H), 1.33-1.22 (m, 10H), 0.87 (t, J=6.8 Hz, 3H). LCMS m/z 299.3 (M+H)⁺ (ES⁺).

Example 5—4-octyl 1-(2-(2-oxopyrrolidin-1-yl)ethyl) 2-methylenesuccinate

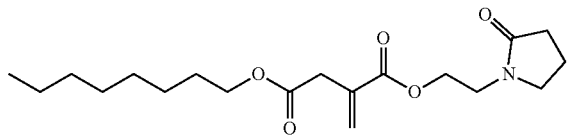 [SMILES: C=C(CC(=O)OCCCCCCCC)C(=O)OCCN1CCCC1=O]

Example 5 was prepared according to General Procedure 2, using 4-octyl itaconate as itaconic acid monoester and 1-(2-hydroxyethyl)pyrrolidin-2-one as R²—OH. ¹H NMR (500 MHz, DMSO-d6) δ 6.19 (d, J=1.3 Hz, 1H), 5.84 (d, J=1.3 Hz, 1H), 4.19 (t, J=5.4 Hz, 2H), 4.01 (t, J=6.6 Hz, 2H), 3.45 (t, J=5.4 Hz, 2H), 3.39-3.32 (m, 4H), 2.20 (t, J=8.1 Hz, 2H), 1.95-1.87 (m, 2H), 1.59-1.50 (m, 2H), 1.33-1.22 (m, 10H), 0.89-0.82 (m, 3H). LCMS m/z 354.3 (M+H)⁺ (ES⁺).

Example 6—1-(3-(dimethylamino)-3-oxopropyl) 4-octyl 2-methylenesuccinate

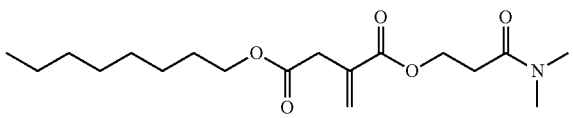 [SMILES: C=C(CC(=O)OCCCCCCCC)C(=O)OCCC(=O)N(C)C]

Example 6 was prepared according to General Procedure 2, using 4-octyl itaconate as itaconic acid monoester and 3-hydroxy-N,N-dimethylpropanamide as R²—OH. ¹H NMR (500 MHz, DMSO-d6) δ 6.17 (d, J=1.4 Hz, 1H), 5.82 (d, J=1.3 Hz, 1H), 4.28 (t, J=6.6 Hz, 2H), 4.00 (t, J=6.6 Hz, 2H), 3.34 (s, 2H), 2.96 (s, 3H), 2.82 (s, 3H), 2.67 (t, J=6.6 Hz, 2H), 1.58-1.50 (m, 2H), 1.33-1.22 (m, 10H), 0.89-0.84 (m, 3H). LCMS m/z 342.3 (M+H)⁺ (ES⁺).

Example 7—4-butyl 1-(2-(methylsulfonyl)ethyl) 2-methylenesuccinate

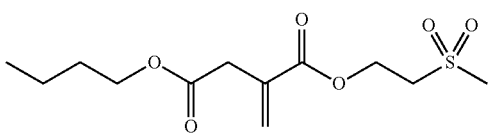 [SMILES: C=C(CC(=O)OCCCC)C(=O)OCCS(C)(=O)=O]

Example 7 was prepared according to General Procedure 2, using 4-butyl itaconate as itaconic acid monoester and 2-(methylsulfonyl)ethan-1-ol as R²—OH. ¹H NMR (500 MHz, DMSO-d6) δ 6.25 (d, J=1.3 Hz, 1H), 5.90 (d, J=1.2 Hz, 1H), 4.48-4.43 (m, 2H), 4.03 (t, J=6.6 Hz, 2H), 3.57- 3.51 (m, 2H), 3.38 (d, J=1.0 Hz, 2H), 3.03 (s, 3H), 1.59-1.50 (m, 2H), 1.37-1.27 (m, 2H), 0.89 (t, J=7.4 Hz, 3H). LCMS m/z 315.2 (M+Na)⁺ (ES⁺).

Example 8—1-(2-cyanoethyl) 4-butyl 2-methylenesuccinate

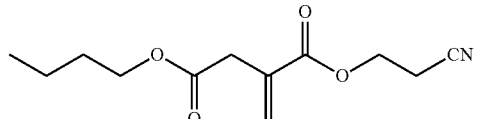

Example 8 was prepared according to General Procedure 2, using 4-butyl itaconate as itaconic acid monoester and 3-hydroxypropanenitrile as R²—OH. ¹H NMR (500 MHz, DMSO-d6) δ 6.26 (d, J=1.2 Hz, 1H), 5.91 (d, J=1.2 Hz, 1H), 4.27 (t, J=6.0 Hz, 2H), 4.03 (t, J=6.6 Hz, 2H), 3.39 (s, 2H), 2.92 (t, J=6.0 Hz, 2H), 1.58-1.51 (m, 2H), 1.37-1.27 (m, 2H), 0.89 (t, J=7.4 Hz, 3H). LCMS m/z 240.1 (M+H)⁺ (ES⁺).

Example 9—1-(2-(2,5-dioxopyrrolidin-1-yl)ethyl) 4-octyl 2-methylenesuccinate

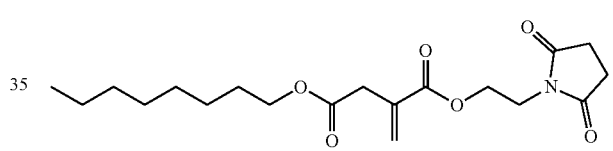

Example 9 was prepared according to General Procedure 2, using 4-octyl itaconate as itaconic acid monoester and 1-(2-hydroxyethyl)pyrrolidine-2,5-dione as R²—OH. ¹H NMR (500 MHz, DMSO-d6) δ 6.16 (d, J=1.4 Hz, 1H), 5.83 (d, J=1.3 Hz, 1H), 4.19 (t, J=5.5 Hz, 2H), 4.00 (t, J=6.6 Hz, 2H), 3.65 (t, J=5.6 Hz, 2H), 3.32 (s, 2H), 2.63 (s, 4H), 1.57-1.50 (m, 2H), 1.32-1.21 (m, 10H), 0.89-0.84 (m, 3H). LCMS m/z 368.3 (M+H)⁺ (ES⁺).

Example 10—1-(2-cyanoethyl) 4-methyl 2-methylenesuccinate

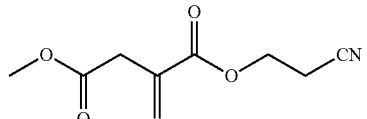

Example 10 was prepared according to General Procedure 2, using 4-methyl itaconate as itaconic acid monoester and 3-hydroxypropanenitrile as R²—OH. ¹H NMR (500 MHz, DMSO-d6) δ 6.27 (d, J=1.2 Hz, 1H), 5.91 (d, J=1.2 Hz, 1H), 4.28 (t, J=5.9 Hz, 2H), 3.62 (s, 3H), 3.40 (d, J=1.0 Hz, 2H), 2.92 (t, J=5.9 Hz, 2H). LCMS m/z 220.1 (M+H)⁺ (ES⁺).

Example 11—1-(2-cyanoethyl) 4-hexyl 2-methylenesuccinate

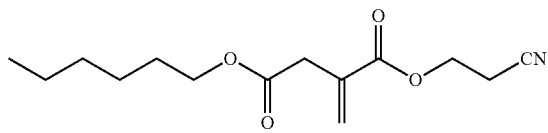 [SMILES: C=C(CC(=O)OCCCCCC)C(=O)OCCC#N]

Example 11 was prepared according to General Procedure 2, using 4-(hexyloxy)-2-methylene-4-oxobutanoic acid (Intermediate 3) as itaconic acid monoester and 3-hydroxypropanenitrile as $R^2$—OH. $^1$H NMR (500 MHz, DMSO-d6) δ 6.26 (d, J=1.2 Hz, 1H), 5.90 (d, J=1.3 Hz, 1H), 4.27 (t, J=6.0 Hz, 2H), 4.02 (t, J=6.6 Hz, 2H), 3.39 (s, 2H), 2.91 (t, J=6.0 Hz, 2H), 1.60-1.51 (m, 2H), 1.34-1.22 (m, 6H), 0.91-0.83 (m, 3H). LCMS m/z 268.1 (M+H)$^+$ (ES$^+$).

Example 12—4-methyl 1-(2-(methylsulfonyl)ethyl) 2-methylenesuccinate

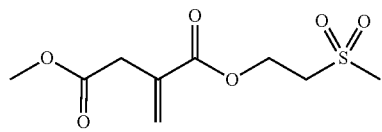

Example 12 was prepared according to General Procedure 2, using 4-methyl itaconate as itaconic acid monoester and 2-(methylsulfonyl)ethan-1-ol as $R^2$—OH. $^1$H NMR (500 MHz, DMSO-d6) δ 6.27 (d, J=1.2 Hz, 1H), 5.90 (d, J=1.3 Hz, 1H), 4.46 (t, J=5.8 Hz, 2H), 3.61 (s, 3H), 3.54 (t, J=5.8 Hz, 2H), 3.39 (d, J=1.0 Hz, 2H), 3.03 (s, 3H). LCMS m/z 273.1 (M+Na)$^+$ (ES$^+$).

Example 13—4-octyl 1-(2-(trifluoromethoxy)ethyl) 2-methylenesuccinate

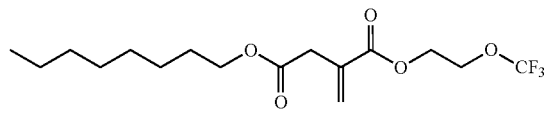 [SMILES: C=C(CC(=O)OCCCCCCCC)C(=O)OCCOC(F)(F)F]

Example 13 was prepared according to General Procedure 2, using 4-octyl itaconate as itaconic acid monoester and 2-(trifluoromethoxy)ethan-1-ol as $R^2$—OH. $^1$H NMR (500 MHz, DMSO-d6) δ 6.24 (d, J=1.2 Hz, 1H), 5.89 (d, J=1.3 Hz, 1H), 4.36-4.29 (m, 4H), 4.00 (t, J=6.6 Hz, 2H), 3.38 (s, 2H), 1.58-1.50 (m, 2H), 1.32-1.21 (m, 10H), 0.86 (t, J=6.9 Hz, 3H). LCMS m/z 355.3 (M+H)$^+$ (ES$^+$).

Example 14—4-hexyl 1-(2-(methylsulfonyl)ethyl) 2-methylenesuccinate

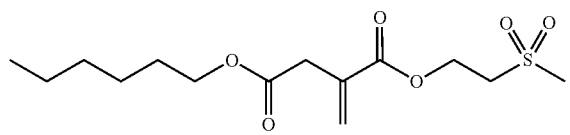 [SMILES: C=C(CC(=O)OCCCCCC)C(=O)OCCS(C)(=O)=O]

Example 14 was prepared according to General Procedure 2, using 4-(hexyloxy)-2-methylene-4-oxobutanoic acid (Intermediate 3) as itaconic acid monoester and 2-(methylsulfonyl)ethan-1-ol as $R^2$—OH. $^1$H NMR (500 MHz, DMSO-d6) δ 6.25 (d, J=1.2 Hz, 1H), 5.89 (d, J=1.2 Hz, 1H), 4.48-4.43 (m, 2H), 4.02 (t, J=6.6 Hz, 2H), 3.54 (t, J=5.8 Hz, 2H), 3.38 (s, 2H), 3.03 (s, 3H), 1.58-1.51 (m, 2H), 1.34-1.22 (m, 6H), 0.92-0.84 (m, 3H). LCMS m/z 343.2 (M+Na)$^+$ (ES$^+$).

Example 15—4-methyl 1-(oxetan-3-yl) 2-methylenesuccinate

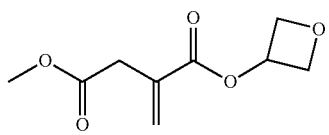

Example 15 was prepared according to General Procedure 2, using 4-methyl itaconate as itaconic acid monoester and oxetan-3-ol as $R^2$—OH. $^1$H NMR (500 MHz, DMSO-d6) δ 6.31 (d, J=1.2 Hz, 1H), 5.93 (d, J=1.1 Hz, 1H), 5.44 (tt, J=6.3, 5.0 Hz, 1H), 4.82 (ddd, J=7.4, 6.3, 1.0 Hz, 2H), 4.49 (ddd, J=7.6, 5.0, 1.0 Hz, 2H), 3.62 (s, 3H), 3.41 (s, 2H). LCMS m/z 201.1 (M+H)$^+$ (ES$^+$).

Example 16—1-(2-(N,N-dimethylsulfamoyl)ethyl) 4-octyl 2-methylenesuccinate

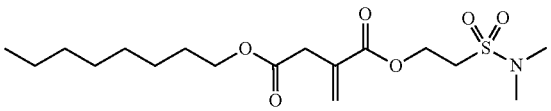 [SMILES: C=C(CC(=O)OCCCCCCCC)C(=O)OCCS(=O)(=O)N(C)C]

Example 16 was prepared according to General Procedure 2, using 4-octyl itaconate as itaconic acid monoester and 2-hydroxy-N,N-dimethylethane-1-sulfonamide as $R^2$—OH. $^1$H NMR (500 MHz, DMSO-d6) δ 6.26 (d, J=1.3 Hz, 1H), 5.90 (d, J=1.3 Hz, 1H), 4.41 (t, J=6.0 Hz, 2H), 4.01 (t, J=6.6 Hz, 2H), 3.45 (t, J=6.0 Hz, 2H), 3.37 (s, 2H), 2.78 (s, 6H), 1.58-1.51 (m, 2H), 1.32-1.21 (m, 10H), 0.89-0.84 (m, 3H). LCMS m/z 378.3 (M+H)$^+$ (ES$^+$).

Example 17—1-(2-(dimethylamino)ethyl) 4-octyl 2-methylenesuccinate

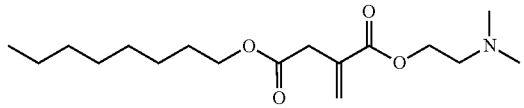 [SMILES: C=C(CC(=O)OCCCCCCCC)C(=O)OCCN(C)C]

Example 17 was prepared according to General Procedure 2, using 4-octyl itaconate as itaconic acid monoester and 2-(dimethylamino)ethan-1-ol as $R^2$—OH. $^1$H NMR (500 MHz, DMSO-d6) δ 6.19 (d, J=1.4 Hz, 1H), 5.84-5.81 (m, 1H), 4.16 (t, J=5.8 Hz, 2H), 4.00 (t, J=6.6 Hz, 2H), 3.35 (s, 2H), 2.52-2.47 (m, 2H), 2.17 (s, 6H), 1.58-1.51 (m, 2H), 1.32-1.23 (m, 10H), 0.89-0.84 (m, 3H). LCMS m/z 314.3 (M+H)$^+$ (ES$^+$).

Example 18—1-(3-(methylsulfonyl)propyl) 4-octyl 2-methylenesuccinate

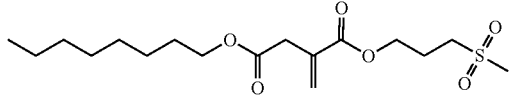 [SMILES: C=C(CC(=O)OCCCCCCCC)C(=O)OCCCS(C)(=O)=O]

Example 18 was prepared according to General Procedure 2, using 4-octyl itaconate as itaconic acid monoester and 3-(methylsulfonyl)propan-1-ol as R²—OH. ¹H NMR (500 MHz, DMSO-d6) δ 6.25 (d, J=1.3 Hz, 1H), 5.85 (d, J=1.3 Hz, 1H), 4.19 (t, J=6.4 Hz, 2H), 4.01 (t, J=6.7 Hz, 2H), 3.38 (s, 2H), 3.22-3.16 (m, 2H), 2.99 (s, 3H), 2.08-2.00 (m, 2H), 1.59-1.51 (m, 2H), 1.33-1.22 (m, 10H), 0.87 (t, J=6.8 Hz, 3H). LCMS m/z 385.2 (M+Na)⁺ (ES⁺).

Example 19—1-(1-(methylsulfonyl)propan-2-yl) 4-octyl 2-methylenesuccinate

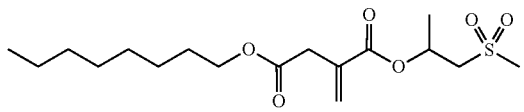 [SMILES: C=C(CC(=O)OCCCCCCCC)C(=O)OC(C)CS(C)(=O)=O]

Example 19 was prepared according to General Procedure 2, using 4-octyl itaconate as itaconic acid monoester and 1-(methylsulfonyl)propan-2-ol as R²—OH. ¹H NMR (500 MHz, DMSO-d6) δ 6.24 (d, J=1.3 Hz, 1H), 5.87 (d, J=1.3 Hz, 1H), 5.34-5.24 (m, 1H), 4.06-3.96 (m, 2H), 3.61 (dd, J=14.8, 8.3 Hz, 1H), 3.47 (dd, J=14.8, 3.8 Hz, 1H), 3.37 (s, 2H), 2.99 (s, 3H), 1.59-1.51 (m, 2H), 1.31 (d, J=6.4 Hz, 3H), 1.29-1.24 (m, 10H), 0.87 (t, J=6.8 Hz, 3H). LCMS m/z 385.2 (M+Na)⁺ (ES⁺).

Example 20—1-(2-(methylsulfonyl)ethyl) 4-(3-phenoxypropyl) 2-methylenesuccinate

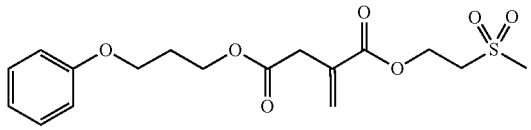 [SMILES: C=C(CC(=O)OCCCOc1ccccc1)C(=O)OCCS(C)(=O)=O]

Example 20 was prepared according to General Procedure 2, using 2-methylene-4-oxo-4-(3-phenoxypropoxy)butanoic acid (Intermediate 2) as itaconic acid monoester and 2-(methylsulfonyl)ethan-1-ol as R²—OH. ¹H NMR (500 MHz, CDCl₃) δ 7.33-7.29 (m, 2H), 7.00-6.95 (m, 1H), 6.95-6.89 (m, 2H), 6.34 (s, 1H), 5.80 (d, J=1.2 Hz, 1H), 4.62 (t, J=5.8 Hz, 2H), 4.33 (t, J=6.3 Hz, 2H), 4.06 (t, J=6.1 Hz, 2H), 3.38 (s, 2H), 3.34 (t, J=5.8 Hz, 2H), 2.98 (s, 3H), 2.18-2.11 (m, 2H). LCMS m/z 393.1 (M+Na)⁺ (ES⁺).

Example 21—1-(2-(dimethylamino)-2-oxoethyl) 4-octyl 2-methylenesuccinate

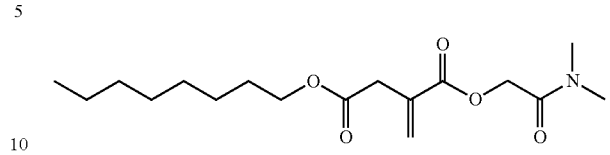

Example 21 was prepared according to General Procedure 2, using 4-octyl itaconate as itaconic acid monoester and 2-hydroxy-N,N-dimethylacetamide as R²—OH. ¹H NMR (500 MHz, DMSO-d6) δ 6.27 (d, J=1.3 Hz, 1H), 5.89 (d, J=1.3 Hz, 1H), 4.84 (s, 2H), 4.00 (t, J=6.6 Hz, 2H), 3.37 (s, 2H), 2.93 (s, 3H), 2.82 (s, 3H), 1.58-1.51 (m, 2H), 1.32-1.22 (m, 10H), 0.89-0.84 (m, 3H). LCMS m/z 328.2 (M+H)⁺ (ES⁺).

Example 22—4-isopropyl 1-(2-(methylsulfonyl)ethyl) 2-methylenesuccinate

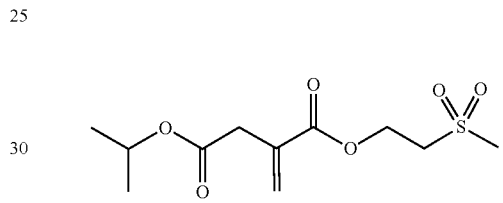

Example 22 was prepared according to General Procedure 2, using 4-isopropoxy-2-methylene-4-oxobutanoic acid (intermediate 4) as itaconic acid monoester and 2-(methylsulfonyl)ethan-1-ol as R²—OH. ¹H NMR (500 MHz, DMSO-d6) δ 6.24 (d, J=1.2 Hz, 1H), 5.89-5.87 (m, 1H), 4.89 (hept, J=6.3 Hz, 1H), 4.47-4.44 (m, 2H), 3.54 (t, J=5.7 Hz, 2H), 3.34 (s, 2H), 3.03 (s, 3H), 1.18 (d, J=6.3 Hz, 6H). LCMS m/z 301.1 (M+Na)⁺ (ES⁺).

Example 23—(S)-4-octyl 1-(tetrahydrofuran-3-yl) 2-methylenesuccinate

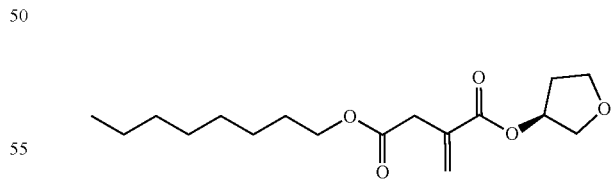

Example 23 was prepared according to General Procedure 2, using 4-octyl itaconate as itaconic acid monoester and (S)-tetrahydrofuran-3-ol as R²—OH. ¹H NMR (500 MHz, DMSO-d6) δ 6.20 (d, J=1.3 Hz, 1H), 5.84-5.82 (m, 1H), 5.29-5.25 (m, 1H), 4.00 (t, J=6.6 Hz, 2H), 3.82 (dd, J=10.4, 4.6 Hz, 1H), 3.77-3.73 (m, 2H), 3.68-3.64 (m, 1H), 3.36 (s, 2H), 2.19-2.11 (m, 1H), 1.92-1.85 (m, 1H), 1.58-1.51 (m, 2H), 1.31-1.22 (m, 10H), 0.89-0.82 (m, 3H). LCMS m/z 313.2 (M+H)⁺ (ES⁺).

Example 24—(R)-4-octyl 1-(tetrahydrofuran-3-yl) 2-methylenesuccinate

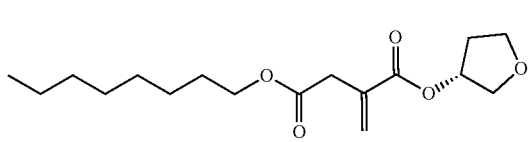 [SMILES: C=C(CC(=O)OCCCCCCCC)C(=O)O[C@@H]1CCOC1]

Example 24 was prepared according to General Procedure 2, using 4-octyl itaconate as itaconic acid monoester and (R)-tetrahydrofuran-3-ol as $R^2$—OH. $^1$H NMR (500 MHz, DMSO-d6) δ 6.20 (d, J=1.3 Hz, 1H), 5.84-5.82 (m, 1H), 5.29-5.24 (m, 1H), 4.00 (t, J=6.6 Hz, 2H), 3.82 (dd, J=10.4, 4.7 Hz, 1H), 3.77-3.73 (m, 2H), 3.69-3.63 (m, 1H), 3.36 (s, 2H), 2.20-2.10 (m, 1H), 1.93-1.85 (m, 1H), 1.58-1.51 (m, 2H), 1.31-1.22 (m, 10H), 0.89-0.84 (m, 3H). LCMS m/z 313.2 (M+H)$^+$ (ES$^+$).

Example 25—4-cyclooctyl 1-(2-(methylsulfonyl)ethyl) 2-methylenesuccinate

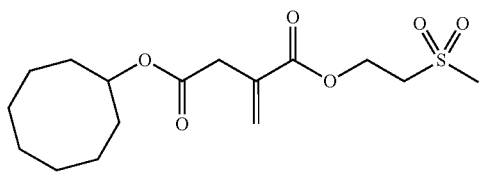 [SMILES: C=C(CC(=O)OC1CCCCCCC1)C(=O)OCCS(C)(=O)=O]

Example 25 was prepared according to General Procedure 2, using 4-(cyclooctyloxy)-2-methylene-4-oxobutanoic acid as itaconic acid monoester and 2-(methylsulfonyl)ethan-1-ol as $R^2$—OH. $^1$H NMR (500 MHz, DMSO-d6) δ 6.24 (d, J=1.3 Hz, 1H), 5.89-5.86 (m, 1H), 4.83 (tt, J=8.1, 3.9 Hz, 1H), 4.45 (t, J=5.8 Hz, 2H), 3.53 (t, J=5.7 Hz, 2H), 3.33 (s, 2H), 3.03 (s, 3H), 1.78-1.40 (m, 14H). LCMS m/z 369.1 (M+Na)$^+$ (ES$^+$).

Example 26—4-octyl 1-(tetrahydro-2H-pyran-4-yl) 2-methylenesuccinate

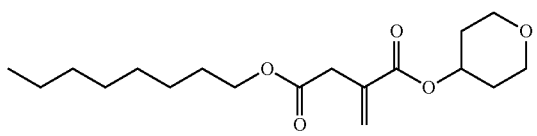 [SMILES: C=C(CC(=O)OCCCCCCCC)C(=O)OC1CCOCC1]

Example 26 was prepared according to General Procedure 2, using as 4-octyl itaconate as itaconic acid monoester and tetrahydro-2H-pyran-4-ol as $R^2$—OH. $^1$H NMR (500 MHz, DMSO-d6) δ 6.22 (d, J=1.4 Hz, 1H), 5.83-5.82 (m, 1H), 4.93 (tt, J=8.0, 4.0 Hz, 1H), 4.01 (t, J=6.5 Hz, 2H), 3.78-3.72 (m, 2H), 3.52-3.46 (m, 2H), 3.38 (s, 2H), 1.88-1.81 (m, 2H), 1.57-1.50 (m, 4H), 1.33-1.22 (m, 10H), 0.89-0.84 (m, 3H). LCMS m/z 349.2 (M+Na)$^+$ (ES$^+$).

Example 27—1-(1-cyanopropan-2-yl) 4-octyl 2-methylenesuccinate

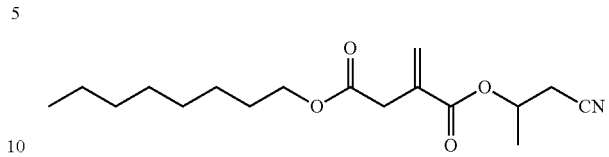

Example 27 was prepared according to General Procedure 2, using as 4-octyl itaconate as itaconic acid monoester and 3-hydroxybutanenitrile as $R^2$—OH. $^1$H NMR (500 MHz, DMSO-d6) δ 6.23 (d, J=1.3 Hz, 1H), 5.88 (q, J=1.2 Hz, 1H), 5.09-5.02 (m, 1H), 4.02 (t, J=6.6 Hz, 2H), 3.37 (s, 2H), 2.93-2.89 (m, 2H), 1.59-1.51 (m, 2H), 1.29 (d, J=6.3 Hz, 3H), 1.28-1.21 (m, 10H), 0.90-0.84 (m, 3H). LCMS m/z 332.5 (M+Na)$^+$ (ES$^+$).

Example 28—1-(1-(methylsulfonyl)piperidin-4-yl) 4-octyl 2-methylenesuccinate

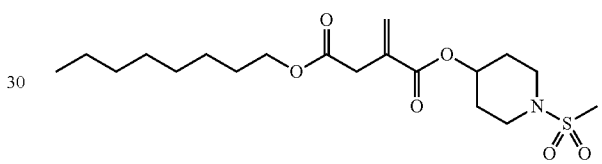

Example 28 was prepared according to General Procedure 2, using as 4-octyl itaconate as itaconic acid monoester and 1-(methylsulfonyl)piperidin-4-ol as $R^2$—OH. $^1$H NMR (500 MHz, DMSO-d6) δ 6.25 (d, J=1.4 Hz, 1H), 5.85 (d, J=1.4 Hz, 1H), 4.94-4.88 (m, 1H), 4.01 (t, J=6.6 Hz, 2H), 3.39 (s, 2H), 3.27-3.13 (m, 4H), 2.89 (s, 3H), 1.95-1.88 (m, 2H), 1.72-1.64 (m, 2H), 1.58-1.51 (m, 2H), 1.33-1.21 (m, 10H), 0.89-0.84 (m, 3H). LCMS m/z 426.3 (M+Na)+(ES$^+$).

Example 29—1-(2-methoxyethyl) 4-octyl 2-methylenesuccinate

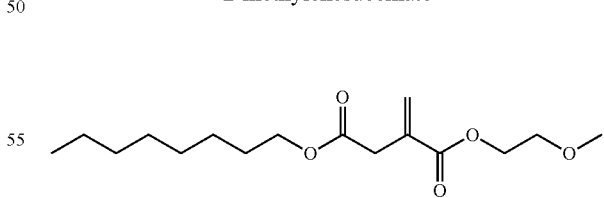

Example 29 was prepared according to General Procedure 2, using as 4-octyl itaconate as itaconic acid monoester and 2-methoxyethan-1-ol as $R^2$—OH. $^1$H NMR (500 MHz, DMSO-d6) δ 6.20 (d, J=1.4 Hz, 1H), 5.85 (q, J=1.2 Hz, 1H), 4.22-4.18 (m, 2H), 4.00 (t, J=6.6 Hz, 2H), 3.57-3.52 (m, 2H), 3.38-3.34 (m, 2H), 3.27 (s, 3H), 1.57-1.51 (m, 2H), 1.32-1.21 (m, 10H), 0.90-0.84 (m, 3H). LCMS m/z 323.1 (M+Na)$^+$ (ES$^+$).

Example 30—1-(2-cyano-2-methylpropyl) 4-octyl 2-methylenesuccinate

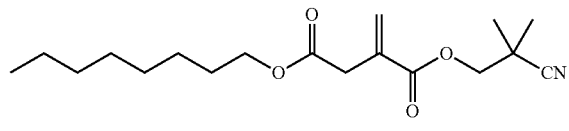 [SMILES: C=C(CC(=O)OCCCCCCCC)C(=O)OCC(C)(C)C#N]

Example 30 was prepared according to General Procedure 2, using as 4-octyl itaconate as itaconic acid monoester and 3-hydroxy-2,2-dimethylpropanenitrile as $R^2$—OH. $^1$H NMR (500 MHz, DMSO-d6) δ 6.29 (d, J=1.3 Hz, 1H), 5.91 (q, J=1.2 Hz, 1H), 4.14 (s, 2H), 4.01 (t, J=6.6 Hz, 2H), 3.41 (s, 2H), 1.55 (t, J=7.0 Hz, 2H), 1.35 (s, 6H), 1.31-1.22 (m, 10H), 0.89-0.85 (m, 3H). LCMS m/z 346.2 (M+Na)$^+$ (ES$^+$).

Example 31—1-(1-methoxypropan-2-yl) 4-octyl 2-methylenesuccinate

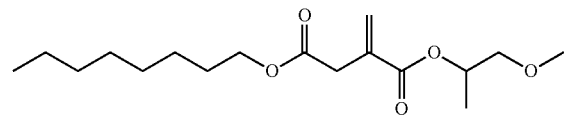 [SMILES: C=C(CC(=O)OCCCCCCCC)C(=O)OC(C)COC]

Example 31 was prepared according to General Procedure 2, using as 4-octyl itaconate as itaconic acid monoester and 1-methoxypropan-2-ol as $R^2$—OH. $^1$H NMR (500 MHz, DMSO-d6) δ 6.18 (d, J=1.4 Hz, 1H), 5.83-5.81 (m, 1H), 5.02-4.96 (m, 1H), 4.05-3.96 (m, 2H), 3.45-3.35 (m, 2H), 3.34 (s, 2H), 3.26 (s, 3H), 1.58-1.51 (m, 2H), 1.33-1.22 (m, 10H), 1.16 (d, J=6.5 Hz, 3H), 0.89-0.84 (m, 3H). LCMS m/z 337.2 (M+Na)$^+$ (ES$^+$).

Example 32—1-((1-cyanocyclopropyl)methyl) 4-octyl 2-methylenesuccinate

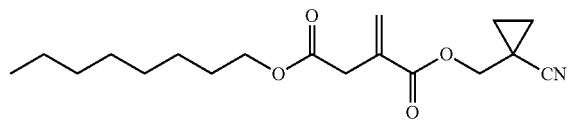 [SMILES: C=C(CC(=O)OCCCCCCCC)C(=O)OCC1(C#N)CC1]

Example 32 was prepared according to General Procedure 2, using as 4-octyl itaconate as itaconic acid monoester and 1-(hydroxymethyl)cyclopropane-1-carbonitrile as $R^2$—OH. $^1$H NMR (500 MHz, CDCl3) δ 6.46 (d, J=0.8 Hz, 1H), 5.82 (q, J=1.1 Hz, 1H), 4.18 (s, 2H), 4.12 (t, J=6.8 Hz, 2H), 3.39 (s, 2H), 1.69-1.61 (m, 2H), 1.40-1.37 (m, 2H), 1.36-1.27 (m, 10H), 1.13-1.09 (m, 2H), 0.93-0.88 (m, 3H). LCMS m/z 344.2 (M+Na)$^+$ (ES$^+$).

Example 33—1-(2-methoxypropyl) 4-octyl 2-methylenesuccinate

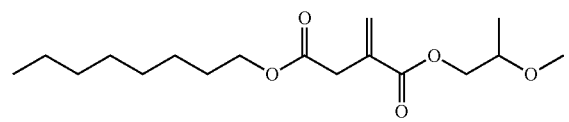 [SMILES: C=C(CC(=O)OCCCCCCCC)C(=O)OCC(C)OC]

Example 33 was prepared according to General Procedure 2, using as 4-octyl itaconate as itaconic acid monoester and 2-methoxypropan-1-ol as $R^2$—OH. $^1$H NMR (500 MHz, CDCl3) δ 6.38 (d, J=1.0 Hz, 1H), 5.74 (q, J=1.1 Hz, 1H), 4.19 (dd, J=11.5, 4.4 Hz, 1H), 4.14 (dd, J=11.5, 5.8 Hz, 1H), 4.10 (t, J=6.8 Hz, 2H), 3.64-3.58 (m, 1H), 3.41 (s, 3H), 3.37 (s, 2H), 1.68-1.61 (m, 2H), 1.38-1.26 (m, 10H), 1.21 (d, J=6.4 Hz, 3H), 0.92-0.89 (m, 3H). LCMS m/z 337.3 (M+Na)$^+$ (ES$^+$).

Example 34—1-(2-methoxy-2-methylpropyl) 4-octyl 2-methylenesuccinate

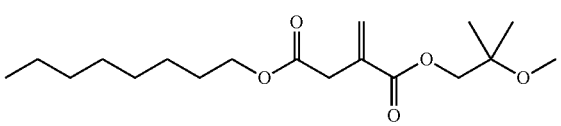 [SMILES: C=C(CC(=O)OCCCCCCCC)C(=O)OCC(C)(C)OC]

Example 34 was prepared according to General Procedure 2, using as 4-octyl itaconate as itaconic acid monoester and 2-methoxy-2-methylpropan-1-ol as $R^2$—OH. $^1$H NMR (500 MHz, DMSO-d6) δ 6.23 (d, J=1.4 Hz, 1H), 5.84 (q, J=1.2 Hz, 1H), 4.01-3.98 (m, 4H), 3.38 (s, 2H), 3.12 (s, 3H), 1.57-1.51 (m, 2H), 1.30-1.23 (m, 10H), 1.12 (s, 6H), 0.89-0.84 (m, 3H). LCMS m/z 351.2 (M+Na)$^+$ (ES$^+$).

Example 35—1-(2-morpholinoethyl) 4-octyl 2-methylenesuccinate

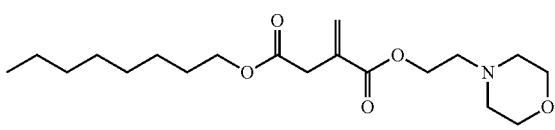 [SMILES: C=C(CC(=O)OCCCCCCCC)C(=O)OCCN1CCOCC1]

Example 35 was prepared according to General Procedure 2, using as 4-octyl itaconate as itaconic acid monoester and 2-morpholinoethan-1-ol as $R^2$—OH. $^1$H NMR (500 MHz, DMSO-d6) δ 6.20 (d, J=1.4 Hz, 1H), 5.83 (d, J=1.3 Hz, 1H), 4.20 (t, J=5.8 Hz, 2H), 4.01 (t, J=6.6 Hz, 2H), 3.57-3.53 (m, 4H), 3.36 (s, 2H), 2.57 (t, J=5.8 Hz, 2H), 2.43-2.39 (m, 4H), 1.58-1.51 (m, 2H), 1.26 (d, J=5.5 Hz, 10H), 0.89-0.84 (m, 3H). LCMS m/z 356.2 (M+H)$^+$ (ES$^+$).

Example 36—4-(2-(2-ethoxyethoxy)ethyl) 1-(2-(methylsulfonyl)ethyl) 2-methylenesuccinate

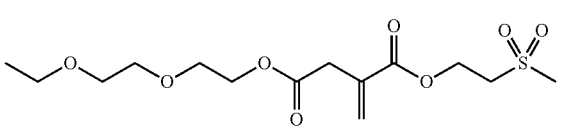 [SMILES: C=C(CC(=O)OCCOCCOCC)C(=O)OCCS(C)(=O)=O]

Example 36 was prepared according to General Procedure 2, using as 4-(2-(2-ethoxyethoxy)ethoxy)-2-methylene-4-oxobutanoic acid (Intermediate 5) as itaconic acid monoester and 2-(methylsulfonyl)ethan-1-ol as $R^2$—OH. $^1$H NMR (500 MHz, DMSO-d6) δ 6.27 (d, J=1.2 Hz, 1H), 5.91 (d, J=1.2 Hz, 1H), 4.49-4.43 (m, 2H), 4.16-4.12 (m, 2H), 3.62-3.58 (m, 2H), 3.56-3.51 (m, 4H), 3.49-3.46 (m, 2H), 3.43 (q, J=7.0 Hz, 2H), 3.41 (s, 2H), 3.03 (s, 3H), 1.11 (t, J=7.0 Hz, 3H). LCMS m/z 375.1 (M+Na)⁺ (ES⁺).

Example 37—4-butyl 1-(oxetan-3-yl) 2-methylenesuccinate

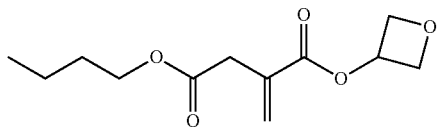 [SMILES: C=C(CC(=O)OCCCC)C(=O)OC1COC1]

Example 37 was prepared according to General Procedure 3, using 4-butyl itaconate as itaconic acid monoester and oxetan-3-ol as R²—OH. ¹H NMR (500 MHz, DMSO-d6) δ 6.30 (d, J=1.2 Hz, 1H), 5.92 (d, J=1.2 Hz, 1H), 5.44 (tt, J=6.3, 5.0 Hz, 1H), 4.82 (ddd, J=7.4, 6.3, 1.0 Hz, 2H), 4.49 (ddd, J=7.6, 5.0, 1.0 Hz, 2H), 4.04 (t, J=6.5 Hz, 2H), 3.40 (s, 2H), 1.58-1.50 (m, 2H), 1.36-1.27 (m, 2H), 0.88 (t, J=7.4 Hz, 3H). LCMS m/z 243.2 (M+H)⁺ (ES⁺).

Example 38—4-hexyl 1-(oxetan-3-yl) 2-methylenesuccinate

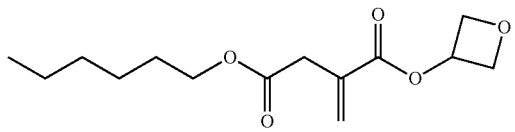 [SMILES: C=C(CC(=O)OCCCCCC)C(=O)OC1COC1]

Example 38 was prepared according to General Procedure 3, using 4-(hexyloxy)-2-methylene-4-oxobutanoic acid (Intermediate 3) as itaconic acid monoester and oxetan-3-ol as R²—OH. ¹H NMR (500 MHz, DMSO-d6) δ 6.30 (d, J=1.2 Hz, 1H), 5.92 (d, J=1.2 Hz, 1H), 5.43 (tt, J=6.3, 5.0 Hz, 1H), 4.82 (ddd, J=7.4, 6.2, 1.0 Hz, 2H), 4.49 (ddd, J=7.5, 5.0, 1.0 Hz, 2H), 4.02 (t, J=6.6 Hz, 2H), 3.40 (s, 2H), 1.59-1.51 (m, 2H), 1.33-1.22 (m, 6H), 0.91-0.83 (m, 3H). LCMS m/z 271.2 (M+H)⁺ (ES⁺).

Example 39—4-butyl 1-(2-tosylethyl) 2-methylenesuccinate

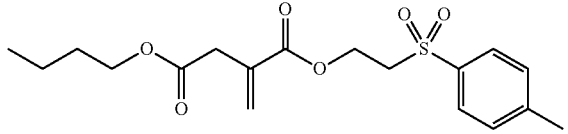 [SMILES: C=C(CC(=O)OCCCC)C(=O)OCCS(=O)(=O)c1ccc(C)cc1]

Example 39 was prepared according to General Procedure 3, using 4-butyl itaconate as itaconic acid monoester and 2-tosylethan-1-ol as R²—OH. ¹H NMR (500 MHz, DMSO-d6) δ 7.81-7.75 (m, 2H), 7.48-7.43 (m, 2H), 5.76 (d, J=1.4 Hz, 1H), 5.71 (d, J=1.2 Hz, 1H), 4.35-4.31 (m, 2H), 4.00 (t, J=6.5 Hz, 2H), 3.73 (dd, J=6.1, 5.1 Hz, 2H), 3.19 (s, 2H), 2.41 (s, 3H), 1.55-1.48 (m, 2H), 1.35-1.25 (m, 2H), 0.90-0.85 (m, 3H). LCMS m/z 391.2 (M+Na)⁺ (ES⁺).

Example 40—4-octyl 1-(2-tosylethyl) 2-methylenesuccinate

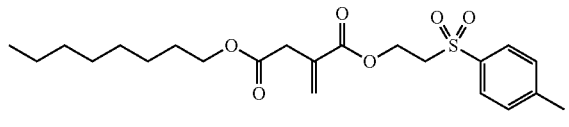 [SMILES: C=C(CC(=O)OCCCCCCCC)C(=O)OCCS(=O)(=O)c1ccc(C)cc1]

Example 40 was prepared according to General Procedure 3, using 4-octyl itaconate as itaconic acid monoester and 2-tosylethan-1-ol as R²—OH. ¹H NMR (500 MHz, DMSO-d6) δ 7.78 (d, J=8.2 Hz, 2H), 7.45 (d, J=8.0 Hz, 2H), 5.77 (s, 1H), 5.71 (s, 1H), 4.33 (t, J=5.6 Hz, 2H), 3.99 (t, J=6.6 Hz, 2H), 3.73 (t, J=5.6 Hz, 2H), 3.18 (s, 2H), 2.41 (s, 3H), 1.60-1.47 (m, 2H), 1.25 (s, 10H), 0.86 (t, J=6.8 Hz, 3H). LCMS m/z 447.2 (M+Na)⁺ (ES⁺).

Example 41—4-cyclooctyl 1-methyl 2-methylenesuccinate

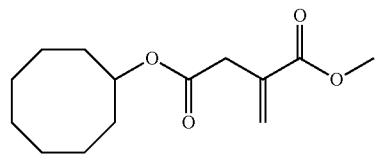 [SMILES: C=C(CC(=O)OC1CCCCCCC1)C(=O)OC]

Example 41 was prepared according to General Procedure 4, using 4-(cyclooctyloxy)-2-methylene-4-oxobutanoic acid (Intermediate 1) as itaconic acid monoester. ¹H NMR (500 MHz, CDCl₃) δ 6.32 (d, J=1.1 Hz, 1H), 5.72-5.70 (m, 1H), 4.98 (tt, J=8.3, 3.9 Hz, 1H), 3.79 (s, 3H), 3.32 (s, 2H), 1.87-1.46 (m, 14H). LCMS m/z 277.2 (M+Na)⁺ (ES⁺).

Example 42—1-methyl 4-octyl 2-methylenesuccinate

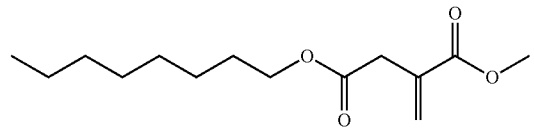 [SMILES: C=C(CC(=O)OCCCCCCCC)C(=O)OC]

Example 42 was prepared according to General Procedure 4, using 4-octyl itaconate as itaconic acid monoester. ¹H NMR (500 MHz, CDCl3) δ 6.32 (d, J=1.0 Hz, 1H), 5.70 (q, J=1.2 Hz, 1H), 4.08 (t, J=6.7 Hz, 2H), 3.76 (s, 3H), 3.33 (s, 2H), 1.66-1.56 (m, 2H), 1.33-1.23 (m, 10H), 0.90-0.85 (m, 3H). LCMS m/z 279.2 (M+Na)⁺ (ES⁺).

Example 43—dicyclobutyl 2-methylenesuccinate

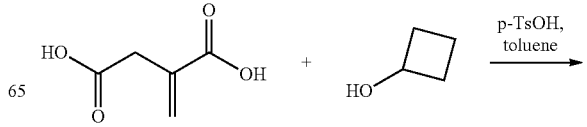

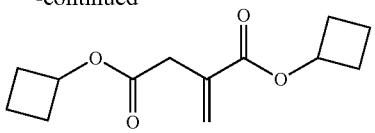

A mixture of itaconic acid (0.10 g, 0.78 mmol), cyclobutanol (0.186 g, 2.58 mmol) and p-TsOH. H₂O (2 mg, 0.008 mmol) in toluene was stirred at 110° C. for 18 h. The mixture was cooled to RT and concentrated onto silica gel. The crude product was purified by chromatography on silica gel (0-20% EtOAc/isohexane), then re-purified by chromatography on silica gel (0-50% EtOAc/isohexane) to afford the title compound as a colourless oil. ¹H NMR (500 MHz, CDCl3) δ 6.33 (d, J=1.1 Hz, 1H), 5.70 (q, J=1.2 Hz, 1H), 5.14-4.97 (m, 2H), 3.31 (d, J=1.1 Hz, 2H), 2.45-2.32 (m, 4H), 2.18-2.03 (m, 4H), 1.89-1.75 (m, 2H), 1.71-1.57 (m, 2H). LCMS m/z 261.2 (M+Na)⁺ (ES⁺).

Example 44—di(oxetan-3-yl) 2-methylenesuccinate

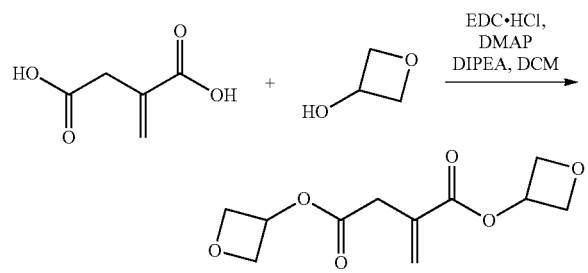

A solution of itaconic acid (200 mg, 1.54 mmol) in DCM was treated with EDC.HCl (590 mg, 3.10 mmol) and DMAP (38 mg, 0.31 mmol). A solution of oxetan-3-ol (0.2 mL, 3.1 mmol) in DCM was added, followed by DIPEA (0.8 mL, 4.6 mmol). The mixture was stirred at RT for 24 hours, then diluted with DCM (10 mL). The solution was washed with 1 N HCl (10 mL), sat. aq. NaHCO₃ (10 mL) and brine (10 mL). The organic phase was dried (MgSO₄) and concentrated. The crude product was purified by preparative HPLC (Waters, Acidic (0.1% Formic acid), Acidic, Waters X-Select Prep-C18, 5 μm, 19×50 mm column, 5-95% MeCN in Water) to afford the title compound as a clear colourless oil. ¹H NMR (500 MHz, MeOD) δ 6.42 (d, J=0.9 Hz, 1H), 5.91 (q, J=1.1 Hz, 1H), 5.51 (tt, J=6.3, 5.0 Hz, 1H), 5.45 (tt, J=6.4, 5.0 Hz, 1H), 4.94 (ddd, J=7.4, 6.3, 1.0 Hz, 2H), 4.90 (ddd, J=7.4, 6.3, 1.0 Hz, 2H), 4.65 (ddd, J=7.7, 5.0, 1.0 Hz, 2H), 4.61 (ddd, J=7.6, 5.0, 1.0 Hz, 2H), 3.49 (s, 2H). LCMS m/z 243.1 (M+H)⁺ (ES⁺).

Example 45—1-cyclobutyl 4-octyl 2-methylenesuccinate

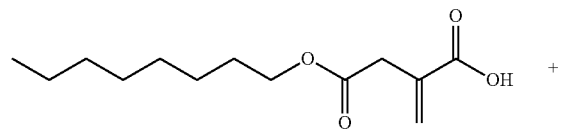

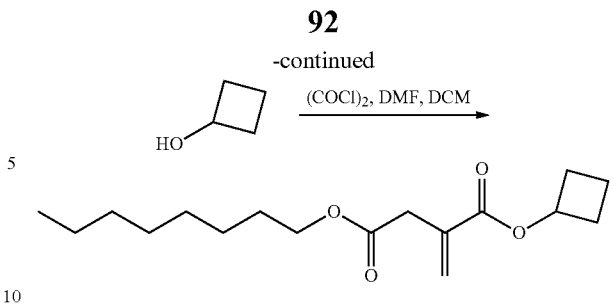

Oxalyl chloride (0.11 mL, 1.2 mmol) was added dropwise to a solution of 4-octyl itaconate (0.15 g, 0.62 mmol), cyclobutanol (0.1 mL, 1.2 mmol) and dimethylformamide (0.1 mL, 1.2 mmol) in DCM. The mixture was stirred for 16 h. Water (10 mL) was added, the phases were separated and the aqueous phase was extracted with DCM (3×10 mL). The combined organic extracts were washed with brine (2×10 mL), dried (MgSO₄) and concentrated. The crude product which was purified by chromatography on silica gel (0-10% MeOH/DCM) to afford the title compound as a pale yellow oil. ¹H NMR (500 MHz, DMSO-d6) δ 6.19 (d, J=1.4 Hz, 1H), 5.80 (d, J=1.3 Hz, 1H), 4.92-4.85 (m, 1H), 4.08 (t, J=6.5 Hz, 2H), 3.33 (s, 2H), 2.29-2.22 (m, 2H), 2.02-1.93 (m, 2H), 1.78-1.69 (m, 1H), 1.63-1.52 (m, 3H), 1.35-1.22 (m, 10H), 0.90-0.84 (m, 3H). LCMS m/z 319.3 (M+Na)⁺ (ES⁺).

Example 46—1-(1-acetoxyethyl) 4-octyl 2-methylenesuccinate

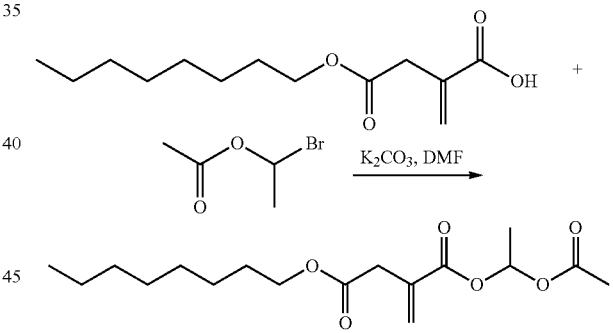

1-bromoethyl acetate (0.103 g, 0.62 mmol) was added dropwise to a suspension of 4-octyl itaconate (0.15 g, 0.62 mmol) and potassium carbonate (0.171 g, 1.24 mmol) in dimethylformamide (5 mL) at RT. The mixture was stirred for 16 h, before water (10 mL) was added and the mixture was extracted with DCM (3×10 mL). The combined organic extracts were washed with brine (2×10 mL), dried (MgSO₄) and concentrated in vacuo. The crude product was purified by chromatography on silica gel (0-10% MeOH/DCM) to afford the title compound as a yellow oil. ¹H NMR (500 MHz, DMSO-d6) δ 6.78 (q, J=5.4 Hz, 1H), 6.24 (d, J=1.1 Hz, 1H), 5.92 (d, J=1.3 Hz, 1H), 4.01 (t, J=6.6 Hz, 2H), 3.36 (s, 2H), 2.04 (s, 3H), 1.58-1.51 (m, 2H), 1.44 (d, J=5.4 Hz, 3H), 1.33-1.21 (m, 10H), 0.90-0.84 (m, 3H). LCMS m/z 351.3 (M+Na)⁺ (ES⁺).

Example 47—1-(1,1-dioxidothietan-3-yl) 4-octyl 2-methylenesuccinate

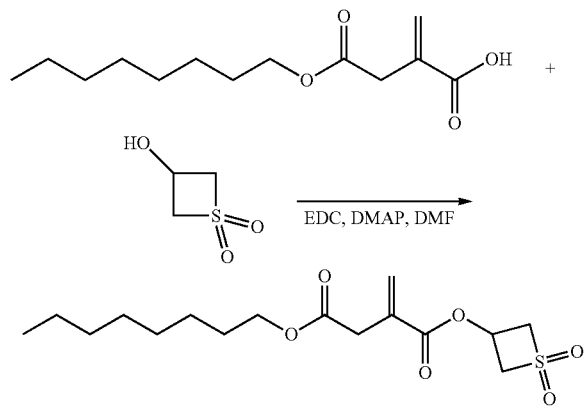

EDC (0.13 mL, 0.74 mmol) was added to a solution of 4-octyl itaconate (0.15 g, 0.62 mmol), DMAP (4 mg, 0.03 mmol) and 3-hydroxythietane 1,1-dioxide (0.11 g, 0.93 mmol) in dimethylformamide (2 mL). The mixture was stirred overnight at RT then diluted with EtOAc (10 mL) and water (10 mL). The phases were separated and the organic phase was washed with brine (2×10 mL), dried (MgSO$_4$) and concentrated. The crude product was purified by chromatography on silica gel (0-10% MeOH/DCM) to afford the title compound as a colourless oil. $^1$H NMR (500 MHz, DMSO-d6) δ 6.78 (q, J=5.4 Hz, 1H), 6.24 (d, J=1.1 Hz, 1H), 5.92 (d, J=1.3 Hz, 1H), 4.01 (t, J=6.6 Hz, 2H), 3.36 (s, 2H), 2.04 (s, 3H), 1.58-1.51 (m, 2H), 1.44 (d, J=5.4 Hz, 3H), 1.33-1.21 (m, 10H), 0.90-0.84 (m, 3H). LCMS m/z 369.2 (M+Na)$^+$ (ES$^+$).

Example 48—1-(2-(tert-butoxy)-2-oxoethyl) 4-octyl 2-methylenesuccinate

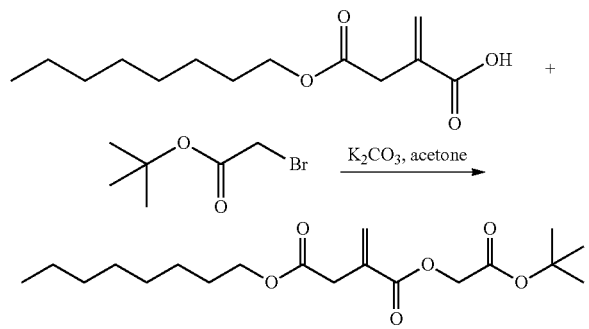

tert-Butyl bromoacetate (0.37 mL, 2.5 mmol) was added to a mixture of 4-octyl itaconate (0.50 g, 2.1 mmol) and potassium carbonate (0.35 g, 2.5 mmol) in acetone (10 mL). The mixture was stirred for 16 h at RT. The mixture was diluted with EtOAc (20 mL), filtered and concentrated onto silica gel. The crude product was purified by chromatography on silica gel (0-30% EtOAc/isohexane) to afford the title compound as a colourless oil. $^1$H NMR (500 MHz, DMSO-d6) δ 6.29 (d, J=1.3 Hz, 1H), 5.95-5.92 (m, 1H), 4.61 (s, 2H), 4.01 (t, J=6.6 Hz, 2H), 3.38 (s, 2H), 1.60-1.50 (m, 2H), 1.42 (s, 9H), 1.34-1.21 (m, 10H), 0.90-0.83 (m, 3H). LCMS m/z 379.3 (M+Na)$^+$ (ES$^+$).

Example 49—2-((2-methylene-4-(octyloxy)-4-oxobutanoyl)oxy)acetic acid

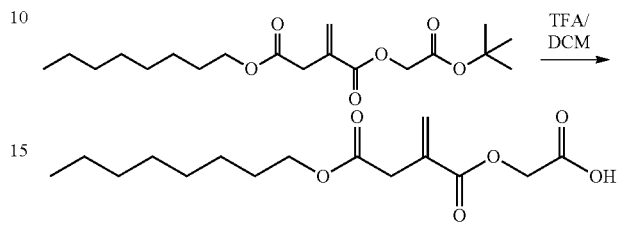

TFA (5 mL, 65 mmol) was added to a solution of 1-(2-(tert-butoxy)-2-oxoethyl) 4-octyl 2-methylenesuccinate (Example 48, 0.65 g, 1.82 mmol) in DCM (5 mL). The reaction mixture was stirred for 30 minutes, diluted with toluene (10 mL) and concentrated. The crude product was purified by chromatography on silica gel (0-4% MeOH/DCM) to afford the title compound as a colourless oil. $^1$H NMR (500 MHz, DMSO-d6) δ 13.08 (s, 1H), 6.29 (d, J=1.2 Hz, 1H), 5.93 (q, J=1.2 Hz, 1H), 4.64 (s, 2H), 4.01 (t, J=6.6 Hz, 2H), 3.38 (s, 2H), 1.60-1.48 (m, 2H), 1.32-1.20 (m, 10H), 0.92-0.82 (m, 3H). LCMS m/z 323.2 (M+Na)$^+$ (ES$^+$).

Example 50—1-(1-acetylazetidin-3-yl) 4-octyl 2-methylenesuccinate

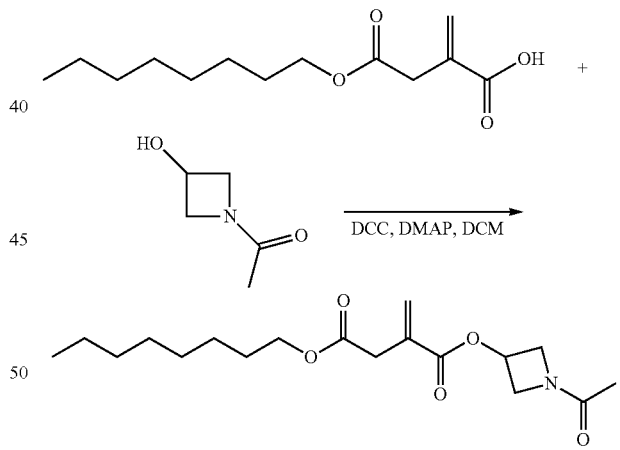

DCC (0.224 g, 1.08 mmol) was added to a mixture of 4-octyl itaconate (0.25 g, 1.03 mmol), DMAP (6 mg, 0.05 mmol) and 1-(3-hydroxyazetidin-1-yl)ethanone (0.143 g, 1.24 mmol in DCM (3 mL). The mixture was stirred for 16 h at RT, before the solid was removed by filtration. The filtrate concentrated and purified by chromatography on silica gel (0-10% MeOH/DCM) to afford a colourless oil. The oil was taken up in DCM/hexane (1:5, 3 mL) and the resulting solid was removed by filtration. The filtrate was concentrated to and the residue was purified by chromatography on silica gel (0-5% MeOH/DCM) to afford the title compound as a colourless oil. $^1$H NMR (500 MHz, DMSO-d6) δ 6.29 (d, J=1.2 Hz, 1H), 5.93-5.90 (m, 1H), 5.21-5.15

Example 51—1-(2-(4-methylpiperazin-1-yl)ethyl) 4-octyl 2-methylenesuccinate

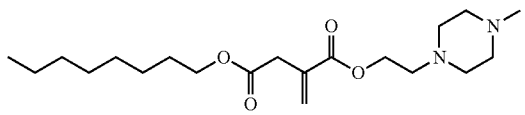 [SMILES: C=C(CC(=O)OCCCCCCCC)C(=O)OCCN1CCN(C)CC1]

Example 51 was prepared according to General Procedure 2, using 4-octyl itaconate as itaconic acid monoester and 2-(4-methylpiperazin-1-yl)ethanol as $R^2$—OH. $^1$H NMR (500 MHz, CDCl$_3$) δ 6.31 (d, J=1.0 Hz, 1H), 5.70 (q, J=1.2 Hz, 1H), 4.29 (t, J=6.1 Hz, 2H), 4.08 (t, J=6.8 Hz, 2H), 3.33 (s, 2H), 2.68 (t, J=6.1 Hz, 2H), 2.65-2.31 (m, 8H), 2.29 (s, 3H), 1.67-1.56 (m, 2H), 1.32-1.23 (m, 10H), 0.88 (t, J=6.8 Hz, 3H). LCMS m/z 369.3 (M+H)$^+$ (ES$^+$).

Example 52—1-(2-(1,1-dioxidothiomorpholino)ethyl) 4-octyl 2-methylenesuccinate

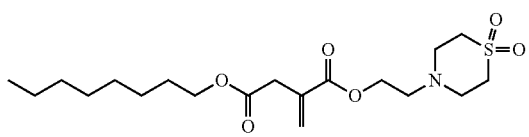 [SMILES: C=C(CC(=O)OCCCCCCCC)C(=O)OCCN1CCS(=O)(=O)CC1]

Example 52 was prepared according to General Procedure 2, using 4-octyl itaconate as itaconic acid monoester and 4-(2-hydroxyethyl)thiomorpholine 1,1-dioxide as $R^2$—OH. $^1$H NMR (500 MHz, DMSO-d6) δ 6.21 (d, J=1.3 Hz, 1H), 5.85 (d, J=1.3 Hz, 1H), 4.19 (t, J=5.6 Hz, 2H), 4.01 (t, J=6.6 Hz, 2H), 3.37 (s, 2H), 3.09-3.03 (m, 4H), 2.97 (dd, J=6.9, 3.5 Hz, 4H), 2.80 (t, J=5.6 Hz, 2H), 1.54 (q, J=6.8 Hz, 2H), 1.32-1.23 (m, 10H), 0.90-0.83 (m, 3H). LCMS m/z 404.2 (M+H)+(ES$^+$).

Example 53—1-(2-(methylsulfonamido)ethyl) 4-octyl 2-methylenesuccinate

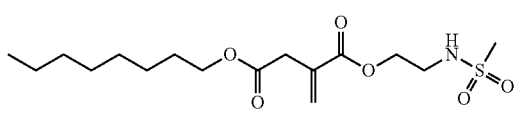 [SMILES: C=C(CC(=O)OCCCCCCCC)C(=O)OCCNS(C)(=O)=O]

Example 53 was prepared according to General Procedure 2, using 4-octyl itaconate as itaconic acid monoester and N-(2-hydroxyethyl)methanesulfonamide as $R^2$—OH. $^1$H NMR (500 MHz, DMSO-d6) δ 7.26 (t, J=6.0 Hz, 1H), 6.30 (d, J=1.3 Hz, 1H), 5.87 (q, J=1.2 Hz, 1H), 4.12 (t, J=5.7 Hz, 2H), 4.01 (t, J=6.6 Hz, 2H), 3.38 (s, 2H), 3.23 (q, J=5.7 Hz, 2H), 2.92 (s, 3H), 1.54 (q, J=6.8 Hz, 2H), 1.32-1.23 (m, 10H), 0.90-0.83 (m, 3H). LCMS m/z 386.2 (M+Na)$^+$ (ES$^+$).

Example 54—4-cyclooctyl 1-(1,1-dioxidothietan-3-yl) 2-methylenesuccinate

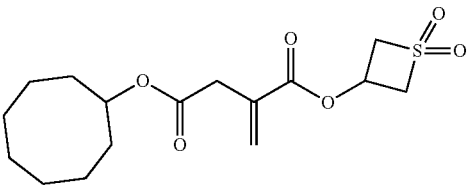 [SMILES: C=C(CC(=O)OC1CCCCCCC1)C(=O)OC1CS(=O)(=O)C1]

Example 54 was prepared according to General Procedure 2, using 4-(cyclooctyloxy)-2-methylene-4-oxobutanoic acid (Intermediate 1) as itaconic acid monoester and 3-hydroxythietane 1,1-dioxide as $R^2$—OH. $^1$H NMR (500 MHz, DMSO-d6) δ 6.28 (d, J=1.1 Hz, 1H), 5.92 (d, J=1.3 Hz, 1H), 5.32 (tt, J=7.7, 2.8 Hz, 1H), 4.84 (tt, J=8.2, 3.9 Hz, 1H), 4.79-4.69 (m, 2H), 4.25-4.16 (m, 2H), 3.36 (s, 2H), 1.78-1.39 (m, 14H). LCMS m/z 367.5 (M+Na)$^+$ (ES$^+$).

Example 55—(R)-1-(2-(methylsulfonyl)ethyl) 4-(octan-2-yl) 2-methylenesuccinate

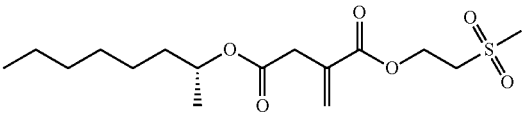 [SMILES: C=C(CC(=O)O[C@H](C)CCCCCC)C(=O)OCCS(C)(=O)=O]

Example 55 was prepared according to General Procedure 2, using (R)-2-methylene-4-(octan-2-yloxy)-4-oxobutanoic acid (Intermediate 8) as itaconic acid monoester and 2-(methylsulfonyl)ethanol as $R^2$—OH. $^1$H NMR (500 MHz, DMSO-d6) δ 6.24 (d, J=1.2 Hz, 1H), 5.88 (d, J=1.3 Hz, 1H), 4.84-4.63 (m, 1H), 4.44 (t, J=5.8 Hz, 2H), 3.53 (t, J=5.8 Hz, 2H), 3.34 (s, 2H), 3.02 (s, 3H), 1.54-1.38 (m, 2H), 1.31-1.20 (m, 8H), 1.14 (d, J=6.2 Hz, 3H), 0.86 (t, J=6.8 Hz, 3H). LCMS m/z 371.5 (M+Na)$^+$ (ES$^+$).

Example 56—1-(1-(methylsulfonyl)propan-2-yl) 4-((R)-octan-2-yl) 2-methylenesuccinate

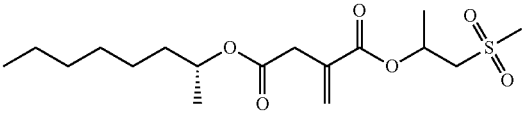 [SMILES: C=C(CC(=O)O[C@H](C)CCCCCC)C(=O)OC(C)CS(C)(=O)=O]

Example 56 was prepared according to General Procedure 2, using (R)-2-methylene-4-(octan-2-yloxy)-4-oxobutanoic acid (Intermediate 8) as itaconic acid monoester and 1-(methylsulfonyl)propan-2-ol as $R^2$—OH. $^1$H NMR (500 MHz, DMSO-d6) δ6.23 (s, 1H), 5.85 (s, 1H), 5.34-5.21 (m, 1H), 4.84-4.69 (m, 1H), 3.63-3.54 (m, 1H), 3.50-3.42 (m, 1H), 3.34-3.32 (m, 2H), 2.98 (s, 3H), 1.52-1.38 (m, 2H), 1.35-1.19 (m, 11H), 1.16-1.10 (m, 3H), 0.85 (t, J=6.8 Hz, 3H). LCMS m/z 385.6 (M+Na)$^+$ (ES$^+$).

Example 57—(R)-1-(1,1-dioxidothietan-3-yl) 4-(octan-2-yl) 2-methylenesuccinate

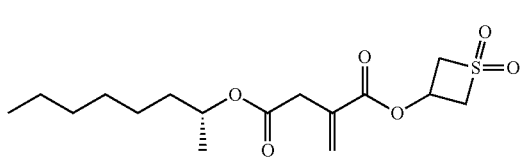 [SMILES: C=C(CC(=O)O[C@H](C)CCCCCC)C(=O)OC1CS(=O)(=O)C1]

Example 57 was prepared according to General Procedure 2, using (R)-2-methylene-4-(octan-2-yloxy)-4-oxobutanoic acid (Intermediate 8) as itaconic acid monoester and 3-hydroxythietane 1,1-dioxide as $R^2$—OH. $^1$H NMR (500 MHz, DMSO-d6) δ 6.28 (d, J=1.1 Hz, 1H), 5.93 (d, J=1.2 Hz, 1H), 5.36-5.22 (m, 1H), 4.83-4.66 (m, 3H), 4.23-4.05 (m, 2H), 3.36 (s, 2H), 1.53-1.41 (m, 2H), 1.30-1.20 (m, 8H), 1.14 (d, J=6.3 Hz, 3H), 0.86 (t, J=6.8 Hz, 3H). LCMS m/z 369.2 (M+Na)$^+$ (ES$^+$).

Example 58—(R)-1-(1-acetylazetidin-3-yl) 4-(octan-2-yl) 2-methylenesuccinate

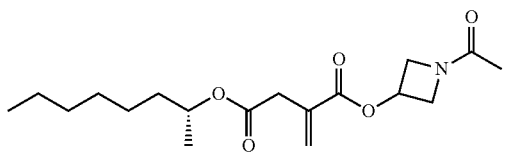 [SMILES: C=C(CC(=O)O[C@H](C)CCCCCC)C(=O)OC1CN(C(C)=O)C1]

Example 58 was prepared according to General Procedure 2, using (R)-2-methylene-4-(octan-2-yloxy)-4-oxobutanoic acid (Intermediate 8) as itaconic acid monoester and 1-(3-hydroxyazetidin-1-yl)ethanone as $R^2$—OH. $^1$H NMR (500 MHz, DMSO-d6) δ 6.28 (d, J=1.2 Hz, 1H), 5.90 (d, J=1.2 Hz, 1H), 5.21-5.11 (m, 1H), 4.85-4.73 (m, 1H), 4.53-4.41 (m, 1H), 4.19-4.13 (m, 1H), 4.06-3.98 (m, 1H), 3.77-3.67 (m, 1H), 3.37 (s, 2H), 1.77 (s, 3H), 1.52-1.39 (m, 2H), 1.30-1.18 (m, 8H), 1.14 (d, J=6.2 Hz, 3H), 0.86 (t, J=6.8 Hz, 3H). LCMS m/z 362.3 (M+Na)$^+$ (ES$^+$).

Example 59—4-cyclohexyl 1-(1-(methylsulfonyl)propan-2-yl) 2-methylenesuccinate

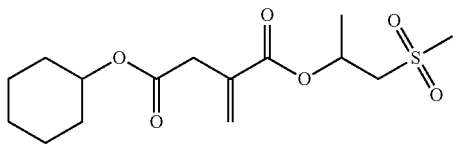 [SMILES: C=C(CC(=O)OC1CCCCC1)C(=O)OC(C)CS(C)(=O)=O]

Example 59 was prepared according to General Procedure 2, using 4-(cyclohexyloxy)-2-methylene-4-oxobutanoic acid (Intermediate 6) as itaconic acid monoester and 1-(methylsulfonyl)propan-2-ol as $R^2$—OH. $^1$H NMR (500 MHz, DMSO-d6) δ 6.24 (d, J=1.3 Hz, 1H), 5.86 (d, J=1.3 Hz, 1H), 5.36-5.16 (m, 1H), 4.68-4.58 (m, 1H), 3.70-3.55 (m, 1H), 3.51-3.42 (m, 1H), 3.35 (s, 2H), 2.99 (s, 3H), 1.78-1.69 (m, 2H), 1.66-1.54 (m, 2H), 1.51-1.43 (m, 1H), 1.41-1.13 (m, 8H). LCMS m/z 355.2 (M+Na)$^+$ (ES$^+$).

Example 60—4-cyclohexyl 1-(1,1-dioxidothietan-3-yl) 2-methylenesuccinate

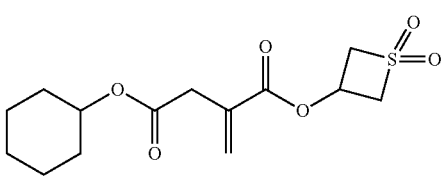 [SMILES: C=C(CC(=O)OC1CCCCC1)C(=O)OC1CS(=O)(=O)C1]

Example 60 was prepared according to General Procedure 2, using 4-(cyclohexyloxy)-2-methylene-4-oxobutanoic acid (Intermediate 6) as itaconic acid monoester and 3-hydroxythietane 1,1-dioxide as $R^2$—OH. $^1$H NMR (500 MHz, DMSO-d6) δ 6.29 (d, J=1.2 Hz, 1H), 5.93 (d, J=1.3 Hz, 1H), 5.32 (tt, J=7.7, 2.8 Hz, 1H), 4.80-4.69 (m, 2H), 4.71-4.58 (m, 1H), 4.26-4.16 (m, 2H), 3.38 (s, 2H), 1.80-1.72 (m, 2H), 1.70-1.59 (m, 2H), 1.54-1.44 (m, OH), 1.44-1.19 (m, 6H). LCMS m/z 339.2 (M+Na)$^+$ (ES$^+$).

Example 61—4-cyclohexyl 1-(2-(methylsulfonyl)ethyl) 2-methylenesuccinate

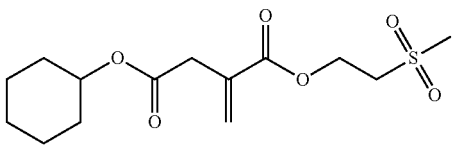 [SMILES: C=C(CC(=O)OC1CCCCC1)C(=O)OCCS(C)(=O)=O]

Example 61 was prepared according to General Procedure 2, using 4-(cyclohexyloxy)-2-methylene-4-oxobutanoic acid (Intermediate 6) as itaconic acid monoester and 2-(methylsulfonyl)ethanol as $R^2$—OH. $^1$H NMR (500 MHz, DMSO-d6) δ 6.23 (d, J=1.2 Hz, 1H), 5.87 (d, J=1.3 Hz, 1H), 4.69-4.61 (m, 1H), 4.44 (t, J=5.8 Hz, 2H), 3.52 (t, J=5.8 Hz, 2H), 3.35 (s, 2H), 3.02 (s, 3H), 1.78-1.69 (m, 2H), 1.65-1.56 (m, 2H), 1.50-1.41 (m, 1H), 1.38-1.12 (m, 5H). LCMS m/z 341.2 (M+Na)$^+$ (ES$^+$).

Example 62—4-cyclooctyl 1-(1-(methylsulfonyl)propan-2-yl) 2-methylenesuccinate

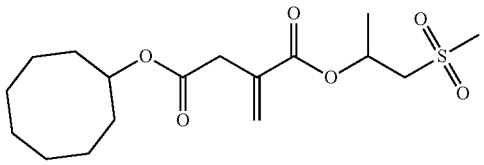 [SMILES: C=C(CC(=O)OC1CCCCCCC1)C(=O)OC(C)CS(C)(=O)=O]

Example 62 was prepared according to General Procedure 2, using 4-(cyclooctyloxy)-2-methylene-4-oxobutanoic acid (Intermediate 1) as itaconic acid monoester and 1-(methylsulfonyl)propan-2-ol as $R^2$—OH. $^1$H NMR (500 MHz, CDCl$_3$) δ 6.32 (s, 1H), 5.76 (d, J=1.1 Hz, 1H), 5.49-5.41 (m, 1H), 5.00-4.94 (m, 1H), 3.47 (dd, J=14.8, 6.6 Hz, 1H), 3.39-3.29 (m, 2H), 3.24-3.14 (m, 1H), 3.00 (s, 3H), 1.87-1.66 (m, 6H), 1.66-1.46 (m, 11H). LCMS m/z 383.5 (M+Na)$^+$ (ES$^+$).

Example 63—1-(1-acetylazetidin-3-yl) 4-cyclooctyl 2-methylenesuccinate

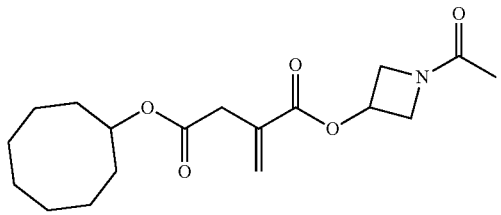 [SMILES: C=C(CC(=O)OC1CCCCCCC1)C(=O)OC1CN(C(C)=O)C1]

Example 63 was prepared according to General Procedure 2, using 4-(cyclooctyloxy)-2-methylene-4-oxobutanoic acid (Intermediate 1) as itaconic acid monoester and 1-(3-hydroxyazetidin-1-yl)ethanone as $R^2$—OH. $^1$H NMR (500 MHz, CDCl$_3$) δ 6.39 (s, 1H), 5.80 (s, 1H), 5.28 (ddd, J=11.1, 6.9, 4.1 Hz, 1H), 4.98 (tt, J=8.3, 3.9 Hz, 1H), 4.54-4.45 (m, 1H), 4.36 (dd, J=11.2, 6.9 Hz, 1H), 4.12 (dd, J=9.8, 4.1 Hz, 1H), 4.04 (dd, J=11.2, 4.3 Hz, 1H), 3.34 (s, 2H), 1.91 (s, 3H), 1.85-1.66 (m, 6H), 1.60-1.52 (m, 8H). LCMS m/z 360.3 (M+Na)$^+$ (ES$^+$).

Example 64—4-cyclohexyl 1-(tetrahydro-2H-pyran-4-yl) 2-methylenesuccinate

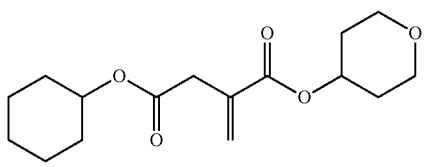 [SMILES: C=C(CC(=O)OC1CCCCC1)C(=O)OC1CCOCC1]

Example 64 was prepared according to General Procedure 2, using 4-(cyclohexyloxy)-2-methylene-4-oxobutanoic acid (Intermediate 6) as itaconic acid monoester and tetrahydro-2H-pyran-4-ol as $R^2$—OH. $^1$H NMR (500 MHz, DMSO-d6) δ 6.21 (s, 1H), 5.81 (s, 1H), 4.95-4.88 (m, 1H), 4.72-4.50 (m, 1H), 3.79-3.70 (m, 2H), 3.53-3.45 (m, 2H), 3.35 (s, 2H), 1.88-1.80 (m, 2H), 1.76-1.68 (m, 2H), 1.66-1.59 (m, 2H), 1.57-1.18 (m, 8H). LCMS m/z 319.2 (M+Na)$^+$ (ES$^+$).

Example 65—4-cyclohexyl 1-(2-(2-oxopyrrolidin-1-yl)ethyl) 2-methylenesuccinate

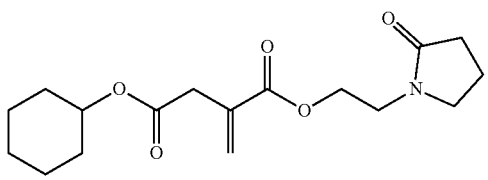 [SMILES: C=C(CC(=O)OC1CCCCC1)C(=O)OCCN1CCCC1=O]

Example 65 was prepared according to General Procedure 2, using 4-(cyclohexyloxy)-2-methylene-4-oxobutanoic acid (Intermediate 6) as itaconic acid monoester and 1-(2-hydroxyethyl)pyrrolidin-2-one as $R^2$—OH. $^1$H NMR (500 MHz, DMSO-d6) δ 6.18 (s, 1H), 5.83 (s, 1H), 4.69-4.53 (m, 1H), 4.18 (t, J=5.5 Hz, 2H), 3.44 (t, J=5.4 Hz, 2H), 3.37 (t, J=7.0 Hz, 2H), 3.32 (s, 2H), 2.19 (t, J=8.1 Hz, 2H), 1.93-1.83 (m, 2H), 1.77-1.68 (m, 2H), 1.65-1.54 (m, 2H), 1.49-1.42 (m, 1H), 1.39-1.15 (m, 5H). LCMS m/z 346.3 (M+Na)$^+$ (ES$^+$).

Example 66—(S)-1-(1-acetylazetidin-3-yl) 4-(octan-2-yl) 2-methylenesuccinate

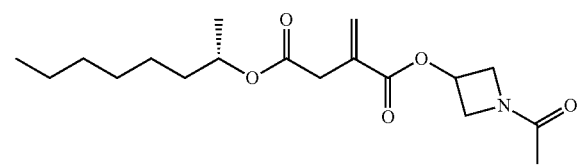 [SMILES: C=C(CC(=O)O[C@@H](C)CCCCCC)C(=O)OC1CN(C(C)=O)C1]

Example 66 was prepared according to General Procedure 2, using (S)-2-methylene-4-(octan-2-yloxy)-4-oxobutanoic acid (Intermediate 9) as itaconic acid monoester and 1-(3-hydroxyazetidin-1-yl)ethanone as $R^2$—OH. $^1$H NMR (500 MHz, DMSO-d6) δ 6.28 (d, J=1.2 Hz, 1H), 5.90 (d, J=1.3 Hz, 1H), 5.21-5.14 (m, 1H), 4.83-4.76 (m, 1H), 4.47 (ddd, J=9.8, 6.7, 1.4 Hz, 1H), 4.20-4.14 (m, 1H), 4.05-4.01 (m, 1H), 3.77-3.69 (m, 1H), 3.37 (s, 2H), 1.77 (s, 3H), 1.48 (dddt, J=13.7, 10.5, 7.6, 5.1 Hz, 2H), 1.31-1.20 (m, 8H), 1.14 (d, J=6.3 Hz, 3H), 0.86 (t, J=6.9 Hz, 3H). LCMS m/z 340.5 (M+H)$^+$ (ES$^+$).

Example 67—(S)-1-(1,1-dioxidothietan-3-yl) 4-(octan-2-yl) 2-methylenesuccinate

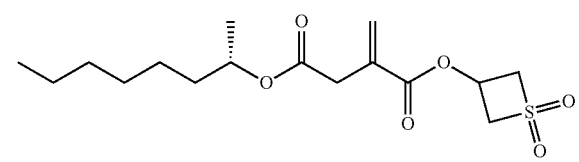 [SMILES: C=C(CC(=O)O[C@@H](C)CCCCCC)C(=O)OC1CS(=O)(=O)C1]

Example 67 was prepared according to General Procedure 2, using (S)-2-methylene-4-(octan-2-yloxy)-4-oxobutanoic acid (Intermediate 9) as itaconic acid monoester and 3-hydroxythietane 1,1-dioxide as $R^2$—OH. $^1$H NMR (500 MHz, DMSO-d6) δ 6.29 (d, J=1.1 Hz, 1H), 5.93 (d, J=1.2 Hz, 1H), 5.31 (tt, J=7.7, 2.8 Hz, 1H), 4.83-4.70 (m, 3H), 4.24-4.17 (m, 2H), 3.37 (s, 2H), 1.49 (dddd, J=19.5, 14.0, 7.8, 4.7 Hz, 2H), 1.31-1.19 (m, 8H), 1.15 (d, J=6.3 Hz, 3H), 0.86 (t, J=6.8 Hz, 3H). LCMS m/z 369.2 (M+Na)$^+$ (ES$^+$).

Example 68—1-(3-methyloxetan-3-yl) 4-octyl 2-methylenesuccinate

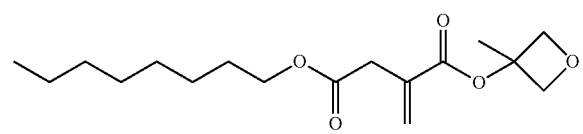 [SMILES: C=C(CC(=O)OCCCCCCCC)C(=O)OC1(C)COC1]

Example 68 was prepared according to General Procedure 2, using 4-octyl itaconate as itaconic acid monoester and 3-methyloxetan-3-ol as $R^2$—OH. $^1$H NMR (500 MHz, DMSO-d6) δ 6.23 (d, J=1.2 Hz, 1H), 5.87 (d, J=1.3 Hz, 1H), 4.61 (d, J=7.1 Hz, 2H), 4.51-4.41 (m, 2H), 4.02 (t, J=6.6 Hz, 2H), 3.38 (s, 2H), 1.63 (s, 3H), 1.59-1.50 (m, 2H), 1.31-1.22 (m, 10H), 0.92-0.83 (m, 3H). LCMS m/z 313.2 (M+H)+ (ES+).

Example 69—4-cyclooctyl 1-(1-(methylsulfonyl)piperidin-4-yl) 2-methylenesuccinate

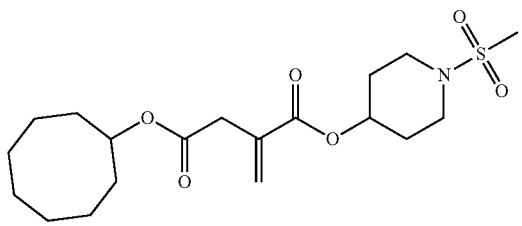 [SMILES: C=C(CC(=O)OC1CCCCCCC1)C(=O)OC1CCN(S(C)(=O)=O)CC1]

Example 69 was prepared according to General Procedure 2, using 4-(cyclooctyloxy)-2-methylene-4-oxobutanoic acid (Intermediate 1) as itaconic acid monoester and 1-(methylsulfonyl)piperidin-4-ol as $R^2$—OH. $^1$H NMR (500 MHz, DMSO-d6) δ 6.24 (d, J=1.4 Hz, 1H), 5.83 (d, J=1.3 Hz, 1H), 4.91 (tt, J=7.2, 3.6 Hz, 1H), 4.83 (tt, J=8.1, 3.9 Hz, 1H), 3.35 (s, 2H), 3.25 (ddd, J=11.7, 7.7, 3.7 Hz, 2H), 3.17 (ddd, J=11.8, 7.4, 3.9 Hz, 2H), 2.90 (s, 3H), 1.97-1.88 (m, 2H), 1.76-1.43 (m, 16H). LCMS m/z 424.2 (M+Na)+ (ES+).

Example 70—4-cyclooctyl 1-(tetrahydro-2H-pyran-4-yl) 2-methylenesuccinate

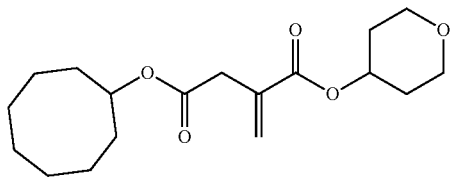 [SMILES: C=C(CC(=O)OC1CCCCCCC1)C(=O)OC1CCOCC1]

Example 70 was prepared according to General Procedure 2, using 4-(cyclooctyloxy)-2-methylene-4-oxobutanoic acid (Intermediate 1) as itaconic acid monoester and tetrahydro-2H-pyran-4-ol as $R^2$—OH. $^1$H NMR (500 MHz, DMSO-d6) δ 6.21 (d, J=1.4 Hz, 1H), 5.81 (d, J=1.4 Hz, 1H), 4.94 (tt, J=8.0, 4.0 Hz, 1H), 4.83 (tt, J=8.1, 3.9 Hz, 1H), 3.76 (ddd, J=10.7, 6.2, 3.9 Hz, 2H), 3.50 (ddd, J=11.6, 8.2, 3.3 Hz, 2H), 3.34 (s, 2H), 1.89-1.81 (m, 2H), 1.76-1.60 (m, 6H), 1.58-1.42 (m, 10H). LCMS m/z 347.5 (M+Na)+ (ES+).

Example 71—4-cyclooctyl 1-(2-(2-oxopyrrolidin-1-yl)ethyl) 2-methylenesuccinate

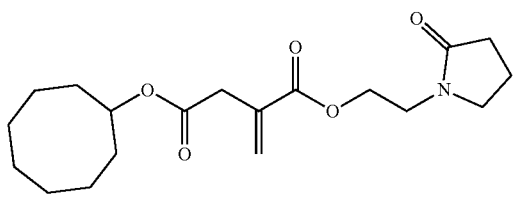 [SMILES: C=C(CC(=O)OC1CCCCCCC1)C(=O)OCCN1CCCC1=O]

Example 71 was prepared according to General Procedure 2, using 4-(cyclooctyloxy)-2-methylene-4-oxobutanoic acid (Intermediate 1) as itaconic acid monoester and 1-(2-hydroxyethyl)pyrrolidin-2-one as $R^2$—OH. $^1$H NMR (500 MHz, DMSO-d6) δ 6.18 (d, J=1.3 Hz, 1H), 5.82 (d, J=1.3 Hz, 1H), 4.83 (tt, J=8.2, 3.9 Hz, 1H), 4.19 (t, J=5.4 Hz, 2H), 3.45 (t, J=5.4 Hz, 2H), 3.38 (t, J=7.0 Hz, 2H), 3.31 (s, 2H), 2.20 (t, J=8.1 Hz, 2H), 1.91 (ddd, J=15.2, 8.1, 6.8 Hz, 2H), 1.77-1.43 (m, 14H). LCMS m/z 374.4 (M+Na)+ (ES+).

Example 72—(R)-4-(octan-2-yl) 1-(2-(2-oxopyrrolidin-1-yl)ethyl) 2-methylenesuccinate

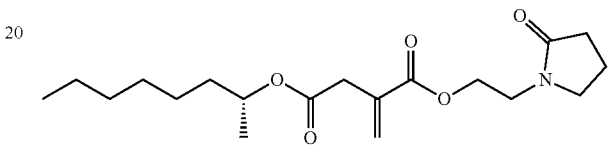

Example 72 was prepared according to General Procedure 2, using (R)-4-(octan-2-yl) 1-(2-(2-oxopyrrolidin-1-yl)ethyl) 2-methylenesuccinate (Intermediate 8) as itaconic acid monoester and 1-(2-hydroxyethyl)pyrrolidin-2-one as $R^2$—OH. $^1$H NMR (500 MHz, DMSO-d6) δ 6.17 (d, J=1.3 Hz, 1H), 5.82 (d, J=1.4 Hz, 1H), 4.81-4.66 (m, 1H), 4.23-4.11 (m, 2H), 3.44 (t, J=5.4 Hz, 2H), 3.37 (t, J=7.0 Hz, 2H), 3.31 (s, 2H), 2.19 (t, J=8.1 Hz, 2H), 1.95-1.84 (m, 2H), 1.52-1.40 (m, 2H), 1.27-1.18 (m, 8H), 1.13 (d, J=6.3 Hz, 3H), 0.85 (t, J=6.8 Hz, 3H). LCMS m/z 354.3 (M+H)+ (ES+).

Example 73—(R)-4-(octan-2-yl) 1-(tetrahydro-2H-pyran-4-yl) 2-methylenesuccinate

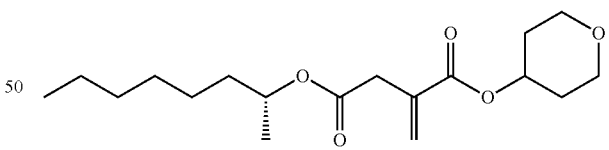

Example 73 was prepared according to General Procedure 2, using (R)-4-(octan-2-yl) 1-(2-(2-oxopyrrolidin-1-yl)ethyl) 2-methylenesuccinate (Intermediate 8) as itaconic acid monoester and tetrahydro-2H-pyran-4-ol as $R^2$—OH. $^1$H NMR (500 MHz, DMSO-d6) δ 6.21 (d, J=1.4 Hz, 1H), 5.81 (d, J=1.4 Hz, 1H), 4.96-4.88 (m, 1H), 4.81-4.72 (m, 1H), 3.79-3.72 (m, 2H), 3.52-3.44 (m, 2H), 3.35-3.33 (m, 2H), 1.87-1.78 (m, 2H), 1.59-1.39 (m, 4H), 1.29-1.19 (m, 8H), 1.13 (d, J=6.3 Hz, 3H), 0.85 (t, J=6.8 Hz, 3H). LCMS m/z 349.3 (M+H)+ (ES+).

Example 74—1-(1-acetylazetidin-3-yl) 4-cyclohexyl 2-methylenesuccinate

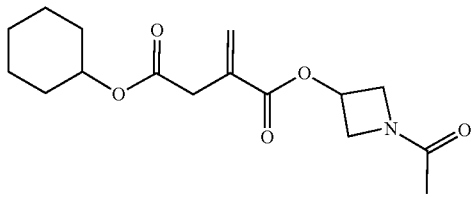 [SMILES: C=C(CC(=O)OC1CCCCC1)C(=O)OC1CN(C(C)=O)C1]

Example 74 was prepared according to General Procedure 2, using 4-(cyclohexyloxy)-2-methylene-4-oxobutanoic acid (Intermediate 6) as itaconic acid monoester and 1-(3-hydroxyazetidin-1-yl)ethanone as $R^2$—OH. $^1$H NMR (500 MHz, DMSO-d6) δ 6.28 (d, J=1.2 Hz, 1H), 5.90 (d, J=1.2 Hz, 1H), 5.20-5.11 (m, 1H), 4.70-4.62 (m, 1H), 4.52-4.41 (m, 1H), 4.20-4.09 (m, 1H), 4.06-3.93 (m, 1H), 3.79-3.68 (m, 1H), 3.38 (s, 2H), 1.80-1.70 (m, 5H), 1.65-1.58 (m, 2H), 1.49-1.12 (m, 6H). LCMS m/z 310.3 (M+H)+ (ES$^+$).

Example 75—4-cyclohexyl 1-(1-(methylsulfonyl)piperidin-4-yl) 2-methylenesuccinate

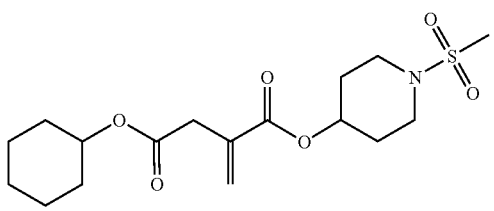 [SMILES: C=C(CC(=O)OC1CCCCC1)C(=O)OC1CCN(S(C)(=O)=O)CC1]

Example 75 was prepared according to General Procedure 2, using 4-(cyclohexyloxy)-2-methylene-4-oxobutanoic acid (Intermediate 6) as itaconic acid monoester and 1-(methylsulfonyl)piperidin-4-ol as $R^2$—OH. $^1$H NMR (500 MHz, DMSO-d6) δ 6.24 (d, J=1.3 Hz, 1H), 5.84 (d, J=1.4 Hz, 1H), 4.95-4.86 (m, 1H), 4.69-4.58 (m, 1H), 3.37 (s, 2H), 3.28-3.21 (m, 2H), 3.19-3.08 (m, 2H), 2.89 (s, 3H), 1.96-1.82 (m, 2H), 1.78-1.57 (m, 6H), 1.49-1.19 (m, 6H). LCMS m/z 395.9 (M+Na)$^+$ (ES$^+$).

Example 76—4-hexyl 1-(1-(methylsulfonyl)piperidin-4-yl) 2-methylenesuccinate

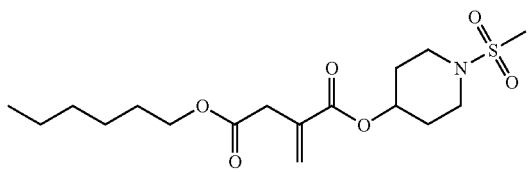 [SMILES: C=C(CC(=O)OCCCCCC)C(=O)OC1CCN(S(C)(=O)=O)CC1]

Example 76 was prepared according to General Procedure 2, using 4-(hexyloxy)-2-methylene-4-oxobutanoic acid (Intermediate 3) as itaconic acid monoester and 1-(methylsulfonyl)piperidin-4-ol as $R^2$—OH. $^1$H NMR (500 MHz, DMSO-d6) δ 6.24 (d, J=1.4 Hz, 1H), 5.84 (d, J=1.3 Hz, 1H), 4.95-4.79 (m, 1H), 4.01 (t, J=6.6 Hz, 2H), 3.38 (s, 2H), 3.27-3.10 (m, 4H), 2.88 (s, 3H), 1.97-1.84 (m, 2H), 1.73-1.60 (m, 2H), 1.58-1.44 (m, 2H), 1.37-1.17 (m, 6H), 0.86 (t, J=7.1 Hz, 3H). LCMS m/z 398.4 (M+Na)$^+$ (ES$^+$).

Example 77—4-hexyl 1-(2-(2-oxopyrrolidin-1-yl)ethyl) 2-methylenesuccinate

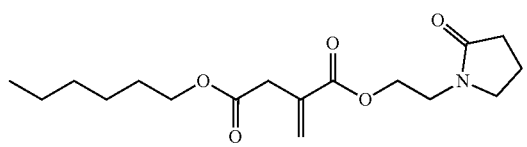 [SMILES: C=C(CC(=O)OCCCCCC)C(=O)OCCN1CCCC1=O]

Example 77 was prepared according to General Procedure 2, using 4-(hexyloxy)-2-methylene-4-oxobutanoic acid (Intermediate 3) as itaconic acid monoester and 1-(2-hydroxyethyl)pyrrolidin-2-one as $R^2$—OH. $^1$H NMR (500 MHz, DMSO-d6) δ 6.19 (d, J=1.3 Hz, 1H), 5.84 (d, J=1.3 Hz, 1H), 4.18 (t, J=5.4 Hz, 2H), 4.00 (t, J=6.6 Hz, 2H), 3.44 (t, J=5.4 Hz, 2H), 3.39-3.34 (m, 4H), 2.19 (t, J=8.1 Hz, 2H), 1.97-1.81 (m, 2H), 1.60-1.47 (m, 2H), 1.37-1.19 (m, 6H), 0.93-0.71 (m, 3H). LCMS m/z 348.3 (M+H)$^+$ (ES$^+$).

Example 78—1-(2-(1H-tetrazol-5-yl)ethyl) 4-hexyl 2-methylenesuccinate

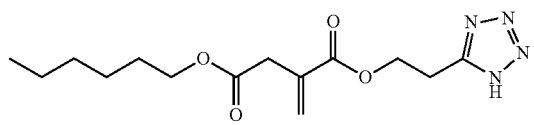 [SMILES: C=C(CC(=O)OCCCCCC)C(=O)OCCc1nnn[nH]1]

Example 78 was prepared according to General Procedure 2, using 4-(hexyloxy)-2-methylene-4-oxobutanoic acid (Intermediate 3) as itaconic acid monoester and 2-(1H-tetrazol-5-yl)ethanol as $R^2$—OH. $^1$H NMR (500 MHz, DMSO-d6) δ 6.13 (d, J=1.3 Hz, 1H), 5.81 (d, J=1.2 Hz, 1H), 4.45 (t, J=6.3 Hz, 2H), 3.94 (t, J=6.6 Hz, 2H), 3.31 (s, 2H), 3.27 (t, J=6.3 Hz, 2H), 1.59-1.47 (m, 2H), 1.30-1.21 (m, 6H), 0.90-0.83 (m, 3H) (1 exchangeable proton not seen). LCMS m/z 311.0 (M+H)$^+$ (ES$^+$).

Example 79—2-((2-methylene-4-(octyloxy)-4-oxobutanoyl)oxy)propanoic acid

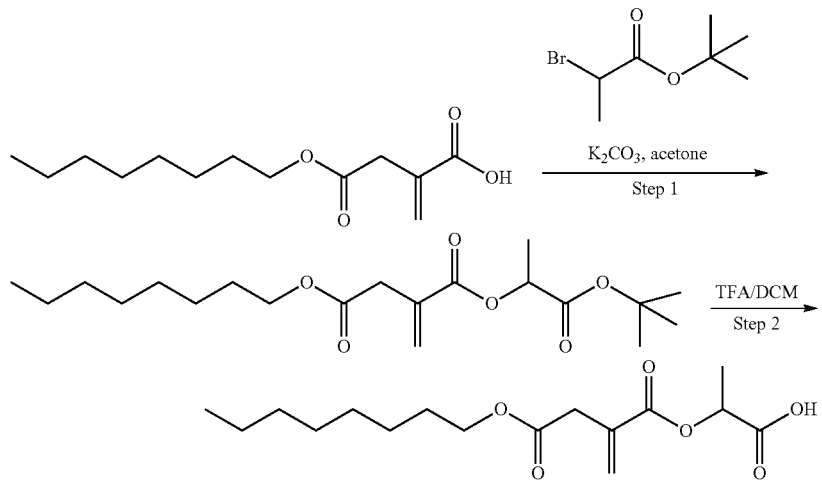

Step 1 tert-Butyl 2-bromopropanoate (1.03 g, 4.95 mmol) was added to a suspension of 4-octyl itaconate (1.00 g, 4.13 mmol) and potassium carbonate (0.696 g, 5.03 mmol) in acetone (20 mL). The reaction mixture was stirred at RT for 18 h, then heated to 50° C. and stirred for a further 5 h. The reaction mixture was diluted with ethyl acetate (40 mL), filtered and concentrated to afford 1-(1-(tert-butoxy)-1-oxopropan-2-yl) 4-octyl 2-methylenesuccinate (1.7 g, 3.07 mmol). $^1$H NMR (500 MHz, DMSO-d6) δ 6.27 (d, J=1.3 Hz, 1H), 5.95-5.88 (m, 1H), 4.88 (q, J=7.0 Hz, 1H), 4.00 (t, J=6.6 Hz, 2H), 3.41-3.32 (m, 2H), 1.59-1.51 (m, 2H), 1.43-1.35 (m, 12H), 1.32-1.18 (m, 10H), 0.89-0.84 (m, 3H). LCMS m/z 393.2 (M+Na)$^+$ (ES$^+$).

Step 2

TFA (11 mL) was added to a solution of 1-(1-(tert-butoxy)-1-oxopropan-2-yl) 4-octyl 2-methylenesuccinate (1.53 g, 4.13 mmol) in DCM (11 mL) and the mixture was stirred for 30 min at RT. The reaction was diluted with toluene (20 mL) and concentrated. The residue was dissolved in ethyl acetate (40 mL) and washed with water (10×25 mL). The organic phase was dried (MgSO$_4$) and concentrated to afford the title compound (1.00 g, 3.15 mmol) as a colourless oil. $^1$H NMR (500 MHz, DMSO-d6) δ 13.06 (s, 1H), 6.27 (d, J=1.3 Hz, 1H), 5.90 (d, J=1.3 Hz, 1H), 4.96 (q, J=7.1 Hz, 1H), 4.00 (t, J=6.6 Hz, 2H), 3.36 (s, 2H), 1.59-1.50 (m, 2H), 1.42 (d, J=7.0 Hz, 3H), 1.31-1.22 (m, 10H), 0.86 (t, J=6.8 Hz, 3H). LCMS m/z 337.2 (M+Na)$^+$ (ES$^+$).

Example 80—3-((2-methylene-4-(octyloxy)-4-oxobutanoyl)oxy)propanoic Acid

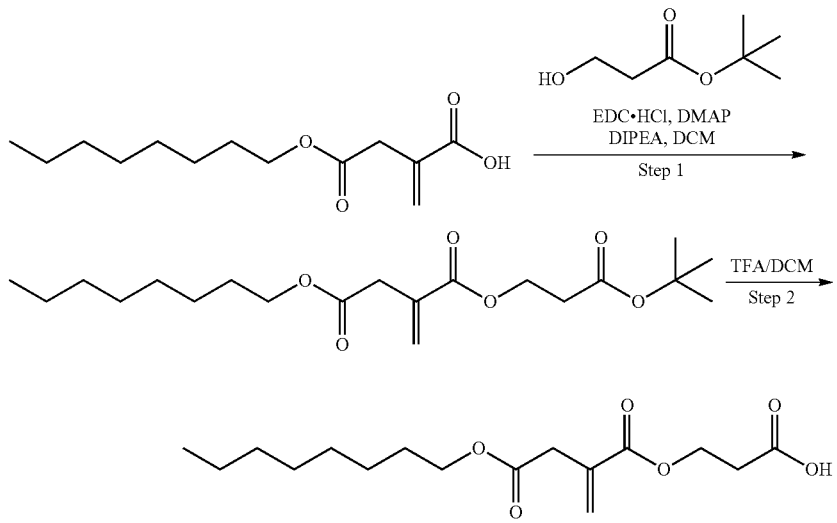

Step 1

A solution of 4-octyl itaconate (2.00 g, 8.25 mmol), tert-butyl 3-hydroxypropanoate (1.49 mL, 9.90 mmol), N-(3-dimethylaminopropyl)-N'-ethylcarbodiimide hydrochloride (3.16 g, 16.5 mmol) and DMAP (0.101 g, 0.83 mmol) in DCM (60 mL) was treated with DIPEA (2.88 mL, 16.5 mmol). The resulting solution was stirred at RT for 20 h. The reaction mixture was concentrated onto silica gel and the crude product purified by chromatography on silica gel (0-20% EtOAc/DCM or 0-20% EtOAc/DCM) to afford 1-(3-(tert-butoxy)-3-oxopropyl) 4-octyl 2-methylenesuccinate (1.56 g, 4.13 mmol) as a clear colourless oil. $^1$H NMR (500 MHz, DMSO-d6) δ 6.30 (d, J=1.0 Hz, 1H), 5.70 (d, J=1.2 Hz, 1H), 4.39 (t, J=6.5 Hz, 2H), 4.08 (t, J=6.8 Hz, 2H), 3.32 (s, 2H), 2.59 (t, J=6.5 Hz, 2H), 1.63-1.51 (m, 2H), 1.45 (s, 9H), 1.32-1.13 (m, 10H), 0.88 (t, J=6.9 Hz, 3H). LCMS m/z 392.9 (M+Na)$^+$ (ES$^+$).

Step 2

TFA (15 mL) was added to a solution of 1-(3-(tert-butoxy)-3-oxopropyl) 4-octyl 2-methylenesuccinate (1.56 g, 4.21 mmol) in DCM (15 mL) and the mixture was stirred for 2 h at RT. The reaction was diluted with toluene (50 mL) and concentrated. The residue was co-evaporated with toluene (2×20 mL) and dried in vacuo to afford the title compound (1.546 g, 4.87 mmol) as a colourless solid. $^1$H NMR (500 MHz, DMSO-d6) δ 12.37 (s, 1H), 6.16 (d, J=1.3 Hz, 1H), 5.82 (d, J=1.4 Hz, 1H), 4.25 (t, J=6.2 Hz, 2H), 4.00 (t, J=6.6 Hz, 2H), 3.32 (s, 2H), 2.59 (t, J=6.2 Hz, 2H), 1.58-1.47 (m, 2H), 1.36-1.16 (m, 10H), 0.86 (t, J=6.8 Hz, 3H). LCMS m/z 337.2 (M+Na)$^+$ (ES$^+$).

Example 81—3-((4-((4-fluorobenzyl)oxy)-2-methylene-4-oxobutanoyl)oxy)propanoic acid

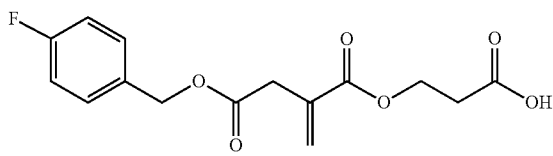 [SMILES: C=C(CC(=O)OCc1ccc(F)cc1)C(=O)OCCC(=O)O]

Example 81 was prepared according to the procedure of Example 80, but using 4-isopropoxy-2-methylene-4-oxobutanoic acid (Intermediate 7) instead of 4-octyl itaconate. $^1$H NMR (500 MHz, DMSO-d6) δ 12.39 (br s, 1H), 7.44-7.38 (m, 2H), 7.25-7.17 (m, 2H), 6.18 (d, J=1.3 Hz, 1H), 5.85 (d, J=1.3 Hz, 1H), 5.08 (s, 2H), 4.24 (t, J=6.2 Hz, 2H), 3.41 (s, 2H), 2.57 (t, J=6.2 Hz, 2H). LCMS m/z 333.3 (M+Na)$^+$ (ES$^+$).

Example 82—3-((4-(cyclooctyloxy)-2-methylene-4-oxobutanoyl)oxy)propanoic acid

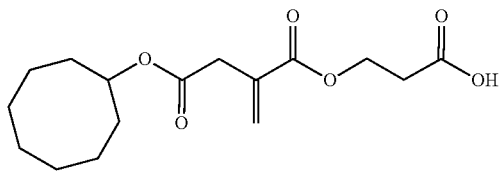 [SMILES: C=C(CC(=O)OC1CCCCCCC1)C(=O)OCCC(=O)O]

Example 82 was prepared according to the procedure of Example 80, but using 4-(cyclooctyloxy)-2-methylene-4-oxobutanoic acid (Intermediate 1) instead of 4-octyl itaconate. $^1$H NMR (500 MHz, DMSO-d6) δ 12.39 (s, 1H), 6.15 (d, J=1.4 Hz, 1H), 5.85-5.74 (m, 1H), 4.83 (tt, J=8.1, 3.9 Hz, 1H), 4.26 (t, J=6.2 Hz, 2H), 3.30 (s, 2H), 2.60 (t, J=6.2 Hz, 2H), 1.77-1.41 (m, 14H). LCMS m/z 335.3 (M+Na)$^+$ (ES$^+$).

Example 83—3-((2-methylene-4-(neopentyloxy)-4-oxobutanoyl)oxy)propanoic acid

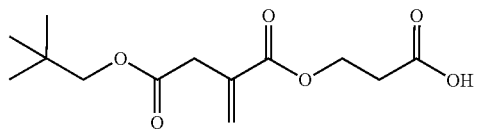 [SMILES: C=C(CC(=O)OCC(C)(C)C)C(=O)OCCC(=O)O]

Example 83 was prepared according to the procedure of Example 80, but using 2-methylene-4-(neopentyloxy)-4-oxobutanoic acid (Intermediate 10) instead of 4-octyl itaconate. $^1$H NMR (400 MHz, DMSO-d6) δ 12.38 (s, 1H), 6.18 (d, J=1.4 Hz, 1H), 5.88-5.82 (m, 1H), 4.26 (t, J=6.2 Hz, 2H), 3.72 (s, 2H), 3.38 (s, 2H), 2.59 (t, J=6.2 Hz, 2H), 0.88 (s, 9H). LCMS m/z 295.7 (M+Na)+(ES$^+$).

Example 84—(S)-3-((2-methylene-4-(octan-2-yloxy)-4-oxobutanoyl)oxy)propanoic acid

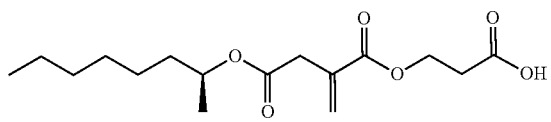 [SMILES: C=C(CC(=O)O[C@@H](C)CCCCCC)C(=O)OCCC(=O)O]

Example 84 was prepared according to the procedure of Example 80, but using S)-2-methylene-4-(octan-2-yloxy)-4-oxobutanoic acid (Intermediate 9) instead of 4-octyl itaconate. $^1$H NMR (400 MHz, DMSO-d6) δ 12.39 (s, 1H), 6.15 (d, J=1.3 Hz, 1H), 5.81 (d, J=1.3 Hz, 1H), 4.84-4.70 (m, 1H), 4.25 (t, J=6.2 Hz, 2H), 3.30 (s, 2H), 2.59 (t, J=6.2 Hz, 2H), 1.54-1.37 (m, 2H), 1.25 (dd, J=10.7, 5.2 Hz, 8H), 1.13 (d, J=6.2 Hz, 3H), 0.85 (t, J=6.4 Hz, 3H). LCMS m/z 336.9 (M+Na)$^+$ (ES$^+$).

Example 85—3-((4-(hexyloxy)-2-methylene-4-oxobutanoyl)oxy)propanoic acid

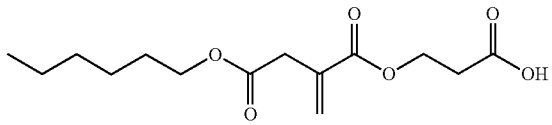 [SMILES: C=C(CC(=O)OCCCCCC)C(=O)OCCC(=O)O]

Example 85 was prepared according to the procedure of Example 80, but using 4-(hexyloxy)-2-methylene-4-oxobutanoic acid (Intermediate 3) instead of 4-octyl itaconate. $^1$H NMR (400 MHz, DMSO-d6) δ 12.39 (s, 1H), 6.16 (d, J=1.4 Hz, 1H), 5.82 (d, J=1.3 Hz, 1H), 4.25 (t, J=6.2 Hz, 2H), 4.00 (t, J=6.6 Hz, 2H), 3.33 (s, 2H), 2.59 (t, J=6.2 Hz, 2H), 1.61-1.47 (m, 2H), 1.32-1.19 (m, 6H), 0.93-0.78 (m, 3H). LCMS m/z 309.7 (M+Na)$^+$ (ES$^+$).

Example 86—3-((2-methylene-4-oxo-4-(3-phenoxy-propoxy)butanoyl)oxy)propanoic acid

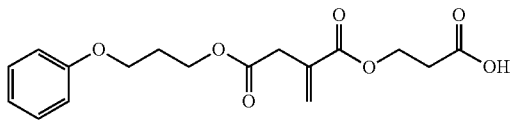 [SMILES: C=C(CC(=O)OCCCOc1ccccc1)C(=O)OCCC(=O)O]

Example 86 was prepared according to the procedure of Example 80, but using 2-methylene-4-oxo-4-(3-phenoxypropoxy)butanoic acid (Intermediate 2) instead of 4-octyl itaconate. $^1$H NMR (400 MHz, DMSO-d6) δ 12.41 (s, 1H), 7.35-7.24 (m, 2H), 6.99-6.88 (m, 3H), 6.17 (d, J=1.3 Hz, 1H), 5.83 (q, J=1.2 Hz, 1H), 4.24 (t, J=6.2 Hz, 2H), 4.19 (t, J=6.4 Hz, 2H), 4.01 (t, J=6.3 Hz, 2H), 3.37 (s, 2H), 2.58 (t, J=6.2 Hz, 2H), 2.06-1.97 (m, 2H). LCMS m/z 359.3 (M+Na)+(ES$^+$).

Example 87—3-((4-(cyclohexyloxy)-2-methylene-4-oxobutanoyl)oxy)propanoic acid

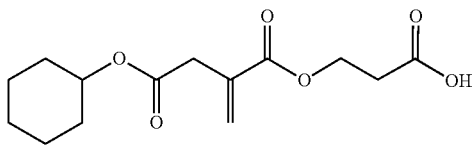 [SMILES: C=C(CC(=O)OC1CCCCC1)C(=O)OCCC(=O)O]

Example 87 was prepared according to the procedure of Example 80, but using 4-(cyclohexyloxy)-2-methylene-4-oxobutanoic acid (Intermediate 6) instead of 4-octyl itaconate. $^1$H NMR (400 MHz, DMSO-d6) δ 12.40 (s, 1H), 6.15 (d, J=1.4 Hz, 1H), 5.81 (d, J=1.3 Hz, 1H), 4.70-4.59 (m, 1H), 4.25 (t, J=6.2 Hz, 2H), 3.31 (s, 2H), 2.59 (t, J=6.2 Hz, 2H), 1.77-1.70 (m, 2H), 1.65-1.55 (m, 2H), 1.49-1.16 (m, 6H). LCMS m/z 307.4 (M+Na)$^+$ (ES$^+$).

Example 88—(R)-3-((2-methylene-4-(octan-2-yloxy)-4-oxobutanoyl)oxy)propanoic acid

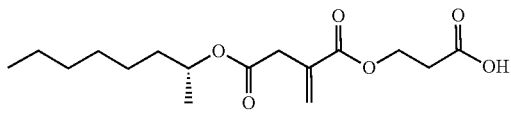 [SMILES: C=C(CC(=O)O[C@H](C)CCCCCC)C(=O)OCCC(=O)O]

Example 88 was prepared according to the procedure of Example 80, but using (R)-2-methylene-4-(octan-2-yloxy)-4-oxobutanoic acid (Intermediate 8) instead of 4-octyl itaconate. $^1$H NMR (400 MHz, DMSO-d6) δ 12.38 (s, 1H), 6.15 (d, J=1.4 Hz, 1H), 5.81 (d, J=1.4 Hz, 1H), 4.83-4.72 (m, 1H), 4.25 (t, J=6.2 Hz, 2H), 3.30 (s, 2H), 2.59 (t, J=6.3 Hz, 2H), 1.54-1.39 (m, 2H), 1.29-1.16 (m, 8H), 1.13 (d, J=6.3 Hz, 3H), 0.85 (t, J=6.4 Hz, 3H). LCMS m/z 337.4 (M+Na)$^+$ (ES$^+$).

Example 89—(S)-2-((2-methylene-4-(octan-2-yloxy)-4-oxobutanoyl)oxy)acetic acid

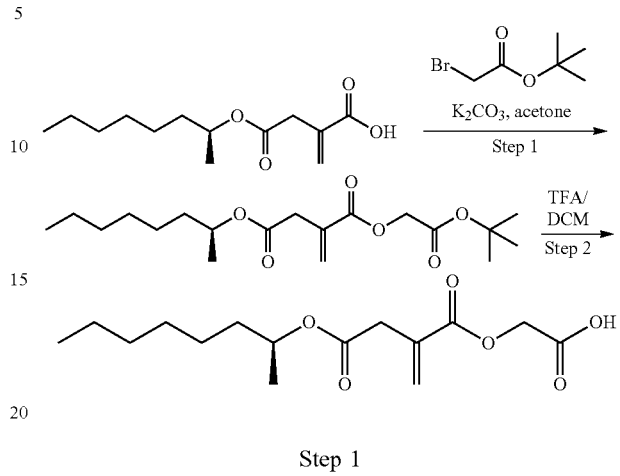

Step 1

A mixture of (S)-2-methylene-4-(octan-2-yloxy)-4-oxobutanoic acid (Intermediate 9, 1 g, 4.13 mmol), tert-butyl bromoacetate (0.64 mL, 4.3 mmol) and potassium carbonate (0.684 g, 4.95 mmol) in acetone (20 mL) was stirred at RT overnight. The reaction mixture was concentrated and the residue was partitioned between water (20 mL) and EtOAc (10 mL). The phases were separated and the aqueous phase was extracted with EtOAc (10 mL). The combined organic phases were washed with brine (10 mL), dried (MgSO$_4$) and concentrated to afford (S)-1-(2-(tert-butoxy)-2-oxoethyl) 4-octan-2-yl 2-methylenesuccinate (1.56 g, 4.07 mmol) as a colourless oil. $^1$H NMR (500 MHz, DMSO-d6) δ 6.28 (s, 1H), 5.92 (s, 1H), 4.82-4.75 (m, 1H), 4.60 (s, 2H), 3.35 (s, 2H), 1.42 (s, 9H), 1.31-1.20 (m, 10H), 1.14 (d, J=6.3 Hz, 3H), 0.88-0.84 (m, 3H).

Step 2

TFA (7.5 mL) was added to a solution of (S)-1-(2-(tert-butoxy)-2-oxoethyl) 4-octan-2-yl 2-methylenesuccinate (1.5 g, 3.79 mmol) in DCM (7.5 mL). The reaction mixture was stirred for 2 h, partitioned between EtOAc (50 mL) and water (50 mL) and the phases separated. The organic phase was washed with water (2×20 mL), brine (20 mL), dried (MgSO$_4$) and concentrated. The residue was redissolved in DCM (10 mL), washed with water (2×10 mL), dried (MgSO$_4$) and concentrated to afford the title compound (0.922 g, 3.04 mmol) as a colourless oil. $^1$H NMR (500 MHz, DMSO-d6) δ 13.08 (br. s, 1H), 6.28 (d, J=1.2 Hz, 1H), 5.92 (d, J=1.3 Hz, 1H), 4.83-4.74 (m, 1H), 4.64 (s, 2H), 3.35 (s, 2H), 1.55-1.40 (m, 2H), 1.31-1.18 (m, 8H), 1.14 (d, J=6.2 Hz, 3H), 0.86 (t, J=6.9 Hz, 3H). LCMS m/z 323.2 (M+H)$^+$ (ES$^+$).

Example 90—2-((4-(cyclooctyloxy)-2-methylene-4-oxobutanoyl)oxy)acetic acid

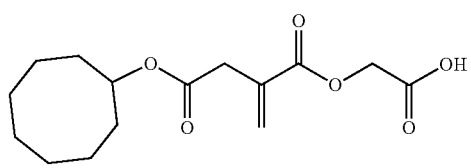 [SMILES: C=C(CC(=O)OC1CCCCCCC1)C(=O)OCC(=O)O]

Example 90 was prepared according to the procedure of Example 89, but using 4-(cyclooctyloxy)-2-methylene-4-oxobutanoic acid (Intermediate 1) instead of (S)-2-methylene-4-(octan-2-yloxy)-4-oxobutanoic acid. ¹H NMR (500 MHz, DMSO-d6) δ 13.11 (s, 1H), 6.27 (d, J=1.2 Hz, 1H), 5.91 (d, J=1.4 Hz, 1H), 4.82 (tt, J=8.1, 3.9 Hz, 1H), 4.63 (s, 2H), 3.33 (s, 2H), 1.75-1.42 (m, 14H). LCMS m/z 321.3 (M+Na)⁺ (ES⁺).

Example 91—2-((4-(cyclohexyloxy)-2-methylene-4-oxobutanoyl)oxy)acetic acid

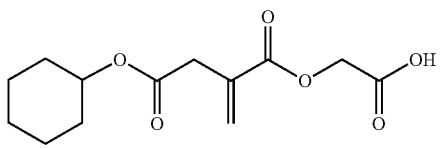 [SMILES: C=C(CC(=O)OC1CCCCC1)C(=O)OCC(=O)O]

Example 91 was prepared according to the procedure of Example 89, but using 4-(cyclohexyloxy)-2-methylene-4-oxobutanoic acid (Intermediate 6) instead of (S)-2-methylene-4-(octan-2-yloxy)-4-oxobutanoic acid. ¹H NMR (500 MHz, DMSO-d6) δ 13.09 (s, 1H), 6.27 (d, J=1.3 Hz, 1H), 5.91 (d, J=1.3 Hz, 1H), 4.68-4.59 (m, 3H), 3.35 (s, 2H), 1.77-1.70 (m, 2H), 1.65-1.58 (m, 2H), 1.50-1.17 (m, 6H). LCMS m/z 293.6 (M+Na)⁺ (ES⁺).

Example 92—2-((2-methylene-4-(neopentyloxy)-4-oxobutanoyl)oxy)acetic acid

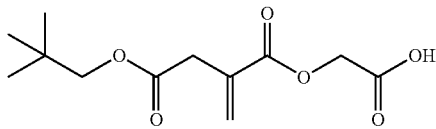 [SMILES: C=C(CC(=O)OCC(C)(C)C)C(=O)OCC(=O)O]

Example 92 was prepared according to the procedure of Example 89, but using 2-methylene-4-(neopentyloxy)-4-oxobutanoic acid (Intermediate 10) instead of (S)-2-methylene-4-(octan-2-yloxy)-4-oxobutanoic acid. ¹H NMR (500 MHz, DMSO-d6) δ 13.08 (s, 1H), 6.30 (d, J=1.2 Hz, 1H), 5.95 (d, J=1.2 Hz, 1H), 4.64 (s, 2H), 3.73 (s, 2H), 3.42 (s, 2H), 0.88 (s, 9H). LCMS m/z 280.7 (M+Na)⁺ (ES⁺).

Example 93—2-((4-((4-fluorobenzyl)oxy)-2-methylene-4-oxobutanoyl)oxy)acetic acid

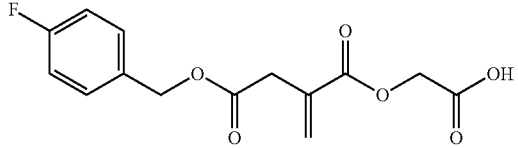 [SMILES: C=C(CC(=O)OCc1ccc(F)cc1)C(=O)OCC(=O)O]

Example 93 was prepared according to the procedure of Example 89, but using 4-isopropoxy-2-methylene-4-oxobutanoic acid (Intermediate 7) instead of (S)-2-methylene-4-(octan-2-yloxy)-4-oxobutanoic acid. ¹H NMR (400 MHz, DMSO-d6) δ 13.10 (br. s, 1H), 7.44-7.37 (m, 2H), 7.25-7.17 (m, 2H), 6.30 (d, J=1.2 Hz, 1H), 5.95 (d, J=1.2 Hz, 1H), 5.09 (s, 2H), 4.63 (s, 2H), 3.45 (s, 2H). LCMS m/z 297.3 (M+H)⁺ (ES⁺).

Example 94—2-((4-(hexyloxy)-2-methylene-4-oxobutanoyl)oxy)acetic acid

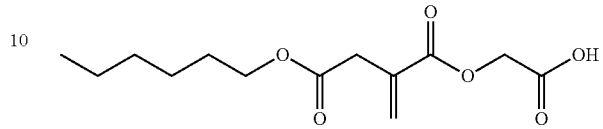

Example 94 was prepared according to the procedure of Example 89, but using 4-(hexyloxy)-2-methylene-4-oxobutanoic acid (Intermediate 3) instead of (S)-2-methylene-4-(octan-2-yloxy)-4-oxobutanoic acid. ¹H NMR (400 MHz, DMSO-d6) δ 13.10 (s, 1H), 6.28 (d, J=1.2 Hz, 1H), 5.92 (d, J=1.2 Hz, 1H), 4.63 (s, 2H), 4.00 (t, J=6.6 Hz, 2H), 3.37 (s, 2H), 1.58-1.42 (m, 2H), 1.31-1.11 (m, 6H), 0.86 (t, J=6.8 Hz, 3H). LCMS m/z 295.3 (M+Na)⁺ (ES⁺).

Example 95—2-((2-methylene-4-oxo-4-(3-phenoxypropoxy)butanoyl)oxy)acetic acid

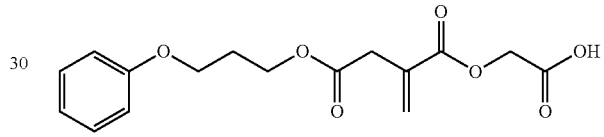

Example 95 was prepared according to the procedure of Example 89, but using 2-methylene-4-oxo-4-(3-phenoxypropoxy)butanoic acid (Intermediate 2) instead of (S)-2-methylene-4-(octan-2-yloxy)-4-oxobutanoic acid. ¹H NMR (400 MHz, DMSO-d6) δ 13.09 (s, 1H), 7.33-7.25 (m, 2H), 6.98-6.90 (m, 3H), 6.29 (d, J=1.2 Hz, 1H), 5.97-5.90 (m, 1H), 4.62 (s, 2H), 4.19 (t, J=6.4 Hz, 2H), 4.01 (t, J=6.3 Hz, 2H), 3.41 (s, 2H), 2.07-1.97 (m, 2H). LCMS m/z 345.3 (M+Na)⁺ (ES⁺).

Example 96—2-((2-methylene-4-oxo-4-(spiro[3.3]heptan-2-yloxy)butanoyl)oxy)acetic acid

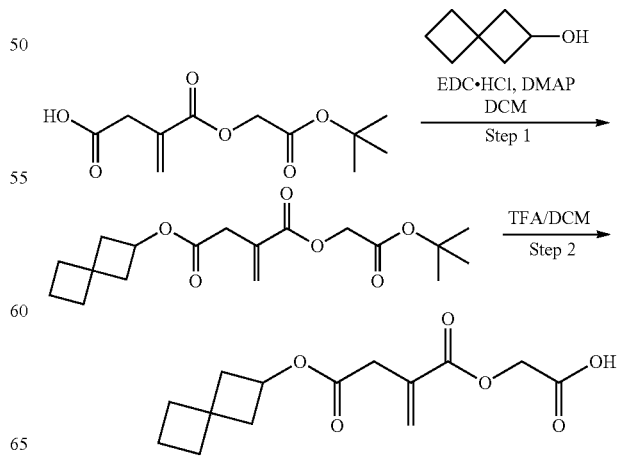

Step 1

N-(3-dimethylaminopropyl)-N'-ethylcarbodiimide hydrochloride (0.471 g, 2.46 mmol) was added to a solution of 3-((2-(tert-butoxy)-2-oxoethoxy)carbonyl)but-3-enoic acid (Intermediate 11, 0.400 g, 1.64 mmol), spiro[3.3]heptan-2-ol (0.220 g, 1.97 mmol) and DMAP (0.300 g, 2.46 mmol) in DCM (10 mL). The reaction mixture was stirred at RT for 18 h. The reaction mixture was concentrated and the crude product was purified by chromatography on silica gel (0-10% EtOAc/DCM) to afford impure product. The crude product was purified by chromatography on silica gel (0-10% EtOAc/isohexane) to afford 1-(2-(tert-butoxy)-2-oxoethyl) 4-spiro[3.3]heptan-2-yl 2-methylenesuccinate (146 mg, 0.41 mmol) as a pale yellow oil.

Step 2

TFA (1 mL) was added to a solution of 1-(2-(tert-butoxy)-2-oxoethyl) 4-spiro[3.3]heptan-2-yl 2-methylenesuccinate (146 mg, 0.41 mmol) in DCM (1 mL). The reaction mixture was stirred for 1 h, diluted with toluene (5 mL) and concentrated. The residue was taken up in EtOAc (10 mL), washed with brine (10 mL), dried (MgSO4) and concentrated to afford the title compound (90 mg, 0.316 mmol) as a colourless oil. $^1$H NMR (400 MHz, DMSO-d6) δ 13.08 (br. s, 1H), 6.28 (d, J=1.2 Hz, 1H), 5.91 (d, J=1.2 Hz, 1H), 4.82-4.73 (m, 1H), 4.64 (s, 2H), 3.34 (s, 2H), 2.43-2.34 (m, 2H), 2.02-1.90 (m, 6H), 1.85-1.74 (m, 2H). LCMS m/z 305.3 (M+Na)$^+$ (ES$^+$).

Example 97—2-((2-methylene-4-oxo-4-(2-tosylethoxy)butanoyl)oxy)acetic acid

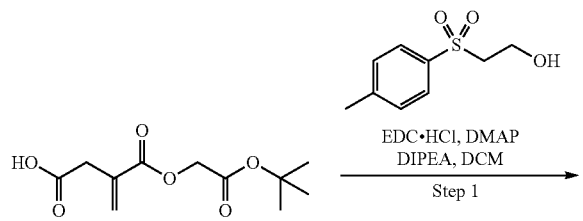

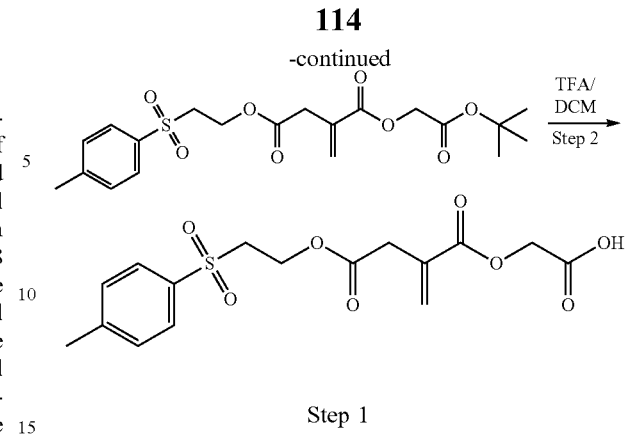

Step 1

N-(3-dimethylaminopropyl)-N'-ethylcarbodiimide hydrochloride (0.447 g, 2.33 mmol) was added to a solution of 3-((2-(tert-butoxy)-2-oxoethoxy)carbonyl)but-3-enoic acid (Intermediate 11, 0.475 g, 1.95 mmol) in DCM (8 mL) 2-tosylethanol (0.47 g, 2.33 mmol), DMAP (0.024 g, 0.19 mmol) followed by DIPEA (0.41 mL, 2.33 mmol). The reaction mixture was stirred for 16 h at RT, then concentrated. The crude product was purified by chromatography on silica gel (0-10% EtOAc: DCM) to afford impure product. The crude material was purified by chromatography on RP Flash C18 (0-100% MeCN/Water 0.1% Formic Acid) to afford 1-(2-(tert-butoxy)-2-oxoethyl) 4-(2-tosylethyl) 2-methylenesuccinate (0.116 g, 0.26 mmol) as a clear colourless oil. $^1$H NMR (400 MHz, DMSO-d6) δ 7.82-7.76 (m, 2H), 7.50-7.44 (m, 2H), 6.26 (d, J=1.1 Hz, 1H), 5.84 (d, J=1.2 Hz, 1H), 4.61 (s, 2H), 4.26 (t, J=5.9 Hz, 2H), 3.67 (t, J=5.9 Hz, 2H), 3.12 (s, 2H), 2.43 (s, 3H), 1.41 (s, 9H). LCMS m/z 449.3 (M+Na)$^+$ (ES$^+$).

Step 2

TFA (0.75 mL) was added to a solution of 1-(2-(tert-butoxy)-2-oxoethyl) 4-(2-tosylethyl) 2-methylenesuccinate (0.116 g, 0.27 mmol) in DCM (0.75 mL). The reaction mixture was stirred for 2 h, diluted with toluene (10 mL) and concentrated. The residue was co-evaporated with toluene (2×10 mL) to afford the title compound (0.054 g, 0.14 mmol) as a colourless oil. $^1$H NMR (400 MHz, DMSO-d6) δ 13.10 (s, 1H), 7.82-7.75 (m, 2H), 7.50-7.45 (m, 2H), 6.25 (d, J=1.1 Hz, 1H), 5.83 (d, J=1.2 Hz, 1H), 4.64 (s, 2H), 4.26 (t, J=5.9 Hz, 2H), 3.68 (t, J=5.9 Hz, 2H), 3.12 (s, 2H), 2.43 (s, 3H). LCMS m/z 393.3 (M+Na)$^+$ (ES$^+$).

Example 98—2—(N-methyl-2-((2-methylene-4-(octyloxy)-4-oxobutanoyl)oxy)acetamido)acetic acid

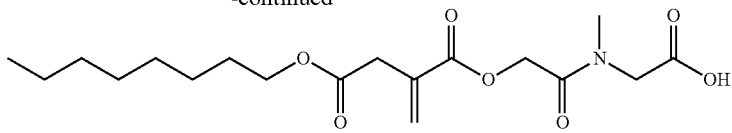

Step 1

HATU (0.209 g, 0.55 mmol) was added to a mixture of 2-((2-methylene-4-(octyloxy)-4-oxobutanoyl)oxy)acetic acid (Example 49, 0.15 g, 0.50 mmol), tert-butyl 2-(methylamino)acetate hydrochloride (0.100 g, 0.549 mmol) and N-methylmorpholine (0.15 mL, 1.36 mmol) in dimethylformamide (2.5 mL). The mixture was stirred for 2 h, then 1M HCl (10 mL) was added. The mixture was extracted with EtOAc (2×10 mL). The combined organic phases were washed with brine (2×20 mL), dried (MgSO$_4$) and concentrated. The crude product was purified by chromatography on silica gel (0-5% MeOH/DCM) to afford 1-(2-((2-(tert-butoxy)-2-oxoethyl)(methyl)amino)-2-oxoethyl) 4-octyl 2-methylenesuccinate (184 mg, 0.43 mmol) as a pale yellow oil. $^1$H NMR (500 MHz, DMSO-d6) δ 6.29 (d, J=1.2 Hz, 1H), 5.93-5.90 (m, 1H), 5.21-5.15 (m, 1H), 4.47 (ddd, J=9.8, 6.7, 1.4 Hz, 1H), 4.17 (ddd, J=10.7, 6.9, 1.4 Hz, 1H), 4.05-3.99 (m, 3H), 3.74 (dd, J=10.8, 4.0 Hz, 1H), 3.40 (s, 2H), 1.77 (s, 3H), 1.58-1.50 (m, 2H), 1.32-1.21 (m, 10H), 0.90-0.84 (m, 3H). LCMS m/z 450.1 (M+Na)$^+$ (ES$^+$).

Step 2

TFA (1 mL, 13 mmol) was added to a solution of 1-(2-((2-(tert-butoxy)-2-oxoethyl)(methyl)amino)-2-oxoethyl) 4-octyl 2-methylenesuccinate (184 mg, 0.43 mmol) in DCM (1 mL). The reaction mixture was stirred for 2 h, diluted with toluene (10 mL) and concentrated. The residue was co-evaporated with toluene (2×5 mL) and dried in vacuo to afford 2-(N-methyl-2-((2-methylene-4-(octyloxy)-4-oxobutanoyl)oxy)acetamido)acetic acid (123 mg, 0.33 mmol) as a colourless oil. $^1$H NMR (500 MHz, DMSO-d6, 373 K) δ 12.37 (br. s, 1H), 6.28 (s, 1H), 5.86 (t, J=1.2 Hz, 1H), 4.86 (br m, 2H), 4.12-3.96 (m, 4H), 3.36 (s, 2H), 3.01 (br. m, 3H), 1.65-1.53 (m, 2H), 1.38-1.23 (m, 10H), 0.89 (t, J=6.8 Hz, 3H). LCMS m/z 372.2 (M+H)$^+$ (ES$^+$).

Example 99—(2-((2-methylene-4-(octyloxy)-4-oxobutanoyl)oxy)acetyl)-L-proline

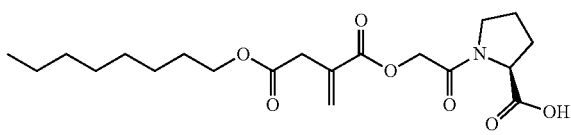

Example 99 was prepared according to the procedure described in Example 98, but using L-proline tert-butyl ester instead of tert-butyl 2-(methylamino)acetate hydrochloride. $^1$H NMR (500 MHz, DMSO-d6) δ 12.55 (br. s, 1H), 6.29-6.25 (m, 1H), 5.93-5.87 (m, 1H), 4.90-4.76 (m, 2H), 4.58-4.20 (m, 1H), 4.01 (t, J=6.6 Hz, 2H), 3.58-3.36 (m, 4H), 2.27-2.08 (m, 1H), 1.97-1.65 (m, 3H), 1.60-1.50 (m, 2H), 1.34-1.21 (m, 10H), 0.91-0.81 (m, 3H). LCMS m/z 398.2 (M+H)+ (ES$^+$).

Example 100—N-methyl-N-(2-((2-methylene-4-(octyloxy)-4-oxobutanoyl)oxy)propanoyl)glycine

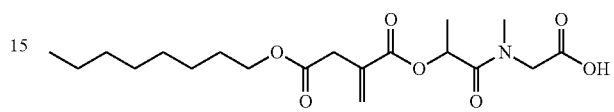

Example 100 was prepared using the same procedure as described in Example 98, but using 2-((2-methylene-4-(octyloxy)-4-oxobutanoyl)oxy)propanoic acid (Example 79) instead of 2-((2-methylene-4-(octyloxy)-4-oxobutanoyl)oxy)acetic acid. $^1$H NMR (500 MHz, DMSO-d6, 363 K) δ 12.30 (br. s, 1H), 6.25 (s, 1H), 5.88-5.80 (m, 1H), 5.49 (s, 1H), 4.18-3.80 (m, 4H), 2.89 (s, 5H), 1.65-1.52 (m, 2H), 1.40-1.27 (m, 13H), 0.92-0.85 (m, 3H). LCMS m/z 386.2 (M+H)$^+$ (ES$^+$).

Example 101—(2-((2-methylene-4-(octyloxy)-4-oxobutanoyl)oxy)propanoyl)-L-proline

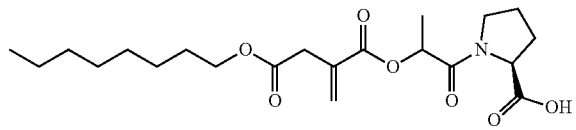 [SMILES: C=C(CC(=O)OCCCCCCCC)C(=O)OC(C)C(=O)N1CCC[C@H]1C(=O)O]

Example 101 was prepared using the same procedure as described in Example 98, but using 2-((2-methylene-4-(octyloxy)-4-oxobutanoyl)oxy)propanoic acid (Example 79) instead of 2-((2-methylene-4-(octyloxy)-4-oxobutanoyl)oxy)acetic acid, and using L-proline tert-butyl ester instead of tert-butyl 2-(methylamino)acetate hydrochloride. $^1$H NMR (500 MHz, DMSO-d6) δ 12.42 (br. s, 1H), 6.28-6.22 (m, 1H), 5.92-5.86 (m, 1H), 5.37-4.61 (m, 1H), 4.27-4.17 (m, 1H), 4.05-3.96 (m, 2H), 3.67-3.39 (m, 2H), 3.36 (s, 1H), 2.24-2.06 (m, 1H), 2.05-1.66 (m, 3H), 1.60-1.48 (m, 2H), 1.37-1.21 (m, 14H), 0.92-0.82 (m, 3H). LCMS m/z 412.3 (M+H)$^+$ (ES$^+$).

Example 102—(2-((2-methylene-4-(octyloxy)-4-oxobutanoyl)oxy)propanoyl)glycine

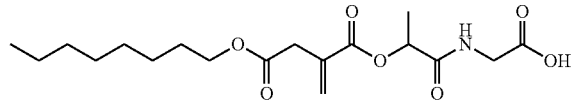 [SMILES: C=C(CC(=O)OCCCCCCCC)C(=O)OC(C)C(=O)NCC(=O)O]

Example 102 was prepared using the same procedure as described in Example 98, but using 2-((2-methylene-4-(octyloxy)-4-oxobutanoyl)oxy)propanoic acid (Example 79) instead of 2-((2-methylene-4-(octyloxy)-4-oxobutanoyl)

oxy)acetic acid, and using glycine tert-butyl ester instead of tert-butyl 2-(methylamino)acetate hydrochloride. ¹H NMR (500 MHz, DMSO-d6) δ 12.57 (s, 1H), 8.25 (t, J=5.9 Hz, 1H), 6.32 (d, J=1.2 Hz, 1H), 5.89 (d, J=1.3 Hz, 1H), 5.07 (q, J=6.8 Hz, 1H), 4.01 (td, J=6.6, 1.6 Hz, 2H), 3.82-3.71 (m, 2H), 3.46-3.35 (m, 2H), 1.59-1.50 (m, 2H), 1.36 (d, J=6.8 Hz, 3H), 1.30-1.22 (m, 10H), 0.86 (t, J=6.8 Hz, 3H). LCMS m/z 372.4 (M+H)+ (ES+).

Example 103—N-(2-((4-(cyclooctyloxy)-2-methylene-4-oxobutanoyl)oxy)acetyl)-N-methylglycine

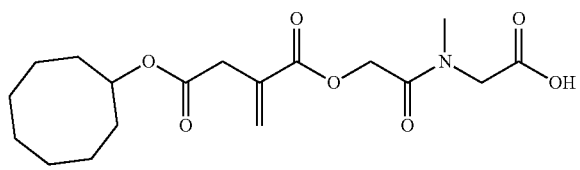 [SMILES: C=C(CC(=O)OC1CCCCCCC1)C(=O)OCC(=O)N(C)CC(=O)O]

Example 103 was prepared using the same procedure as described in Example 98, but using 2-((4-(cyclooctyloxy)-2-methylene-4-oxobutanoyl)oxy)acetic acid (Example 90) instead of 2-((2-methylene-4-(octyloxy)-4-oxobutanoyl)oxy)acetic acid. ¹H NMR (500 MHz, DMSO-d6, 363 K) δ 12.70 (s, 1H), 6.27-6.23 (m, 1H), 5.89-5.83 (m, 1H), 4.94-4.75 (m, 3H), 4.15-3.96 (m, 2H), 3.33 (s, 2H), 3.01-2.79 (m, 3H), 1.77-1.40 (m, 14H). LCMS m/z 392.2 (M+H)+ (ES+).

Example 104—(2-((4-(cyclooctyloxy)-2-methylene-4-oxobutanoyl)oxy)acetyl)-L-proline

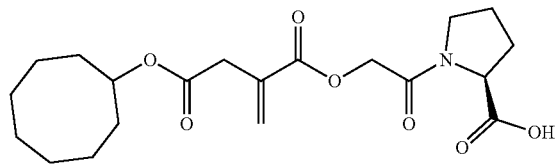 [SMILES: C=C(CC(=O)OC1CCCCCCC1)C(=O)OCC(=O)N1CCC[C@H]1C(=O)O]

Example 104 was prepared using the same procedure as described in Example 98, but using 2-((4-(cyclooctyloxy)-2-methylene-4-oxobutanoyl)oxy)acetic acid (Example 90) instead of 2-((2-methylene-4-(octyloxy)-4-oxobutanoyl)oxy)acetic acid, and using L-proline tert-butyl ester instead of tert-butyl 2-(methylamino)acetate hydrochloride. ¹H NMR (500 MHz, DMSO-d6, 363 K) δ 12.47 (s, 1H), 6.27-6.23 (m, 1H), 5.91-5.84 (m, 1H), 4.91-4.57 (m, 3H), 4.54-4.17 (m, 1H), 3.57-3.36 (m, 3H), 2.23-1.80 (m, 5H), 1.76-1.43 (m, 14H). LCMS m/z 418.2 (M+Na)+ (ES+).

Example 105—(S)—N-methyl-N-(2-((2-methylene-4-(octan-2-yloxy)-4-oxobutanoyl)oxy)acetyl)glycine

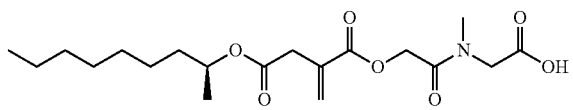 [SMILES: C=C(CC(=O)O[C@@H](C)CCCCCCC)C(=O)OCC(=O)N(C)CC(=O)O]

Example 105 was prepared using the same procedure as described in Example 98, but using (S)-2-((2-methylene-4-(octan-2-yloxy)-4-oxobutanoyl)oxy)acetic acid (Example 89) instead of 2-((2-methylene-4-(octyloxy)-4-oxobutanoyl)oxy)acetic acid. ¹H NMR (500 MHz, DMSO-d6, 363 K) δ 6.28 (s, 1H), 5.85 (d, J=1.3 Hz, 1H), 4.93-4.74 (br. m, 3H), 4.03 (br. s, 2H), 3.33 (s, 2H), 3.08-2.83 (br. m, 3H), 1.59-1.43 (m, 2H), 1.35-1.24 (m, 8H), 1.17 (d, J=6.3 Hz, 3H), 0.89 (t, J=6.7 Hz, 3H), 1 exchangeable proton not visible. LCMS m/z 394.4 (M+Na)+ (ES+).

Example 106—(S)-(2-((2-methylene-4-(octan-2-yloxy)-4-oxobutanoyl)oxy)acetyl)glycine

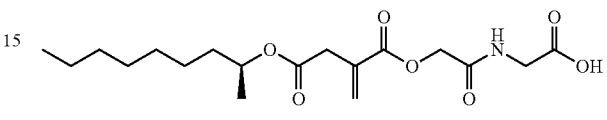

Example 106 was prepared using the same procedure as described in Example 98, but using (S)-2-((2-methylene-4-(octan-2-yloxy)-4-oxobutanoyl)oxy)acetic acid (Example 89) instead of 2-((2-methylene-4-(octyloxy)-4-oxobutanoyl)oxy)acetic acid, and using glycine tert-butyl ester instead of tert-butyl 2-(methylamino)acetate hydrochloride. ¹H NMR (500 MHz, DMSO-d6) δ 8.30 (t, J=5.7 Hz, 1H), 6.34 (d, J=1.2 Hz, 1H), 5.91 (d, J=1.4 Hz, 1H), 4.84-4.74 (m, 1H), 4.59 (s, 2H), 3.80 (d, J=5.8 Hz, 2H), 3.38 (s, 2H), 1.56-1.39 (m, 2H), 1.25 (d, J=10.8 Hz, 8H), 1.14 (d, J=6.2 Hz, 3H), 0.86 (t, J=6.8 Hz, 3H), 1 exchangeable proton not visible. LCMS m/z 380.3 (M+Na)+(ES+).

Example 107—1-(2-(4-methylpiperazin-1-yl)-2-oxoethyl) 4-octyl 2-methylenesuccinate

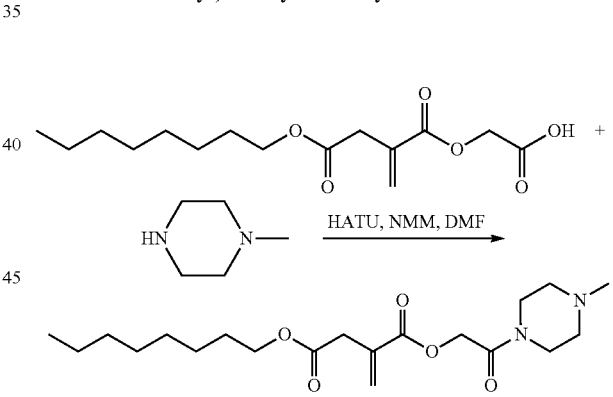

HATU (0.139 g, 0.37 mmol) was added to a mixture of 2-((2-methylene-4-(octyloxy)-4-oxobutanoyl)oxy)acetic acid (Example 49, 0.10 g, 0.33 mmol), 1-methylpiperazine (0.041 mL, 0.37 mmol) and N-methylmorpholine (0.1 mL, 0.91 mmol) in dimethylformamide (2.5 mL). The mixture was stirred for 2 h, then sat. aq. NH₄Cl (10 mL) was added. The mixture was extracted with EtOAc (2×10 mL). The combined organic phases were washed with brine (2×20 mL), dried (MgSO₄) and concentrated. The crude product was purified by chromatography on silica gel (0-10% MeOH/DCM) to afford the title compound (70 mg, 0.174 mmol) as a pale yellow oil. ¹H NMR (500 MHz, DMSO-d6) δ 6.27 (d, J=1.3 Hz, 1H), 5.90 (q, J=1.2 Hz, 1H), 4.86 (s, 2H), 4.00 (t, J=6.6 Hz, 2H), 3.46-3.34 (m, 6H), 2.34-2.24 (m, 4H), 2.19 (s, 3H), 1.59-1.51 (m, 2H), 1.26 (m, 10H), 0.89-0.83 (m, 3H). LCMS m/z 383.2 (M+H)+ (ES+).

Example 108—1-(3-morpholino-3-oxopropyl) 4-octyl 2-methylenesuccinate

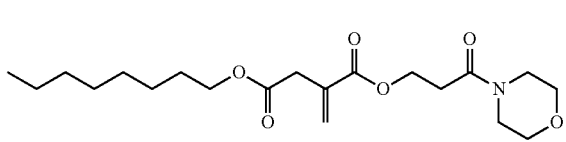 [SMILES: C=C(CC(=O)OCCCCCCCC)C(=O)OCCC(=O)N1CCOCC1]

Example 108 was prepared using the same procedure as described in Example 107, but using morpholine instead of 1-methylpiperazine. $^1$H NMR (500 MHz, DMSO-d6) δ 6.16 (d, J=1.4 Hz, 1H), 5.82 (t, J=1.3 Hz, 1H), 4.29 (t, J=6.6 Hz, 2H), 4.00 (t, J=6.6 Hz, 2H), 3.55 (dt, J=12.8, 4.9 Hz, 4H), 3.46-3.40 (m, 4H), 3.33 (s, 2H), 2.73-2.67 (m, 2H), 1.57-1.49 (m, 2H), 1.31-1.22 (m, 10H), 0.86 (t, J=6.9 Hz, 3H). LCMS m/z 384.3 (M+H)$^+$ (ES$^+$).

Example 109—1-(3-(diethylamino)-3-oxopropyl) 4-octyl 2-methylenesuccinate

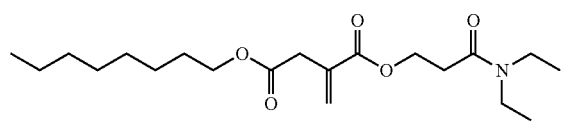 [SMILES: C=C(CC(=O)OCCCCCCCC)C(=O)OCCC(=O)N(CC)CC]

Example 109 was prepared using the same procedure as described in Example 107, but using diethylamine instead of 1-methylpiperazine. $^1$H NMR (500 MHz, DMSO-d6) δ 6.15 (d, J=1.4 Hz, 1H), 5.82 (d, J=1.4 Hz, 1H), 4.30 (t, J=6.5 Hz, 2H), 4.00 (t, J=6.6 Hz, 2H), 3.33 (s, 2H), 3.30-3.24 (m, 4H), 2.65 (t, J=6.5 Hz, 2H), 1.59-1.46 (m, 2H), 1.31-1.21 (m, 10H), 1.10 (t, J=7.1 Hz, 3H), 1.01 (t, J=7.1 Hz, 3H), 0.86 (t, J=6.8 Hz, 3H). LCMS m/z 370.3 (M+H)+ (ES$^+$).

Example 110—1-(3-(methylamino)-3-oxopropyl) 4-octyl 2-methylenesuccinate

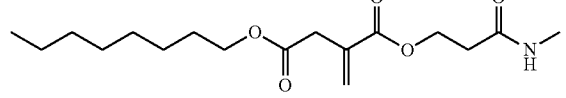

Example 110 was prepared using the same procedure as described in Example 107, but using methylamine instead of 1-methylpiperazine. $^1$H NMR (500 MHz, DMSO-d6) δ 7.86 (d, J=4.6 Hz, 1H), 6.15 (d, J=1.4 Hz, 1H), 5.81 (d, J=1.4 Hz, 1H), 4.25 (t, J=6.4 Hz, 2H), 3.99 (t, J=6.6 Hz, 2H), 3.32 (s, 2H), 2.57 (d, J=4.6 Hz, 3H), 2.42 (t, J=6.4 Hz, 2H), 1.57-1.47 (m, 2H), 1.31-1.18 (m, 10H), 0.86 (t, J=6.8 Hz, 3H). LCMS m/z 350.3 (M+Na)$^+$ (ES$^+$).

Example 111—2-((4-(cyclohexyloxy)-2-methylene-4-oxobutanoyl)oxy)propanoic acid

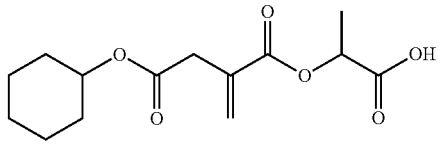 [SMILES: C=C(CC(=O)OC1CCCCC1)C(=O)OC(C)C(=O)O]

Example 111 was prepared using the same procedure as described in Example 79, but using 4-(cyclohexyloxy)-2-methylene-4-oxobutanoic acid (Intermediate 6) instead of 4-octyl itaconate. $^1$H NMR (400 MHz, DMSO-d6) δ 13.03 (s, 1H), 6.26 (d, J=1.3 Hz, 1H), 5.89 (d, J=1.3 Hz, 1H), 4.96 (q, J=7.0 Hz, 1H), 4.65 (dq, J=8.6, 4.0 Hz, 1H), 3.40-3.29 (m, 2H), 1.80-1.70 (m, 2H), 1.64 (ddd, J=13.0, 6.9, 3.9 Hz, 2H), 1.42 (d, J=7.1 Hz, 3H), 1.52-1.19 (m, 6H). LCMS m/z 307.6 (M+Na)$^+$ (ES$^+$).

Example 112—(R)-2-((2-methylene-4-(octan-2-yloxy)-4-oxobutanoyl)oxy)acetic acid

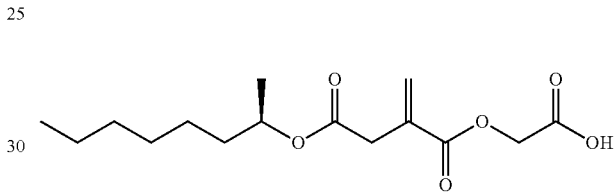

Example 112 was prepared according to the procedure of Example 89, but using (R)-2-methylene-4-(octan-2-yloxy)-4-oxobutanoic acid (Intermediate 8) instead of (S)-2-methylene-4-(octan-2-yloxy)-4-oxobutanoic acid. $^1$H NMR (400 MHz, DMSO-d6) δ 13.09 (s, 1H), 6.28 (d, J=1.2 Hz, 1H), 5.92 (d, J=1.2 Hz, 1H), 4.84-4.74 (m, 1H), 4.64 (s, 2H), 3.35 (s, 2H), 1.58-1.39 (m, 2H), 1.31-1.18 (m, 8H), 1.14 (d, J=6.3 Hz, 3H), 0.91-0.82 (m, 3H). LCMS m/z 323.0 (M+Na)$^+$ (ES$^+$).

The sodium salt of Example 112 was made as follows:

Example 112a: (R)-2-((2-methylene-4-(octan-2-yloxy)-4-oxobutanoyl)oxy)acetic Acid Sodium Salt

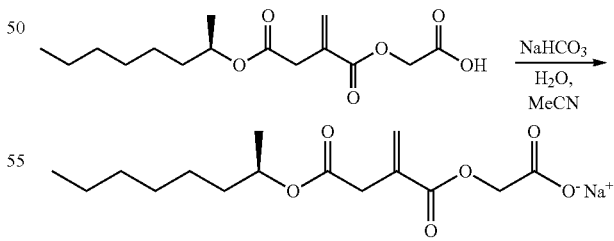

To a solution of (R)-2-((2-methylene-4-(octan-2-yloxy)-4-oxobutanoyl)oxy)acetic acid (1.0 g, 3.3 mmol) in MeCN (10 mL) was added a solution of NaHCO$_3$ in water (0.5 M, 6.27 mL, 3.14 mmol), and the mixture was stirred at room temperature for 10 min. The mixture was then concentrated under reduced pressure at 30° C. to remove the MeCN, and the remaining aqueous solution was washed with MTBE. The aqueous solution was then concentrated under reduced pressure at 30° C. to remove residual dissolved MTBE, and finally lyophilized to give (R)-2-((2-methylene-4-(octan-2-yloxy)-4-oxobutanoyl)oxy)acetic acid sodium salt (1.0 g, 3.1 mmol, 94% yield) as a white solid. LCMS (System 2, Method B) m/z 323.2 (M+H)⁺ (ES⁺). ¹H NMR (400 MHz, DMSO-d6) δ: 6.18 (d, J=0.8 Hz, 1H), 5.75 (d, J=0.8 Hz, 1H), 4.82-4.74 (m, 1H), 4.14 (d, J=1.2 Hz, 2H), 3.25 (s, 2H), 1.52-1.38 (m, 2H), 1.27-1.23 (m, 8H), 1.13 (d, J=6.4 Hz, 3H), 0.85 (t, J=6.4 Hz, 3H).

Example 113—2-((4-((4,4-difluorocyclohexyl)methoxy)-2-methylene-4-oxobutanoyl)oxy)acetic Acid

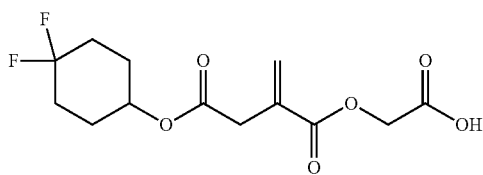 [SMILES: C=C(CC(=O)OC1CCC(F)(F)CC1)C(=O)OCC(=O)O]

Example 113 was prepared according to the procedure of Example 96, but using 4,4-difluorocyclohexanol instead of spiro[3.3]heptan-2-ol. ¹H NMR (400 MHz, DMSO-d6) δ 13.08 (s, 1H), 6.30 (d, J=1.2 Hz, 1H), 5.94 (d, J=1.3 Hz, 1H), 4.65 (s, 2H), 3.92 (d, J=6.1 Hz, 2H), 3.41 (s, 2H), 2.07-1.93 (m, 2H), 1.89-1.68 (m, 5H), 1.28-1.14 (m, 2H). LCMS m/z 319.1 (M−H)⁻ (ES⁻).

Example 114—2-((4-(3-ethoxypropoxy)-2-methylene-4-oxobutanoyl)oxy)acetic acid

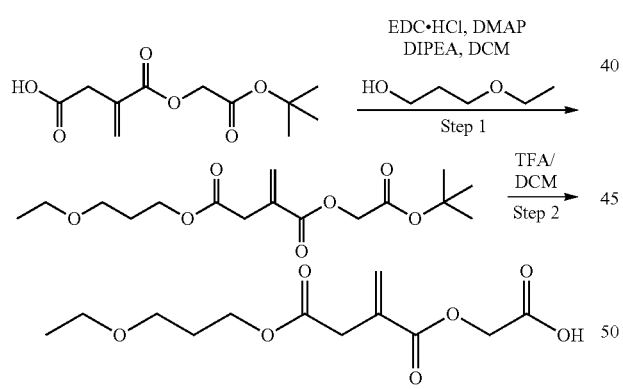

Step 1

EDC.HCl (0.371 g, 1.935 mmol) was added to a solution of 3-((2-(tert-butoxy)-2-oxoethoxy)carbonyl)but-3-enoic acid (Intermediate 11, 0.35 g, 1.29 mmol), 3-ethoxypropan-1-ol (0.18 mL, 1.56 mmol), DMAP (0.016 g, 0.13 mmol) and DIPEA (0.34 mL, 1.95 mmol) in DCM (10 mL). The reaction mixture was stirred at RT for 18 h. The reaction mixture was diluted with water (50 mL) and extracted with DCM (3×20 mL). The organic layers were combined and passed through a phase separator and concentrated in vacuo. The crude product was purified by chromatography on silica gel (0-10% EtOAc/DCM) to afford impure product. The crude product was purified by chromatography on silica gel (0-20% EtOAc/DCM) to afford 1-(2-(tert-butoxy)-2-oxoethyl) 4-(3-ethoxypropyl) 2-methylenesuccinate (260 mg, 0.71 mmol) as a colourless oil. ¹H NMR (400 MHz, DMSO-d6) δ 6.30 (d, J=1.2 Hz, 1H), 5.95-5.92 (m, 1H), 4.62 (s, 2H), 4.07 (t, J=6.5 Hz, 2H), 3.43-3.35 (m, 6H), 1.82-1.71 (m, 2H), 1.42 (s, 9H), 1.10 (t, J=7.0 Hz, 3H). LCMS m/z 353.3 (M+Na)⁺ (ES⁺).

Step 2

TFA (2.5 mL) was added to a solution of 1-(2-(tert-butoxy)-2-oxoethyl) 4-(3-ethoxypropyl) 2-methylenesuccinate (260 mg, 0.71 mmol) in DCM (2.5 mL). The reaction mixture was stirred for 2 h, then concentrated. The crude product was purified by chromatography on RP Flash C18 (5-75% MeCN/Water 0.1% Formic Acid) followed by chromatography on silica gel (0-10% MeOH/DCM) to afford the title compound (0.015 g, 0.052 mmol) as a clear and colourless gum. ¹H NMR (400 MHz, DMSO-d6) δ 6.21 (d, J=1.5 Hz, 1H), 5.82-5.77 (m, 1H), 4.20 (s, 2H), 4.06 (t, J=6.5 Hz, 2H), 3.45-3.36 (m, 4H), 3.34 (s, 2H), 1.82-1.71 (m, 2H), 1.10 (t, J=7.0 Hz, 3H). LCMS m/z 275.3 (M+H)⁺ (ES⁺).

Example 115—2-((4-(bicyclo[2.2.1]heptan-2-yloxy)-2-methylene-4-oxobutanoyl)oxy)acetic acid

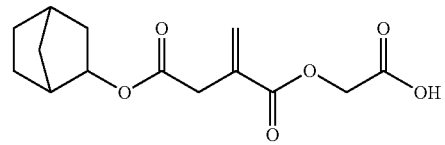 [SMILES: C=C(CC(=O)OC1CC2CCC1C2)C(=O)OCC(=O)O]

Example 115 was prepared according to the procedure of Example 114, but using bicyclo[2.2.1]heptan-2-ol instead of 3-ethoxypropan-1-ol. ¹H NMR (400 MHz, DMSO-d6) δ 13.10 (s, 1H), 6.27 (d, J=1.2 Hz, 1H), 5.96-5.86 (m, 1H), 4.64 (s, 2H), 4.55-4.47 (m, 1H), 3.33 (s, 2H), 2.29-2.17 (m, 2H), 1.69-1.61 (m, 1H), 1.52-1.29 (m, 4H), 1.16-1.03 (m, 3H). LCMS m/z 305.2 (M+Na)⁺ (ES⁺).

Example 116—2-((4-cyclobutoxy-2-methylene-4-oxobutanoyl)oxy)acetic acid

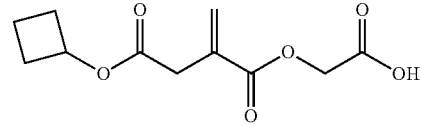 [SMILES: C=C(CC(=O)OC1CCC1)C(=O)OCC(=O)O]

Example 116 was prepared according to the procedure of Example 114, but using cyclobutanol instead of 3-ethoxypropan-1-ol. ¹H NMR (400 MHz, DMSO-d6) δ 13.08 (s, 1H), 6.29 (s, 1H), 5.92 (d, J=1.5 Hz, 1H), 4.89 (p, J=7.4 Hz, 1H), 4.65 (s, 2H), 3.36 (s, 2H), 2.30-2.19 (m, 2H), 2.06-1.92 (m, 2H), 1.79-1.68 (m, 1H), 1.65-1.50 (m, 1H). LCMS m/z 265.1 (M+Na)⁺ (ES⁺).

Example 117—3-((4-(cyclohexyloxy)-2-methylene-4-oxobutanoyl)oxy)-2,2-dimethylpropanoic acid

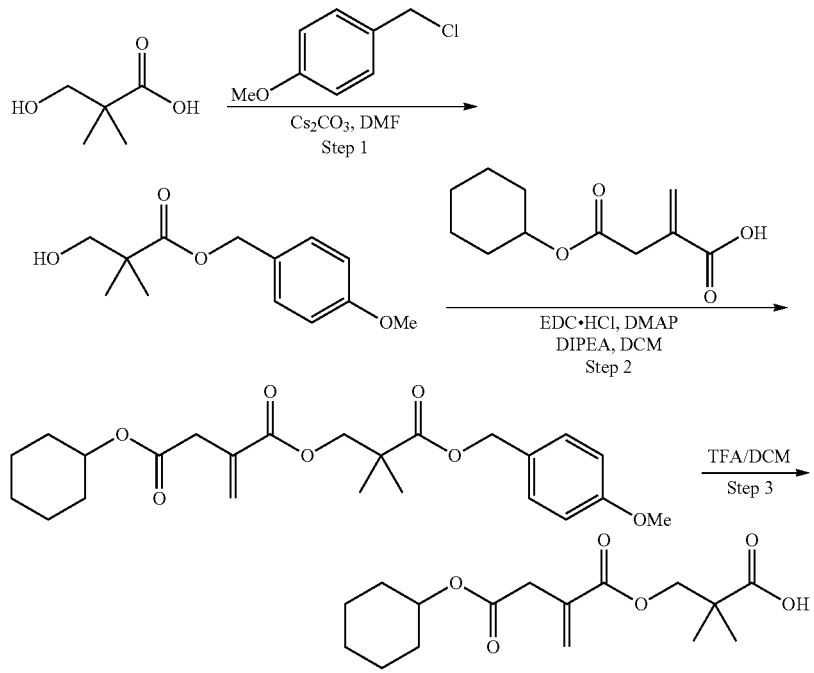

Step 1

1-(chloromethyl)-4-methoxybenzene (1 mL, 7.4 mmol) was added to a mixture of 3-hydroxy-2,2-dimethylpropanoic acid (1.00 g, 8.47 mmol) and cesium carbonate (2.76 g, 8.47 mmol) in dimethylformamide (40 mL). The mixture was stirred at RT for 3 h, then heated to 70° C. for 2 h, then cooled to RT and stirred for 18 h. The mixture was poured onto water (50 mL) and extracted with EtOAc (3×50 mL). The combined organic phases were washed with brine (100 mL), dried (MgSO$_4$) and concentrated. The crude product was purified by chromatography on silica gel (0-50% EtOAc/isohexane) to afford 4-methoxybenzyl 3-hydroxy-2,2-dimethylpropanoate (1.45 g, 5.78 mmol) as a colourless oil. $^1$H NMR (400 MHz, DMSO-d6) δ 7.32-7.27 (m, 2H), 6.97-6.90 (m, 2H), 5.01 (s, 2H), 4.85 (t, J=5.5 Hz, 1H), 3.76 (s, 3H), 3.42 (d, J=5.5 Hz, 2H), 1.08 (s, 6H).

Step 2

EDC.HCl (0.248 g, 1.30 mmol) was added to a solution of 4-(cyclohexyloxy)-2-methylene-4-oxobutanoic acid (Intermediate 6, 250 mg, 1.18 mmol), 4-methoxybenzyl 3-hydroxy-2,2-dimethylpropanoate (337 mg, 1.41 mmol), DMAP (0.014 g, 0.12 mmol) and DIPEA (0.31 mL, 1.77 mmol) in DCM (5 mL). The reaction mixture was stirred at RT for 18 h. The reaction mixture was diluted with 1 M HCl (30 mL). The phases were separated and the aqueous phase was extracted with DCM (10 mL). The combined organic phases were washed with brine (30 mL), dried (MgSO$_4$) and concentrated. The crude product was purified by chromatography on silica gel (0-30% EtOAc/isohexane) to afford 4-cyclohexyl 1-(3-((4-methoxybenzyl)oxy)-2,2-dimethyl-3-oxopropyl) 2-methylenesuccinate (213 mg, 0.47 mmol) as a colourless oil. $^1$H NMR (400 MHz, DMSO-d6) δ 7.31-7.24 (m, 2H), 6.94-6.89 (m, 2H), 6.08 (d, J=1.4 Hz, 1H), 5.78 (d, J=1.3 Hz, 1H), 5.04 (s, 2H), 4.68-4.61 (m, 1H), 4.11 (s, 2H), 3.75 (s, 3H), 3.28 (s, 2H), 1.78-1.70 (m, 2H), 1.66-1.57 (m, 2H), 1.51-1.41 (m, 1H), 1.40-1.21 (m, 5H), 1.17 (s, 6H).

Step 3

TFA (1.5 mL) was added to a solution of 4-cyclohexyl 1-(3-((4-methoxybenzyl)oxy)-2,2-dimethyl-3-oxopropyl) 2-methylenesuccinate (213 mg, 0.47 mmol) in DCM (3 mL). The reaction mixture was stirred for 1 h, diluted with toluene (5 mL) and concentrated. The crude product was purified by chromatography on silica gel (0-60% EtOAc/isohexane) to afford the title compound (87 mg, 0.28 mmol) as a colourless oil. $^1$H NMR (400 MHz, DMSO-d6) δ 12.45 (s, 1H), 6.18 (d, J=1.4 Hz, 1H), 5.83 (d, J=1.3 Hz, 1H), 4.65 (td, J=8.5, 3.9 Hz, 1H), 4.08 (s, 2H), 3.33 (s, 2H), 1.80-1.70 (m, 2H), 1.69-1.57 (m, 2H), 1.52-1.17 (m, 6H), 1.14 (s, 6H). LCMS m/z 335.3 (M+Na)$^+$ (ES$^+$).

Example 118—1-(2-((N,N-dimethylsulfamoyl)amino)-2-oxoethyl) 4-hexyl 2-methylenesuccinate

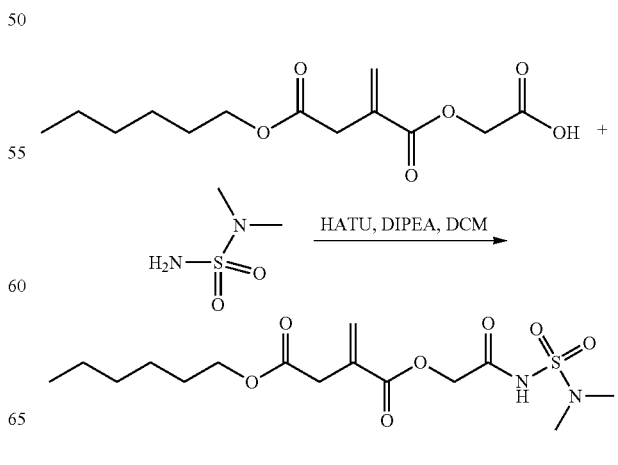

To a solution of 2-((4-(hexyloxy)-2-methylene-4-oxobutanoyl)oxy)acetic acid (Example 94, 498 mg, 1.83 mmol) in DCM (13 mL), was added HATU (696 mg, 1.83 mmol), DIPEA (0.64 mL, 3.66 mmol), followed by dimethylsulfamide (273 mg, 2.20 mmol). The resulting solution was stirred at RT for 16 h. Water (50 mL) was added and the mixture was extracted with EtOAc (3×20 mL). The combined organic layers were washed with brine (50 mL), dried (MgSO$_4$) and concentrated. The crude product was purified by chromatography on silica gel (0-100% EtOAc/isohexane) to afford the title compound (221 mg, 0.53 mmol) as a colourless oil. $^1$H NMR (400 MHz, DMSO-d6) δ 11.70 (s, 1H), 6.29 (d, J=1.2 Hz, 1H), 5.93 (d, J=1.2 Hz, 1H), 4.68 (s, 2H), 4.00 (t, J=6.6 Hz, 2H), 3.38 (s, 2H), 2.79 (s, 6H), 1.59-1.47 (m, 2H), 1.33-1.15 (m, 6H), 0.86 (t, J=6.4 Hz, 3H). LCMS m/z 401.4 (M+Na)$^+$ (ES$^+$).

Example 119—4-hexyl 1-(2-(methylsulfonamido)-2-oxoethyl) 2-methylenesuccinate

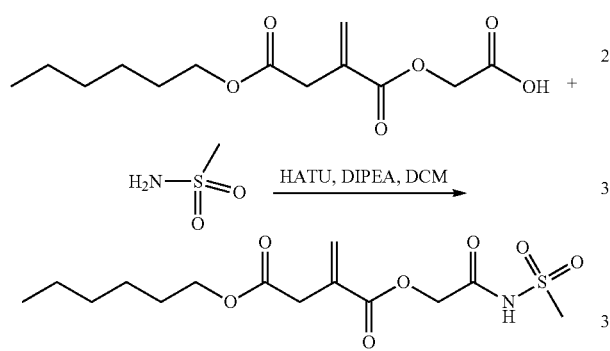

To a solution of 2-((4-(hexyloxy)-2-methylene-4-oxobutanoyl)oxy)acetic acid (Example 94, 477 mg, 1.75 mmol) in DCM (13 mL), was added HATU (666 mg, 1.75 mmol), DIPEA (0.61 mL, 3.50 mmol), followed by methanesulfonamide (200 mg, 2.10 mmol). The resulting solution was stirred at RT for 72 h. Water (50 mL) was added and the mixture was extracted with EtOAc (3×20 mL). The combined organic layers were washed with brine (50 mL), dried (MgSO$_4$) and concentrated. The crude product was purified by chromatography on silica gel (0-100% EtOAc/isohexane) to afford the title compound (221 mg, 0.53 mmol) as a colourless oil. $^1$H NMR (400 MHz, DMSO-d6) δ 12.06 (s, 1H), 6.30 (d, J=1.2 Hz, 1H), 5.94 (d, J=1.2 Hz, 1H), 4.70 (s, 2H), 4.01 (t, J=6.6 Hz, 2H), 3.39 (s, 2H), 3.24 (s, 3H), 1.58-1.45 (m, 2H), 1.33-1.19 (m, 6H), 0.86 (t, J=6.2 Hz, 3H). LCMS m/z 372.3 (M+Na)$^+$ (ES$^+$).

Example 120—4-hexyl 1-(3-(methylsulfonamido)-2-oxoethyl) 2-methylenesuccinate

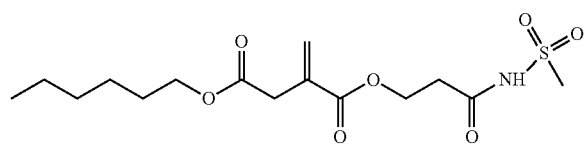 [SMILES: C=C(CC(=O)OCCCCCC)C(=O)OCCC(=O)NS(C)(=O)=O]

Example 120 was prepared according to the procedure of Example 119, but using 3-((4-(hexyloxy)-2-methylene-4-oxobutanoyl)oxy)propanoic acid (Example 85) instead of 2-((4-(hexyloxy)-2-methylene-4-oxobutanoyl)oxy)acetic acid. $^1$H NMR (400 MHz, DMSO-d6) δ 11.83 (s, 1H), 6.17 (d, J=1.4 Hz, 1H), 5.83 (d, J=1.2 Hz, 1H), 4.28 (t, J=6.1 Hz, 2H), 4.00 (t, J=6.6 Hz, 2H), 3.33 (s, 2H), 3.22 (s, 3H), 2.65 (t, J=6.1 Hz, 2H), 1.58-1.49 (m, 2H), 1.34-1.18 (m, 6H), 0.86 (t, J=6.0 Hz, 3H). LCMS m/z 386.3 (M+H)$^+$ (ES$^+$).

Example 121—2-((4-(cyclohexyloxy)-2-methylene-4-oxobutanoyl)oxy)-3,3,3-trifluoropropanoic acid

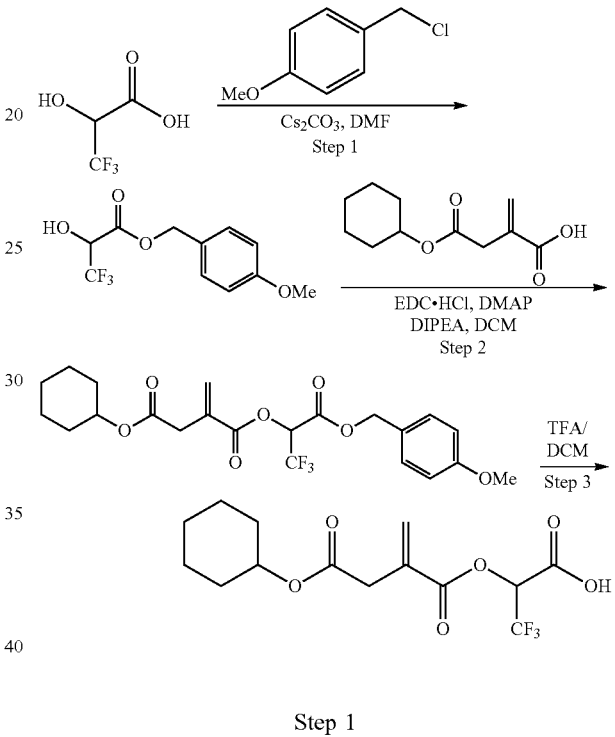

Step 1

1-(chloromethyl)-4-methoxybenzene (0.90 mL, 6.64 mmol) was added to a mixture of 3,3,3-trifluoro-2-hydroxypropanoic acid (1.00 g, 6.94 mmol) and cesium carbonate (2.26 g, 6.94 mmol) in dimethylformamide (30 mL). The mixture was stirred at RT for 3 h, then heated to 70° C. for 2 h, then cooled to RT and stirred for 18 h. The mixture was poured onto water (50 mL) and extracted with EtOAc (3×50 mL). The combined organic phases were washed with brine (100 mL), dried (MgSO$_4$) and concentrated. The crude product was purified by chromatography on silica gel (0-50% EtOAc/isohexane) to afford 4-methoxybenzyl 3,3,3-trifluoro-2-hydroxypropanoate (640 mg, 2.30 mmol) as a colourless oil. $^1$H NMR (400 MHz, DMSO-d6) δ 7.36-7.30 (m, 2H), 7.14 (d, J=7.4 Hz, 1H), 7.00-6.91 (m, 2H), 5.22-5.14 (m, 2H), 4.92-4.83 (m, 1H), 3.76 (s, 3H).

Step 2

EDC.HCl (0.348 g, 1.81 mmol) was added to a solution of 4-(cyclohexyloxy)-2-methylene-4-oxobutanoic acid (Intermediate 6, 0.35 g, 1.65 mmol), 4-methoxybenzyl 3,3,3-trifluoro-2-hydroxypropanoate (0.523 g, 1.98 mmol), DMAP (0.020 g, 0.17 mmol) and DIPEA (0.43 mL, 2.47 mmol) in DCM (8 mL) at 0° C. The reaction mixture was allowed to warm to RT and stirred for 72 h. The reaction mixture was diluted with 1 M HCl (30 mL). The phases were separated and the aqueous phase was extracted with DCM (10 mL). The combined organic phases were washed with brine (30 mL), dried (MgSO₄) and concentrated. The crude product was purified by chromatography on silica gel (0-20% EtOAc/isohexane) to afford 4-cyclohexyl 1-(1,1,1-trifluoro-3-((4-methoxybenzyl)oxy)-3-oxopropan-2-yl) 2-methylenesuccinate (302 mg, 0.593 mmol) as a colourless oil. ¹H NMR (400 MHz, DMSO-d6) δ 7.34-7.29 (m, 2H), 6.98-6.92 (m, 2H), 6.36 (d, J=0.9 Hz, 1H), 6.15 (q, J=7.3 Hz, 1H), 6.06 (d, J=1.1 Hz, 1H), 5.23 (s, 2H), 4.70-4.61 (m, 1H), 3.76 (s, 3H), 3.41 (s, 2H), 1.79-1.71 (m, 2H), 1.68-1.59 (m, 2H), 1.54-1.42 (m, 1H), 1.41-1.21 (m, 5H). LCMS m/z 481.3 (M+Na)⁺ (ES⁺).

Example 122—2-((4-(cyclooctyloxy)-2-methylene-4-oxobutanoyl)oxy)-3,3,3-trifluoropropanoic acid

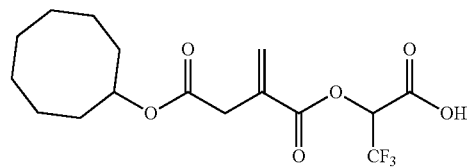 [SMILES: C=C(CC(=O)OC1CCCCCCC1)C(=O)OC(C(=O)O)C(F)(F)F]

Example 122 was prepared according to the procedure of Example 121, but using 4-(cyclooctyloxy)-2-methylene-4-oxobutanoic acid (Intermediate 1) instead of 4-(cyclohexyloxy)-2-methylene-4-oxobutanoic acid. ¹H NMR (400 MHz, DMSO-d6) δ 14.47 (s, 1H), 6.34 (s, 1H), 6.03 (s, 1H), 5.86 (q, J=7.6 Hz, 1H), 4.82 (tt, J=8.2, 4.0 Hz, 1H), 3.37 (d, J=2.1 Hz, 2H), 1.80-1.32 (m, 12H). LCMS m/z 390.0 (M+H)⁺ (ES⁺).

Example 123—(E)-4-((4-(cyclohexyloxy)-2-methylene-4-oxobutanoyl)oxy)but-2-enoic acid

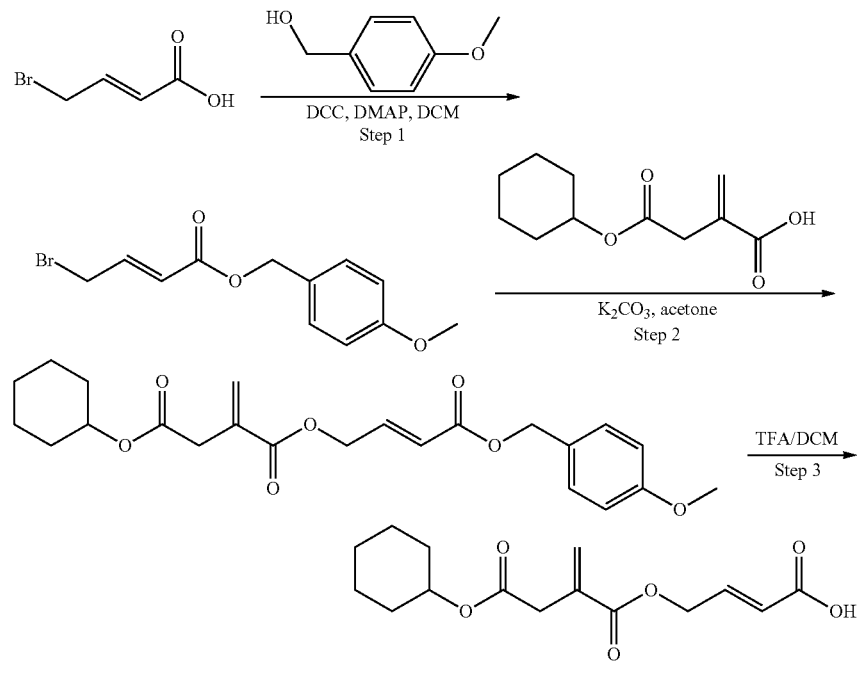

Step 3

TFA (1 mL) was added to a solution of 4-cyclohexyl 1-(1,1,1-trifluoro-3-((4-methoxybenzyl)oxy)-3-oxopropan-2-yl) 2-methylenesuccinate (302 mg, 0.659 mmol) in DCM (2 mL). The reaction mixture was stirred for 1 h, diluted with toluene (5 mL) and concentrated. The crude product was purified by chromatography on silica gel (0-60% EtOAc/isohexane) to afford the title compound (38 mg, 0.107 mmol, 16.20% yield) as a colourless oil. ¹H NMR (400 MHz, DMSO-d6) δ 14.49 (br. s, 1H), 6.35 (d, J=0.9 Hz, 1H), 6.04 (d, J=1.1 Hz, 1H), 5.87 (q, J=7.6 Hz, 1H), 4.70-4.60 (m, 1H), 3.47-3.35 (m, 2H), 1.80-1.71 (m, 2H), 1.69-1.58 (m, 2H), 1.52-1.43 (m, 1H), 1.42-1.18 (m, 5H). LCMS m/z 337.2 (M–H)⁻ (ES⁻).

Step 1

DCC (1.87 g, 9.06 mmol) was added to a stirred solution of (E)-4-bromobut-2-enoic acid (1.00 g, 6.06 mmol), 4-methoxybenzyl alcohol (0.90 mL, 7.2 mmol) and DMAP (0.074 g, 0.61 mmol) in DCM (30 mL) at 0° C. The mixture was allowed to warm to RT and stirred for 18 h. The precipitate was removed by filtration and the filtrate concentrated. The crude product was purified by chromatography on silica gel (0-100% DCM/isohexane) to afford (E)-4-methoxybenzyl 4-bromobut-2-enoate (1.07 g, 3.49 mmol) as a colourless gum. ¹H NMR (400 MHz, DMSO-d6) δ 7.37-7.30 (m, 2H), 7.00-6.88 (m, 3H), 6.23-6.15 (m, 1H), 5.10 (s, 2H), 4.32-4.23 (m, 2H), 3.76 (s, 3H).

Step 2

(E)-4-methoxybenzyl 4-bromobut-2-enoate (1.00 g, 3.26 mmol) was added to a mixture of 4-(cyclohexyloxy)-2-methylene-4-oxobutanoic acid (Intermediate 6, 0.923 g, 3.91 mmol) and potassium carbonate (0.586 g, 4.24 mmol) in acetone (20 mL). The reaction mixture was stirred for 20 h at RT then concentrated in vacuo. The residue was taken up in EtOAc (80 mL), then washed with a saturated solution of $NaHCO_3$ (3×50 mL). The organic layer was dried (phase separator) and concentrated. The crude product was purified by chromatography on silica gel (0-100% EtOAc/isohexane) to afford (E)-4-cyclohexyl 1-(4-((4-methoxybenzyl)oxy)-4-oxobut-2-en-1-yl) 2-methylenesuccinate (1.57 g, 3.26 mmol, 85% purity) as a colourless oil. $^1$H NMR (400 MHz, DMSO-d6) δ 7.33 (d, J=8.2 Hz, 2H), 6.99-6.88 (m, 3H), 6.28 (s, 1H), 6.06-5.97 (m, 1H), 5.88 (s, 1H), 5.10 (s, 2H), 4.87-4.81 (m, 2H), 4.69-4.59 (m, 1H), 3.76 (s, 3H), 3.39 (s, 2H), 1.76-1.65 (m, 2H), 1.62-1.52 (m, 2H), 1.48-1.39 (m, 1H), 1.38-1.14 (m, 5H). LCMS m/z 439.3 (M+Na)$^+$ (ES$^+$).

Step 3

TFA (0.8 mL, 10.4 mmol) was added dropwise to a solution of (E)-4-cyclohexyl 1-(4-((4-methoxybenzyl)oxy)-4-oxobut-2-en-1-yl) 2-methylenesuccinate (1.57 g, 3.26 mmol) in DCM (30 mL) at 0° C. The mixture was warmed to RT and stirred for 20 h, then concentrated in vacuo. The crude product was purified by chromatography on RP Flash C18 (5-75% MeCN/Water 0.1% Formic Acid) to afford the title compound (0.54 g, 1.73 mmol) as a white solid. $^1$H NMR (400 MHz, DMSO-d6) δ 12.47 (s, br. 1H), 6.88-6.78 (m, 1H), 6.28 (d, J=1.2 Hz, 1H), 5.96-5.90 (m, 1H), 5.90-5.88 (m, 1H), 4.84-4.80 (m, 2H), 4.70-4.62 (m, 1H), 3.39 (s, 2H), 1.81-1.69 (m, 2H), 1.68-1.57 (m, 2H), 1.51-1.42 (m, 1H), 1.41-1.16 (m, 5H). LCMS m/z 297.3 (M+H)$^+$ (ES$^+$).

Example 124—3-((2-((4-(cyclohexyloxy)-2-methylene-4-oxobutanoyl)oxy)ethyl)sulfonyl)propanoic acid

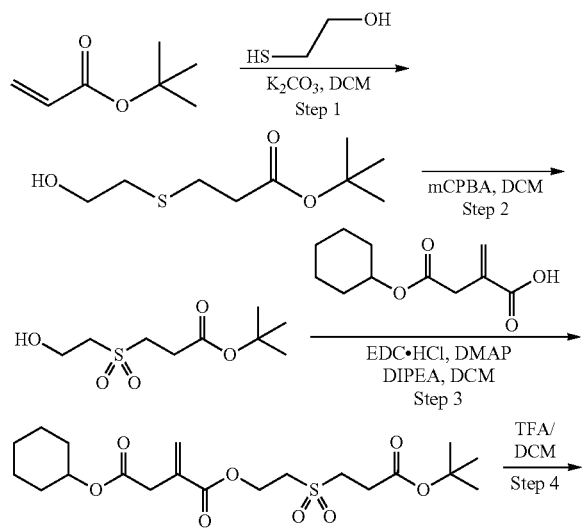

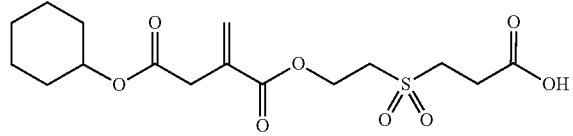

Step 1

Tert-butyl acrylate (4.50 mL, 30.7 mmol) was added dropwise to a mixture of 2-mercaptoethanol (1.79 mL, 25.6 mmol) and potassium carbonate (0.177 g, 1.28 mmol) in DCM (24 mL) at 0° C. The reaction mixture was warmed to RT and stirred for 48 h. The reaction was quenched with sat. aq. $NH_4Cl$ (100 mL) and the aqueous layer was extracted with DCM (3×50 mL). The combined organic layers were passed through a hydrophobic phase separator and concentrated. The crude product was purified by chromatography on silica gel (0-10% MeOH/DCM) to afford tert-butyl 3-((2-hydroxyethyl)thio)propanoate (5.80 g, 23.3 mmol, 91% yield) as a colourless oil. $^1$H NMR (400 MHz, DMSO-d6) δ 4.75 (t, J=5.5 Hz, 1H), 3.56-3.46 (m, 2H), 2.68 (t, J=6.7 Hz, 2H), 2.56 (t, J=6.9 Hz, 2H), 2.50-2.44 (m, 2H), 1.40 (s, 9H). LCMS m/z 229.2 (M+Na)$^+$ (ES$^+$).

Step 2

3-Chlorobenzoperoxoic acid ((mCPBA) 8.15 g, 36.4 mmol) was added portionwise to a solution of tert-butyl 3-((2-hydroxyethyl)thio)propanoate (3.00 g, 14.5 mmol) in DCM (100 mL) at 0° C. The mixture was warmed to RT and stirred for 20 h. The reaction was cooled to 0° C. and quenched with sat. aq. $NaHCO_3$ (300 mL). The aqueous layer was extracted with DCM (3×80 mL). The combined organic layers were washed with sat. aq. $Na_2S_2O_5$ (120 mL), passed through a hydrophobic phase separator and concentrated. The crude product was purified by chromatography on silica gel (0-100% EtOAc/isohexane) to afford tert-butyl 3-((2-hydroxyethyl)sulfonyl)propanoate (1.60 g, 6.18 mmol) as a colourless oil. $^1$H NMR (400 MHz, DMSO-d6) δ 5.13 (t, J=5.0 Hz, 1H), 3.78 (q, J=5.4 Hz, 2H), 3.38-3.32 (m, 2H), 3.24 (t, J=5.7 Hz, 2H), 2.65 (t, J=7.5 Hz, 2H), 1.41 (d, J=1.2 Hz, 9H).

Step 3

EDC.HCl (1.20 g, 6.3 mmol) was added to a solution of 4-(cyclohexyloxy)-2-methylene-4-oxobutanoic acid (Intermediate 6, 663 mg, 3.12 mmol), tert-butyl 3-((2-hydroxyethyl)sulfonyl)propanoate (809 mg, 3.12 mmol), DMAP (38 mg, 0.31 mmol) and DIPEA (1.1 mL, 6.3 mmol) in DCM (16 mL). The mixture was stirred at RT for 20 h. The reaction mixture was concentrated onto silica and purified by chromatography on silica gel (0-30% EtOAc/iso-hexane) to afford 1-(2-((3-(tert-butoxy)-3-oxopropyl)sulfonyl)ethyl) 4-cyclohexyl 2-methylenesuccinate (405 mg, 0.84 mmol, 90% purity) as a colourless oil. $^1$H NMR (400 MHz, DMSO-d6) δ 6.22 (d, J=1.3 Hz, 1H), 5.88 (d, J=1.2 Hz, 1H), 4.71-4.56 (m, 1H), 4.44 (t, J=6.2, 5.2, 4.4 Hz, 2H), 3.57 (t, J=5.7 Hz, 2H), 3.41-3.32 (m, 4H), 2.67 (t, J=7.5 Hz, 2H), 1.80-1.68 (m, 2H), 1.66-1.58 (m, 2H), 1.53-1.09 (m, 15H). LCMS m/z 455.3 (M+Na)$^+$ (ES$^+$).

Step 4

TFA (3.0 mL, 39 mmol) was added to a solution of 1-(2-((3-(tert-butoxy)-3-oxopropyl)sulfonyl)ethyl) 4-cyclohexyl 2-methylenesuccinate (405 mg, 0.84 mmol) in DCM (3 mL) at RT. The mixture was stirred for 1 h, diluted with toluene (20 mL) and concentrated. The residue was taken up in EtOAc (50 mL), washed with brine (20 mL), dried (MgSO$_4$) and concentrated to afford the title compound (278 mg, 0.716 mmol) as a yellow gum. $^1$H NMR (400 MHz, DMSO-d6) δ 6.23 (d, J=1.2 Hz, 1H), 5.87 (d, J=1.3 Hz, 1H), 4.69-4.61 (m, 1H), 4.44 (t, J=5.7 Hz, 2H), 3.58 (t, J=5.7 Hz, 2H), 3.45-3.32 (m, 4H), 2.68 (t, J=7.5 Hz, 2H), 1.79-1.71 (m, 2H), 1.66-1.55 (m, 2H), 1.50-1.16 (m, 6H) (1 exchangeable proton not visible). LCMS m/z 375.3 (M+Na)$^+$ (ES$^+$).

Example 125—1-((2H-tetrazol-5-yl)methyl) 4-cyclohexyl 2-methylenesuccinate

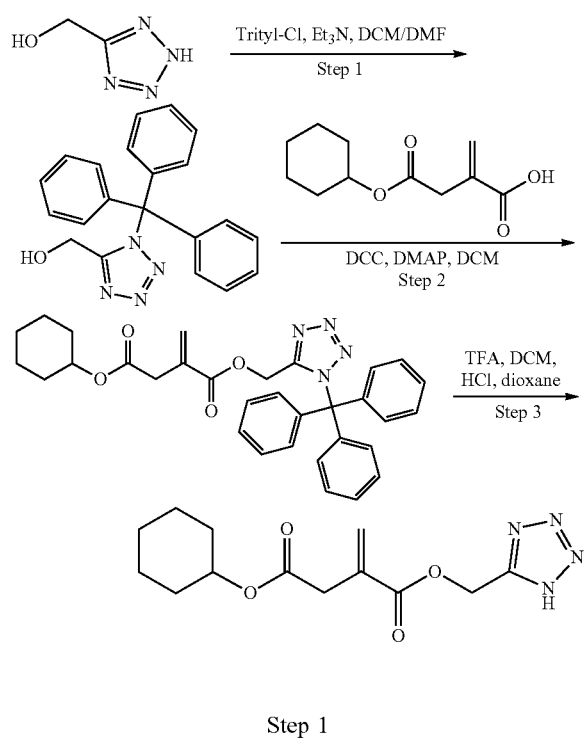

Step 1

To a solution of (2H-tetrazol-5-yl)methanol (0.50 g, 5.0 mmol) in DCM (10 mL) and DMF (2.5 mL) were added triethylamine (0.78 mL, 5.6 mmol) and trityl chloride (1.39 g, 5.00 mmol). The resulting mixture was stirred at RT for 1 h, diluted with water (50 mL), and extracted with DCM (3×40 mL). The combined organic phases were dried (phase separator) and concentrated. The crude product was purified by chromatography on silica gel (0-50% EtOAc/isohexane) to afford (2-trityl-2H-tetrazol-5-yl)methanol (1.40 g, 3.76 mmol) as a white solid. $^1$H NMR (400 MHz, DMSO-d6) δ 7.48-7.33 (m, 10H), 7.09-6.95 (m, 5H), 5.66 (t, J=6.0 Hz, 1H), 4.71 (d, J=5.9 Hz, 2H).

Step 2

DCC (0.583 g, 2.83 mmol) was added to a stirred solution of 4-(cyclohexyloxy)-2-methylene-4-oxobutanoic acid (Intermediate 6, 0.400 g, 1.88 mmol), (2-trityl-2H-tetrazol-5-yl)methanol (0.772 g, 2.07 mmol) and DMAP (0.023 g, 0.19 mmol) in DCM (12 mL) at 0° C. The mixture was warmed to RT and stirred for 18 h. The precipitate was removed by filtration and filtrate was concentrated. The crude product was purified by chromatography on silica gel (0-50% EtOAc/isohexane) to afford 4-cyclohexyl 1-((2-trityl-2H-tetrazol-5-yl)methyl) 2-methylenesuccinate (0.16 g, 0.27 mmol) as a colourless gum. $^1$H NMR (400 MHz, DMSO-d6) δ 7.41 (m, 10H), 7.04-6.98 (m, 5H), 6.22 (d, J=1.2 Hz, 1H), 5.90-5.86 (m, 1H), 5.46 (s, 2H), 4.58 (m, 1H), 3.32 (s, 2H), 1.60 (m, 5H), 1.48-1.35 (m, 1H), 1.32-1.08 (m, 4H). LCMS m/z 559.2 (M+Na)$^+$ (ES$^+$).

Step 3

TFA (0.55 mL, 7.1 mmol) was added dropwise to a solution of 4-cyclohexyl 1-((2-trityl-2H-tetrazol-5-yl)methyl) 2-methylenesuccinate (0.16 g, 0.27 mmol) in DCM (3 mL) at 0° C. The mixture was stirred at RT for 20 h, before 4 N HCl in 1,4-dioxane (0.2 mL, 0.8 mmol) was added and the reaction mixture stirred for a further 18 h then concentrated. The crude product was purified by chromatography on RP Flash C18 (5-75% MeCN/Water 0.1% Formic Acid) to afford the title compound as a colourless gum. $^1$H NMR (400 MHz, DMSO-d6) δ 6.31 (d, J=1.2 Hz, 1H), 5.95-5.90 (m, 1H), 5.49 (s, 2H), 4.70-4.53 (m, 1H), 3.38 (s, 2H), 1.74-1.52 (m, 4H), 1.51-1.39 (m, 1H), 1.35-1.16 (m, 5H) (1 exchangeable proton not visible). LCMS m/z 295.2 (M+H)$^+$ (ES$^+$).

Example 126—2-((3-((2-((3-chlorophenyl)sulfonyl) ethoxy)carbonyl)but-3-enoyl)oxy)acetic acid

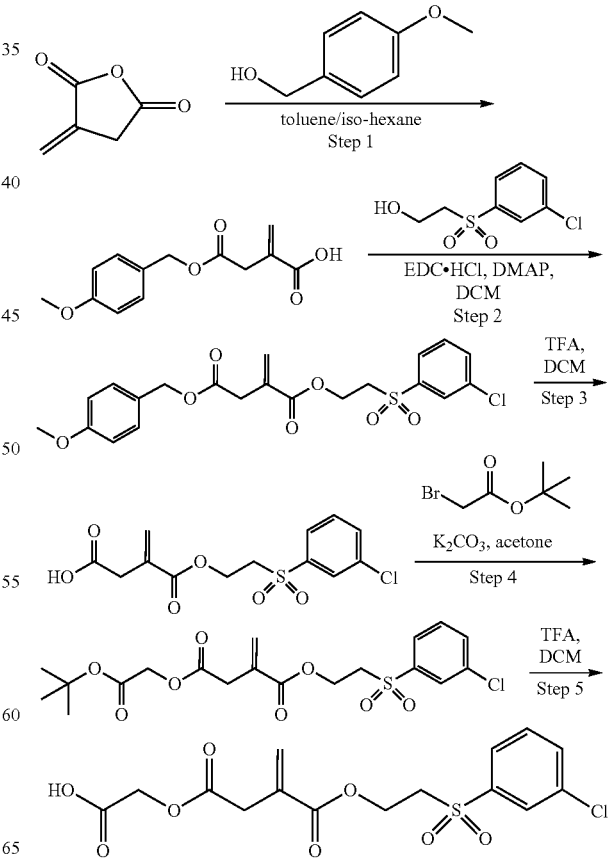

Step 1

A mixture of (4-methoxyphenyl)methanol (17.3 g, 125 mmol) and itaconic anhydride (16.8 g, 150 mmol) in toluene/iso-hexane (1:1, 300 mL) was heated at 70° C. for 16 h. The mixture was cooled to RT and the precipitate was filtered. The solid was taken up in EtOAc (200 mL) and washed with water (3×100 mL), brine (100 mL), dried (MgSO₄) and concentrated. The crude product was recrystallized from a mixture of toluene/iso-hexane (200 mL/200 mL) to afford 4-((4-methoxybenzyl)oxy)-2-methylene-4-oxobutanoic acid (19.1 g, 73.4 mmol) as a colourless solid. $^1$H NMR (400 MHz, DMSO-d6) δ 12.63 (s, 1H), 7.29 (d, J=8.7 Hz, 2H), 6.92 (d, J=8.6 Hz, 2H), 6.16 (d, J=1.6 Hz, 1H), 5.77 (d, J=1.4 Hz, 1H), 5.02 (s, 2H), 3.76 (s, 3H), 3.34 (s, 2H). LCMS m/z 272.9 (M+Na)$^+$ (ES$^+$).

Step 2

A slurry of EDC.HCl (0.920 g, 4.80 mmol) in DCM (1 mL) was added dropwise to a solution of 4-((4-methoxybenzyl)oxy)-2-methylene-4-oxobutanoic acid (1.00 g, 4.00 mmol), 2-((3-chlorophenyl)sulfonyl)ethanol (1.06 g, 4.80 mmol) and DMAP (0.586 g, 4.80 mmol) in DCM (6 mL) at 0° C. The mixture was allowed to slowly warm to RT and stirred for 16 h. The reaction mixture was poured into 1M HCl (5 mL) and extracted with EtOAc (3×15 mL). The combined organic extracts were washed with brine (20 mL), dried (Na₂SO₄) and concentrated. The crude product was purified by chromatography on silica gel (0-10% EtOAc/DCM) to afford 1-(2-((3-chlorophenyl)sulfonyl)ethyl) 4-(4-methoxybenzyl) 2-methylenesuccinate (0.439 g, 0.960 mmol) as a colourless oil. LCMS m/z 475.1 (M+Na)$^+$ (ES$^+$).

Step 3

TFA (0.22 mL, 2.9 mmol) was added dropwise to a solution of 1-(2-((3-chlorophenyl)sulfonyl)ethyl) 4-(4-methoxybenzyl) 2-methylenesuccinate (0.439 g, 0.97 mmol) in DCM (11 mL) at 0° C. The mixture was slowly warmed to RT and stirred for 16 h. The solvent was removed and the residue was co-evaporated with toluene (2×10 mL). The crude product was purified by chromatography on silica gel (0-10% MeOH/DCM) to afford 3-((2-((3-chlorophenyl)sulfonyl)ethoxy)carbonyl)but-3-enoic acid (0.274 g, 0.81 mmol) as a colourless oil. $^1$H NMR (400 MHz, DMSO-d6) δ 12.33 (s, 1H), 7.96 (t, J=1.9 Hz, 1H), 7.88 (dt, J=7.8, 1.4 Hz, 1H), 7.83 (ddd, J=8.1, 2.1, 1.0 Hz, 1H), 7.68 (t, J=7.9 Hz, 1H), 5.71 (d, J=1.3 Hz, 1H), 5.67 (d, J=1.3 Hz, 1H), 4.42-4.35 (m, 2H), 3.93-3.86 (m, 2H), 3.13-3.08 (m, 2H). LCMS m/z 355.1 (M+Na)$^+$ (ES$^+$).

Step 4

Tert-butyl bromoacetate (0.13 mL, 0.87 mmol) was added dropwise to a mixture of 3-((2-((3-chlorophenyl)sulfonyl)ethoxy)carbonyl)but-3-enoic acid (0.274 g, 0.82 mmol) and potassium carbonate (0.12 g, 0.87 mmol) in acetone (3.5 mL). The reaction was stirred at RT for 16 h. The mixture was filtered and concentrated. The crude product was purified by chromatography on silica gel (0-100% EtOAc/isohexane) to afford 4-(2-(tert-butoxy)-2-oxoethyl) 1-(2-((3-chlorophenyl)sulfonyl)ethyl) 2-methylenesuccinate (0.294 g, 0.65 mmol) as a colourless oil. $^1$H NMR (400 MHz, DMSO-d6) δ 7.96 (t, J=1.9 Hz, 1H), 7.88 (ddd, J=7.8, 1.8, 1.0 Hz, 1H), 7.83 (ddd, J=8.1, 2.1, 1.0 Hz, 1H), 7.69 (t, J=7.9 Hz, 1H), 5.83 (d, J=1.2 Hz, 1H), 5.81-5.76 (m, 1H), 4.52 (s, 2H), 4.42-4.36 (m, 2H), 3.94-3.87 (m, 2H), 3.27 (s, 2H), 1.41 (s, 9H). LCMS m/z 469.1 (M+Na)$^+$ (ES$^+$).

Step 5

TFA (1.8 mL) was added to a solution of 4-(2-(tert-butoxy)-2-oxoethyl) 1-(2-((3-chlorophenyl)sulfonyl)ethyl) 2-methylenesuccinate (0.294 g, 0.65 mmol) in DCM (1.8 mL). The mixture was stirred for 30 min. The solvent was removed and the residue was co-evaporated with toluene (2×10 mL). The crude product was purified by chromatography on silica gel (0-10% MeOH/DCM) to afford the title compound (0.132 g, 0.33 mmol) as a colourless gum. $^1$H NMR (400 MHz, DMSO-d6) δ 13.07 (s, 1H), 7.96 (t, J=1.9 Hz, 1H), 7.88 (ddd, J=7.8, 1.7, 1.0 Hz, 1H), 7.83 (ddd, J=8.1, 2.2, 1.0 Hz, 1H), 7.69 (t, J=7.9 Hz, 1H), 5.83 (d, J=1.2 Hz, 1H), 5.81-5.77 (m, 1H), 4.56 (s, 2H), 4.41-4.35 (m, 2H), 3.93-3.87 (m, 2H), 3.25 (s, 2H). LCMS m/z 389.0 (M−Na)$^-$ (ES$^-$).

Example 127—(R)-2-((4-(cyclohexyloxy)-2-methylene-4-oxobutanoyl)oxy)-2-phenylacetic acid

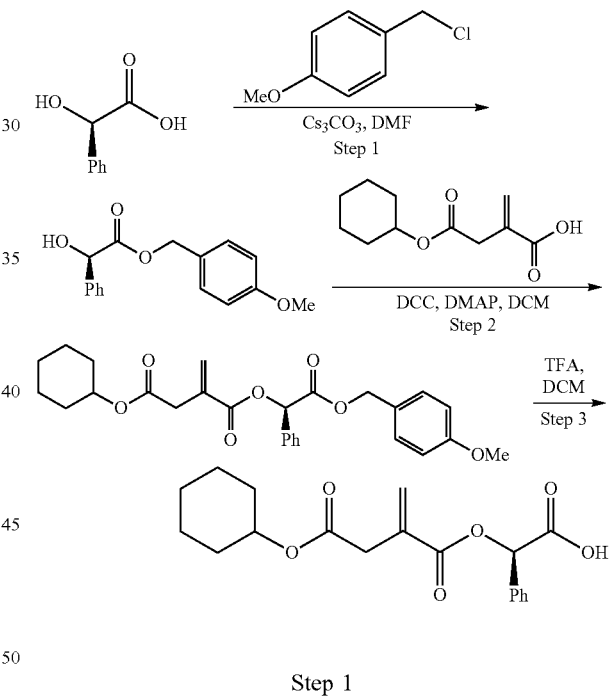

Step 1

Cesium carbonate (1.07 g, 3.29 mmol) was added to a solution of (R)-mandelic acid (1.00 g, 6.57 mmol) in methanol (8 mL) at 0° C. The suspension was stirred for 1 h at 0° C., then concentrated. Dimethylformamide (4 mL) was added and the mixture was cooled to 0° C., 4-methoxybenzyl chloride (1.1 mL, 8.1 mmol) was added dropwise. The mixture was warmed to RT and stirred for 18 h. EtOAc (100 mL) was added and the organic layer was washed with sat. aq. NH₄Cl (2×100 mL) followed by sat. aq. NaHCO₃ (100 mL). The organic layer was dried (phase separator) and concentrated. The resulting oil was cooled in an ice-bath which initiated precipitation of a white solid. Isohexane (50 mL) was added and the resulting suspension filtered. The solid was washed with isohexane (3×20 mL) and dried to afford (R)-4-methoxybenzyl 2-hydroxy-2-phenylacetate (1.61 g, 5.32 mmol) as a white solid. $^1$H NMR (400 MHz, DMSO-d6) δ 7.45-7.26 (m, 5H), 7.25-7.15 (m, 2H), 6.92-6.85 (m, 2H), 6.11-6.04 (m, 1H), 5.16 (d, J=5.4 Hz, 1H), 5.04 (q, J=12.1 Hz, 2H), 3.74 (s, 3H).

Step 2

DCC (0.583 g, 2.83 mmol) was added to a stirred solution of (R)-4-methoxybenzyl 2-hydroxy-2-phenylacetate (0.570 g, 1.89 mmol), 4-(cyclohexyloxy)-2-methylene-4-oxobutanoic acid (Intermediate 6, 0.40 g, 1.89 mmol) and DMAP (0.023 g, 0.19 mmol) in DCM (10 mL) at 0° C. The mixture was allowed to warm to RT and stirred for 18 h. The mixture was filtered, washing with toluene (3×5 mL) and the filtrate was concentrated. The residue was suspended in toluene (20 mL) and filtered, washing with toluene (3×5 mL) and the filtrate was concentrated. The crude product was purified by chromatography on silica gel (0-100% EtOAc/isohexane) followed by chromatography on RP Flash C18 (5-75% MeCN/Water 0.1% Formic Acid) to afford (R)-4-cyclohexyl 1-(2-((4-methoxybenzyl)oxy)-2-oxo-1-phenylethyl) 2-methylenesuccinate (0.47 g, 0.85 mmol, 84% purity) as a colourless oil. $^1$H NMR (400 MHz, DMSO-d6) δ 7.50-7.45 (m, 2H), 7.44-7.38 (m, 3H), 7.21-7.14 (m, 2H), 6.90-6.84 (m, 2H), 6.34 (d, J=1.2 Hz, 1H), 6.06 (s, 1H), 5.97-5.92 (m, 1H), 5.15-5.01 (m, 2H), 4.63-4.53 (m, 1H), 3.74 (s, 3H), 3.39 (s, 2H), 1.73-1.51 (m, 3H), 1.49-1.37 (m, 1H), 1.34-1.13 (m, 6H). LCMS m/z 489.1 (M+Na)$^+$ (ES$^+$).

Step 3

TFA (0.15 mL, 1.9 mmol) was added dropwise to a solution of (R)-4-cyclohexyl 1-(2-((4-methoxybenzyl)oxy)-2-oxo-1-phenylethyl) 2-methylenesuccinate (0.47 g, 0.85 mmol) in DCM (8 mL) at 0° C. The mixture was stirred at RT for 20 h, then concentrated. The crude product was purified by chromatography on RP Flash C18 (5-75% MeCN/Water 0.1% Formic Acid) to afford the title compound (0.209 g, 0.54 mmol) as a colourless gum. $^1$H NMR (400 MHz, DMSO-d6) δ 13.29 (s, 1H), 7.53-7.46 (m, 2H), 7.46-7.39 (m, 3H), 6.33 (d, J=1.2 Hz, 1H), 5.95-5.91 (m, 1H), 5.89 (s, 1H), 4.64-4.52 (m, 1H), 3.39 (s, 2H), 1.74-1.51 (m, 4H), 1.51-1.38 (m, 1H), 1.34-1.13 (m, 5H). LCMS m/z 369.1 (M+Na)$^+$ (ES$^+$).

Example 128—1-(2-(1H-tetrazol-5-yl)ethyl) 4-cyclohexyl 2-methylenesuccinate

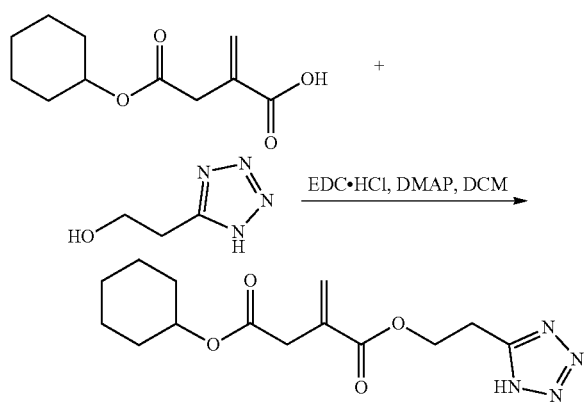

A slurry of EDC.HCl (297 mg, 1.55 mmol) in DCM (3 mL) was added slowly to a solution of 4-(cyclohexyloxy)-2-methylene-4-oxobutanoic acid (Intermediate 6, 219 mg, 1.03 mmol), 2-(1H-tetrazol-5-yl)ethanol (141 mg, 1.24 mmol) and DMAP (189 mg, 1.55 mmol) in DCM (3 mL) at 0° C. The mixture was allowed to warm slowly to RT and stirred for 16 h. The reaction mixture was diluted with 1 M HCl (5 mL) and the phases were separated. The aqueous phase was extracted with DCM (2×5 mL). The combined organic phases were dried (MgSO$_4$) and concentrated. The crude product was purified by chromatography on silica gel (0-100% EtOAc/isohexane) to afford the title compound (77 mg, 0.25 mmol) as a colourless oil. $^1$H NMR (400 MHz, DMSO-d6) δ 6.13 (d, J=1.3 Hz, 1H), 5.81 (d, J=1.3 Hz, 1H), 4.64-4.56 (m, 1H), 4.45 (t, J=6.4 Hz, 2H), 3.30 (s, 2H), 3.27 (t, J=6.4 Hz, 2H), 1.77-1.57 (m, 4H), 1.51-1.42 (m, 1H), 1.38-1.19 (m, 5H) (1 exchangeable proton not visible). LCMS m/z 309.2 (M+H)+ (ES$^+$).

Example 129—(S)-1-(2-(1H-tetrazol-5-yl)ethyl) 4-octan-2-yl 2-methylenesuccinate

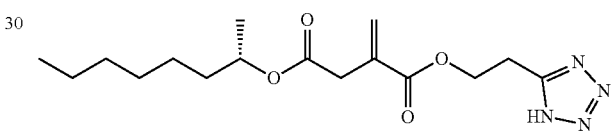

Example 129 was prepared according to the procedure of Example 128, but using (S)-2-methylene-4-(octan-2-yloxy)-4-oxobutanoic acid (Intermediate 9) instead of 4-(cyclohexyloxy)-2-methylene-4-oxobutanoic acid. $^1$H NMR (400 MHz, DMSO-d6) δ 6.12 (d, J=1.3 Hz, 1H), 5.80 (d, J=1.3 Hz, 1H), 4.78-4.68 (m, 1H), 4.44 (t, J=6.4 Hz, 2H), 3.30-3.24 (m, 4H), 1.52-1.37 (m, 2H), 1.30-1.15 (m, 8H), 1.10 (d, J=6.3 Hz, 3H), 0.89-0.81 (m, 3H) (1 exchangeable proton not visible). LCMS m/z 339.2 (M+H)+ (ES$^+$).

Example 130—1-(2-(1H-tetrazol-5-yl)ethyl) 4-cyclooctyl 2-methylenesuccinate

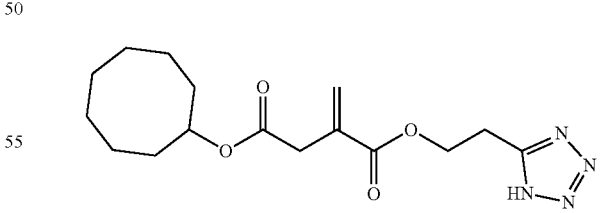

Example 130 was prepared according to the procedure of Example 128, but using 4-(cyclooctyloxy)-2-methylene-4-oxobutanoic acid (Intermediate 1) instead of 4-(cyclohexyloxy)-2-methylene-4-oxobutanoic acid. $^1$H NMR (400 MHz, DMSO-d6) δ 6.12 (d, J=1.4 Hz, 1H), 5.80 (d, J=1.2 Hz, 1H), 4.80-4.73 (m, 1H), 4.45 (t, J=6.3 Hz, 2H), 3.30-3.25 (m, 4H), 1.73-1.38 (m, 14H) (1 exchangeable proton not visible). LCMS m/z 337.2 (M+H)$^+$ (ES$^+$).

Example 131—1-(2-((3-chlorophenyl)sulfonyl)-2-methylpropyl) 4-cyclooctyl 2-methylenesuccinate

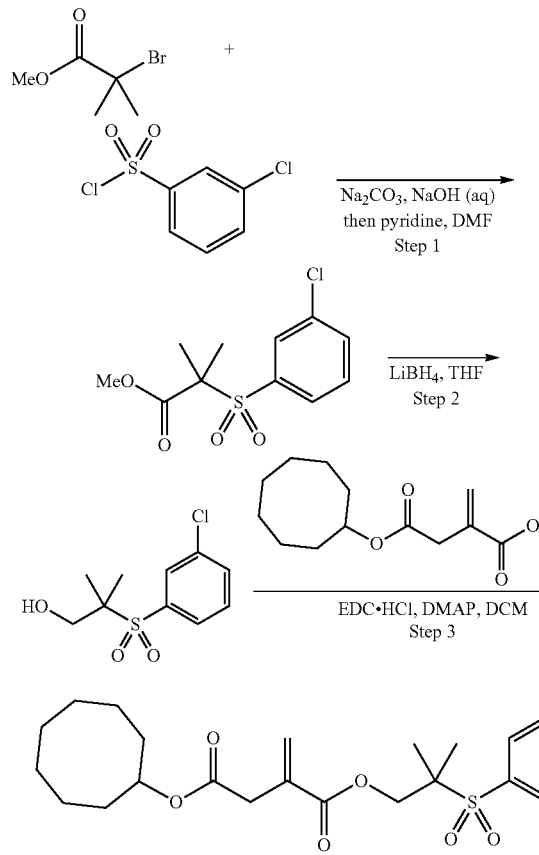

Step 1

3-Chlorobenzene-1-sulfonyl chloride (0.67 mL, 4.76 mmol) was added to a stirred solution of sodium sulfite (1.237 g, 9.52 mmol) and 2 M NaOH (aq.) (4.8 mL, 9.6 mmol) in water (25 mL). The reaction mixture was heated to 100° C. and stirred for 30 min, cooled to RT and concentrated. The residue was suspended in DMF (10 mL) and pyridine (0.85 mL, 10.5 mmol) and methyl 2-bromo-2-methylpropanoate (2.5 mL, 19.3 mmol) were added. The mixture was stirred at 40° C. for 16 h. The mixture was cooled to RT and diluted with brine (100 mL). The mixture was extracted with DCM (3×80 mL), dried (phase separator) and concentrated. The crude product was purified by chromatography on silica gel (0-50% EtOAc/isohexane) to afford methyl 2-((3-chlorophenyl)sulfonyl)-2-methylpropanoate (0.70 g, 2.28 mmol) as a white solid. $^1$H NMR (400 MHz, DMSO-d6) δ 7.96-7.89 (m, 1H), 7.81-7.77 (m, 2H), 7.76-7.69 (m, 1H), 3.62 (s, 3H), 1.53 (s, 6H). LCMS m/z 299.2 (M+Na)$^+$ (ES$^+$).

Step 2

Lithium borohydride (4 M in THF, 1 mL, 4 mmol) was added to a solution of methyl 2-((3-chlorophenyl)sulfonyl)-2-methylpropanoate (0.60 g, 1.95 mmol) in THF (15 mL) at 0° C. The mixture was warmed to RT and stirred for 18 h. The reaction was quenched with acetic acid (20 mL) and concentrated. The residue was partitioned between DCM (50 mL) and water (50 mL). The phases were separated and the aqueous phase was extracted with DCM (3×50 mL). The combined organic phases were dried (phase separator) and concentrated. The crude product was purified by chromatography on silica gel (0-100% EtOAc/isohexane) to afford 2-((3-chlorophenyl)sulfonyl)-2-methylpropan-1-ol (0.57 g, 2.11 mmol) as a white solid. $^1$H NMR (400 MHz, DMSO-d6) δ 7.87-7.79 (m, 3H), 7.71-7.65 (m, 1H), 5.10 (t, J=5.8 Hz, 1H), 3.55-3.50 (m, 2H), 1.22 (s, 6H). LCMS m/z 249.2 (M+H)$^+$ (ES$^+$).

Step 3

EDC.HCl (0.106 g, 0.555 mmol) was added to a solution of 4-(cyclooctyloxy)-2-methylene-4-oxobutanoic acid (Intermediate 1, 0.089 g, 0.37 mmol), 2-((3-chlorophenyl)sulfonyl)-2-methylpropan-1-ol (0.1 g, 0.37 mmol) and DMAP (0.068 g, 0.56 mmol) in DCM (5 mL) at 0° C. The reaction was allowed to warm to RT slowly and stirred for 18 h. The mixture was diluted with 1M HCl (20 mL) and extracted with DCM (3×20 mL). The combined organic phases were dried (phase separator) and concentrated. The crude product was purified by chromatography on silica gel (0-100% EtOAc/isohexane) to afford the title compound (0.046 g, 0.093 mmol) as a colourless gum. $^1$H NMR (400 MHz, DMSO-d6) δ 7.92-7.86 (m, 1H), 7.84-7.79 (m, 2H), 7.75-7.67 (m, 1H), 5.91 (d, J=1.3 Hz, 1H), 5.77-5.73 (m, 1H), 4.85-4.75 (m, 1H), 4.24 (s, 2H), 3.18 (s, 2H), 1.76-1.37 (m, 14H), 1.34 (s, 6H). LCMS m/z 493.2/495.2 (M+Na)$^+$ (ES$^+$).

Example 132—4-cyclooctyl 1-(2-methyl-2-(methylsulfonyl)propyl) 2-methylenesuccinate

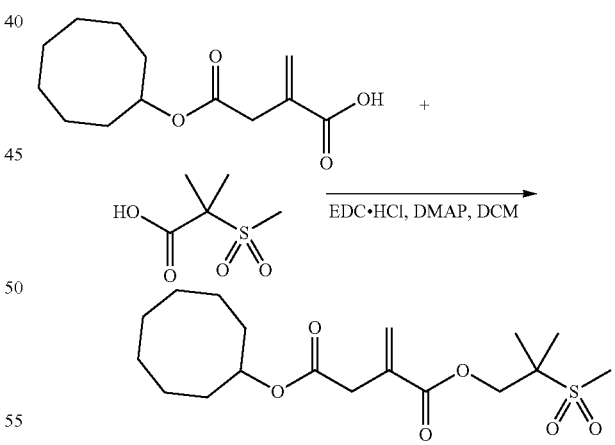

EDC.HCl (0.156 g, 0.812 mmol) in DCM (1.1 mL) was added to a solution of 4-(cyclooctyloxy)-2-methylene-4-oxobutanoic acid (Intermediate 1, 0.13 g, 0.54 mmol), 2-methyl-2-(methylsulfonyl)propan-1-ol (0.099 g, 0.65 mmol), and DMAP (0.099 g, 0.81 mmol) in DCM (1.1 mL) at 0° C. The mixture was allowed to warm slowly to RT and stirred for 16 h. The mixture was poured into 1 M HCl (5 mL) and extracted with EtOAc (3×5 mL). The combined organic extracts were washed with brine (15 mL), dried (Na$_2$SO$_4$) and concentrated. The crude product was purified by chromatography on silica gel (0-100% EtOAc/isohexane) to afford the title compound (0.048 g, 0.13 mmol) as a colourless oil. $^1$H NMR (400 MHz, DMSO-d6) δ 6.27 (d, J=1.2 Hz, 1H), 5.88 (d, J=1.2 Hz, 1H), 4.83 (tt, J=8.1, 4.0 Hz, 1H), 4.29 (s, 2H), 3.36 (s, 2H), 2.97 (s, 3H), 1.79-1.36 (m, 10H), 1.33 (s, 6H). LCMS m/z 397.3 (M+Na)$^+$ (ES$^+$).

Example 133—1-(1-(1H-tetrazol-5-yl)ethyl) 4-cyclooctyl 2-methylenesuccinate

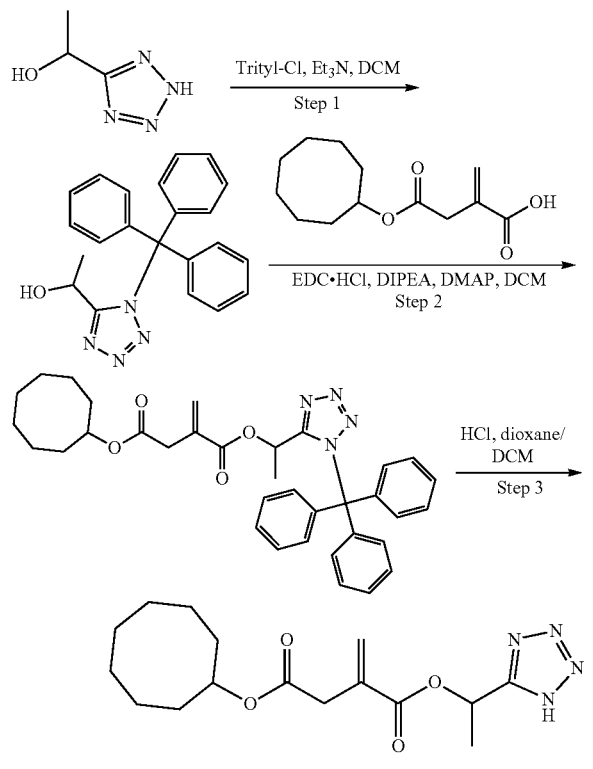

Step 1

Trityl-Cl (0.641 g, 2.30 mmol) was added to a solution of 1-(1H-tetrazol-5-yl)ethanol (0.25 g, 2.19 mmol) and triethylamine (0.35 mL, 2.5 mmol) in DCM (5 mL). The mixture was stirred for 2 h, then diluted with water (10 mL). The phases were separated and the aqueous phase was extracted with EtOAc (2×10 mL). The combined organic phases were washed with brine (30 mL), dried (MgSO$_4$) and concentrated. The crude product was purified by chromatography on silica gel (0-100% EtOAc/isohexane) to afford 1-(1-trityl-1H-tetrazol-5-yl)ethanol (746 mg, 1.67 mmol) as a colourless oil that solidified on standing. $^1$H NMR (400 MHz, DMSO-d6) δ 7.46-7.35 (m, 9H), 7.08-6.98 (m, 6H), 5.69 (d, J=5.4 Hz, 1H), 5.02 (qd, J=6.6, 5.3 Hz, 1H), 1.48 (d, J=6.6 Hz, 3H). LCMS m/z 243.2 (trityl)$^+$ (ES$^+$).

Step 2

A slurry of EDC.HCl (0.50 g, 2.6 mmol) in DCM (3 mL) was added slowly to a solution of 4-(cyclooctyloxy)-2-methylene-4-oxobutanoic acid (Intermediate 1, 0.419 g, 1.74 mmol), 1-(1-trityl-1H-tetrazol-5-yl)ethanol (0.746 g, 2.09 mmol), DIPEA (0.46 mL, 2.6 mmol) and DMAP (0.021 g, 0.17 mmol) in DCM (3 mL) at 0° C. The mixture was allowed to warm slowly to RT and stirred for 3 days. The mixture was diluted with water (5 mL) and the phases were separated. The aqueous phase was extracted with DCM (2×5 mL). The combined organic phases were dried (MgSO$_4$) and concentrated. The crude product was purified by chromatography on silica gel (0-50% EtOAc/isohexane) to afford 4-cyclooctyl 1-(1-(1-trityl-1H-tetrazol-5-yl)ethyl) 2-methylenesuccinate (402 mg, 0.59 mmol, 85% purity) as a colourless gum. $^1$H NMR (400 MHz, DMSO-d6) δ 7.45-7.36 (m, 9H), 7.03-6.97 (m, 6H), 6.20 (d, J=1.3 Hz, 1H), 6.16 (q, J=6.7 Hz, 1H), 5.85 (d, J=1.3 Hz, 1H), 4.76 (tt, J=8.0, 3.9 Hz, 1H), 3.31 (s, 2H), 1.64 (d, J=6.7 Hz, 3H), 1.62-1.31 (m, 14H). LCMS m/z 601.1 (M+Na)$^+$ (ES$^+$).

Step 3

HCl (4 M in 1,4-dioxane, 1.5 mL, 6.00 mmol) was added to a solution of 4-cyclooctyl 1-(1-(1-trityl-1H-tetrazol-5-yl)ethyl) 2-methylenesuccinate (402 mg, 0.59 mmol, 85% purity) in DCM (3.5 mL). The mixture was stirred for 18 h at RT. The mixture was concentrated. The crude product was purified by chromatography on silica gel (0-5% MeOH/DCM) to afford the title compound (152 mg, 0.45 mmol) as a pale yellow oil. $^1$H NMR (400 MHz, DMSO-d6) δ 6.29 (d, J=1.2 Hz, 1H), 6.20 (q, J=6.7 Hz, 1H), 5.90 (d, J=1.2 Hz, 1H), 4.78 (tt, J=7.8, 3.8 Hz, 1H), 3.35 (s, 2H), 1.64 (d, J=6.7 Hz, 3H), 1.63-1.30 (m, 14H) (1 exchangeable proton not visible). LCMS m/z 359.3 (M+Na)$^+$ (ES$^+$).

Example 134—1-((1H-tetrazol-5-yl)methyl) 4-cyclooctyl 2-methylenesuccinate

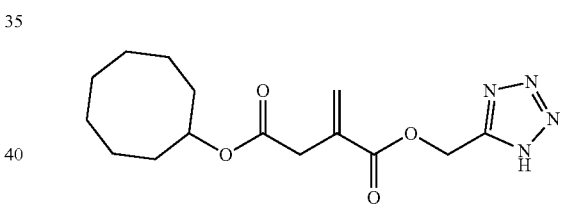

Example 134 was prepared according to the procedure of Example 133, but using (1-trityl-1H-tetrazol-5-yl)methanol instead of 1-(1-trityl-1H-tetrazol-5-yl)ethanol, in step 2. $^1$H NMR (400 MHz, DMSO-d6) δ 6.31 (d, J=1.1 Hz, 1H), 5.92 (d, J=1.2 Hz, 1H), 5.48 (s, 2H), 4.83-4.74 (m, 1H), 3.35 (s, 2H), 1.72-1.36 (m, 14H) (1 exchangeable proton not visible). LCMS m/z 345.3 (M+Na)+(ES$^+$).

Example 135—(R)-1-(2-(1H-tetrazol-5-yl)ethyl) 4-octan-2-yl 2-methylenesuccinate

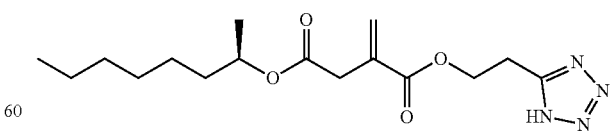

Example 135 was prepared according to the procedure of Example 133, but using 2-(1-trityl-1H-tetrazol-5-yl)ethanol, instead of 1-(1-trityl-1H-tetrazol-5-yl)ethanol, and (R)-2-methylene-4-(octan-2-yloxy)-4-oxobutanoic acid (Intermediate 8) instead of 4-(cyclooctyloxy)-2-methylene-4-oxobutanoic acid in step 2. $^1$H NMR (400 MHz, DMSO-d6) δ 6.12 (d, J=1.3 Hz, 1H), 5.81 (d, J=1.3 Hz, 1H), 4.78-4.69 (m, 1H), 4.44 (t, J=6.4 Hz, 2H), 3.29 (s, 2H), 3.27 (t, J=6.4 Hz, 2H), 1.52-1.38 (m, 2H), 1.30-1.16 (m, 8H), 1.11 (d, J=6.2 Hz, 3H), 0.89-0.82 (m, 3H) (1 exchangeable proton not visible). LCMS m/z 339.2 (M+H)+ (ES+).

Example 136—(2R,3S)-2-acetamido-3-((4-(cyclooctyloxy)-2-methylene-4-oxobutanoyl)oxy)butanoic acid

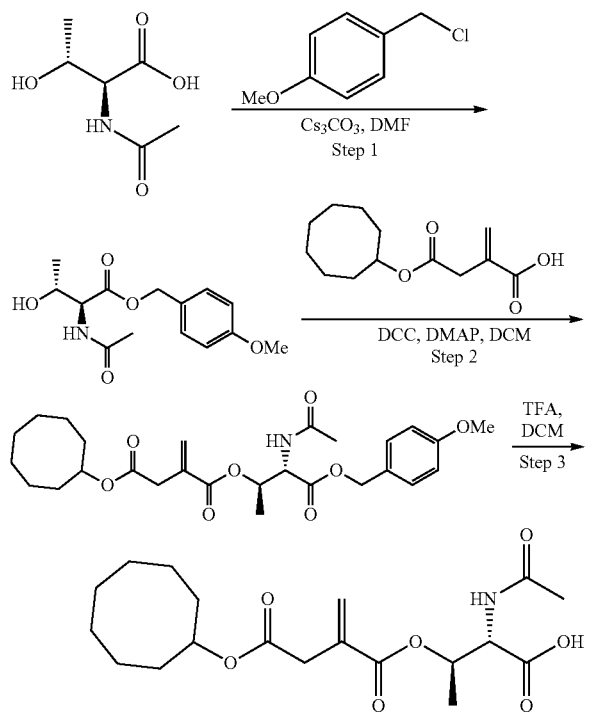

Step 1

1-(chloromethyl)-4-methoxybenzene (0.85 mL, 6.24 mmol) was added to a mixture of (2S,3R)-2-acetamido-3-hydroxybutanoic acid (1.00 g, 6.21 mmol) and cesium carbonate (2.22 g, 6.81 mmol) in dimethylformamide (20 mL) at 0° C. The mixture was stirred at RT for 42 h. The mixture was poured onto water (100 mL) and extracted with DCM (3×50 mL). The combined organic phases were dried (phase separator) and concentrated. The crude product was purified by chromatography on silica gel (0-10% MeOH/DCM) to afford (2S,3R)-4-methoxybenzyl 2-acetamido-3-hydroxybutanoate (0.95 g, 3.21 mmol) as a white solid. $^1$H NMR (400 MHz, DMSO-d6) δ 7.99 (d, J=8.4 Hz, 1H), 7.35-7.26 (m, 2H), 6.97-6.89 (m, 2H), 5.11-4.99 (m, 2H), 4.95 (d, J=5.5 Hz, 1H), 4.34-4.23 (m, 1H), 4.16-4.05 (m, 1H), 3.76 (s, 3H), 1.91 (s, 3H), 1.05 (d, J=6.4 Hz, 3H). LCMS m/z 304.2 (M+Na)+ (ES+).

Step 2

DCC (0.475 g, 2.30 mmol) was added to a solution of 4-(cyclooctyloxy)-2-methylene-4-oxobutanoic acid (0.369 g, 1.536 mmol), (2S,3R)-4-methoxybenzyl 2-acetamido-3-hydroxybutanoate (0.48 g, 1.54 mmol), DMAP (0.019 g, 0.15 mmol) in DCM (15 mL) at 0° C. The reaction mixture was allowed to warm to RT and stirred for 18 h. The reaction mixture was filtered, washing with toluene (3×5 mL) and the filtrate was concentrated. The residue was suspended in toluene (20 mL) and filtered, washing with toluene (3×5 mL) and the filtrate was concentrated. The crude product was purified by chromatography on RP Flash C18 (5-100% MeCN/Water 0.1% Formic Acid, eluting at 100%) to afford a residue which was treated with toluene (20 mL). The solid was removed by filtration and the filtrate was concentrated to afford 1-((2S,3R)-3-acetamido-4-((4-methoxybenzyl)oxy)-4-oxobutan-2-yl) 4-cyclooctyl 2-methylenesuccinate (0.23 g, 0.41 mmol) as a colourless gum. $^1$H NMR (400 MHz, DMSO-d6) δ 8.34 (d, J=9.0 Hz, 1H), 7.30-7.23 (m, 2H), 6.94-6.86 (m, 2H), 6.24 (d, J=1.4 Hz, 1H), 5.81-5.77 (m, 1H), 5.32-5.23 (m, 1H), 5.07-4.96 (m, 2H), 4.87-4.77 (m, 1H), 4.75-4.68 (m, 1H), 3.75 (s, 3H), 3.28 (s, 2H), 1.96 (s, 3H), 1.80-1.34 (m, 14H), 1.15 (d, J=6.4 Hz, 3H). LCMS m/z 526.3 (M+Na)+ (ES+).

Step 3

TFA (0.2 mL) was added to a solution of 1-((2S,3R)-3-acetamido-4-((4-methoxybenzyl)oxy)-4-oxobutan-2-yl) 4-cyclooctyl 2-methylenesuccinate (0.23 g, 0.41 mmol) in DCM (5 mL). The reaction mixture was stirred for 20 h and concentrated. The crude product was purified by chromatography on silica gel (0-10% MeOH/DCM) to afford the title compound (0.044 g, 0.11 mmol) as a pale yellow solid. $^1$H NMR (400 MHz, DMSO-d6) δ 12.91 (s, br. 1H), 8.18 (d, J=9.1 Hz, 1H), 6.32 (d, J=1.4 Hz, 1H), 5.86-5.77 (m, 1H), 5.34-5.20 (m, 1H), 4.88-4.76 (m, 1H), 4.64-4.53 (m, 1H), 3.31 (s, 2H), 1.95 (s, 3H), 1.79-1.35 (m, 14H), 1.15 (d, J=6.4 Hz, 3H). LCMS m/z 406.2 (M+Na)+ (ES+).

Example 137—4-cyclooctyl 1-(3-(2-ethoxy-2-oxoethyl)oxetan-3-yl) 2-methylenesuccinate

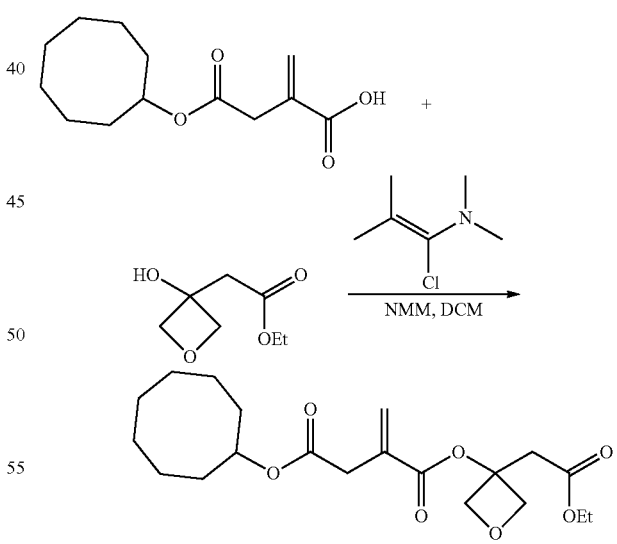

1-Chloro-N,N,2-trimethylprop-1-en-1-amine (0.27 mL, 2.01 mmol) was added to a solution of 4-(cyclooctyloxy)-2-methylene-4-oxobutanoic acid (Intermediate 1, 0.44 g, 1.83 mmol) in DCM (5 mL). The mixture was stirred for 2 h and concentrated. The residue was dissolved in DCM (2 mL) and added dropwise to a solution of ethyl 2-(3-hydroxyoxetan-3-yl)acetate (0.323 g, 2.01 mmol) and NMM (0.28 mL, 2.6 mmol) in DCM (3 mL). The mixture was stirred for 16 h at RT, then poured into water (10 mL) and extracted with EtOAc (3×10 mL). The combined organic extracts were washed with brine (20 mL), dried (Na$_2$SO$_4$) and concentrated. The crude product was purified by chromatography on silica gel (0-100% EtOAc/isohexane) to afford the title compound (0.072 g, 0.19 mmol) as a colourless oil. $^1$H NMR (400 MHz, DMSO-d6) δ 6.20 (d, J=1.3 Hz, 1H), 5.87 (d, J=1.3 Hz, 1H), 4.84 (tt, J=8.2, 3.9 Hz, 1H), 4.71-4.65 (m, 2H), 4.64 (d, J=7.7 Hz, 2H), 4.06 (q, J=7.1 Hz, 2H), 3.32 (s, 2H), 3.20 (s, 2H), 1.79-1.42 (m, 14H), 1.16 (t, J=7.1 Hz, 3H). LCMS m/z 383.3 (M+H)$^+$ (ES$^+$).

Example 138—4-(2-(methylsulfonyl)ethyl) 1-octyl 2-methyl-3-methylenesuccinate

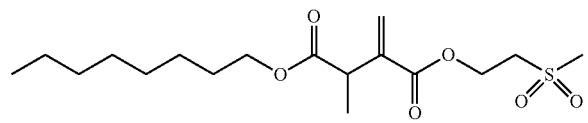 [SMILES: C=C(C(=O)OCCS(C)(=O)=O)C(C)C(=O)OCCCCCCCC]

Example 138 was prepared according to General Procedure 2, using 3-methyl-2-methylene-4-(octyloxy)-4-oxobutanoic acid (Intermediate 12) as itaconic acid monoester and 2-(methylsulfonyl)ethanol as R$^2$—OH. $^1$H NMR (500 MHz, DMSO-d6) δ 6.28 (s, 1H), 5.85 (s, 1H), 4.45 (t, J=5.8 Hz, 2H), 4.00 (t, J=6.6 Hz, 2H), 3.61-3.52 (m, 3H), 3.03 (s, 3H), 1.55-1.49 (m, 2H), 1.30-1.23 (m, 13H), 0.86 (t, J=6.8 Hz, 3H). LCMS m/z 385.5 (M+Na)$^+$ (ES$^+$).

Example 139—1-octyl 4-((S)-tetrahydrofuran-3-yl) 2-methyl-3-methylenesuccinate

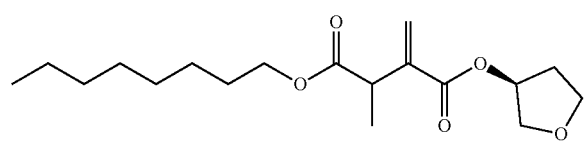 [SMILES: C=C(C(=O)O[C@H]1CCOC1)C(C)C(=O)OCCCCCCCC]

Example 139 was prepared according to General Procedure 2, using 3-methyl-2-methylene-4-(octyloxy)-4-oxobutanoic acid (Intermediate 12) as itaconic acid monoester and (S)-tetrahydrofuran-3-ol as R$^2$—OH. $^1$H NMR (500 MHz, DMSO-d6) δ 6.23 (s, 1H), 5.79 (s, 1H), 5.29-5.25 (m, 1H), 3.98 (t, J=6.5 Hz, 2H), 3.84-3.72 (m, 3H), 3.65 (dd, J=10.5, 3.7 Hz, 1H), 3.56 (q, J=7.2 Hz, 1H), 2.20-2.08 (m, 1H), 1.93-1.84 (m, 1H), 1.57-1.48 (m, 2H), 1.29-1.23 (m, 13H), 0.86 (t, J=6.8 Hz, 3H). LCMS m/z 349.2 (M+Na)$^+$ (ES$^+$).

Example 140—1-(1-(1H-tetrazol-5-yl)propan-2-yl) 4-((R)-octan-2-yl) 2-methylenesuccinate

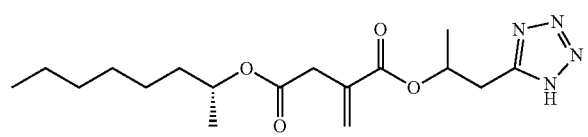 [SMILES: C=C(CC(=O)O[C@H](C)CCCCCC)C(=O)OC(C)Cc1nnn[nH]1]

Example 140 was prepared according to General Procedure 2, using Intermediate 8 as itaconic acid monoester and 1-(1H-tetrazol-5-yl)propan-2-ol as R$^2$—OH. $^1$H NMR (400 MHz, DMSO-d6) δ 6.11 (d, J=1.4 Hz, 1H), 5.78 (d, J=1.4 Hz, 1H), 5.30-5.13 (m, 1H), 4.75 (h, J=6.2 Hz, 1H), 3.37-3.13 (m, 4H), 1.54-1.35 (m, 2H), 1.34-1.16 (m, 11H), 1.11 (dd, J=6.3, 2.4 Hz, 3H), 0.85 (t, J=6.6 Hz, 3H) (1 exchangeable proton not visible). LCMS m/z 353.4 (M+H)$^+$ (ES$^+$).

Example 141—1-(1-(1H-tetrazol-5-yl)propan-2-yl) 4-((S)-octan-2-yl) 2-methylenesuccinate

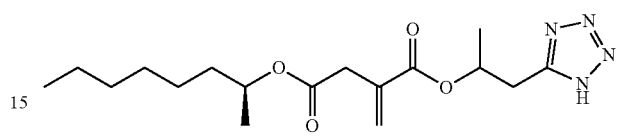

Example 141 was prepared according to General Procedure 2, using Intermediate 9 as itaconic acid monoester and 1-(1H-tetrazol-5-yl)propan-2-ol as R$^2$—OH. $^1$H NMR (400 MHz, DMSO-d6) b 6.11 (d, J=1.4 Hz, 1H), 5.78 (d, J=1.4 Hz, 1H), 5.21 (h, J=6.7 Hz, 1H), 4.75 (h, J=6.3 Hz, 1H), 3.40-3.13 (m, 4H), 1.53-1.35 (m, 2H), 1.33-1.16 (m, 11H), 1.11 (dd, J=6.2, 2.4 Hz, 3H), 0.85 (t, J=6.6 Hz, 3H) (1 exchangeable proton not visible). LCMS m/z 375.4 (M+Na)$^+$ (ES$^+$).

Example 142—4-cyclohexyl 1-((2-methyl-2H-tetrazol-5-yl)methyl) 2-methylenesuccinate

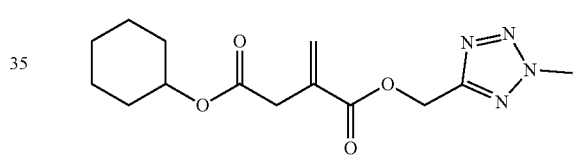

Example 142 was prepared according to the procedure of Example 130, but using Intermediate 6 instead of 4-(cyclooctyloxy)-2-methylene-4-oxobutanoic acid (Intermediate 1). $^1$H NMR (400 MHz, DMSO-d6) δ 6.23 (d, J=1.2 Hz, 1H), 5.91-5.87 (m, 1H), 5.41 (s, 2H), 4.69-4.57 (m, 1H), 4.38 (s, 3H), 3.36 (s, 2H), 1.76-1.55 (m, 4H), 1.52-1.40 (m, 1H), 1.38-1.14 (m, 5H). LCMS m/z 309 (M+H)$^+$ (ES$^+$).

Example 143—4-cyclohexyl 1-((1-methyl-1H-tetrazol-5-yl)methyl) 2-methylenesuccinate

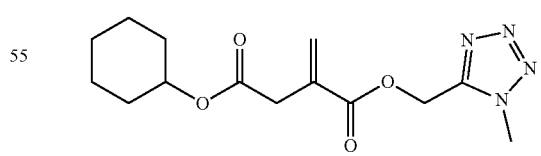

Example 142 was prepared according to the procedure of Example 130, but using Intermediate 6 instead of 4-(cyclooctyloxy)-2-methylene-4-oxobutanoic acid (Intermediate 1). $^1$H NMR (400 MHz, DMSO-d6) δ 6.30 (d, J=1.1 Hz, 1H), 5.95-5.90 (m, 1H), 5.52 (s, 2H), 4.66-4.54 (m, 1H), 4.10 (s, 3H), 3.38 (s, 2H), 1.73-1.40 (m, 5H), 1.37-1.12 (m, 5H). LCMS m/z 309 (M+H)$^+$ (ES$^+$).

Example 144—3-((4-(cyclooctyloxy)-2-methylene-4-oxobutanoyl)oxy)-4,4,4-trifluorobutanoic acid

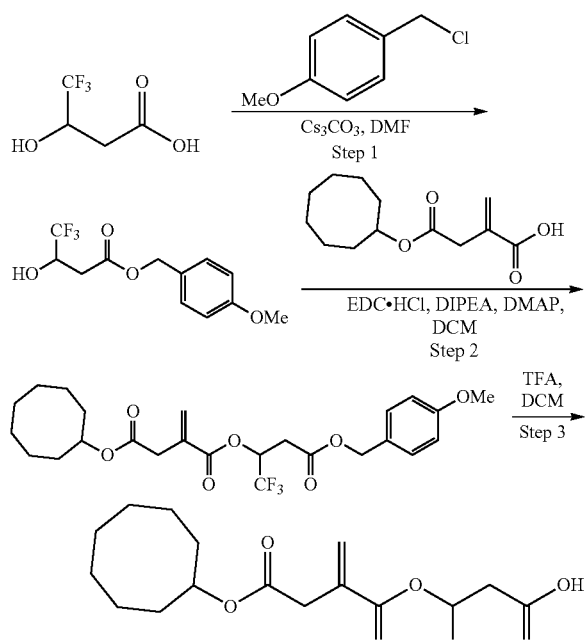

Step 1

1-(chloromethyl)-4-methoxybenzene (0.86 ml, 6.3 mmol) was added to a mixture of 4,4,4-trifluoro-3-hydroxybutanoic acid (1.00 g, 6.33 mmol) and cesium carbonate (2.06 g, 6.33 mmol) in DMF (27 mL). The mixture was stirred at RT for 1 h, then heated to 70° C. for 2 h. The mixture was cooled to RT and stirred for 18 h. The mixture was poured onto water (50 mL) and extracted with EtOAc (3×50 mL). The combined organic phases were washed with brine (100 mL), dried (MgSO4) and concentrated. The crude product was purified by chromatography on silica gel (0-100% EtOAc/isohexane) to afford 4-methoxybenzyl 4,4,4-trifluoro-3-hydroxybutanoate (0.283 g, 0.97 mmol) as a colourless oil. 1H NMR (400 MHz, DMSO-d6) δ 7.37-7.26 (m, 2H), 6.98-6.87 (m, 2H), 6.58 (d, J=6.7 Hz, 1H), 5.08 (d, J=13.5 Hz, 1H), 5.05 (d, J=13.6 Hz, 1H), 4.35 (dtt, J=17.3, 7.2, 3.3 Hz, 1H), 3.75 (s, 3H), 2.77 (dd, J=15.8, 3.3 Hz, 1H), 2.57-2.52 (m, 1H).

Step 2

A slurry of N-(3-dimethylaminopropyl)-N'-ethylcarbodiimide hydrochloride (0.28 g, 1.5 mmol) in DCM (1.6 mL) was added slowly to a solution of 4-(cyclooctyloxy)-2-methylene-4-oxobutanoic acid (0.233 g, 0.97 mmol), 4-methoxybenzyl 4,4,4-trifluoro-3-hydroxybutanoate (0.283 g, 0.97 mmol), DIPEA (0.25 mL, 1.5 mmol) and DMAP (0.012 g, 0.097 mmol) in DCM (1.6 mL) at 0° C. The mixture was allowed to warm slowly to RT and stirred for 18 h. The mixture was diluted with 1 M HCl (10 mL) and extracted with EtOAc (3×10 mL). The combined organic phases were washed with brine (15 mL), dried (Na2SO4) and concentrated. The crude product was purified by chromatography on silica gel (0-50% EtOAc/isohexane) to afford 4-cyclooctyl 1-(1,1,1-trifluoro-4-((4-methoxybenzyl)oxy)-4-oxobutan-2-yl) 2-methylenesuccinate (0.304 g, 0.56 mmol) as a colourless oil. LCMS m/z 523.2 (M+Na)+ (ES+). 1H NMR (400 MHz, DMSO-d6) δ 7.34-7.22 (m, 2H), 6.96-6.85 (m, 2H), 6.23 (d, J=1.0 Hz, 1H), 5.93 (d, J=1.1 Hz, 1H), 5.81 (dqd, J=10.3, 6.7, 3.6 Hz, 1H), 5.04 (s, 2H), 4.80 (tt, J=8.2, 4.0 Hz, 1H), 3.75 (s, 3H), 3.31 (s, 2H), 3.10 (dd, J=16.8, 3.6 Hz, 1H), 2.87 (dd, J=16.8, 9.5 Hz, 1H), 1.78-1.33 (m, 14H).

Step 3

Trifluoroacetic acid (1.4 mL) was added to a solution of 4-cyclooctyl 1-(1,1,1-trifluoro-4-((4-methoxybenzyl)oxy)-4-oxobutan-2-yl) 2-methylenesuccinate (0.304 g, 0.56 mmol) in DCM (5 mL) at 0° C. The reaction mixture was warmed to RT, stirred for 30 min and concentrated. The residue was co-evaporated with toluene (2×10 mL). The crude product was purified by chromatography on silica gel (0-50% EtOAc/DCM) to afford 3-((4-(cyclooctyloxy)-2-methylene-4-oxobutanoyl)oxy)-4,4,4-trifluorobutanoic acid (0.127 g, 0.32 mmol) as a colourless oil. LCMS m/z 403.3 (M+Na)+ (ES+). 1H NMR (400 MHz, DMSO-d6) δ 12.84 (s, 1H), 6.29 (d, J=1.1 Hz, 1H), 5.96 (d, J=1.2 Hz, 1H), 5.83-5.71 (m, 1H), 4.82 (tt, J=8.1, 3.9 Hz, 1H), 3.35 (s, 2H), 2.96 (dd, J=16.9, 3.8 Hz, 1H), 2.74 (dd, J=16.9, 9.2 Hz, 1H), 1.79-1.34 (m, 14H).

Example 145—2-(4-(cycloheptyloxy)-2-methylene-4-oxobutanoyloxy)acetic acid

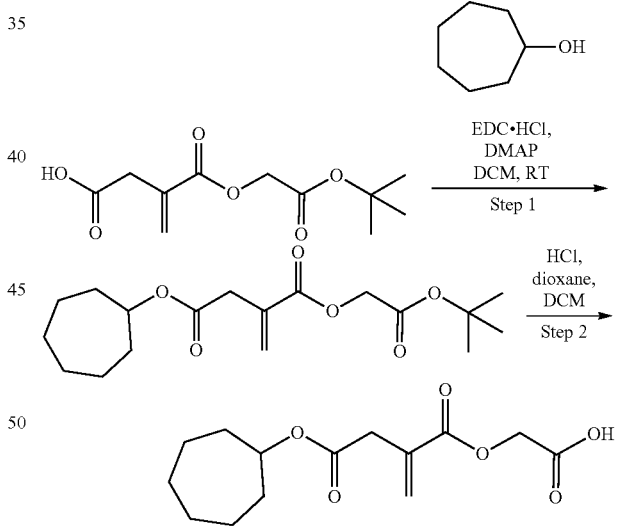

Step 1

To a solution of 3-((2-tert-butoxy-2-oxoethoxy)carbonyl)but-3-enoic acid (234 mg, 0.96 mmol), cycloheptanol (110 mg, 0.96 mmol) and DMAP (117 mg, 0.96 mmol) in DCM (4 mL) was added EDC.HCl (276 mg, 1.44 mmol) at 0° C., and the resulting mixture was stirred at room temperature for 1 h. The mixture was quenched with aqueous NH4Cl (2 mL), the phases were separated, and the aqueous phase was extracted with DCM (2×3 mL). The combined organic phases were washed with brine, dried over Na2SO4 and filtered. The filtrate was concentrated under reduced pressure at 40° C., and the residue was purified by flash column chromatography (25 g silica, 0-10% MTBE/petroleum ether) to give 1-(2-tert-butoxy-2-oxoethyl) 4-cycloheptyl 2-methylenesuccinate (130 mg, 0.38 mmol, 40%) as a pale-yellow oil. LCMS (System 2, Method B) m/z 363.3 (M+Na)$^+$ (ES$^+$).

Step 2

A mixture of 1-(2-tert-butoxy-2-oxoethyl) 4-cycloheptyl 2-methylenesuccinate (130 mg, 0.38 mmol) and HCl solution in 1,4-dioxane (4 M, 3 mL, 12 mmol) in DCM (2 mL) was stirred at room temperature for 4 h. The mixture was concentrated under reduced pressure at 40° C. and the residue was purified by preparative HPLC (Column: Waters X-Bridge C18 OBD 10 μm 19×250 mm; Flow Rate: 20 mL/min; solvent system: MeCN/(0.05% TFA/water); gradient: 15-95% MeCN; collection wavelength: 214 nm). The collected fractions were concentrated at 40° C. under reduced pressure to remove MeCN, and the residue was lyophilized to give 2-(4-(cycloheptyloxy)-2-methylene-4-oxobutanoyloxy)acetic acid (76 mg, 0.27 mmol, 70%) as a pale-yellow oil. LCMS (System 2, Method B) m/z 307.1 (M+Na)$^+$ (ES$^+$). $^1$H NMR (400 MHz, DMSO-d6) δ: 13.06 (br, 1H), 6.27 (d, J=0.8 Hz, 1H), 5.91 (d, J=0.8 Hz, 1H), 4.83-4.78 (m, 1H), 4.63 (s, 2H), 3.33 (s, 2H), 1.83-1.76 (m, 2H), 1.62-1.51 (m, 4H), 1.50-1.48 (m, 4H), 1.42-1.37 (m, 2H).

The following compounds were made using a similar procedure:

| Example No. | Alcohol Intermediate/ Example Structure/Name | LCMS/$^1$H NMR data |
| --- | --- | --- |
| 146 | octan-3-ol<br>2-(2-methylene-4-(octan-3-yloxy)-4-oxobutanoyloxy)acetic acid | LCMS (System 2, Method B) m/z 323.2 (M + Na)$^+$ (ES$^+$).<br>$^1$H NMR (400 MHz, DMSO-d6) δ: 13.09 (br, 1H), 6.28 (d, J = 0.8 Hz, 1H), 5.93 (d, J = 0.8 Hz, 1H), 4.73-4.66 (m, 1H), 4.62 (s, 2H), 3.37 (s, 2H), 1.56-1.40 (m, 4H), 1.25-1.14 (m, 6H), 0.84 (t, J = 6.4 Hz, 3H), 0.80 (d, J = 7.2 Hz, 3H). |
| 147 | octan-4-ol<br>2-(2-methylene-4-(octan-4-yloxy)-4-oxobutanoyloxy)acetic acid | LCMS (System 2, Method B) m/z 323.2 (M + Na)$^+$ (ES$^+$).<br>$^1$H NMR (400 MHz, DMSO-d6) δ: 13.09 (br, 1H), 6.28 (d, J = 1.2 Hz, 1H), 5.92 (d, J = 1.2 Hz, 1H), 4.81-4.74 (m, 1H), 4.62 (s, 2H), 3.36 (s, 2H), 1.49-1.42 (m, 4H), 1.32-1.14 (m, 6H), 0.84 (t, J = 7.2 Hz, 6H). |
| 148 | heptan-4-ol<br>2-((4-(heptan-4-yloxy)-2-methylene-4-oxobutanoyl)oxy) acetic acid | LCMS (System 2, Method B) m/z 309.3 (M + Na)$^+$ (ES$^+$).<br>$^1$H NMR (400 MHz, DMSO-d6) δ: 13.09 (br, 1H), 6.28 (d, J = 1.2 Hz, 1H), 5.93 (d, J = 0.8 Hz, 1H), 4.82-4.77 (m, 1H), 4.62 (s, 2H), 3.37 (s, 2H), 1.48-1.42 (m, 4H), 1.32-1.16 (m, 4H), 0.85 (t, J = 7.2 Hz, 6H). |
| 149 | adamantan-2-ol<br>2-((4-((adamantan-2-yl)oxy)-2-methylene-4-oxobutanoyl)oxy)acetic acid | LCMS (System 2, Method B) m/z 323.2 (M + H)$^+$ (ES$^+$).<br>$^1$H NMR (400 MHz, DMSO-d6) δ: 13.01 (br, 1H), 6.29 (s, 1H), 5.94 (s, 1H), 4.80 (m, 1H), 4.63 (s, 2H), 3.41 (s, 2H), 1.89-1.86 (m, 4H), 1.80-1.78 (m, 4H), 1.72-1.68 (m, 4H), 1.49 (d, J = 12.4 Hz, 2H). |

| Example No. | Alcohol Intermediate/ Example Structure/Name | LCMS/¹H NMR data |
|---|---|---|
| 150 | 1-cyclohexylethan-1-ol 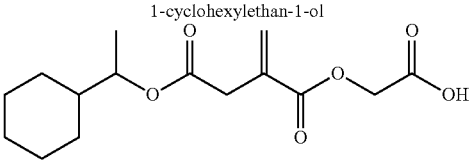 2-((4-(1-cyclohexylethoxy)-2-methylene-4-oxobutanoyl)oxy) acetic acid | LCMS (System 2, Method B) m/z 321.3 (M + Na)⁺ (ES⁺). ¹H NMR (400 MHz, DMSO-d6) δ: 13.11 (br, 1H), 6.28 (s, 1H), 5.92 (s, 1H), 4.64-4.58 (m, 1H), 4.62 (s, 2H), 3.40 (s, 2H), 1.68 (d, $J$ = 10.0 Hz, 3H), 1.59 (t, $J$ = 10.8 Hz, 2H), 1.42-1.35 (m, 1H), 1.21-1.12 (m, 3H), 1.09 (d, $J$ = 6.0 Hz, 3H), 1.06-0.84 (m, 2H). |
| 151 | 1-cycloheptylethan-1-ol 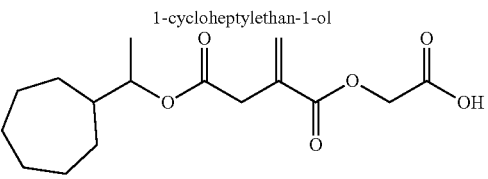 2-((4-(1-cycloheptylethoxy)-2-methylene-4-oxobutanoyl)oxy)acetic acid | LCMS (System 2, Method B) m/z 335.2 (M + Na)⁺ (ES⁺). ¹H NMR (400 MHz, DMSO-d6) δ: 13.08 (br, 1H), 6.27 (s 1H), 5.92 (s 1H), 4.70-4.65 (m, 1H), 4.63 (s, 2H), 3.34 (s, 2H), 1.63-1.61 (m, 5H), 1.57-1.33 (m, 6H), 1.22-1.14 (m, 2H), 1.07 (d, $J$ = 6.0 Hz, 3H). |
| 152 | spiro[3.4]octan-2-ol 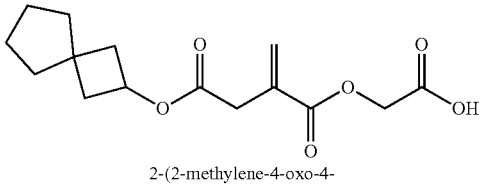 2-(2-methylene-4-oxo-4-(spiro[3.4]octan-2-yloxy)butanoyloxy)acetic acid | LCMS (System 2, Method B) m/z 319.1 (M + Na)⁺ (ES⁺). ¹H NMR (400 MHz, DMSO-d6) δ: 13.08 (br, 1H), 6.28 (d, $J$ = 0.8 Hz, 1H), 5.91 (d, $J$ = 0.8 Hz, 1H), 4.90-4.83 (m, 1H), 4.64 (s, 2H), 3.35 (s, 2H), 2.23-2.18 (m, 2H), 1.92-1.87 (m, 2H), 1.57-1.47 (m, 8H). |
| 153 | spiro[3.5]nonan-2-ol 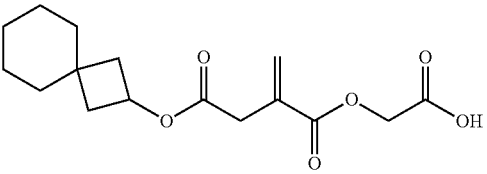 [SMILES: C=C(CC(=O)OC1CC2(CCCCC2)C1)C(=O)OCC(=O)O] 2-(2-methylene-4-oxo-4-(spiro[3.5]nonan-2-yloxy)butanoyloxy)acetic acid | LCMS (System 2, Method B) m/z 333.3 (M + Na)⁺ (ES⁺). ¹H NMR (400 MHz, DMSO-d6) δ: 13.08 (br, 1H), 6.28 (s, 1H), 5.91 (s, 1H), 4.91-4.83 (m, 1H), 4.64 (s, 2H), 3.35 (s, 2H), 2.19-2.14 (m, 2H), 1.68-1.63 (m, 2H), 1.40-1.30 (m, 10H). |
| 154 | spiro[3.5]nonan-7-ol 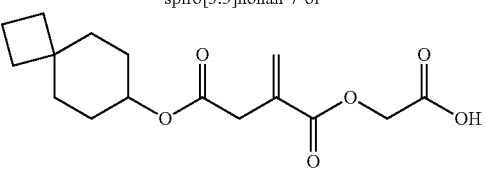 2-(2-methylene-4-oxo-4-(spiro[3.5]nonan-7-yloxy)butanoyloxy)acetic acid | LCMS (System 2, Method B) m/z 333.3 (M + Na)⁺ (ES⁺). ¹H NMR (400 MHz, DMSO-d6) δ: 13.10 (br, 1H), 6.26 (s, 1H), 5.90 (s, 1H), 4.62 (s, 3H), 3.34 (s, 2H), 1.83-1.77 (m, 2H), 1.70-1.61 (m, 8H), 1.37-1.34 (m, 4H). |
| 155 | 2,2-dimethylcyclohexan-1-ol 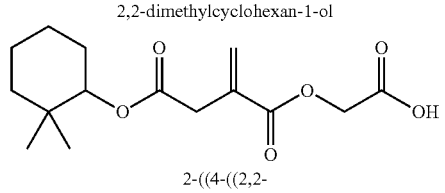 2-((4-((2,2-dimethylcyclohexyl)oxy)-2-methylene-4-oxobutanoyl)oxy)acetic acid | LCMS (System 2, Method B) m/z 321.3 (M + Na)⁺ (ES⁺). ¹H NMR (400 MHz, DMSO-d6) δ: 13.09 (br, 1H), 6.28 (s, 1H), 5.93 (s, 1H), 4.62 (s, 2H), 4.47-4.44 (m, 1H), 3.38 (s, 2H), 1.62-1.58 (m, 2H), 1.42-1.34 (m, 4H), 1.29-1.18 (m, 2H), 0.84 (s, 6H). |

| Example No. | Alcohol Intermediate/ Example Structure/Name | LCMS/¹H NMR data |
|---|---|---|
| 169 | 2,2,4,4-tetramethylcyclobutan-1-ol<br>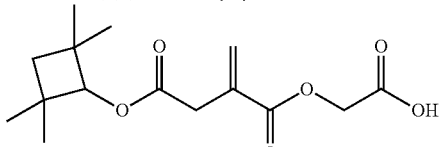<br>2-((2-methylene-4-oxo-4-(2,2,4,4-tetramethylcyclobutoxy)butanoyl)oxy) acetic acid | LCMS (System 2, Method B)<br>m/z 321.2 (M + Na)⁺ (ES⁺).<br>¹H NMR (400 MHz, DMSO-d6) δ: 13.11 (br, 1H), 6.29 (s, 1H), 5.95 (s, 1H), 4.63 (s, 2H), 4.35 (s, 1H), 3.43 (s, 2H), 1.51 (d, J = 11.6 Hz, 1H), 1.41 (d, J = 11.6 Hz, 1H), 1.10 (s, 6H), 1.00 (s, 6H). |
| 170 | (S)-octan-3-ol<br>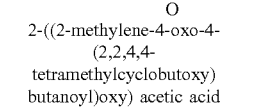<br>(S)-2-(2-methylene-4-(octan-3-yloxy)-4-oxobutanoyloxy)acetic acid | LCMS (System 2, Method B)<br>m/z 323.2 (M + Na)⁺ (ES⁺).<br>¹H NMR (400 MHz, DMSO-d6) δ: 13.09 (br, 1H), 6.28 (d, J = 0.8 Hz, 1H), 5.93 (d, J = 0.8 Hz, 1H), 4.73-4.66 (m, 1H), 4.62 (s, 2H), 3.37 (s, 2H), 1.56-1.40 (m, 4H), 1.25-1.14 (m, 6H), 0.84 (t, J = 6.4 Hz, 3H), 0.80 (d, J = 7.2 Hz, 3H). |
| 173 | (R)-heptan-2-ol<br>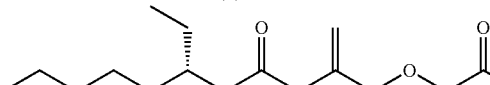<br>(R)-2-((4-(heptan-2-yloxy)-2-methylene-4-oxobutanoyl)oxy)acetic acid | LCMS (System 2, Method B)<br>m/z 309.3 (M + Na)⁺ (ES⁺).<br>¹H NMR (400 MHz, DMSO-d6) δ: 13.14 (br, 1H), 6.27 (d, J = 0.8 Hz, 1H), 5.91 (d, J = 0.8 Hz, 1H), 4.80-4.75 (m, 1H), 4.63 (s, 2H), 3.34 (s, 2H), 1.49-1.43 (m, 2H), 1.29-1.23 (m, 6H), 1.13 (d, J = 6.4 Hz, 3H), 0.85 (t, J = 6.4 Hz, 3H). |
| 174 | nonan-2-ol<br>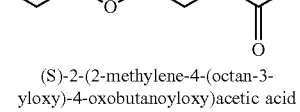<br>2-((2-methylene-4-(nonan-2-yloxy)-4-oxobutanoyl)oxy)acetic acid | LCMS (System 2, Method B)<br>m/z 337.3 (M + Na)⁺ (ES⁺).<br>¹H NMR (400 MHz, DMSO-d6) δ: 13.09 (br, 1H), 6.27 (d, J = 1.2 Hz, 1H), 5.91 (d, J = 1.2 Hz, 1H), 4.82-4.74 (m, 1H), 4.62 (s, 2H), 3.50 (s, 2H), 1.48-1.43 (m, 2H), 1.29-1.23 (m, 10H), 1.13 (d, J = 6.4 Hz, 3H), 0.86 (t, J = 6.8 Hz, 3H). |
| 175 | nonan-5-ol<br>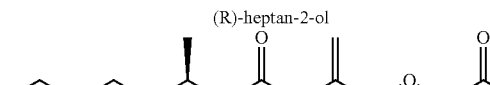<br>2-((2-methylene-4-(nonan-5-yloxy)-4-oxobutanoyl)oxy)acetic acid | LCMS (System 2, Method B)<br>m/z 337.3 (M + Na)⁺ (ES⁺).<br>¹H NMR (400 MHz, DMSO-d6) δ: 13.14 (br, 1H), 6.28 (d, J = 1.2 Hz, 1H), 5.92 (d, J = 0.8 Hz, 1H), 4.79-4.74 (m, 1H), 4.62 (s, 2H), 3.37 (s, 2H), 1.52-1.42 (m, 4H), 1.31-1.14 (m, 8H), 0.85 (t, J = 6.8 Hz, 6H). |
| 176 | 1-(3,5-dichlorophenyl)ethan-1-ol<br>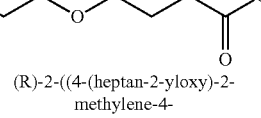<br>2-((4-(1-(3,5-dichlorophenyl)ethoxy)-2-methylene-4-oxobutanoyl)oxy)acetic acid | LCMS (System 2, Method B)<br>m/z 383.0 (M + Na)⁺ (ES⁺).<br>¹H NMR (400 MHz, DMSO-d6) δ: 13.12 (br, 1H), 7.54 (t, J = 2.0 Hz, 1H), 7.41 (d, J = 1.6 Hz, 2H), 6.31 (d, J = 0.8 Hz, 1H), 5.96 (d, J = 0.8 Hz, 1H), 5.77 (q, J = 6.4 Hz, 1H), 4.63 (s, 2H), 3.47 (s, 2H), 1.44 (d, J = 6.4 Hz, 3H). |

| Example No. | Alcohol Intermediate/ Example Structure/Name | LCMS/¹H NMR data |
|---|---|---|
| 177 | 1-(3,5-dichlorophenyl)propan-2-ol<br>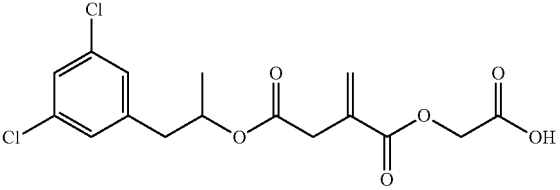 [SMILES: C=C(CC(=O)OC(C)Cc1cc(Cl)cc(Cl)c1)C(=O)OCC(=O)O]<br>2-((4-((1-(3,5-dichlorophenyl)propan-2-yl)oxy)-2-methylene-4-oxobutanoyl)oxy)acetic acid | LCMS (System 2, Method B)<br>m/z 397.1 (M + Na)⁺ (ES⁺).<br>¹H NMR (400 MHz, DMSO-d6) δ: 13.07 (br, 1H), 7.46 (t, J = 2.0 Hz, 1H), 7.29 (d, J = 1.6 Hz, 2H), 6.27 (s, 1H), 5.87 (d, J = 0.8 Hz, 1H), 4.99 (q, J = 6.4 Hz, 1H), 4.61 (d, J = 1.6 Hz, 2H), 3.31 (s, 2H), 2.88-2.78 (m, 2H), 1.14 (d, J = 6.4 Hz, 3H). |
| 178 | (R)-octan-3-ol<br>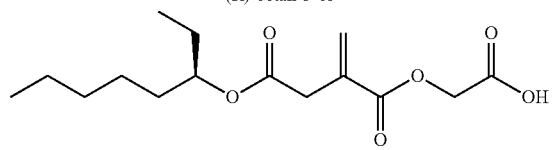<br>(R)-2-(2-methylene-4-(octan-3-yloxy)-4-oxobutanoyloxy)acetic acid | LCMS (System 2, Method B)<br>m/z 323.2 (M + Na)⁺ (ES⁺).<br>¹H NMR (400 MHz, DMSO-d6) δ: 13.11 (br, 1H), 6.28 (d, J = 0.8 Hz, 1H), 5.93 (d, J = 0.8 Hz, 1H), 4.73-4.66 (m, 1H), 4.62 (s, 2H), 3.37 (s, 2H), 1.56-1.40 (m, 4H), 1.25-1.14 (m, 6H), 0.84 (t, J = 6.4 Hz, 3H), 0.80 (d, J = 7.2 Hz, 3H). |
| 179 | (1R,2S,4R)-1,7,7-trimethylbicyclo[2.2.1]heptan-2-ol<br>(CAS No. 464-43-7)<br>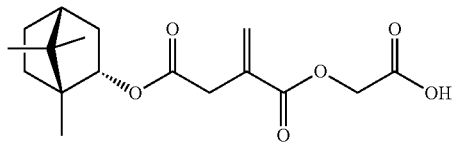 [SMILES: C=C(CC(=O)O[C@H]1C[C@H]2CC[C@]1(C)C2(C)C)C(=O)OCC(=O)O]<br>2-((2-methylene-4-oxo-4-(((1R,2S,4R)-1,7,7-trimethylbicyclo[2.2.1]heptan-2-yl)oxy)butanoyl)oxy)acetic acid | LCMS (System 2, Method B)<br>m/z 347.2 (M + Na)⁺ (ES⁺).<br>¹H NMR (400 MHz, DMSO-d6) δ: 13.13 (br, 1H), 6.29 (s, 1H), 5.94 (d, J = 0.8 Hz, 1H), 4.79-4.77 (m, 1H), 4.64 (s, 2H), 3.40 (s, 2H), 2.27-2.20 (m, 1H), 1.84-1.77 (m, 1H), 1.72-1.63 (m, 2H), 1.27-1.12 (m, 2H), 0.91 (dd, J = 13.6, 3.6 Hz, 1H), 0.84 (d, J = 8.8 Hz, 6H), 0.76 (s, 3H). |
| 180 | 1-cyclohexyl-2,2,2-trifluoroethan-1-ol<br>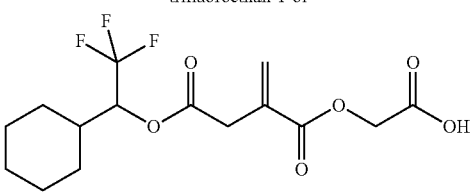<br>2-((4-(1-cyclohexyl-2,2,2-trifluoroethoxy)-2-methylene-4-oxobutanoyl)oxy)acetic acid | LCMS (System 2, Method B)<br>m/z 375.3 (M + Na)⁺ (ES⁺).<br>¹H NMR (400 MHz, DMSO-d6) δ: 13.08 (br, 1H), 6.33 (s, 1H), 6.01 (s, 1H), 5.27-5.18 (m, 1H), 4.63 (s, 2H), 3.56 (s, 2H), 1.88-1.75 (m, 1H), 1.71-1.51 (m, 5H), 1.29-0.96 (m, 5H). |
| 181 | bicyclo[3.3.1]nonan-9-ol<br>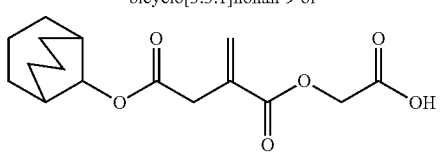<br>2-((4-(bicyclo[3.3.1]nonan-9-yloxy)-2-methylene-4-oxobutanoyl)oxy)acetic acid | LCMS (System 2, Method B)<br>m/z 333.2 (M + Na)⁺ (ES⁺).<br>¹H NMR (400 MHz, DMSO-d6) δ: 13.08 (br, 1H), 6.29 (d, J = 1.2 Hz, 1H), 5.94 (d, J = 1.2 Hz, 1H), 4.66 (s, 1H), 4.63 (s, 2H), 3.41 (s, 2H), 1.83-1.75 (m, 6H), 1.73 (d, J = 13.2 Hz, 4H), 1.45 (d, J = 6.0 Hz, 4H). |

-continued

| Example No. | Alcohol Intermediate/ Example Structure/Name | LCMS/$^1$H NMR data |
|---|---|---|
| 182 | (S)-1,1,1-trifluorooctan-2-ol<br>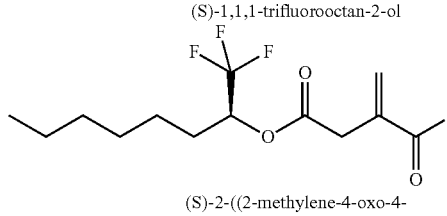<br>(S)-2-((2-methylene-4-oxo-4-((1,1,1-trifluorooctan-2-yl)oxy)butanoyl)oxy)acetic acid | LCMS (System 2, Method B) m/z 377.1 (M + Na)$^+$ (ES$^+$).<br>$^1$H NMR (400 MHz, DMSO-d6) δ: 13.10 (br, 1H), 6.34 (s, 1H), 6.02 (s, 1H), 5.41-5.36 (m, 1H), 4.62 (s, 2H), 3.54 (s, 2H), 1.75-1.62 (m, 2H), 1.26-1.24 (m, 8H), 0.86 (t, J = 6.4 Hz, 3H). |
| 183 | (R)-nonan-2-ol<br>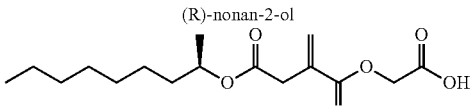<br>(R)-2-((2-methylene-4-(nonan-2-yloxy)-4-oxobutanoyl)oxy)acetic acid | LCMS (System 2, Method B) m/z 337.3 (M + Na)$^+$ (ES$^+$).<br>$^1$H NMR (400 MHz, DMSO-d6) δ: 13.06 (br, 1H), 6.27 (d, J = 1.2 Hz, 1H), 5.91 (d, J = 1.2 Hz, 1H), 4.82-4.74 (m, 1H), 4.62 (s, 2H), 3.50 (s, 2H), 1.48-1.43 (m, 2H), 1.29-1.23 (m, 10H), 1.13 (d, J = 6.4 Hz, 3H), 0.86 (t, J = 6.8 Hz, 3H). |
| 184 | (R)-1-cyclohexylethan-1-ol<br>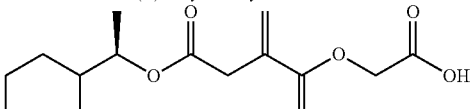<br>(R)-2-((4-(1-cyclohexylethoxy)-2-methylene-4-oxobutanoyl)oxy)acetic acid | LCMS (System 2, Method B) m/z 321.3 (M + Na)$^+$ (ES$^+$).<br>$^1$H NMR (400 MHz, DMSO-d6) δ: 13.14 (br, 1H), 6.28 (s, 1H), 5.92 (s, 1H), 4.62 (s, 2H), 4.66-4.58 (m, 1H), 3.26 (s, 2H), 1.69-1.67 (m, 3H), 1.62-1.53 (m, 2H), 1.42-1.35 (m, 1H), 1.25-1.08 (m, 3H), 1.15 (d, J = 6.4 Hz, 3H), 1.04-0.82 (m, 2H). |

Example 156—bis((endo)-3-(methylsulfonyl)-3-azabicyclo[3.2.1]octan-8-yl) 2-methylenesuccinate

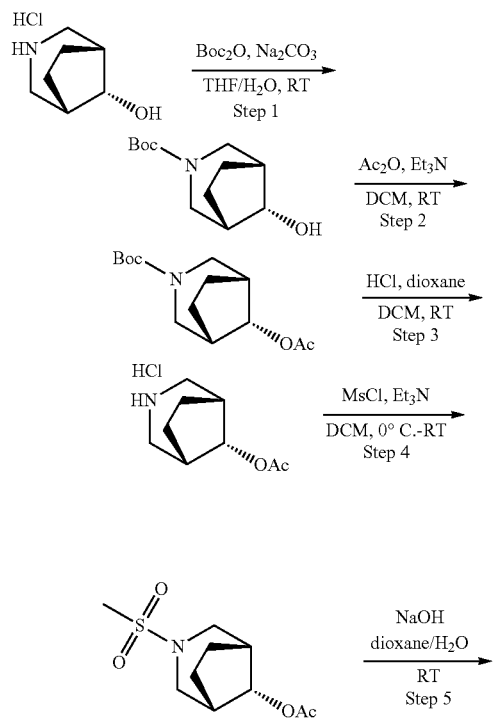

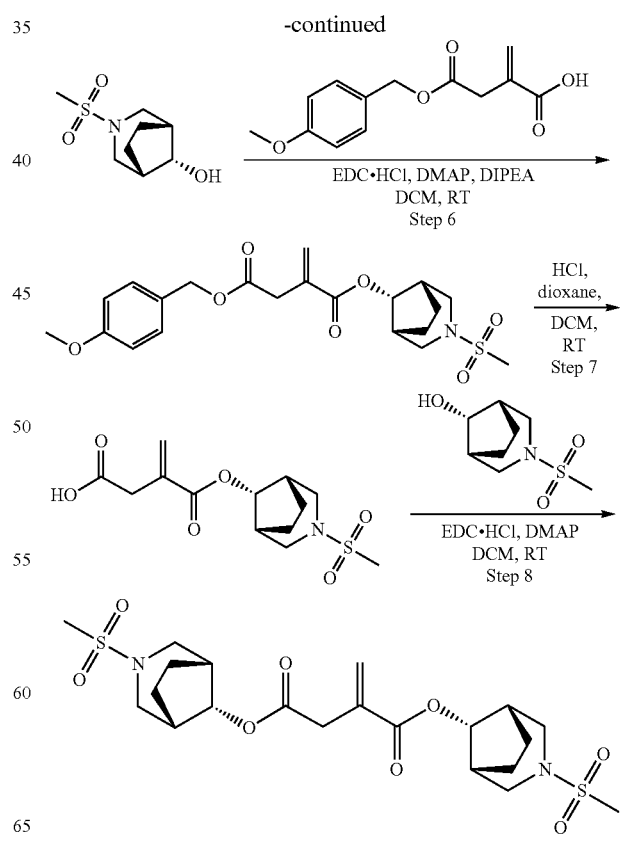

Step 1

To a solution of (endo)-3-azabicyclo[3.2.1]octan-8-ol hydrochloride (3.8 g, 23.2 mmol) in a mixture of THF (40 mL) and $H_2O$ (10 mL) was added $Na_2CO_3$ (7.38 g, 69.7 mmol), followed by $Boc_2O$ (10.1 g, 46.4 mmol) added portionwise at 0° C. The reaction mixture was stirred at room temperature for 3 h, then diluted with water (100 mL) and extracted with MTBE. The separated organic layers were washed with brine, dried over $Na_2SO_4$ and filtered. The filtrate was concentrated under reduced pressure at 30° C., and the residue was purified by flash column chromatography (120 g silica, 0-50% ethyl acetate/petroleum ether) to give tert-butyl (endo)-8-hydroxy-3-azabicyclo[3.2.1]octane-3-carboxylate (4.7 g, 20.7 mmol, 89%) as a colorless oil. $^1H$ NMR (400 MHz, $CDCl_3$) δ: 4.03 (t, d=5.2 Hz, 1H), 3.67 (d, d=12.0 Hz, 1H), 3.54 (d, d=12.0 Hz, 1H), 3.33 (dd, d=32.8, 12.4 Hz, 2H), 2.01 (d, d=20.0 Hz, 1H), 1.70-1.54 (m, 4H), 1.43 (s, 9H).

Step 2

To a solution of tert-butyl (endo)-8-hydroxy-3-azabicyclo[3.2.1]octane-3-carboxylate (4.7 g, 20.7 mmol) in DCM (50 mL) was added triethylamine (6.3 g, 62.1 mmol) and acetic anhydride (6.3 g, 62.1 mmol) at 0° C. The reaction mixture was stirred at room temperature for 3 h, then washed with water (2×50 mL) and brine, dried over $Na_2SO_4$ and filtered. The filtrate was concentrated under reduced pressure at 30° C. to give tert-butyl (endo)-8-acetoxy-3-azabicyclo[3.2.1]octane-3-carboxylate (5.5 g, 20.4 mmol, 99%) as a pale-yellow oil. LCMS (System 2, Method C) m/z 214.4 (M−56+H)$^+$ (ES$^+$). $^1H$ NMR (400 MHz, $CDCl_3$) δ: 4.77 (t, d=4.8 Hz, 1H), 3.70 (d, d=12.8 Hz, 1H), 3.56 (d, d=12.0 Hz, 1H), 3.15 (dd, d=29.2, 12.8 Hz, 2H), 2.20 (d, d=20.0 Hz, 1H), 2.10 (s, 3H), 1.73-1.70 (m, 2H), 1.62-1.56 (m, 2H), 1.45 (s, 9H).

Step 3

To a solution of tert-butyl (endo)-8-acetoxy-3-azabicyclo[3.2.1]octane-3-carboxylate (5.5 g, 20.4 mmol) in DCM (50 mL) was added HCl solution in 1,4-dioxane (3 M, 20.4 mL, 61.2 mmol), and the reaction mixture was stirred at room temperature for 3 h. The reaction mixture was then concentrated under reduced pressure at 40° C. to give (endo)-3-azabicyclo[3.2.1]octan-8-yl acetate hydrochloride (4.2 g, 20.4 mmol, 98%) as a pale-yellow solid. LCMS (System 2, Method C) m/z 170.3 (M+H)$^+$ (ES$^+$).

Step 4

To a mixture of (endo)-3-azabicyclo[3.2.1]octan-8-yl acetate hydrochloride (4.2 g, 20.4 mmol) and triethylamine (6.2 g, 61.2 mmol) in DCM (50 mL) was added methanesulfonyl chloride (4.7 g, 40.8 mmol) at 0° C., and the reaction mixture was stirred at room temperature overnight. The reaction mixture was then washed with water (2×50 mL) and brine, dried over $Na_2SO_4$ and filtered. The filtrate was concentrated under reduced pressure at 30° C. to give (endo)-3-(methylsulfonyl)-3-azabicyclo[3.2.1]octan-8-yl acetate (4.8 g, 19.4 mmol, 95%) as pale-brown oil. LCMS (System 2, Method C) m/z 248.3 (M+H)$^+$ (ES$^+$). $^1H$ NMR (400 MHz, $CDCl_3$) δ: 4.82 (t, d=5.2 Hz, 1H), 3.65 (dd, d=11.6, 3.6 Hz, 2H), 3.13 (d, d=11.2 Hz, 2H), 2.80 (s, 3H), 2.33 (s, 2H), 2.12 (s, 3H), 1.78 (d, d=1.6 Hz, 4H).

Step 5

To a mixture of (endo)-3-(methylsulfonyl)-3-azabicyclo[3.2.1]octan-8-yl acetate (4.8 g, 19.4 mmol) and 1,4-dioxane (50 mL) was added aqueous NaOH solution (2.5 M, 19.4 mL, 48.5 mmol) at 0° C., and the reaction mixture was stirred at room temperature for 5 h. The reaction mixture was then acidified with conc. aqueous HCl to pH~7 and extracted with EtOAc (3×50 mL). The combined organic layers were dried over $Na_2SO_4$, filtered, and concentrated under reduced pressure at 40° C. to give (endo)-3-(methylsulfonyl)-3-azabicyclo[3.2.1]octan-8-ol (4 g, 19.5 mmol, 100%) as a pale-brown solid. LCMS (System 1, Method A) m/z 206.3 (M+H)+(ES$^+$). $^1H$ NMR (400 MHz, $CDCl_3$) δ: 4.07 (t, d=5.2 Hz, 1H), 3.31 (d, d=2.4 Hz, 4H), 2.79 (s, 3H), 2.33 (s, 2H), 2.11 (q, d=2.4 Hz, 3H), 1.79-1.71 (m, 4H).

Step 6

To a solution of 4-(4-methoxybenzyloxy)-2-methylene-4-oxobutanoic acid (1.70 g, 6.82 mmol), (endo)-3-(methylsulfonyl)-3-azabicyclo[3.2.1]octan-8-ol (1.40 g, 6.82 mmol), DMAP (832 mg, 6.82 mmol) and DIPEA (2.64 g, 20.46 mmol) in DCM (20 mL) was added EDC.HCl (1.96 g, 10.23 mmol) at 0° C., and the resulting pale-yellow mixture was stirred at room temperature overnight. The mixture was then quenched with dilute aqueous HCl (0.5 M, 10 mL), the phases were separated, and the aqueous phase extracted with DCM (2×20 mL). The combined organic phases were washed with brine, dried over $Na_2SO_4$ and filtered. The filtrate was concentrated under reduced pressure at 40° C., and the residue was purified by flash column chromatography (80 g silica, 30-60% MTBE/petroleum ether) to give 4-(4-methoxybenzyl) 1-((endo)-3-(methylsulfonyl)-3-azabicyclo[3.2.1]octan-8-yl) 2-methylenesuccinate (2.40 g, 5.49 mmol, 80%) as a colorless oil. LCMS (System 2, Method B) m/z 460.1 (M+Na)$^+$ (ES$^+$).

Step 7

A mixture of 4-(4-methoxybenzyl) 1-((endo)-3-(methylsulfonyl)-3-azabicyclo[3.2.1]octan-8-yl) 2-methylenesuccinate (2.40 g, 5.49 mmol), HCl solution in 1,4-dioxane (4 M, 5 mL, 20 mmol) and DCM (5 mL) was stirred at room temperature for 2 h. The mixture was then concentrated under reduced pressure at 40° C. and the residue was purified by reversed phase column chromatography (120 g C18 silica; flow rate: 40 mL/min; 40-75% MeCN/(10 mM HCl/water); collection wavelength: 214 nm). The collected fractions were concentrated under reduced pressure at 40° C. to remove MeCN, and the residue was lyophilized to give 3-(((endo)-3-(methylsulfonyl)-3-azabicyclo[3.2.1]octan-8-yloxy)carbonyl)but-3-enoic acid (1.00 g, 3.15 mmol, 57%) as a white solid. LCMS (System 2, Method B) m/z 318.3 (M+H)$^+$ (ES$^+$).

Step 8

To a solution of 3-(((endo)-3-(methylsulfonyl)-3-azabicyclo[3.2.1]octan-8-yloxy)carbonyl)but-3-enoic acid (200 mg, 0.63 mmol), (endo)-3-(methylsulfonyl)-3-azabicyclo[3.2.1]octan-8-ol (129 mg, 0.63 mmol), and DMAP (76 mg, 0.63 mmol) in DCM (3 mL) was added EDC.HCl (182 mg, 0.94 mmol) at 0° C., and the resulting clear colorless mixture was stirred at room temperature for 2 h. The mixture was then quenched with dilute aqueous HCl (0.5 M, 1 mL), the phases were separated, and the aqueous phase was extracted with DCM (2×2 mL). The combined organic phases were washed with brine, dried over $Na_2SO_4$ and filtered. The filtrate was concentrated under reduced pressure at 40° C., and the residue was purified by preparative HPLC (Column: Waters X-Bridge C18 OBD 10 μm 19×250 mm; Flow Rate: 20 mL/min; solvent system: MeCN/(0.05% TFA/water); gradient: 50-95% MeCN; collection wavelength: 214 nm). The collected fractions were concentrated under reduced pressure at 40° C. to remove MeCN, and the residue was lyophilized to give bis((endo)-3-(methylsulfonyl)-3-azabicyclo[3.2.1]octan-8-yl) 2-methylenesuccinate (145 mg, 0.29 mmol, 45%) as a white solid. LCMS (System 2, Method B) m/z 505.3 (M+H)+ (ES+). ¹H NMR (400 MHz, DMSO-d6) δ: 6.36 (s, 1H), 5.95 (s, 1H), 4.82 (t, J=5.2 Hz, 1H), 4.72 (t, J=4.8 Hz, 1H), 3.55 (s, 2H), 3.17-3.09 (m, 6H), 3.01 (d, J=11.2 Hz, 2H), 2.90 (s, 3H), 2.86 (s, 3H), 2.29-2.26 (m, 4H), 1.76-1.70 (m, 4H), 1.61-1.54 (m, 4H).

The following compounds were made using a similar procedure:

| Example No. | Alcohol used in Step 8/ Example Structure/Name | LCMS/¹H NMR data |
|---|---|---|
| 157 | 2-oxaspiro[3.3]heptan-6-ol<br><br>1-((endo)-3-(methylsulfonyl)-3-azabicyclo[3.2.1]octan-8-yl) 4-(2-oxaspiro[3.3]heptan-6-yl) 2-methylenesuccinate | LCMS (System 2, Method B) m/z 414.3 (M + H)+ (ES+).<br>¹H NMR (400 MHz, DMSO-d6) δ: 6.32 (s, 1H), 5.88 (s, 1H), 4.81-4.75 (m, 2H), 4.56 (s, 2H), 4.49 (s, 2H), 3.40 (s, 2H) 3.18-3.15 (m, 2H), 3.08-3.06 (m, 2H), 2.89 (s, 3H), 2.64-2.59 (m, 2H), 2,29 (m, 2H), 2,17-2.11 (m, 2H), 1.76-1.73 (m, 2H), 1.62-1.57 (m, 2H). |
| 158 | oxepan-4-ol<br><br>1-((endo)-3-(methylsulfonyl)-3-azabicyclo[3.2.1]octan-8-yl) 4-(oxepan-4-yl) 2-methylenesuccinate | LCMS (System 2, Method B) m/z 438.2 (M + Na)+ (ES+).<br>¹H NMR (400 MHz, DMSO-d6) δ: 6.33 (s, 1H), 5.90 (s, 1H), 4.94-4.88 (m, 1H), 4.80 (t, J = 5.2 Hz, 1H), 3.65-3.52 (m 4H) 3.38 (s, 2H), 3.17 (dd, J = 11.2, 2.8 Hz, 2H), 3.09 (d, J = 11.2 Hz, 2H), 2.90 (s, 3H), 2.30 (m, 2H), 1.94-1.89 (m, 1H), 1.84-1.80 (m, 1H), 1.76-1.62 (m, 5H), 1.60-1.55 (m, 3H). |
| 159 | 1-butoxypropan-2-ol<br><br>4-(1-butoxypropan-2-yl) 1-((endo)-3-(methylsulfonyl)-3-azabicyclo[3.2.1]octan-8-yl) 2-methylenesuccinate | LCMS (System 2, Method B) m/z 432.3 (M + H)+ (ES+).<br>¹H NMR (400 MHz, DMSO-d6) δ: 6.32 (s, 1H), 5.89 (s, 1H), 4.94-4.90 (m, 1H), 4.79 (t, J = 5.2 Hz, 1H), 3.41 (s, 2H), 3.40-3.39 (m, 2H), 3.36-3.32 (m, 2H), 3.18-3.15 (m, 2H), 3.11-3.08 (m, 2H), 2.89 (s, 3H), 2.30 (m, 2H), 1.76-1.73 (m, 2H), 1.62-1.57 (m, 2H), 1.49-1.42 (m, 2H), 1.34-1.25 (m, 2H), 1.12 (d, J = 6.4 Hz, 3H), 0.87 (t, J = 7.6 Hz, 3H). |

Example 160—4-spiro[3.3]heptan-2-yl 1-(3,3,3-trifluoro-2,2-dihydroxypropyl) 2-methylenesuccinate Hydrate

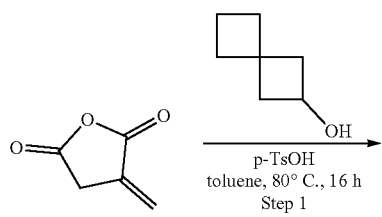

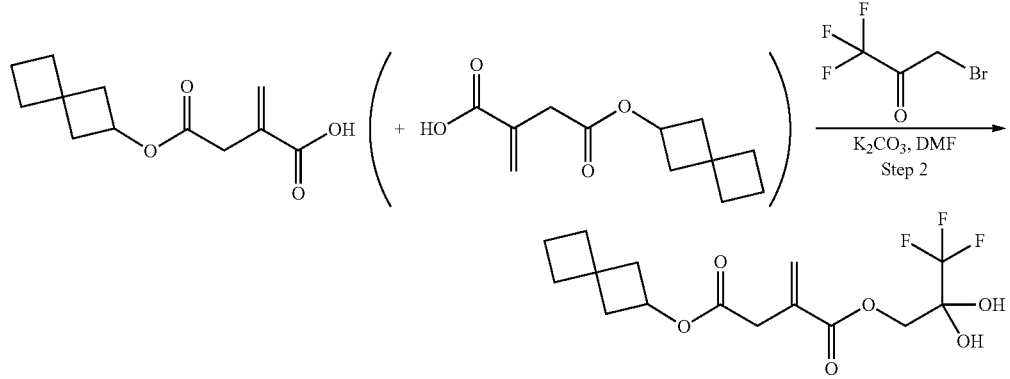

Step 1

A mixture of 3-methylenedihydrofuran-2,5-dione (300 mg, 2.68 mmol), spiro[3.3]heptan-2-ol (250 mg, 2.23 mmol) and p-toluenesulfonic acid monohydrate (26 mg, 0.13 mmol) in toluene (90 mL) was stirred at 80° C. for 16 h. The reaction mixture was then cooled to room temperature and concentrated under reduced pressure at 50° C. The residue was purified by reversed phase column chromatography (120 g C18 silica; flow rate: 40 mL/min; 50-80% MeCN/(10 mM HCl/water); collection wavelength: 214 nm). The collected fractions were concentrated under reduced pressure at 40° C. to remove MeCN, and the residue was lyophilized to give 2-methylene-4-oxo-4-(spiro[3.3]heptan-2-yloxy)butanoic acid (450 mg, 90%) as a white solid that contained 8% of the regioisomeric 3-((spiro[3.3]heptan-2-yloxy)carbonyl)but-3-enoic acid as measured by $^1$H NMR. The solid was stirred in a mixture of n-hexane (5 mL) and MTBE (0.5 mL) at room temperature overnight, then filtered, and the wet filter cake was dried under reduced pressure at 40° C. to give pure 2-methylene-4-oxo-4-(spiro[3.3]heptan-2-yloxy)butanoic acid (400 mg, 1.78 mmol, 80%). LCMS (System 2, Method C) m/z 247.4 (M+Na)$^+$ (ES$^+$). $^1$H NMR (400 MHz, DMSO-d6) δ: 12.60 (br, 1H), 6.14 (d, J=1.2 Hz, 1H), 5.74 (s, 1H), 4.79-4.72 (m, 1H), 3.25 (s, 2H), 2.40-2.35 (m, 2H), 1.99-1.89 (m, 6H), 1.81-1.74 (m, 2H).

Step 2

To a solution of 2-methylene-4-oxo-4-(spiro[3.3]heptan-2-yloxy)butanoic acid (200 mg, 0.89 mmol) in DMF (5 mL) was added potassium carbonate (110 mg, 0.89 mmol) and the reaction mixture was stirred at room temperature for 30 min, then 3-bromo-1,1,1-trifluoropropan-2-one (171 mg, 0.89 mmol) was added, and the resulting yellow suspension was stirred at room temperature for 6 h. More potassium carbonate (55 mg, 0.45 mmol) and 3-bromo-1,1,1-trifluoropropan-2-one (86 mg, 0.45 mmol) were added, and the mixture was stirred at room temperature overnight. The mixture was then diluted with EtOAc (10 mL) and water (10 mL), the phases were separated, and the aqueous phase was extracted with EtOAc (2×5 mL). The separated organic phases were washed with brine, dried over Na$_2$SO$_4$ and filtered. The filtrate was concentrated under reduced pressure at 40° C., and the residue was purified by preparative HPLC (Column: Waters X-Bridge C18 OBD 10 μm 19×250 mm; Flow Rate: 20 mL/min; solvent system: MeCN/(0.05% TFA/water); gradient: 45-95% MeCN; collection wavelength: 214 nm). The collected fractions were concentrated under reduced pressure at 40° C. to remove MeCN, and the residue was lyophilized to give 4-spiro[3.3]heptan-2-yl 1-(3,3,3-trifluoro-2,2-dihydroxypropyl) 2-methylenesuccinate hydrate (131 mg, 0.37 mmol, 41%) as a pale-yellow oil. LCMS (System 2, Method B) m/z 375.1 (M+Na)$^+$ (ES$^+$). $^1$H NMR (400 MHz, DMSO-d6) δ: 7.37 (d, J=3.2 Hz, 2H), 6.25 (s, 1H), 5.86 (s, 1H), 4.79-4.72 (m, 1H), 4.15 (s, 2H), 3.32 (s, 2H), 2.39-2.33 (m, 2H), 1.99-1.90 (m, 6H), 1.81-1.73 (m, 2H).

Example 161—(R)-1-((2H-tetrazol-5-yl)methyl) 4-(octan-2-yl) 2-methylenesuccinate

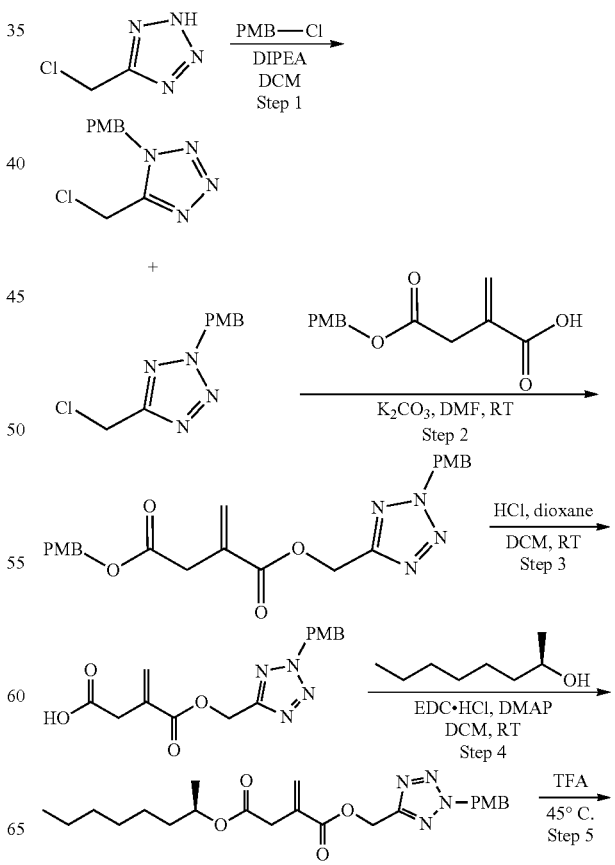

-continued

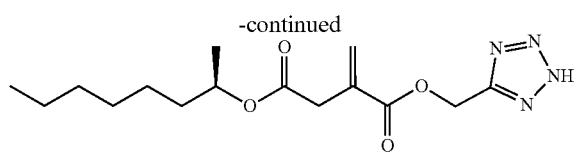

Step 1

A solution of 5-(chloromethyl)-2H-tetrazole (5.5 g, 46.6 mmol) and DIPEA (1.8 g, 139.8 mmol) in dry DCM (80 mL) was stirred for 30 min at room temperature and then 1-(chloromethyl)-4-methoxy benzene (7.3 g, 46.6 mmol) was added. The resulting mixture was stirred at room temperature under a $N_2$ atmosphere for 16 h, then extracted with DCM (4×30 mL) and brine (45 mL). The combined organic layers were dried over $Na_2SO_4$, filtered and the filtrate was concentrated under reduced pressure. The residue was purified by flash column chromatography (120 g silica, 0-60% ethyl acetate/petroleum ether) to give 5-(chloromethyl)-2-(4-methoxybenzyl)-2H-tetrazole (1.25 g, 5.2 mmol, 11%) as a yellow solid and 5-(chloromethyl)-1-(4-methoxybenzyl)-1H-tetrazole (1.0 g, 4.2 mmol, 9%) as a yellow solid.

5-(chloromethyl)-2-(4-methoxybenzyl)-2H-tetrazole: $^1$H NMR (400 MHz, DMSO-d6) δ: 7.33 (d, J=8.4 Hz, 2H), 6.93 (d, J=8.8 Hz, 2H), 5.84 (s, 2H), 4.97 (s, 2H) 3.72 (s, 3H).

5-(chloromethyl)-1-(4-methoxybenzyl)-1H-tetrazole: $^1$H NMR (400 MHz, DMSO-d$_6$) δ: 7.31 (d, J=8.8 Hz, 2H), 6.93 (d, J=8.8 Hz, 2H), 5.63 (s, 2H), 5.20 (s, 2H), 3.72 (s, 3H).

Step 2

A solution of 4-(4-methoxybenzyloxy)-2-methylene-4-oxobutanoic acid (1.33 g, 5.3 mmol) and potassium carbonate (731 mg, 5.3 mmol) in dry DMF (20 mL) was stirred for 30 min at room temperature and then 5-(chloromethyl)-2-(4-methoxybenzyl)-2H-tetrazole (1.25 g, 5.3 mmol) was added. The reaction mixture was stirred at room temperature under a $N_2$ atmosphere for 16 h, then quenched with water (45 mL) and extracted with EtOAc (4×30 mL). The organic layer was dried over $Na_2SO_4$, filtered and the filtrate was concentrated under reduced pressure. The residue was purified by flash column chromatography (80 g silica, 0-60% ethyl acetate/petroleum ether) to give 4-(4-methoxybenzyl) 1-(2-(4-methoxybenzyl)-2H-tetrazol-5-yl)methyl 2-methylenesuccinate (1.9 g, 4.2 mmol, 81%) as a white solid. LCMS (System 2, Method B) m/z 453.3 (M+H)$^+$ (ES$^+$). $^1$H NMR (400 MHz, DMSO-d6) δ: 7.31 (d, J=8.4 Hz, 2H), 7.21 (d, J=8.4 Hz, 2H), 6.90 (m, 4H), 6.20 (s, 1H), 5.87 (s, 1H), 5.83 (m, 2H), 5.36 (s, 2H), 4.93 (s, 2H), 3.73 (s, 3H), 3.71 (s, 3H), 3.38 (s, 2H).

Step 3

To a solution of 4-(4-methoxybenzyl) 1-(2-(4-methoxybenzyl)-2H-tetrazol-5-yl)methyl 2-methylenesuccinate (1.9 g, 4.2 mmol) in dry DCM (20 mL) was added HCl solution in 1,4-dioxane (4 M, 42 mL, 168 mmol) and the mixture was stirred at room temperature for 4 h. The mixture was then concentrated under reduced pressure at 40° C. and the residue was purified by reversed phase column chromatography (120 g C18 silica; flow rate: 40 mL/min; 0-60% MeCN/(10 mM HCl/water); collection wavelength: 214 nm). The collected fractions were concentrated under reduced pressure at 40° C. to remove MeCN, and the residue was lyophilized to give 3-(((2-(4-methoxybenzyl)-2H-tetrazol-5-yl)methoxy)-carbonyl)but-3-enoic acid (1.0 g, 3.0 mmol, 75%) as a colorless oil. LCMS (System 2, Method B) m/z 333.3 (M+H)+(ES$^+$). $^1$H NMR (400 MHz, DMSO-d6) δ: 12.48 (s, 1H), 7.34 (d, J=8.8 Hz, 2H), 6.93 (d, J=8.8 Hz, 2H), 6.17 (d, J=1.2 Hz, 1H), 5.84 (s, 3H), 5.39 (s, 2H), 3.73 (s, 3H), 3.29 (s, 2H).

Step 4

To a solution of 3-(((2-(4-methoxybenzyl)-2H-tetrazol-5-yl)methoxy)carbonyl)but-3-enoic acid (180 mg, 0.54 mmol), (R)-octan-2-ol (70 mg, 0.54 mmol) and DMAP (66 mg, 0.54 mmol) in DCM (3 mL) at 0° C. was added EDC.HCl (156 mg, 0.81 mmol), and the resulting colorless clear mixture was stirred at room temperature for 2 h. The mixture was then quenched with dilute aqueous HCl (0.5 M, 1 mL), the phases were separated, and the aqueous phase was extracted with DCM (2×2 mL). The separated organic phases were washed with brine, dried over $Na_2SO_4$ and filtered. The filtrate was concentrated under reduced pressure at 40° C., and the residue was purified by flash column chromatography (25 g silica, 0-27% MTBE/petroleum ether) to give (R)-1-((2-(4-methoxybenzyl)-2H-tetrazol-5-yl)methyl) 4-(octan-2-yl) 2-methylenesuccinate (130 mg, 0.29 mmol, 54%) as a yellow oil. LCMS (System 2, Method B) m/z 445.3 (M+H)$^+$ (ES$^+$).

Step 5

A solution of (R)-1-((2-(4-methoxybenzyl)-2H-tetrazol-5-yl)methyl) 4-(octan-2-yl) 2-methylenesuccinate (130 mg, 0.29 mmol) in TFA (4 mL) was stirred at 45° C. for 2 h and then concentrated under reduced pressure at 40° C. The residue was purified by preparative HPLC (Column: Waters X-Bridge C18 OBD 10 μm 19×250 mm; Flow Rate: 20 mL/min; solvent system: MeCN/(0.05% TFA/water); gradient: 50-95% MeCN; collection wavelength: 214 nm). The collected fractions were concentrated under reduced pressure at 40° C. to remove MeCN, and the residue was lyophilized to give (R)-1-((2H-tetrazol-5-yl)methyl) 4-(octan-2-yl) 2-methylenesuccinate (65 mg, 0.20 mmol, 68%) as a white solid. LCMS (System 2, Method B) m/z 325.3 (M+H)$^+$ (ES$^+$). $^1$H NMR (400 MHz, DMSO-d6) δ: 16.75 (br, 1H), 6.29 (s, 1H), 5.91 (s, 1H), 5.46 (s, 2H), 4.74-4.69 (m, 1H), 3.35 (s, 2H), 1.43-1.37 (m, 2H), 1.25-1.19 (m, 8H), 1.05 (d, J=6.0 Hz, 3H), 0.83 (t, J=6.8 Hz, 3H).

The following compounds were made using a similar procedure:

| Example No. | Alcohol used in Step 4/ Example Structure/Name | LCMS/$^1$H NMR data |
|---|---|---|
| 162 | cycloheptanol<br><br>1-(2H-tetrazol-5-yl)methyl 4-cycloheptyl 2-methylenesuccinate | LCMS (System 2, Method B) m/z 309.3 (M + H)+ (ES+).<br>$^1$H NMR (400 MHz, DMSO-d6) δ: 16.78 (br, 1H), 6.28 (s, 1H), 5.90 (s, 1H), 5.46 (s, 2H), 4.78-4.71 (m, 1H), 3.33 (s, 2H), 1.74-1.67 (m, 2H), 1.51-1.44 (m, 8H), 1.5-1.31 (m, 2H). |
| 163 | spiro[3.3]heptan-2-ol<br><br>1-(2H-tetrazol-5-yl)methyl 4-spiro[3.3]heptan-2-yl 2-methylenesuccinate | LCMS (System 2, Method B) m/z 307.1 (M + H)$^+$ (ES$^+$).<br>$^1$H NMR (400 MHz, DMSO-d6) δ: 16.80 (br, 1H), 6.29 (s, 1H), 5.90 (s, 1H), 5.46 (s, 2H), 4.73-4.65 (m, 1H), 3.33 (s, 2H), 2.33-2.29 (m, 2H), 1.94-1.87 (m, 4H), 1.85-1.80 (m, 2H), 1.76-1.73 (m, 2H). |

Example 164—(S)-1-(2H-tetrazol-5-yl)methyl 4-octan-2-yl 2-methylenesuccinate

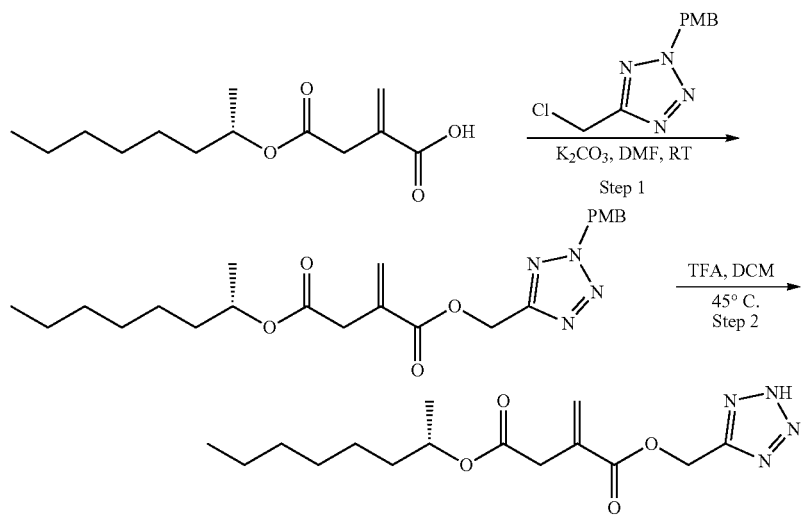

Step 1

Step 2

To a solution of (S)-2-methylene-4-(octan-2-yloxy)-4-oxobutanoic acid (150 mg, 0.62 mmol) in DMF (2 mL) was added potassium carbonate (86 mg, 0.62 mmol) and the mixture was stirred at room temperature for 30 min. 5-(Chloromethyl)-2-(4-methoxybenzyl)-2H-tetrazole (148 mg, 0.62 mmol) was added, and the mixture was stirred at room temperature for 2 h, then diluted with EtOAc (2 mL) and water (2 mL). The phases were separated, and the aqueous phase was extracted with EtOAc (2×2 mL). The combined organic phases were washed with brine, dried over $Na_2SO_4$ and filtered. The filtrate was concentrated under reduced pressure at 40° C., and the residue was purified by flash column chromatography (25 g silica, 0-40% MTBE/petroleum ether) to give (S)-1-(2-(4-methoxybenzyl)-2H-tetrazol-5-yl)methyl 4-octan-2-yl 2-methylenesuccinate (220 mg, 0.49 mmol, 80%) as a colorless oil. LCMS (System 2, Method B) m/z 445.3 (M+H)$^+$ (ES$^+$).

A mixture of (S)-1-(2-(4-methoxybenzyl)-2H-tetrazol-5-yl)methyl 4-octan-2-yl 2-methylenesuccinate (220 mg, 0.49 mmol) in TFA (1 mL) and DCM (1 mL) was stirred at 45° C. for 4 h, then concentrated under reduced pressure at 40° C. The residue was purified by reversed phase column chromatography (120 g C18 silica; flow rate: 40 mL/min; 50-80% MeCN/(10 mM HCl/water); collection wavelength: 214 nm). The collected fractions were concentrated under reduced pressure at 40° C. to remove MeCN, and the residue was lyophilized to give a solid (116 mg), which was twice triturated in a mixture of n-hexane (4 mL) and MTBE (0.5 mL) to give (S)-1-(2H-tetrazol-5-yl)methyl 4-octan-2-yl 2-methylenesuccinate (90 mg, 0.28 mmol, 57%) as a white solid. LCMS (System 2, Method B) m/z 325.3 (M+H)⁺ (ES⁺). ¹H NMR (400 MHz, DMSO-d6) δ: 16.75 (br, 1H), 6.29 (s, 1H), 5.90 (s, 1H), 5.45 (s, 2H), 4.74-4.69 (m, 1H), 3.34 (s, 2H), 1.43-1.38 (m, 2H), 1.25-1.19 (m, 8H), 1.05 (d, J=6.4 Hz, 3H), 0.83 (t, J=6.8 Hz, 3H).

Example 165—1-(1-(1H-tetrazol-5-yl)ethyl) 4-((S)-octan-2-yl) 2-methylenesuccinate

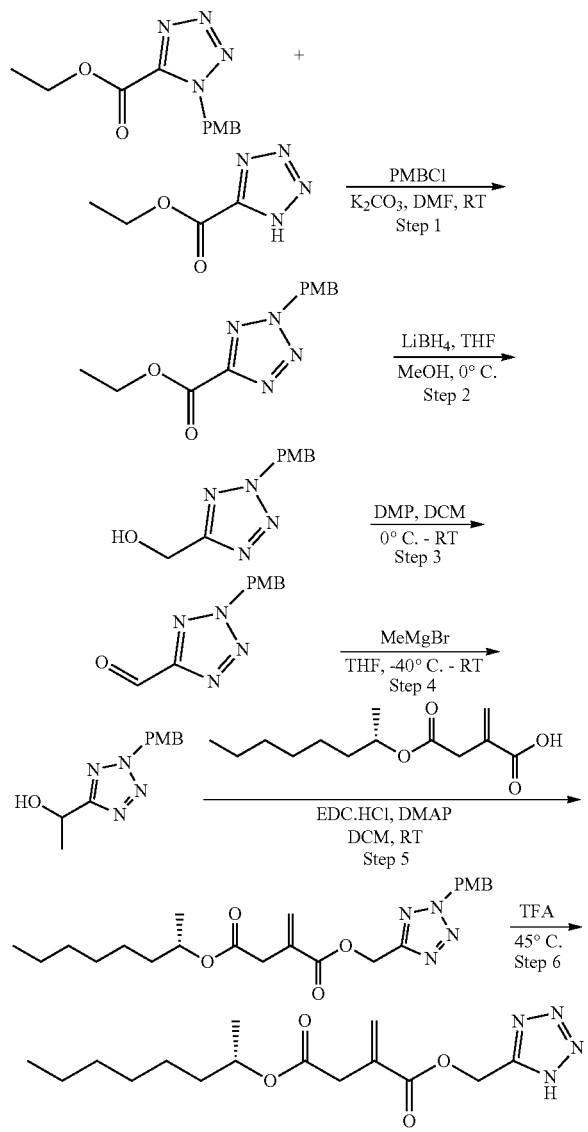

Step 1

A mixture of ethyl 1H-tetrazole-5-carboxylate (4.6 g, 32.4 mmol), 1-(chloromethyl)-4-methoxybenzene (5.1 g, 32.4 mmol) and potassium carbonate (4.5 g, 32.4 mmol) in DMF (50 mL) was stirred at room temperature overnight. The reaction mixture was then diluted with H₂O (150 mL) and extracted with EtOAc (3×50 mL). The combined organic layers were dried over Na₂SO₄, filtered and the filtrate was concentrated under reduced pressure at 40° C. The residue was purified by flash column chromatography (120 g silica, 0-40% ethyl acetate/petroleum ether) to give ethyl 2-(4-methoxybenzyl)-2H-tetrazole-5-carboxylate (2.1 g, 8.0 mmol, 25%) as a white solid and a mixture of ethyl 2-(4-methoxybenzyl)-2H-tetrazole-5-carboxylate and ethyl 1-(4-methoxybenzyl)-1H-tetrazole-5-carboxylate (2.2 g, 8.4 mmol, 26%) as a white solid.

ethyl 2-(4-methoxybenzyl)-2H-tetrazole-5-carboxylate: LCMS (System 2, Method B) m/z 285.3 (M+Na)⁺ (ES⁺). ¹H NMR (400 MHz, DMSO-d6) δ: 7.36 (d, J=8.8 Hz, 2H), 6.93 (d, J=8.8 Hz, 2H), 5.93 (s, 2H), 4.37 (q, J=7.2 Hz, 2H), 3.71 (s, 3H), 1.30 (t, J=7.2 Hz, 3H).

Step 2

To a solution of ethyl 2-(4-methoxybenzyl)-2H-tetrazole-5-carboxylate (1.4 g, 5.35 mmol) in methanol (40 mL) at 0° C. was added lithium borohydride solution in THF (2 M, 5.35 mL, 10.7 mmol) and the reaction mixture was stirred at 0° C. for 1 h. The reaction mixture was quenched with dilute aqueous HCl (0.5 M, 20 mL), and concentrated under reduced pressure at 35° C. to remove methanol. The aqueous residue was extracted with EtOAc (2×20 mL), and the combined organic layers were dried over Na₂SO₄, filtered and the filtrate was concentrated under reduced pressure. The residue was purified by flash column chromatography (120 g silica, 0-60% ethyl acetate/petroleum ether) to give (2-(4-methoxybenzyl)-2H-tetrazol-5-yl)methanol (800 mg, 3.63 mmol, 68%) as a yellow oil. LCMS (System 2, Method B) m/z 243.2 (M+Na)⁺ (ES⁺). ¹H NMR (400 MHz, DMSO-d6) δ: 7.32 (d, J=8.4 Hz, 2H), 6.93 (d, J=8.4 Hz, 3H), 5.79 (s, 2H), 4.61 (s, 2H), 3.72 (s, 3H).

Step 3

To a solution of (2-(4-methoxybenzyl)-2H-tetrazol-5-yl)methanol (800 mg, 3.63 mmol) in dichloromethane (20 mL) was added Dess-Martin periodinane (2.31 g, 5.45 mmol) at 0° C., and the reaction mixture was stirred at room temperature for 0.5 h. The reaction mixture was quenched by the addition of aqueous Na₂S₂O₃/NaHCO₃ mixture (20 mL) and then extracted with DCM (2×20 mL). The combined organic layers were dried over Na₂SO₄, filtered and the filtrate was concentrated to give crude 2-(4-methoxybenzyl)-2H-tetrazole-5-carbaldehyde (750 mg, 3.44 mmol, 94%) as a yellow oil, which was used directly in the next step. LCMS (System 2, Method B) m/z 259.3 2 (M+H₂O+Na)⁺ (ES⁺). ¹H NMR (400 MHz, DMSO-d6) δ: 10.08 (s, 1H), 7.38 (d, J=8.4 Hz, 2H), 6.94 (d, J=8.4 Hz, 2H), 5.97 (s, 2H), 3.72 (s, 3H).

Step 4

To a solution of 2-(4-methoxybenzyl)-2H-tetrazole-5-carbaldehyde (400 mg, 1.83 mmol) in THF (10 mL) at −40° C. was added a solution of methyl magnesium bromide in THF (1 M, 5.46 mL, 5.46 mmol) and the resulting mixture was stirred at room temperature for 2 h. The reaction mixture was then quenched with dilute aqueous HCl (0.5 M, 10 mL) and extracted with EtOAc (2×10 mL). The combined organic layers were dried over Na₂SO₄, filtered and the filtrate was concentrated under reduced pressure. The residue was purified by flash column chromatography (120 g silica, 0-50% ethyl acetate/petroleum ether) to give crude 1-(2-(4-methoxybenzyl)-2H-tetrazol-5-yl)ethan-1-ol (300 mg, 1.28 mmol, 70%) as a yellow oil. LCMS (System 2, Method B) m/z 235.3 (M+H)+ (ES⁺). ¹H NMR (400 MHz, DMSO-d6)

δ: 7.34 (d, J=8.8 Hz, 2H), 6.95 (d, J=8.4 Hz, 3H), 5.81 (s, 2H), 4.96 (q, J=6.4 Hz, 1H), 3.74 (s, 3H), 1.45 (d, J=6.4 Hz, 3H).

Step 5

To a solution of (S)-2-methylene-4-(octan-2-yloxy)-4-oxobutanoic acid (300 mg, 1.28 mmol), 1-(2-(4-methoxybenzyl)-2H-tetrazol-5-yl)ethan-1-ol (300 mg, 1.28 mmol) and DMAP (156 mg, 1.28 mmol) in DCM (7 mL) at 0° C. was added EDC.HCl (369 mg, 1.92 mmol), and the resulting colorless clear mixture was stirred at room temperature for 3 h. The mixture was quenched with dilute aqueous HCl (0.5 M, 1 mL), the phases were separated, and the aqueous phase was extracted with DCM (2×2 mL). The combined organic phases were washed with brine, dried over Na$_2$SO$_4$ and filtered. The filtrate was concentrated under reduced pressure at 40° C., and the residue was purified by flash column chromatography (25 g silica, 0-40% MTBE/petroleum ether) to give 1-(1-(2-(4-methoxybenzyl)-2H-tetrazol-5-yl) ethyl) 4-((S)-octan-2-yl) 2-methylenesuccinate (400 mg, 0.87 mmol, 68%) as a yellow oil. LCMS (System 2, Method B) m/z 459.3 (M+H)$^+$ (ES$^+$).

Step 6

A solution of 1-(1-(2-(4-methoxybenzyl)-2H-tetrazol-5-yl)ethyl) 4-((S)-octan-2-yl) 2-methylenesuccinate (400 mg, 0.87 mmol) in TFA (8 mL) was stirred at 45° C. for 2 h, then concentrated at 40° C. under reduced pressure and the residue was purified by preparative HPLC (Column: Waters X-Bridge C18 OBD 10 μm 19×250 mm; Flow Rate: 20 mL/min; solvent system: MeCN/(0.05% TFA/water); gradient: 30-95% MeCN; collection wavelength: 214 nm). The collected fractions were concentrated under reduced pressure at 40° C. to remove MeCN, and the residue was lyophilized to give 1-(1-(1H-tetrazol-5-yl)ethyl) 4-((S)-octan-2-yl) 2-methylenesuccinate (120 mg, 0.35 mmol, 40%) as a pale-yellow oil. LCMS (System 2, Method B) m/z 339.3 (M+H)+ (ES$^+$). $^1$H NMR (400 MHz, DMSO-d6) δ: 16.75 (br, 1H), 6.29 (s, 1H), 6.19 (q, J=6.4 Hz, 1H), 5.91 (s, 1H), 4.76-4.71 (m, 1H), 3.35 (s, 2H), 1.63 (d, J=6.4 Hz, 3H), 1.44-1.41 (m, 2H), 1.25-1.19 (m, 8H), 1.08 (t, J=5.6 Hz, 3H), 0.85 (t, J=5.6 Hz, 3H).

Example 166—1-(cyclopropyl(1H-tetrazol-5-yl)methyl) 4-((S)-octan-2-yl) 2-methylenesuccinate

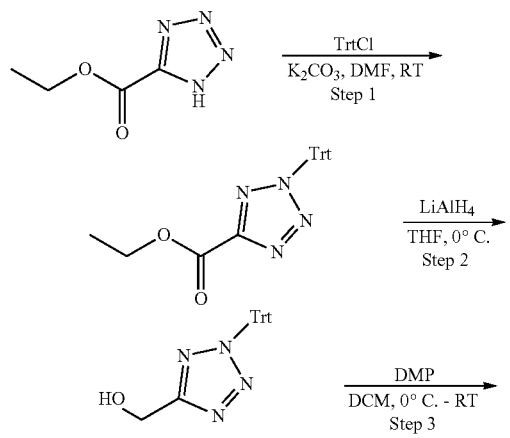

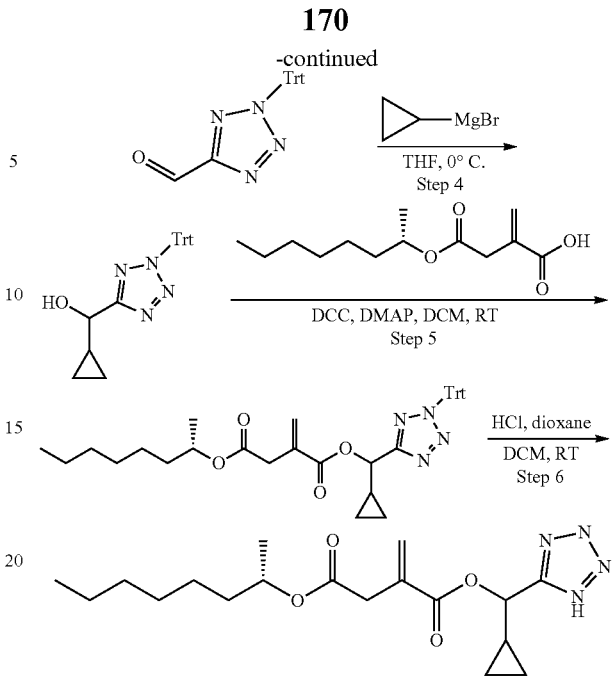

Step 1

A mixture of ethyl 1H-tetrazole-5-carboxylate (4.6 g, 32.4 mmol), triphenylmethyl chloride (9.0 g, 32.4 mmol) and potassium carbonate (4.5 g, 32.4 mmol) in DMF (50 mL) was stirred at room temperature overnight. The reaction mixture was diluted with saturated aqueous NH$_4$Cl solution (150 mL) and extracted with EtOAc (3×50 mL). The combined organic layers were washed with brine (100 mL), dried over Na$_2$SO$_4$, filtered and the filtrate was concentrated under reduced pressure at 40° C. The residual solid was purified by trituration in a mixed of petroleum ether (30 mL) and ethyl acetate (3 ml) to give ethyl 2-trityl-2H-tetrazole-5-carboxylate (6.4 g, 16.6 mmol, 51%) as a white solid. LCMS (System 2, Method C) m/z 407.4 (M+Na)$^+$ (ES$^+$).

Step 2

To a solution of 2-trityl-2H-tetrazole-5-carboxylate (2.1 g, 5.8 mmol) in THF (50 mL) at 0° C. was added lithium aluminium hydride (416 mg, 10.9 mmol), and the reaction mixture was stirred at 0° C. for 1 h. The reaction mixture was quenched by adding Na$_2$SO$_4$.10H$_2$O (2.1 g, 6.5 mmol) in portions, then the mixture was filtered and the filtrate was concentrated under reduced pressure at 35° C. to give (2-trityl-2H-tetrazol-5-yl)methanol (1.4 g, 4.1 mmol, 75%) as a white solid. LCMS (System 2, Method C) m/z 365.4 (M+Na)$^+$ (ES$^+$).

Step 3

To a solution of (2-trityl-2H-tetrazol-5-yl)methanol (1.4 g, 4.1 mmol) in DCM (1 mL) at 0° C. was added Dess-Martin periodinane (2.6 g, 6.1 mmol), and the reaction mixture was stirred at room temperature for 0.5 h. The reaction mixture was quenched by the addition of aqueous Na$_2$S$_2$O$_3$/NaHCO$_3$ mixture (20 mL) and then extracted with DCM (2×50 mL). The combined organic layer was dried over Na$_2$SO$_4$, filtered and the filtrate was concentrated under reduced pressure at 30° C. The residue was purified by flash column chromatography (120 g silica, 0-5% ethyl acetate/ petroleum ether) to give 2-trityl-2H-tetrazole-5-carbaldehyde (720 mg, 2.1 mmol, 51%) as a white solid. $^1$H NMR (400 MHz, DMSO-d6) δ 10.15 (s, 1H), 7.44-7.41 (m, 9H), 7.08-7.05 (m, 6H).

Step 4

To a solution of 2-trityl-2H-tetrazole-5-carbaldehyde (720 mg, 2.12 mmol) in THF (20 mL) at 0° C. was added cyclopropyl magnesium bromide solution in THF (1 M, 3.2 mL, 3.2 mmol), and the reaction mixture was stirred at 0° C. for 1 h. The reaction mixture was quenched by the addition of saturated aqueous NH$_4$Cl solution (30 mL) and extracted with EtOAc (2×30 mL). The combined organic layers were dried over Na$_2$SO$_4$, filtered and the filtrate was concentrated under reduced pressure at 40° C. The residue was purified by basic silica flash column chromatography (0-10% ethyl acetate/petroleum ether) to give cyclopropyl(2-trityl-2H-tetrazol-5-yl) methanol (540 mg, 68%) as a yellow solid. LCMS (System 2, Method C) m/z 405.2 (M+Na)$^+$ (ES$^+$). $^1$H NMR (400 MHz, DMSO-d6) δ: 7.19-7.15 (m, 9H), 6.80-6.76 (m, 6H), 5.52 (br, 1H), 4.10 (d, J=7.6 Hz, 1H), 1.08-1.05 (m, 1H), 0.29-0.26 (m, 1H), 0.18-0.12 (m, 2H), 0.01-0.00 (m, 1H).

Step 5

To a solution of (S)-2-methylene-4-(octan-2-yloxy)-4-oxobutanoic acid (126 mg, 0.52 mmol), cyclopropyl(2-trityl-2H-tetrazol-5-yl) methanol (200 mg, 0.52 mmol) and DMAP (63 mg, 0.52 mmol) in DCM (7 mL) at 0° C. was added dicyclohexylcarbodiimide (150 mg, 0.78 mmol), and the resulting mixture was stirred at room temperature for 3 h. The mixture was filtered, and the filtrate was concentrated under reduced pressure at 30° C. The residue was purified by flash column chromatography (40 g silica, 0-40% MTBE/ petroleum ether) to give 1-(cyclopropyl(2-trityl-2H-tetrazol-5-yl)methyl) 4-((S)-octan-2-yl) 2-methylenesuccinate (240 mg, 0.40 mmol, 76%) as a yellow oil. LCMS (System 2, Method C) m/z 629.2 (M+Na)$^+$ (ES$^+$).

Step 6

A mixture of 1-(cyclopropyl(2-trityl-2H-tetrazol-5-yl) methyl) 4-((S)-octan-2-yl) 2-methylenesuccinate (200 mg, 0.33 mmol) and HCl solution in 1,4-dioxane (4 M, 1 mL, 4 mmol) in DCM (4 mL) was stirred at room temperature for 3 h. The mixture was concentrated under reduced pressure at 30° C. and the residue was purified by flash column chromatography (80 g silica, 0-40% ethyl acetate/petroleum ether) to give the crude product, which was further purified by preparative HPLC (Column: Waters X-Bridge C18 OBD 10 μm 19×250 mm; Flow Rate: 20 mL/min; solvent system: MeCN/(0.05% TFA/water); gradient: 30-95% MeCN; collection wavelength: 214 nm). The collected fractions were concentrated under reduced pressure at 40° C. to remove MeCN, and the residue was lyophilized to give 1-(cyclopropyl(1H-tetrazol-5-yl)methyl) 4-((S)-octan-2-yl) 2-methylenesuccinate (27 mg, 0.074 mmol, 22%) as a pale-yellow oil. LCMS (System 2, Method B) m/z 365.2 (M+H)$^+$ (ES$^+$). $^1$H NMR (400 MHz, DMSO-d6) δ: 6.28 (s, 1H), 5.90 (s, 1H), 5.58 (d, J=9.2 Hz, 1H), 4.76-4.73 (m, 1H), 3.41 (s, 2H), 1.50-1.41 (m, 3H), 1.26 (m, 9H), 1.09 (dd, J=9.6, 6.4 Hz, 3H), 0.85 (t, J=5.6 Hz, 3H), 0.62-0.58 (m, 2H), 0.47 (m, 2H).

Example 167—dicyclohexyl 2-methylenesuccinate

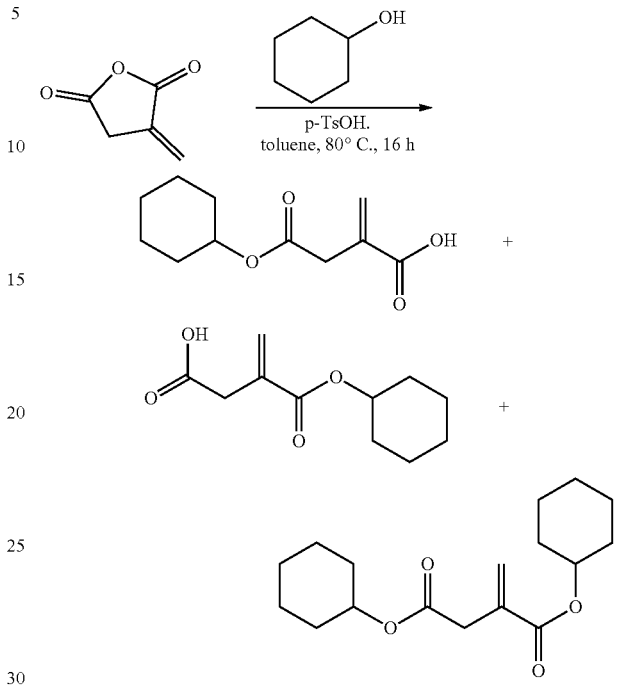

A mixture of 3-methylenedihydrofuran-2,5-dione (3.00 g, 26.8 mmol), cyclohexanol (2.44 g, 24.3 mmol) and p-toluenesulfonic acid monohydrate (255 mg, 1.34 mmol) in toluene (30 mL) was stirred at 80° C. for 16 hours, then cooled to room temperature and concentrated under reduced pressure at 50° C. The residue was purified by reversed phase column chromatography (120 g C18 silica; flow rate: 40 mL/min; 50-70% then 80-90% MeCN/(10 mM HCl/ water); collection wavelength: 214 nm).

The first set of fractions that were collected were concentrated under reduced pressure at 40° C. to remove MeCN, and the residue was lyophilized to give 4-(cyclohexyloxy)-2-methylene-4-oxobutanoic acid that contained ~ 5% (by $^1$H-NMR) of the regioisomeric 3-((cyclohexyloxy) carbonyl)but-3-enoic acid (3.00 g, 14.1 mmol, 58%) as a white solid.

The second set of fractions that were collected were concentrated under reduced pressure at 40° C. to remove MeCN, and the residue was lyophilized to give the crude product, which was further purified by preparative HPLC (Column: Waters X-Bridge C18 OBD 10 μm 19×250 mm; Flow Rate: 20 mL/min; solvent system: MeCN/(0.05% TFA/water); gradient: 70-95% MeCN; collection wavelength: 214 nm). The collected fractions were concentrated under reduced pressure at 40° C. to remove MeCN, and the residue was lyophilized to give dicyclohexyl 2-methylenesuccinate (82 mg, 0.28 mmol, 1%) as a pale-yellow oil.

dicyclohexyl 2-methylenesuccinate: LCMS (System 2, Method B) m/z 295.4 (M+H)$^+$ (ES$^+$). $^1$H NMR (400 MHz, DMSO-d6) δ: 6.17 (s, 1H), 5.78 (s, 1H), 4.75-4.70 (m, 1H), 4.67-4.62 (m, 1H), 3.33 (d, J=2.8 Hz, 2H), 1.73-1.68 (m, 4H), 1.63-1.61 (m, 4H), 1.46-1.37 (m, 4H), 1.35-1.22 (m, 8H).

Example 168—2-((4-(cyclooctyloxy)-3-methyl-2-methylene-4-oxobutanoyl)oxy)acetic acid

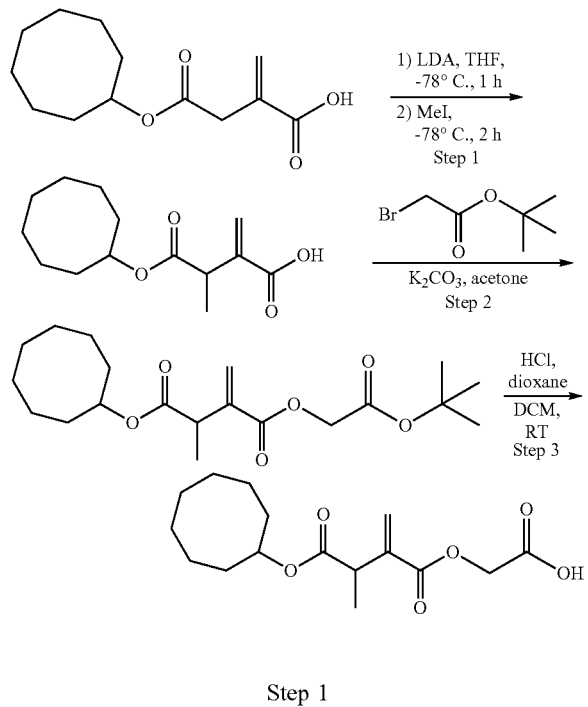

Step 1

To a solution of 4-(cyclooctyloxy)-2-methylene-4-oxobutanoic acid (570 mg, 2.38 mmol) in THF (10 mL) at −78° C. was added a solution of LDA in THF/n-heptane/ethyl benzene (2 M, 2.38 mL, 4.76 mmol), and the reaction mixture was stirred at −78° C. for 1 h. Iodomethane (338 mg, 2.38 mmol) was then added at −78° C., and the reaction mixture was stirred at −78° C. for 2 h. The reaction mixture was quenched with dilute aqueous HCl (0.5 M, 20 mL) and extracted with EtOAc (2×20 mL). The combined organic phases were dried over Na$_2$SO$_4$, filtered and the filtrate was concentrated under reduced pressure at 35° C. to give crude 4-(cyclooctyloxy)-3-methyl-2-methylene-4-oxobutanoic acid (550 mg, 2.16 mmol, 91%) as a colorless oil, which was used in the next step without purification. LCMS (System 2, Method C) m/z 277.4 (M+Na)$^+$ (ES$^+$).

Step 2

To a solution of 4-(cyclooctyloxy)-3-methyl-2-methylene-4-oxobutanoic acid (550 mg, 2.16 mmol) in acetone (10 mL) was added potassium carbonate (329 mg, 2.39 mmol), and the reaction mixture was stirred at room temperature for 30 min. tert-Butyl 2-bromoacetate (464 mg, 2.39 mmol) was then added and the resulting mixture was stirred at room temperature overnight. The reaction mixture was filtered and the filtrate was concentrated under reduced pressure at 40° C. The residue was purified by flash column chromatography (25 g silica, 0-10% MTBE/petroleum ether) to give 1-(2-(tert-butoxy)-2-oxoethyl) 4-cyclooctyl 3-methyl-2-methylenesuccinate (380 mg, 1.0 mmol, 48%) as a yellow oil. LCMS (System 2, Method B) m/z 391.3 (M+Na)$^+$ (ES$^+$).

Step 3

A mixture of 1-(2-(tert-butoxy)-2-oxoethyl) 4-cyclooctyl 3-methyl-2-methylenesuccinate (180 mg, 0.49 mmol) and HCl solution in 1,4-dioxane (4 M, 2 mL, 8.0 mmol) in DCM (2 mL) was stirred at room temperature for 4 h, then concentrated under reduced pressure at 40° C. The residue was purified by preparative HPLC (Column: Waters X-Bridge C18 OBD 10 μm 19×250 mm; Flow Rate: 20 mL/min; solvent system: MeCN/(0.05% TFA/water) gradient: 30-95% MeCN; collection wavelength: 214 nm). The fractions were concentrated under reduced pressure at 40° C. to remove MeCN, and the residue was lyophilized to give 2-((4-(cyclooctyloxy)-3-methyl-2-methylene-4-oxobutanoyl)oxy)acetic acid (117 mg, 0.37 mmol, 77%) as a pale-yellow oil.

LCMS (System 2, Method B) m/z 335.2 (M+Na)$^+$ (ES$^+$).
$^1$H NMR (400 MHz, DMSO-d6) δ: 13.10 (br, 1H), 6.28 (s, 1H), 5.85 (s, 1H), 4.82-4.76 (m, 1H), 4.64 (d, J=1.6 Hz, 2H), 3.51 (q, J=6.8 Hz, 1H), 1.70-1.62 (m, 6H), 1.55-1.41 (m, 8H), 1.27 (d, J=7.2 Hz, 3H).

Example 171—2-((4-(cyclooctyloxy)-3-methoxy-2-methylene-4-oxobutanoyl)oxy)acetic Acid

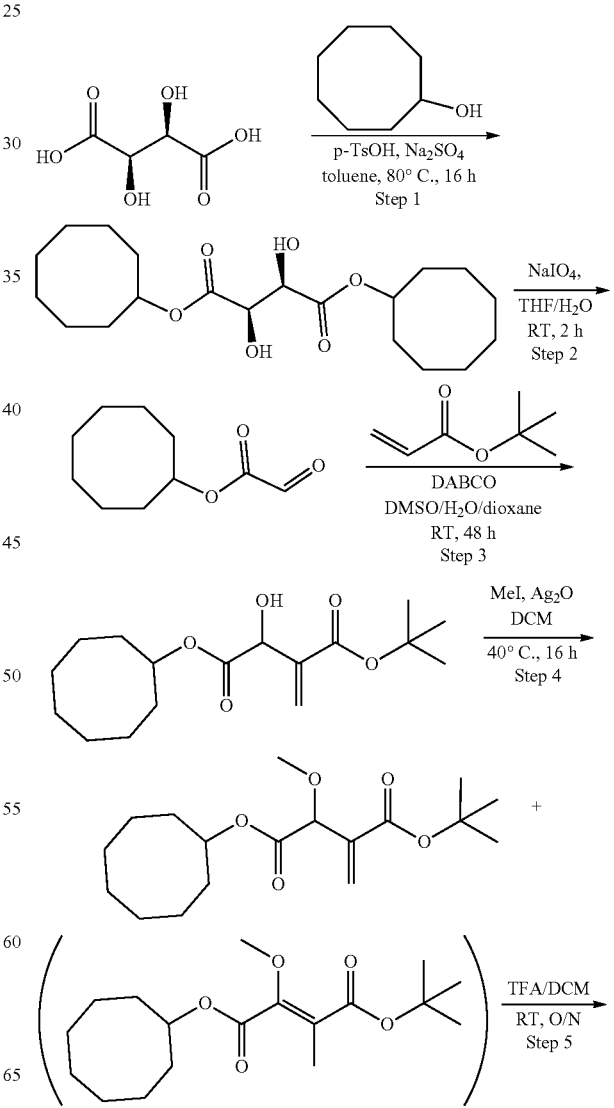

-continued

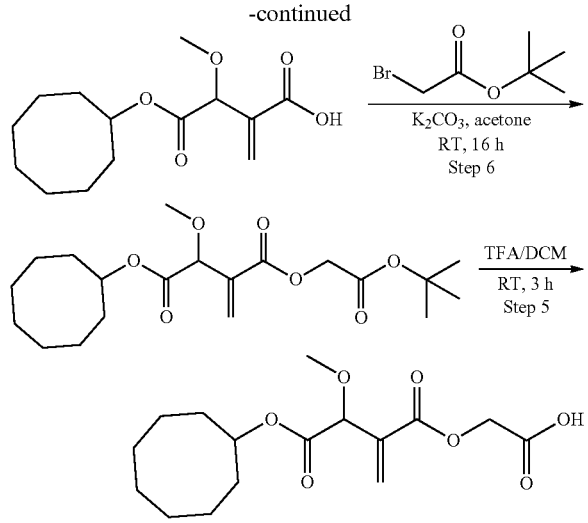

Step 1

A mixture of (2R,3R)-2,3-dihydroxysuccinic acid (3 g, 20 mmol), cyclooctanol (7.7 g, 60 mmol), anhydrous p-toluenesulfonic acid (344 mg, 2 mmol) and anhydrous $Na_2SO_4$ (6 g, 42.2 mmol) in toluene (40 mL) was stirred at 80° C. for 16 h. The reaction mixture was cooled to room temperature and filtered. The filtrate was concentrated under reduced pressure at 45° C. and the residue was purified by reversed phase column chromatography (120 g C18 silica; flow rate: 40 mL/min; 50-70% MeCN/(10 mM HCl/water); collection wavelength: 214 nm). The collected fractions were concentrated under reduced pressure at 40° C. to remove MeCN, and the residue was lyophilized to give dicyclooctyl (2R, 3R)-2,3-dihydroxysuccinate (3.5 g, 9.4 mmol, 47%) as a white solid. LCMS (System 2, Method B) m/z 393.3 (M+Na)$^+$ (ES$^+$). $^1$H NMR (400 MHz, DMSO-d6) δ: 5.38 (d, J=8.0 Hz, 2H), 4.90-4.86 (m, 2H), 4.32 (d, J=7.6 Hz, 2H), 1.77-1.65 (m, 12H), 1.58-1.49 (m, 16H).

Step 2

To a solution of dicyclooctyl (2R,3R)-2,3-dihydroxysuccinate (3.5 g, 9.4 mmol) in THF:$H_2O$ (2:1, 40 mL) was added $NaIO_4$ (2.3 g, 18.8 mmol) at room temperature, and the reaction mixture was stirred at room temperature for 2 h. The reaction mixture was filtered, the filtrate was diluted with EtOAc (30 mL), quenched with saturated aqueous $Na_2S_2O_3$ aq. and separated. The organic layer was washed with saturated aqueous $NaHCO_3$, dried over $Na_2SO_4$, filtered and concentrated under reduced pressure at 30° C. The residue was purified by flash column chromatography (40 g silica, 0-20% EtOAc/petroleum ether) to give crude cyclooctyl 2-oxoacetate (3 g, 16.3 mmol, 87%) as a pale yellow oil, which was used directly in the next step. $^1$H NMR (400 MHz, CDCl$_3$) δ: 9.39 (s, 1H), 5.08-5.03 (m, 1H), 1.91-1.68 (m, 6H), 1.60-1.58 (m, 8H).

Step 3

A mixture of cyclooctyl 2-oxoacetate (3 g, 16.3 mmol), tert-butyl acrylate (3.1 g, 24.4 mmol) and DABCO (914 mg, 8.1 mmol) in a solvent mixture of 1,4-dioxane/DMSO/$H_2O$ (20 mL, 8/2/1) was stirred at room temperature for 48 h. The reaction mixture was filtered and the filtrate was concentrated under reduced pressure at 50° C. The residue was purified by reversed phase column chromatography (120 g C18 silica; flow rate: 40 mL/min; 50-70% MeCN/$H_2O$; collection wavelength: 214 nm). The collected fractions were concentrated under reduced pressure at 40° C. to remove MeCN, and the residue was lyophilized to give 1-(tert-butyl) 4-cyclooctyl 3-hydroxy-2-methylenesuccinate (2.3 g, 7.4 mmol, 45%) as a yellow oil. LCMS (System 2, Method B) m/z 335.2 (M+Na)$^+$ (ES$^+$).

Step 4

To a mixture of 1-(tert-butyl) 4-cyclooctyl 3-hydroxy-2-methylenesuccinate (300 mg, 0.96 mmol) and $Ag_2O$ (445 mg, 1.92 mmol) in DCM (1 mL) was added methyl iodide (818 mg, 5.76 mmol), and the reaction mixture was stirred at 40° C. for 16 h. The mixture was filtered and the filtrate was concentrated under reduced pressure at 30° C. to give the crude product as a 5:1 mixture of 1-(tert-butyl) 4-cyclooctyl 3-methoxy-2-methylenesuccinate and 1-(tert-butyl) 4-cyclooctyl 3-methoxy-2-methylfumarate respectively. The crude product was purified by flash column chromatography (25 g silica, 0-10% MTBE/petroleum ether) to give pure 1-(tert-butyl) 4-cyclooctyl 3-methoxy-2-methylenesuccinate (250 mg, 0.77 mmol, 79%) as a pale yellow oil. LCMS (System 2, Method B) m/z 349.3 (M+Na)$^+$ (ES$^+$). $^1$H NMR (400 MHz, CDCl$_3$) δ: 6.31 (d, J=0.8 Hz, 1H), 5.88 (s, 1H), 5.02-4.98 (m, 1H), 4.58 (s, 1H), 3.44 (s, 3H), 1.86-1.64 (m, 6H), 1.63-1.52 (m, 8H), 1.48 (s, 9H).

Step 5

A mixture of 1-(tert-butyl) 4-cyclooctyl 3-methoxy-2-methylenesuccinate (230 mg, 0.71 mmol) and TFA (2 mL) in DCM (2 mL) was stirred at room temperature overnight. The mixture was concentrated under reduced pressure at 40° C. to give crude 4-(cyclooctyloxy)-3-methoxy-2-methylene-4-oxobutanoic acid (200 mg, 0.71 mmol, >100%) as a pale yellow oil, which was used directly in the next step. LCMS (System 2, Method C) m/z 293.4 (M+Na)$^+$ (ES$^+$).

Step 6

To a solution of crude 4-(cyclooctyloxy)-3-methoxy-2-methylene-4-oxobutanoic acid (200 mg, 0.71 mmol) in acetone (5 mL) was added potassium carbonate (110 mg, 0.74 mmol), and the reaction mixture was stirred at room temperature for 30 min. Tert-butyl 2-bromoacetate (171 mg, 0.89 mmol) was added and the resulting mixture was stirred at room temperature overnight. The reaction mixture was filtered, and the filtrate was concentrated under reduced pressure at 40° C. The residue was purified by flash column chromatography (25 g silica, 0-10% MTBE/petroleum ether) to give 1-(2-(tert-butoxy)-2-oxoethyl) 4-cyclooctyl 3-methoxy-2-methylenesuccinate (200 mg, 0.52 mmol, 73%) as a yellow oil. LCMS (System 2, Method B) m/z 407.3 (M+Na)$^+$ (ES$^+$).

Step 7

A mixture of 1-(2-(tert-butoxy)-2-oxoethyl) 4-cyclooctyl 3-methoxy-2-methylenesuccinate (200 mg, 0.52 mmol) and TFA (2 mL) in DCM (2 mL) was stirred at room temperature for 3 h. The mixture was concentrated under reduced pressure at 40° C. and the residue was purified by preparative HPLC (Column: Waters X-Bridge C18 OBD 10 µm 19×250 mm; Flow Rate: 20 mL/min; solvent system: MeCN/(0.1% TFA/water) gradient: 45-95% MeCN; collection wavelength: 214 nm). The fractions were concentrated under reduced pressure at 40° C. to remove MeCN, and the residue was lyophilized to give 2-((4-(cyclooctyloxy)-3-methoxy-2-methylene-4-oxobutanoyl)oxy)acetic acid (144 mg, 0.44 mmol, 84%) as a white solid. LCMS (System 2, Method B) m/z 351.2 (M+Na)$^+$ (ES$^+$). $^1$H NMR (400 MHz, DMSO-d6) δ: 12.97 (br, 1H), 6.40 (s, 1H), 6.03 (s, 1H), 4.90-4.84 (m, 1H), 4.65 (s, 2H), 4.60 (s, 1H), 3.33 (s, 3H), 1.77-1.54 (m, 6H), 1.49-1.38 (m, 8H).

Example 172—2-((4-((-adamantan-1-yl)oxy)-2-methylene-4-oxobutanoyl)oxy)acetic Acid

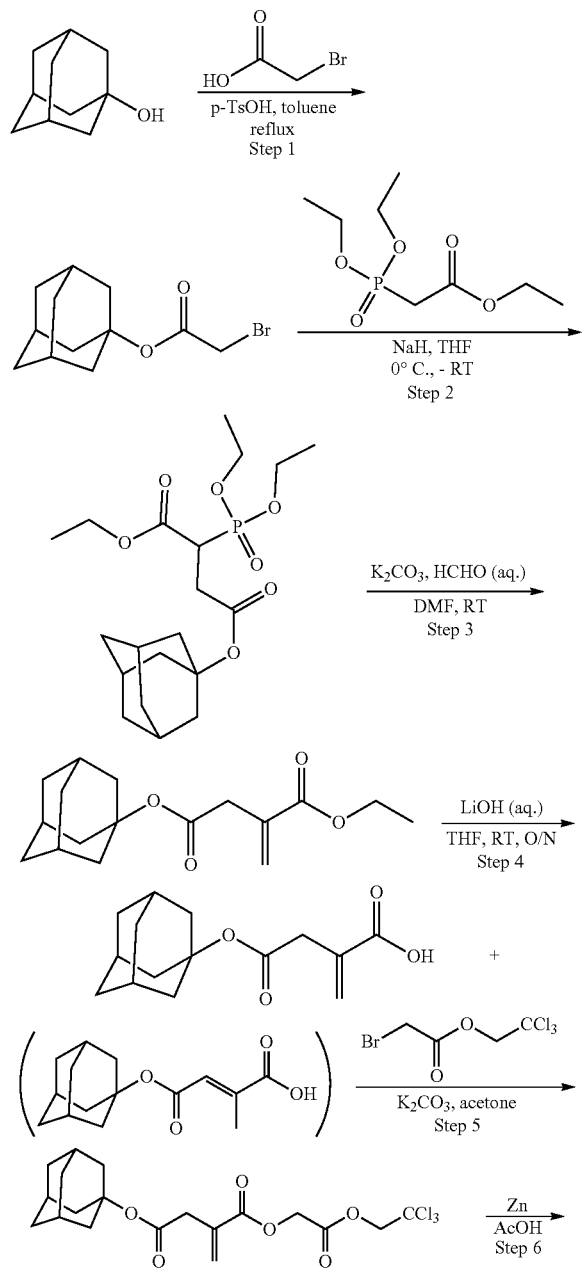

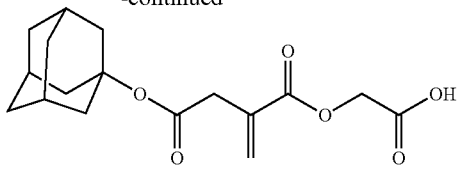

Step 1

A mixture of adamantan-1-ol (3.1 g, 20 mmol), bromoacetic acid (5.5 g, 40 mmol) and anhydrous p-toluenesulfonic acid (172 mg, 1 mmol) in toluene (100 mL) was heated at reflux overnight. The reaction mixture was cooled to room temperature, diluted with saturated aqueous NaHCO$_3$, separated and the aqueous layer was extracted with EtOAc (2×30 mL). The combined organic layers was washed with brine, dried over Na$_2$SO$_4$, filtered and concentrated under reduced pressure at 40° C. The residue was purified by flash column chromatography (80 g silica, 0-5% EtOAc/petroleum ether) to give adamantan-1-yl 2-bromoacetate (4.5 g, 16.5 mmol, 83%) as a white solid. $^1$H NMR (400 MHz, DMSO-d6) δ: 4.02 (s, 2H), 2.50 (m, 3H), 2.05 (d, J=3.2 Hz, 6H), 1.62 (t, J=2.8 Hz, 6H).

Step 2

To a solution of ethyl 2-(diethoxyphosphoryl)acetate (1.2 g, 5.4 mmol) in THF (10 mL) was added NaH suspension in mineral oil (60 wt. %, 236 mg, 5.9 mmol) at 0° C., the reaction mixture was stirred at 0° C. for 0.5 h, then adamantan-1-yl 2-bromoacetate (1.61 g, 5.9 mmol) was added. The reaction mixture was stirred at room temperature for 4 h, then it was quenched by the addition of dilute aqueous HCl (0.5 M, 10 mL), adjusted to pH=5, and extracted with EtOAc (2×10 mL). The combined organic layers were washed with brine, dried over Na$_2$SO$_4$, filtered and concentrated under reduced pressure at 40° C. The residue was purified by flash column chromatography (40 g silica, 0-30% EtOAc/petroleum ether) to give crude 4-(adamantan-1-yl) 1-ethyl 2-(diethoxyphosphoryl)succinate (2 g, 4.8 mmol, 90%) as a yellow oil. LCMS (System 2, Method B) m/z 417.3 (M+H)$^+$ (ES$^+$). $^1$H NMR (400 MHz, DMSO-d6) δ: 4.13-4.00 (m, 6H), 3.37-3.32 (m, 1H), 2.75-2.72 (m, 1H), 2.63-2.60 (m, 1H), 2.11 (m, 3H), 2.01 (s, 6H), 1.60 (m, 6H), 1.26-1.17 (m, 9H).

Step 3

To a solution of 4-(adamantan-1-yl) 1-ethyl 2-(diethoxyphosphoryl)succinate (2 g, 4.8 mmol) and potassium carbonate (1.3 g, 9.6 mmol) in DMF (20 mL) was added formaldehyde solution in water (37 wt. %, 7.8 mL, 96 mmol) at room temperature, and the reaction mixture was stirred at room temperature for 4 h. The reaction mixture was diluted with H$_2$O (60 mL) and extracted with MTBE (2×30 mL). The combined organic layers were washed with H$_2$O and brine, dried over Na$_2$SO$_4$, filtered and concentrated under reduced pressure at 30° C. The residue was purified by flash column chromatography (40 g silica, 0-10% MTBE/petroleum ether) to give 4-(adamantan-1-yl) 1-ethyl 2-methylenesuccinate (800 mg, 3.0 mmol, 57%) as a yellow oil. LCMS (System 2, Method B) m/z 315.3 (M+Na)$^+$ (ES$^+$). $^1$H NMR (400 MHz, DMSO-d6) δ: 6.14 (d, J=1.2 Hz, 1H), 5.75

(d, J=1.2 Hz, 1H), 4.13 (q, J=7.2 Hz, 2H), 3.26 (s, 2H), 2.11 (m, 3H), 2.01 (d, J=2.8 Hz, 6H), 1.60 (s, 6H), 1.21 (t, J=7.8 Hz, 3H).

Step 4

To a solution of 4-(adamantan-1-yl) 1-ethyl 2-methylenesuccinate (800 mg, 3.0 mmol) in THF (10 mL) was added LiOH solution in water (2 M, 4.5 mL, 9 mmol), and the reaction mixture was stirred at room temperature overnight. The reaction mixture was concentrated under reduced pressure at 30° C. to remove THF. The residue was diluted with H$_2$O (20 mL) and washed with MTBE (2×10 mL). The aqueous layer was adjusted to pH=3 using dilute aqueous HCl (0.5 M) and extracted with EtOAc (2×10 mL). The combined EtOAc layers were washed with brine, dried over Na$_2$SO$_4$, filtered and concentrated under reduced pressure at 40° C. to give a 1:1 mixture of 4-((adamantan-1-yl)oxy)-2-methylene-4-oxobutanoic acid and 4-((adamantan-1-yl)oxy)-2-methyl-4-oxobut-2-enoic acid (300 mg, 1.1 mmol, 38%) as a pale yellow oil, which was used directly in the next step. LCMS (System 2, Method C) m/z 287.2 (M+Na)$^+$ (ES$^+$).

Step 5

To a solution of a 1:1 mixture of 4-((adamantan-1-yl)oxy)-2-methylene-4-oxobutanoic acid and 4-((adamantan-1-yl)oxy)-2-methyl-4-oxobut-2-enoic acid (300 mg, 1.1 mmol), and potassium carbonate (157 mg, 1.1 mmol) in acetone (10 mL) was added 2,2,2-trichloroethyl 2-bromoacetate (354 mg, 1.3 mmol) at room temperature, and the reaction mixture was stirred at room temperature overnight. The reaction mixture was then filtered, and the filtrate was concentrated under reduced pressure at 30° C. The residue was purified by flash column chromatography (40 g silica, 0-10% MTBE/petroleum ether) to give 4-(adamantan-1-yl) 1-(2-oxo-2-(2,2,2-trichloroethoxy)ethyl) 2-methylenesuccinate (270 mg, 0.60 mmol, 54%) as a yellow oil. LCMS (System 2, Method B) m/z 475.3 (M+Na)$^+$ (ES$^+$).

Step 6

To a solution of 4-(adamantan-1-yl) 1-(2-oxo-2-(2,2,2-trichloroethoxy)ethyl) 2-methylenesuccinate (270 mg, 0.60 mmol) in AcOH (5 mL) was added zinc powder (195 mg, 3 mmol), and the reaction mixture was stirred at room temperature overnight. The reaction mixture was filtered, and the filtrate was concentrated under reduced pressure at 45° C. The residue was purified by preparative HPLC (Column: Waters X-Bridge C18 OBD 10 μm 19×250 mm; Flow Rate: 20 mL/min; solvent system: MeCN/(0.05% TFA/water) gradient: 50-95% MeCN; collection wavelength: 214 nm). The fractions were concentrated under reduced pressure at 40° C. to remove MeCN, and the residue was lyophilized to give 2-((4-((-adamantan-1-yl)oxy)-2-methylene-4-oxobutanoyl)oxy)acetic acid (72 mg, 37%) as a colorless oil. LCMS (System 2, Method B) m/z 345.3 (M+Na)$^+$ (ES$^+$). $^1$H NMR (400 MHz, DMSO-d6) δ: 13.07 (br, 1H), 6.23 (s, 1H), 5.86 (s, 1H), 4.64 (s, 2H), 3.27 (s, 2H), 2.10 (s, 3H), 2.01 (d, J=2.4 Hz, 6H), 1.60 (m, 6H).

Example 185—1-(3,3-difluorocyclobutyl) 4-octyl 2-methylenesuccinate

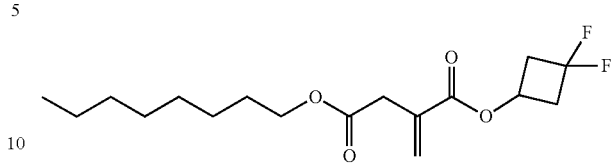

Example 185 was prepared according to General Procedure 2, using 4-octyl itaconate as itaconic acid monoester and 3,3-difluorocyclobutanol as R$^2$—OH. LCMS m/z 333.4 (M+H)$^+$ (ES$^+$). $^1$H NMR (500 MHz, DMSO-d6) δ 6.25 (d, J=1.2 Hz, 1H), 5.89 (d, J=1.3 Hz, 1H), 4.95 (dddd, J=12.3, 7.6, 4.7, 2.8 Hz, 1H), 4.01 (t, J=6.6 Hz, 2H), 3.38 (s, 2H), 3.15-3.05 (m, 2H), 2.72-2.60 (m, 2H), 1.58-1.50 (m, 2H), 1.33-1.19 (m, 10H), 0.89-0.83 (m, 3H).

Example 186—1-((endo)-3-(methylsulfonyl)-3-azabicyclo[3.2.1]octan-8-yl) 4-((R)-octan-2-yl) 2-methylenesuccinate

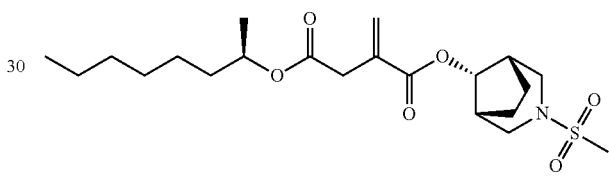

Example 186 was prepared according to General Procedure 2, using (R)-2-methylene-4-(octan-2-yloxy)-4-oxobutanoic acid (Intermediate 8) as itaconic acid monoester and (endo)-3-(methylsulfonyl)-3-azabicyclo[3.2.1]octan-8-ol as R$^2$—OH. LCMS m/z 452.3 (M+Na)$^+$ (ES$^+$). $^1$H NMR (400 MHz, DMSO-d6) δ 6.31 (d, J=0.8 Hz, 1H), 5.85 (d, J=1.2 Hz, 1H), 4.80-4.75 (m, 2H), 3.40 (s, 2H), 3.17 (dd, J=11.6, 3.2 Hz, 2H), 3.10 (dd, J=10.8, 4.4 Hz, 2H), 2.89 (s, 3H), 2.30 (s, 2H), 1.76-1.74 (m, 2H), 1.62-1.57 (m, 2H), 1.48-1.45 (m, 2H), 1.27-1.23 (m, 8H), 1.13 (d, J=6.0 Hz, 3H), 0.85 (t, J=6.4 Hz, 3H).

Example 187—(R)-4-(octan-2-yl) 1-((3-oxo-2,3-dihydroisoxazol-5-yl)methyl) 2-methylenesuccinate

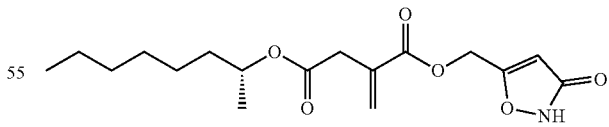

Example 187 was prepared according to General Procedure 2, using (R)-2-methylene-4-(octan-2-yloxy)-4-oxobutanoic acid (Intermediate 8) as itaconic acid monoester as itaconic acid monoester and 5-(hydroxymethyl)isoxazol-3(2H)-one as R$^2$—OH. LCMS m/z 362.2 (M+H)$^+$ (ES$^+$). $^1$H NMR (400 MHz, DMSO-d6) δ 11.42 (br, 1H), 6.25 (s, 1H), 6.06 (s, 1H), 5.89 (d, J=0.8 Hz, 1H), 5.15 (s, 2H), 4.80-4.72 (m, 1H), 3.36 (s, 1H), 3.31 (s, 1H) 1.45 (bs, 2H), 1.22 (t, 8H), 1.11 (d, J=6.4 Hz, 3H), 0.85 (t, J=6.4 Hz, 3H).

5-(hydroxymethyl)isoxazol-3(2H)-one was prepared via reduction of the corresponding methyl ester with LiAlH$_4$ in THF. 1H NMR (400 MHz, DMSO-d6) δ: 5.18 (t, J=6.0 Hz, 1H), 5.15 (s, 1H), 4.16 (d, J=5.6 Hz, 2H), 3.17 (d, J=5.2 Hz, 1H).

Example 188—(R)-4,4,4-trifluoro-3-((2-methylene-4-(((R)-octan-2-yl)oxy)-4-oxobutanoyl)oxy)butanoic Acid and filtered. The filtrate was concentrated under reduced pressure at 40° C., and the residue was purified by flash column chromatography (25 g silica, 0-15% MTBE/petroleum ether) to give 4-((R)-octan-2-yl) 1-((R)-1,1,1-trifluoro-4-((4-methoxybenzyl)oxy)-4-oxobutan-2-yl) 2-methylenesuccinate (300 mg, 0.60 mmol, 52%) as a yellow oil. LCMS (System 2, Method C) m/z 525.3 (M+Na)$^+$ (ES$^+$).

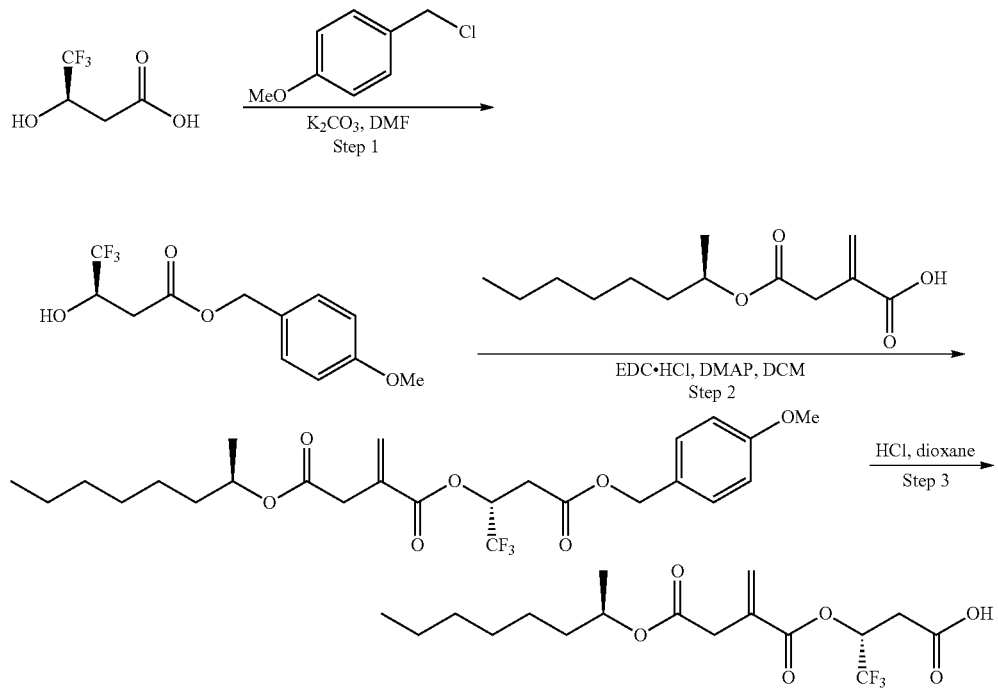

Step 1

To a mixture of (R)-4,4,4-trifluoro-3-hydroxybutanoic acid (300 mg, 1.90 mmol) and K$_2$CO$_3$ (315 mg, 2.28 mmol) in DMF (10 mL) was added PMBCl (327 mg, 2.09 mmol) at 0° C., and the reaction mixture was stirred at room temperature overnight. The reaction mixture was quenched with water and extracted with EtOAc. The organic layers were washed with water and brine, dried over Na2SO4 and filtered. The filtrate was concentrated under reduced pressure at 40° C., and the residue was purified by flash column chromatography (80 g silica, 0-20% MTBE/petroleum ether) to give 4-methoxybenzyl (R)-4,4,4-trifluoro-3-hydroxybutanoate (320 mg, 1.15 mmol, 61%) as a yellow oil. LCMS (System 2, Method B) m/z 301.1 (M+Na)$^+$ (ES$^+$).

Step 2

To a solution of (R)-2-methylene-4-(octan-2-yloxy)-4-oxobutanoic acid (228 mg, 1.15 mmol), 4-methoxybenzyl (R)-4,4,4-trifluoro-3-hydroxybutanoate (320 mg, 1.15 mmol) and DMAP (140 mg, 1.15 mmol) in DCM (3 mL) was added EDC.HCl (331 mg, 1.725 mmol) at 0° C., and the resulting pale yellow mixture was stirred at room temperature for 2 h. The mixture was quenched with saturated aqueous NH$_4$Cl solution (1 mL), separated and the organic phase was extracted with DCM (2×2 mL). The separated organic phases were washed with brine, dried over Na2SO4

Step 3

A solution of 4-((R)-octan-2-yl) 1-((R)-1,1,1-trifluoro-4-((4-methoxybenzyl)oxy)-4-oxobutan-2-yl) 2-methylenesuccinate (300 mg, 0.60 mmol) in HCl solution in 1,4-dioxane (4 M, 3 mL) was stirred at room temperature for 4 h. The mixture was concentrated under reduced pressure at 30° C. and the residue was purified by preparative HPLC (Column: Waters X-Bridge C18 OBD 10 μm 19×250 mm; Flow Rate: 20 mL/min; solvent system: MeCN/(0.05% TFA/water) gradient: 60-95% MeCN; collection wavelength: 214 nm). The fractions were concentrated under reduced pressure at 40° C. to remove MeCN, and the residue was lyophilized to give (R)-4,4,4-trifluoro-3-((2-methylene-4-(((R)-octan-2-yl)oxy)-4-oxobutanoyl)oxy)butanoic acid (134 mg, 0.35 mmol 59%) as a colourless oil. LCMS (System 2, Method B) m/z 405.3 (M+Na)$^+$ (ES$^+$). $^1$H NMR (400 MHz, DMSO-d6) δ: 12.85 (br, 1H), 6.28 (s, 1H), 5.96 (d, J=0.8 Hz, 1H), 5.79-5.73 (m, 1H), 4.80-4.75 (m, 1H), 3.40 (s, 2H), 2.95 (dd, J=22.8, 4.0 Hz, 1H), 2.74 (dd, J=16.8, 9.2 Hz, 1H), 1.48-1.33 (m, 2H), 1.29-1.23 (m, 8H), 1.12 (d, J=6.4 Hz, 3H), 0.85 (t, J=6.4 Hz, 3H).

The following compound was synthesised using a similar procedure but starting from (S)-4,4,4-trifluoro-3-hydroxybutanoic acid:

| Example No. | Example Structure/Name | LCMS/$^1$H NMR data |
|---|---|---|
| 205 | ![structure] (S)-4,4,4-trifluoro-3-((2-methylene-4-(((R)-octan-2-yl)oxy)-4-oxobutanoyl)oxy)butanoic acid | LCMS (System 2, Method B) m/z 405.3 (M + Na)$^+$ (ES$^+$). $^1$H NMR (400 MHz, DMSO-d6) δ: 12.83 (br, 1H), 6.29 (s, 1H), 5.96 (s, 1H), 5.80-5.72 (m, 1H), 4.81-4.73 (m, 1H), 3.40 (s, 2H), 2.95 (dd, J = 22.8, 4.0 Hz, 1H), 2.74 (dd, J = 16.8, 9.2 Hz, 1H), 1.51-1.41 (m, 2H), 1.29-1.23 (m, 8H), 1.12 (d, J = 6.4 Hz, 3H), 0.85 (t, J = 6.4 Hz, 3H). |

Example 189—2-((4-(cyclooctyloxy)-3-hydroxy-2-methylene-4-oxobutanoyl)oxy)acetic acid

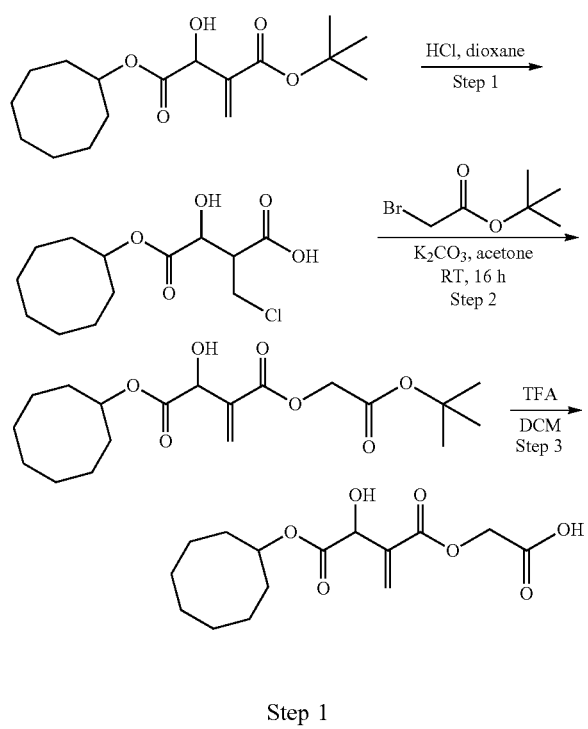

Step 1

A mixture of 1-(tert-butyl) 4-cyclooctyl 3-hydroxy-2-methylenesuccinate (200 mg, 0.64 mmol) and HCl solution in 1,4-dioxane (4 M, 2 mL) in DCM (2 mL) was stirred at room temperature for 4 h. The mixture was concentrated under reduced pressure at 40° C. to give crude 2-(chloromethyl)-4-(cyclooctyloxy)-3-hydroxy-4-oxobutanoic acid (200 mg, 0.68 mmol, >100%) as a pale yellow oil, which was used directly in the next step. LCMS (System 2, Method C) m/z 315.2 (M+Na)$^+$ (ES$^+$).

Step 2

To a solution of the crude 2-(chloromethyl)-4-(cyclooctyloxy)-3-hydroxy-4-oxobutanoic acid (200 mg, 0.68 mmol) in acetone (5 mL) was added potassium carbonate (94 mg, 0.68 mmol) and the reaction mixture was stirred at room temperature for 30 min, then tert-butyl 2-bromoacetate (158 mg, 0.82 mmol) was added, and the resulting mixture was stirred at room temperature overnight. The reaction mixture was filtered, the filtrate was concentrated under reduced pressure at 40° C., and the residue was purified by flash column chromatography (25 g silica, 0-20% MTBE/petroleum ether) to give 1-(2-(tert-butoxy)-2-oxoethyl) 4-cyclooctyl 3-hydroxy-2-methylenesuccinate (200 mg, 0.54 mmol, 79%) as a yellow oil. LCMS (System 2, Method B) m/z 393.3 (M+Na)$^+$ (ES$^+$). $^1$H NMR (400 MHz, CDCl$_3$) δ: 6.47 (s, 1H), 6.00 (s, 1H), 5.30 (m, 1H), 4.85 (d, J=6.0 Hz, 1H), 4.66 (d, J=16.0 Hz, 1H), 4.52 (d, J=16.0 Hz, 1H), 3.56 (d, J=6.0 Hz, 1H), 1.86-1.65 (m, 6H), 1.63-1.52 (m, 8H), 1.42 (s, 9H).

Step 3

A mixture of 1-(2-(tert-butoxy)-2-oxoethyl) 4-cyclooctyl 3-hydroxy-2-methylenesuccinate (200 mg, 0.54 mmol) and TFA (2 mL) in DCM (2 mL) was stirred at room temperature overnight. The mixture was concentrated under reduced pressure at 40° C. and the residue was purified by preparative HPLC (Column: Waters X-Bridge C18 OBD 10 μm 19×250 mm; Flow Rate: 20 mL/min; solvent system: MeCN/(0.1% TFA/water) gradient: 35-95% MeCN; collection wavelength: 214 nm). The fractions were concentrated under reduced pressure at 40° C. to remove MeCN, and the residue was lyophilized to give 2-((4-(cyclooctyloxy)-3-hydroxy-2-methylene-4-oxobutanoyl)oxy)acetic acid (99 mg, 58%) as a colorless oil. LCMS (System 2, Method B) m/z 337.3 (M+Na)$^+$ (ES$^+$). $^1$H NMR (400 MHz, DMSO-d6) δ: 13.10 (br, 1H), 6.30 (s, 1H), 6.07 (m, 1H), 6.03 (s, 1H), 4.85-4.79 (m, 1H), 4.83 (s, 1H), 4.64 (s, 2H), 1.71-1.53 (m, 6H), 1.49-1.36 (m, 8H).

Example 190—2-(3-methylene-5-(4-methylheptan-4-yloxy)-5-oxopent-1-en-2-yloxy)acetic acid

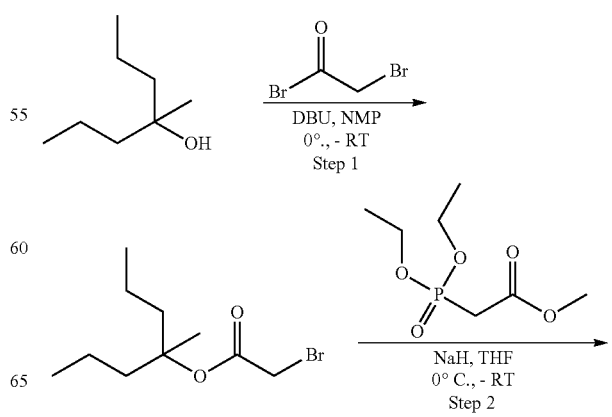

-continued

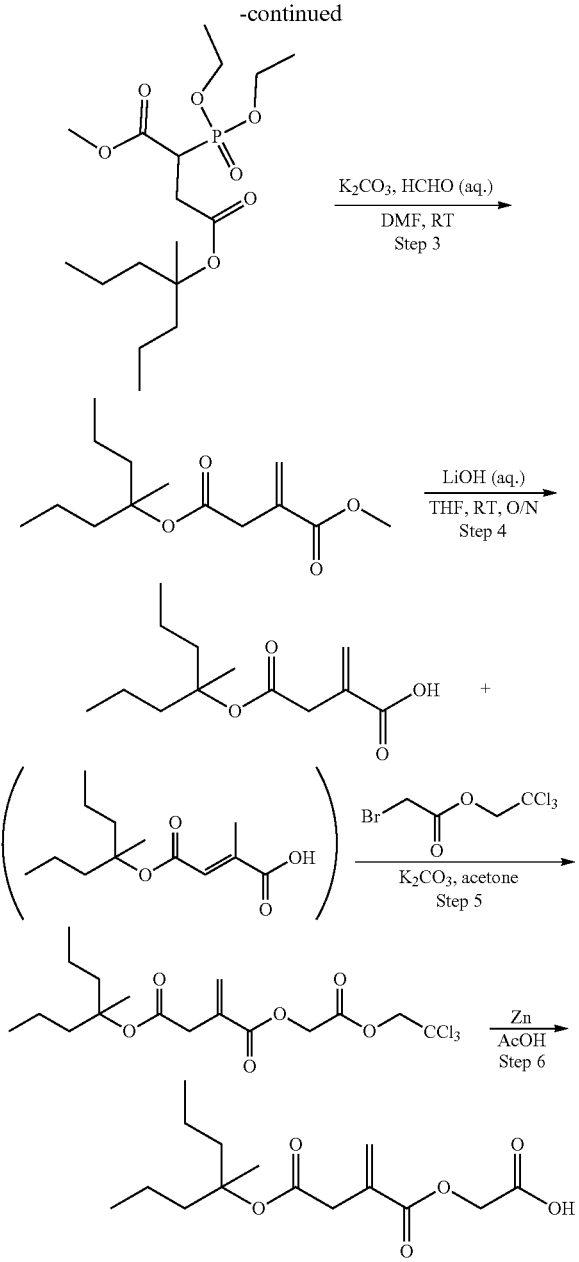

Step 1

To a solution of 4-methylheptan-4-ol (1.50 g, 11.52 mmol) and DBU (2.62 g, 17.28 mmol) in 1-methyl-2-pyrrolidinone (25 mL) was slowly added 2-bromoacetyl bromide (3.49 g, 17.28 mmol) dropwise at 0° C., and the mixture was stirred at room temperature for 1 h. The reaction mixture was diluted with water (20 mL) and MTBE (20 mL), the layers were separated and the aqueous layer was extracted with MTBE (2×10 mL). The combined organic layers were washed with brine, dried over Na$_2$SO$_4$, filtered and concentrated under reduced pressure at 40° C. The residue was purified by flash column chromatography (25 g silica, 0-3% MTBE/petroleum ether) to give 4-methylheptan-4-yl 2-bromoacetate (2.00 g, 7.96 mmol, 69%) as a colourless oil. $^1$H NMR (400 MHz, CDCl3) δ: 3.75 (s, 2H), 1.86-1.78 (m, 2H), 1.74-1.67 (m, 2H), 1.42 (s, 3H), 1.36-1.26 (m, 4H), 0.91 (t, J=7.6 Hz, 6H).

Step 2

To a solution of methyl 2-(diethoxyphosphoryl)acetate (1.52 g, 7.24 mmol) in THF (30 mL) was added NaH suspension in mineral oil (60 wt. %, 290 mg, 7.96 mmol) at 0° C., and the reaction mixture was stirred at 0° C. for 0.5 h. 4-Methylheptan-4-yl 2-bromoacetate (2.00 g, 7.96 mmol) was added and the reaction mixture was stirred at room temperature overnight. The reaction mixture was then quenched with dilute aqueous HCl (0.5 M, 10 mL) to pH=5, and extracted with EtOAc (2×10 mL). The combined organic layers were washed with brine, dried over Na$_2$SO$_4$, filtered and concentrated under reduced pressure at 40° C. The residue was purified by silica gel column chromatography (25 g silica, 1:4-1:2 EtOAc/petroleum ether) to give 1-methyl 4-(4-methylheptan-4-yl) 2-(diethoxyphosphoryl) succinate (2.30 g, 6.0 mmol, 83%) as a light yellow oil. LCMS (System 2, Method C) m/z 403.3 (M+Na)$^+$ (ES$^+$).

Step 3

To a solution of 1-methyl 4-(4-methylheptan-4-yl) 2-(diethoxyphosphoryl)succinate (1.30 g, 3.42 mmmol) and potassium carbonate (945 mg, 6.84 mmol) in DMF (15 mL) was added formaldehyde solution in water (37 wt. %, 5.5 mL, 68.40 mmol) at room temperature, and the reaction mixture was stirred at room temperature for 4 h. The reaction mixture was diluted with H$_2$O (30 mL) and extracted with MTBE (2×20 mL). The combined organic layers were washed with H$_2$O (2×15 mL) and brine, dried over Na$_2$SO$_4$, filtered and concentrated under reduced pressure at 30° C. The residue was purified by flash column chromatography (25 g silica, 0-10% MTBE/petroleum ether) to give 1-methyl 4-(4-methylheptan-4-yl) 2-methylenesuccinate (600 mg, 2.34 mmol, 68%) as a colourless oil. LCMS (System 2, Method C) m/z 279.4 (M+Na)$^+$ (ES$^+$).

Step 4

To a solution of 1-methyl 4-(4-methylheptan-4-yl) 2-methylenesuccinate (600 mg, 2.34 mmol) in THF (10 mL) was added LiOH solution in water (2 M, 4.7 mL, 9.36 mmol), and the reaction mixture was stirred at room temperature overnight. The reaction mixture was acidified with dilute aqueous HCl (0.5 M) to pH=3, and extracted with EtOAc (2×10 mL). The EtOAc layer was washed with brine, dried over Na$_2$SO$_4$, filtered and concentrated under reduced pressure at 40° C. to give a 5:1 mixture of 2-methylene-4-(4-methylheptan-4-yloxy)-4-oxobutanoic acid and 2-methyl-4-(4-methylheptan-4-yloxy)-4-oxobut-2-enoic acid (500 mg, 2.06 mmol, 88%) as a pale yellow oil, which was used directly in the next step. LCMS (System 2, Method B) m/z 265.3 (M+Na)$^+$ (ES$^+$).

Step 5

To a solution of the 5:1 mixture of 2-methylene-4-(4-methylheptan-4-yloxy)-4-oxobutanoic acid and 2-methyl-4-(4-methylheptan-4-yloxy)-4-oxobut-2-enoic acid (500 mg, 2.06 mmol), and potassium carbonate (313 mg, 2.26 mmol) in acetone (10 mL) was added 2,2,2-trichloroethyl 2-bromoacetate (558 mg, 2.06 mmol), and the reaction mixture was stirred at room temperature overnight. The reaction mixture was filtered and the filtrate was concentrated under reduced pressure at 30° C. The residue was purified by flash column chromatography (25 g silica, 0-10% MTBE/petroleum ether) to give 4-(4-methylheptan-4-yl) 1-(2-oxo-2-(2,2,2-trichloroethoxy)ethyl) 2-methylenesuccinate (430 mg, 1.00 mmol, 48%) as a pale yellow oil. LCMS (System 2, Method B) m/z 455.0 (M+Na)$^+$ (ES$^+$).

Step 6

To a solution of 4-(4-methylheptan-4-yl) 1-(2-oxo-2-(2,2,2-trichloroethoxy)ethyl) 2-methylenesuccinate (430 mg, 1.00 mmol) in AcOH (5 mL) was added zinc powder (325 mg, 4.98 mmol), and the reaction mixture was stirred at room temperature overnight. The reaction mixture was filtered and the filtrate was concentrated under reduced pressure at 30° C. The residue was purified by preparative HPLC (Column: Waters X-Bridge C18 OBD 10 μm 19×250 mm; Flow Rate: 20 mL/min; solvent system: MeCN/(0.1% TFA/water) gradient: 50-95% MeCN; collection wavelength: 214 nm). The fractions were concentrated under reduced pressure at 30° C. to remove MeCN, and the residue was lyophilized to give 2-(3-methylene-5-(4-methylheptan-4-yloxy)-5-oxopent-1-en-2-yloxy)acetic acid (72 mg, 0.24 mmol, 24%) as a colourless oil. LCMS (System 2, Method B) m/z 323.2 (M+Na)$^+$ (ES$^+$). $^1$H NMR (400 MHz, DMSO-d6) δ: 13.09 (br, 1H), 6.23 (d, J=1.2 Hz, 1H), 5.86 (d, J=0.4 Hz, 1H), 4.61 (s, 2H), 3.28 (s, 2H), 1.76-1.68 (m, 2H), 1.64-1.56 (m, 2H), 1.30 (s, 3H), 1.28-1.18 (m, 4H), 0.85 (d, J=7.2 Hz, 6H).

The following compounds were made using a similar procedure:

| Example No. | Alcohol used in step 5/ Example Structure/Name | LCMS/$^1$H NMR data |
|---|---|---|
| 191 | 1-cyclohexylcyclobutan-1-ol<br><br>2-((4-(1-cyclohexylcyclobutoxy)-2-methylene-4-oxobutanoyl)oxy)acetic acid | LCMS (System 2, Method B) m/z 347.2 (M + Na)$^+$ (ES$^+$).<br>$^1$H NMR (400 MHz, DMSO-d6) δ: 13.09 (br, 1H), 6.26 (d, J = 1.2 Hz, 1H), 5.90 (d, J = 0.8 Hz, 1H), 4.63 (s, 2H), 3.23 (s, 2H), 2.28-2.15 (m, 4H), 1.88-1.80 (m, 1H), 1.79-1.68 (m, 6H), 1.63-1.61 (m, 1H), 1.54-1.45 (m, 1H), 1.20-1.06 (m, 2H), 1.02-0.92 (m, 2H). |
| 192 | 2-methyloctan-2-ol<br><br>2-((2-methylene-4-((2-methyloctan-2-yl)oxy)-4-oxobutanoyl)oxy)acetic acid | LCMS (System 2, Method B) m/z 337.3 (M + Na)$^+$ (ES$^+$).<br>$^1$H NMR (400 MHz, DMSO-d6) δ: 13.11 (br, 1H), 6.24 (d, J = 0.8 Hz, 1H), 5.87 (d, J = 0.8 Hz, 1H), 4.63 (s, 2H), 3.35 (s, 2H), 1.65-1.63 (m, 2H), 1.34 (s, 6H), 1.27-1.23 (m, 8H), 0.86 (t, J = 7.2 Hz, 3H). |
| 193 | 2-methylheptan-2-ol<br><br>2-((2-methylene-4-((2-methylheptan-2-yl)oxy)-4-oxobutanoyl)oxy)acetic acid | LCMS (System 2, Method B) m/z 323.2 (M + Na)$^+$ (ES$^+$).<br>$^1$H NMR (400 MHz, DMSO-d6) δ: 13.07 (br, 1H), 6.24 (d, J = 1.2 Hz, 1H), 5.87 (d, J = 0.8 Hz, 1H), 4.63 (s, 2H), 3.27 (s, 2H), 1.67-1.63 (m, 2H), 1.34 (s, 6H), 1.29-1.18 (m, 6H), 0.85 (d, J = 6.8 Hz, 3H). |
| 194 | 1-pentylcyclobutan-1-ol<br><br>2-((2-methylene-4-oxo-4-(1-pentylcyclobutoxy)butanoyl)oxy)acetic acid | LCMS (System 2, Method B) m/z 335.2 (M + Na)$^+$ (ES$^+$).<br>$^1$H NMR (400 MHz, DMSO-d6) δ: 13.09 (br, 1H), 6.27 (s, 1H), 5.90 (s, 1H), 4.64 (s, 2H), 3.31 (s, 2H), 2.19-2.13 (m, 2H), 2.09-2.05 (m, 2H), 1.82-1.79 (m, 2H), 1.76-1.72 (m, 1H), 1.63-1.53 (m, 1H), 1.30-1.22 (m, 6H), 0.86 (t, J = 7.2 Hz, 3H). |
| 195 | 2-methylspiro[3.5]nonan-2-ol<br><br>2-((2-methylene-4-((2-methylspiro[3.5]nonan-2-yl)oxy)-4-oxobutanoyl)oxy)acetic acid | LCMS (System 2, Method B) m/z 347.2 (M + Na)$^+$ (ES$^+$).<br>$^1$H NMR (400 MHz, DMSO-d6) δ: 13.08 (br, 1H), 6.26 (s, 1H), 5.90 (s, 1H), 4.64 (s, 2H), 3.34 (s, 2H), 1.95 (q, J = 12.8 Hz, 4H), 1.46 (s, 3H), 1.40 (m, 4H), 1.31-1.30 (m, 6H). |

| Example No. | Alcohol used in step 5/ Example Structure/Name | LCMS/¹H NMR data |
|---|---|---|
| 206 | 1-pentylcyclopropan-1-ol<br>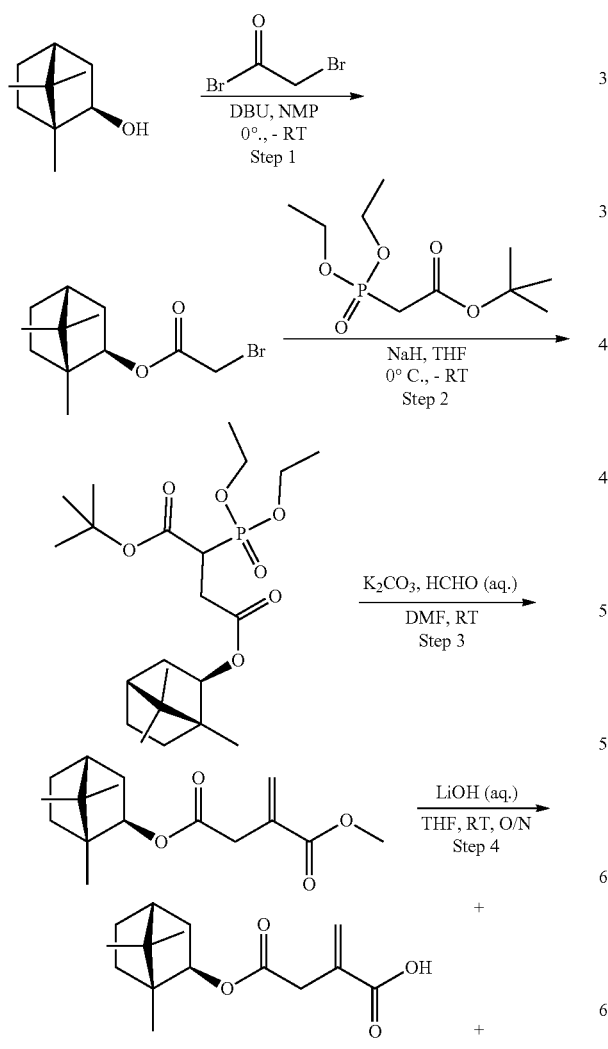<br>2-((2-methylene-4-oxo-4-(1-pentylcyclopropoxy)butanoyl)oxy)acetic acid | LCMS (System 2, Method B)<br>m/z 299.2 (M + H)⁺ (ES⁺).<br>¹H NMR (400 MHz, DMSO-d6) δ: 13.07 (br, 1H), 6.27 (s, 1H), 5.90 (s, 1H), 4.62 (s, 2H), 3.33 (s, 2H), 1.68-1.64 (m, 2H), 1.37-1.24 (m, 6H), 0.86 (t, J = 6.8 Hz, 3H), 0.73 (t, J = 5.2 Hz, 2H), 0.61 (t, J = 5.2 Hz, 2H). |

2-Methylspiro[3.5]nonan-2-ol was made by MeMgBr addition to the corresponding commercially available ketone in THF. ¹H NMR (400 MHz, CDCl₃) δ: 1.92 (d, J=14.6 Hz, 2H), 1.89 (d, J=14.4 Hz, 2H), 1.71 (m, 1H), 1.53-1.50 (m, 2H), 1.43-1.34 (m, 8H), 1.39 (s, 3H).

Example 196—2-((2-methylene-4-oxo-4-(((exo)-1,7,7-trimethylbicyclo[2.2.1]heptan-2-yl)oxy)butanoyl)oxy)acetic acid

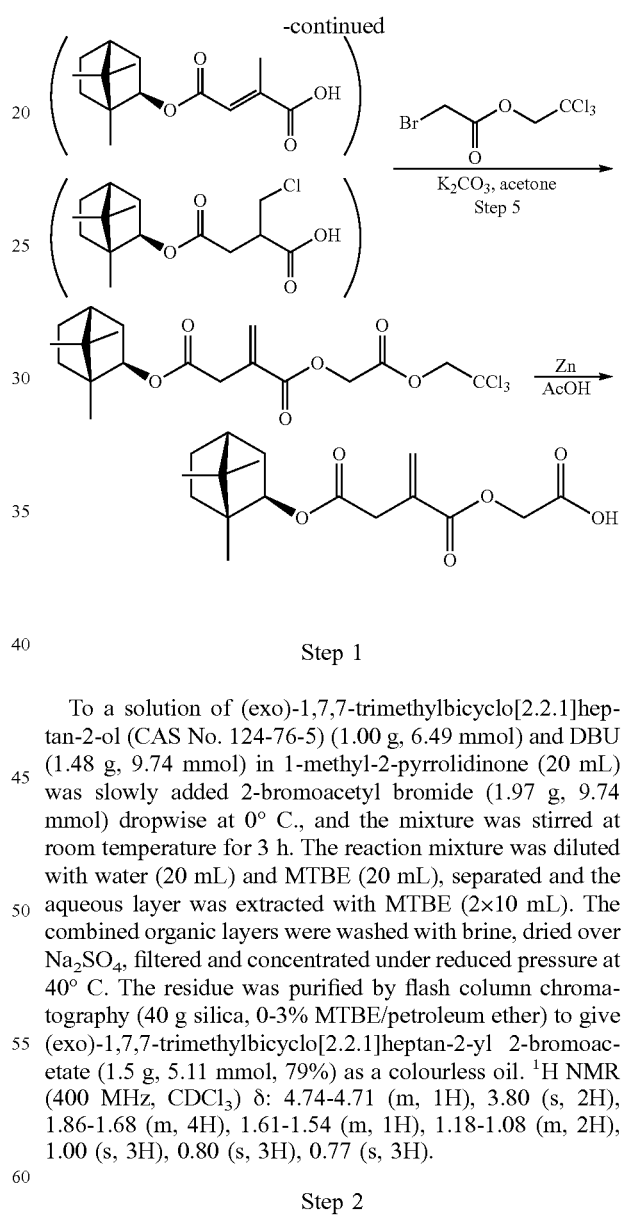

Step 1

To a solution of (exo)-1,7,7-trimethylbicyclo[2.2.1]heptan-2-ol (CAS No. 124-76-5) (1.00 g, 6.49 mmol) and DBU (1.48 g, 9.74 mmol) in 1-methyl-2-pyrrolidinone (20 mL) was slowly added 2-bromoacetyl bromide (1.97 g, 9.74 mmol) dropwise at 0° C., and the mixture was stirred at room temperature for 3 h. The reaction mixture was diluted with water (20 mL) and MTBE (20 mL), separated and the aqueous layer was extracted with MTBE (2×10 mL). The combined organic layers were washed with brine, dried over Na₂SO₄, filtered and concentrated under reduced pressure at 40° C. The residue was purified by flash column chromatography (40 g silica, 0-3% MTBE/petroleum ether) to give (exo)-1,7,7-trimethylbicyclo[2.2.1]heptan-2-yl 2-bromoacetate (1.5 g, 5.11 mmol, 79%) as a colourless oil. ¹H NMR (400 MHz, CDCl₃) δ: 4.74-4.71 (m, 1H), 3.80 (s, 2H), 1.86-1.68 (m, 4H), 1.61-1.54 (m, 1H), 1.18-1.08 (m, 2H), 1.00 (s, 3H), 0.80 (s, 3H), 0.77 (s, 3H).

Step 2

To a solution of tert-butyl 2-(diethoxyphosphoryl)acetate (1.29 g, 5.11 mmol) in THF (20 mL) was added NaH suspension in mineral oil (60 wt. %, 225 mg, 5.62 mmol) at 0° C., and the reaction mixture was stirred at 0° C. for 0.5 h, then (exo)-1,7,7-trimethylbicyclo[2.2.1]heptan-2-yl 2-bromoacetate (1.50 g, 5.11 mmol) was added. The reaction mixture was stirred at room temperature overnight, then quenched with dilute aqueous HCl (0.5 M) to pH=5 and extracted with EtOAc (2×10 mL). The combined organic layers were washed with brine, dried over Na$_2$SO$_4$, filtered and concentrated under reduced pressure at 40° C. The residue was purified by flash column chromatography (40 g silica, 1:4-1:2 EtOAc/petroleum ether) to give 1-(tert-butyl) 4-((exo)-1,7,7-trimethylbicyclo[2.2.1]heptan-2-yl) 2-(diethoxyphosphoryl)succinate (1.60 g, 3.59 mmol, 70%) as a colourless oil. LCMS (System 2, Method C) m/z 469.4 (M+Na)$^+$ (ES$^+$).

Step 3

To a mixture of 1-(tert-butyl) 4-((exo)-1,7,7-trimethylbicyclo[2.2.1]heptan-2-yl) 2-(diethoxyphosphoryl)succinate (1.60 g, 3.59 mmol) and potassium carbonate (990 mg, 7.17 mmol) in DMF (10 mL) was added formaldehyde solution in water (37 wt. %, 2.9 mL, 35.9 mmol) at room temperature, and the reaction mixture was stirred at room temperature for 4 h. The reaction mixture was diluted with H$_2$O (15 mL) and extracted with MTBE (2×20 mL). The combined organic layers were washed with H$_2$O (2×10 mL) and brine, dried over Na$_2$SO$_4$, filtered and concentrated under reduced pressure at 30° C. The residue was purified by flash column chromatography (25 g silica, 0-10% MTBE/petroleum ether) to give 1-(tert-butyl) 4-((exo)-1,7,7-trimethylbicyclo[2.2.1]heptan-2-yl) 2-methylenesuccinate (850 mg, 2.64 mmol, 73%) as a colourless oil. LCMS (System 2, Method C) m/z 345.4 (M+Na)$^+$ (ES$^+$).

Step 4

To a solution of 1-(tert-butyl) 4-((exo)-1,7,7-trimethylbicyclo[2.2.1]heptan-2-yl) 2-methylenesuccinate (400 mg, 1.24 mmol) in DCM (8 mL) was added HCl solution in 1,4-dioxane (4 M, 4.0 mL), and the reaction mixture was stirred at room temperature overnight. The reaction mixture was concentrated under reduced pressure at 40° C. to give a crude 33:20:47 mixture of 2-methylene-4-oxo-4-(((exo)-1,7,7-trimethylbicyclo[2.2.1]heptan-2-yl)oxy)butanoic acid (LCMS (System 2, Method C) m/z 289.4 (M+Na)$^+$ (ES$^+$)), 2-methyl-4-oxo-4-(((exo)-1,7,7-trimethylbicyclo[2.2.1]heptan-2-yl)oxy)but-2-enoic acid (LCMS (System 2, Method C) m/z 289.4 (M+Na)$^+$ (ES$^+$)) and 2-(chloromethyl)-4-oxo-4-(((exo)-1,7,7-trimethylbicyclo[2.2.1]heptan-2-yl)oxy)butanoic acid (LCMS (System 2, Method C) m/z 325.2 (M+Na)$^+$ (ES$^+$)) (400 mg) as a pale yellow oil, which was used directly in the next step.

Step 5

To a crude 33:20:47 mixture of 2-methylene-4-oxo-4-(((exo)-1,7,7-trimethylbicyclo[2.2.1]heptan-2-yl)oxy) butanoic acid, (2-methyl-4-oxo-4-(((exo)-1,7,7-trimethylbicyclo[2.2.1]heptan-2-yl)oxy)but-2-enoic acid and 2-(chloromethyl)-4-oxo-4-(((exo)-1,7,7-trimethylbicyclo[2.2.1] heptan-2-yl)oxy) butanoic acid (400 mg) and potassium carbonate (342 mg, 2.48 mmol) in acetone (10 mL) was added tert-butyl 2-bromoacetate (331 mg, 1.24 mmol), and the reaction mixture was stirred at room temperature overnight. The mixture was then filtered, and the filtrate was concentrated under reduced pressure at 30° C. The residue was purified by flash column chromatography (25 g silica, 0-10% MTBE/petroleum ether) to give 1-(2-oxo-2-(2,2,2-trichloroethoxy)ethyl) 4-((exo)-1,7,7-trimethylbicyclo [2.2.1]heptan-2-yl) 2-methylenesuccinate (450 mg, 0.99 mmol, 80% over two steps) as a pale yellow oil. LCMS (System 2, Method C) m/z 477.0 (M+Na)$^+$ (ES$^+$).

Step 6

To a solution of 1-(2-oxo-2-(2,2,2-trichloroethoxy)ethyl) 4-((exo)-1,7,7-trimethylbicyclo[2.2.1]heptan-2-yl) 2-methylenesuccinate (450 mg, 0.99 mmol) in AcOH (5 mL) was added zinc powder (322 mg, 4.96 mmol), and the reaction mixture was stirred at room temperature overnight. The reaction mixture was filtered and the filtrate was concentrated under reduced pressure at 30° C. The residue was purified by preparative HPLC (Column: Waters X-Bridge C18 OBD 10 μm 19×250 mm; Flow Rate: 20 mL/min; solvent system: MeCN/(0.05% TFA/water) gradient: 40-95% MeCN; collection wavelength: 214 nm). The fractions were concentrated under reduced pressure at 30° C. to remove MeCN, and the residue was lyophilized to give 2-((2-methylene-4-oxo-4-(((exo)-1,7,7-trimethylbicyclo [2.2.1]heptan-2-yl) oxy)butanoyl)oxy)acetic acid (77 mg, 0.23 mmol, 24%) as a colourless oil. LCMS (System 2, Method B) m/z 347.2 (M+Na)$^+$ (ES$^+$). $^1$H NMR (400 MHz, DMSO-d6) δ: 13.06 (br, 1H), 6.27 (d, J=0.8 Hz, 1H), 5.92 (d, J=0.8 Hz, 1H), 4.61 (s, 2H), 4.54 (dd, J=8.0, 3.6 Hz, 1H), 3.35 (s, 2H), 1.74-1.60 (m, 4H), 1.53-1.47 (m, 1H), 1.13-1.01 (m, 2H), 0.88 (s, 3H), 0.79 (s, 3H), 0.75 (s, 3H).

The following compound was made using a similar procedure:

| Example No. | Alcohol/Example Structure/Name | LCMS/$^1$H NMR data |
| --- | --- | --- |
| 197 | 2,2,6,6-tetramethylcyclohexan-1-ol<br><br>2-((2-methylene-4-oxo-4-((2,2,6,6-tetramethylcyclohexyl)oxy)butanoyl)oxy)acetic acid | LCMS (System 2, Method B) m/z 349.3 (M + Na)$^+$ (ES$^+$).<br>$^1$H NMR (400 MHz, DMSO-d6) δ: 13.09 (br, 1H), 6.31 (d, J = 1.2 Hz, 1H), 5.98 (s, 1H), 4.62 (s, 2H), 4.40 (s, 1H), 3.46 (s, 2H), 1.56-1.44 (1H, m), 1.45-1.37 (2H, m), 1.37-1.29 (m, 1H), 1.27-1.16 (m, 2H), 0.86 (s, 6H), 0.75 (s, 6H). |

2,2,6,6-Tetramethyl cyclohexan-1-ol was made by reduction of the corresponding commercially available ketone with NaBH$_4$ in MeOH. $^1$H NMR (400 MHz, DMSO-d6) b: 4.40 (br, 1H), 2.83 (5, 1H), 1.56-1.48 (11H, in), 1.47-1.38 (i, 2H), 1.36-1.28 (in, H), 1.22-1.11 (d, 2H), 0.93 (s, 6H), 0.88 (3, 6H).

The following examples were prepared according to the procedure of Example 114, but using the alcohols described below instead of 3-ethoxypropan-1-ol:

1-(3,5-dichlorophenyl)ethan-1-ol (Isomer 1) was prepared by the following method: Racemic 1-(3,5-dichlorophenyl)ethan-1-ol was resolved using chiral SFC (Column:

| Example No. | Alcohol/Example Structure/Name | LCMS/$^1$H NMR data |
|---|---|---|
| 198 | 1-(3,5-dichlorophenyl)ethan-1-ol (Isomer 1)<br>2-((4-(1-(3,5-dichlorophenyl)ethoxy)-2-methylene-4-oxobutanoyl)oxy)acetic acid (Isomer 1) | LCMS (System 2, Method B) m/z 383.0 (M + Na)$^+$ (ES$^+$).<br>$^1$H NMR (400 MHz, DMSO-d6) δ 13.12 (br, 1H), 7.54 (t, J = 2.0 Hz, 1H), 7.41 (d, J = 1.6 Hz, 2H), 6.31 (d, J = 0.8 Hz, 1H), 5.96 (d, J = 0.8 Hz, 1H), 5.77 (q, J = 6.4 Hz, 1H), 4.63 (s, 2H), 3.47 (s, 2H), 1.44 (d, J = 6.4 Hz, 3H). |
| 199 | 1-(3,5-dichlorophenyl)ethan-1-ol (Isomer 2)<br>2-((4-(1-(3,5-dichlorophenyl)ethoxy)-2-methylene-4-oxobutanoyl)oxy)acetic acid (Isomer 2) | LCMS (System 2, Method B) m/z 383.0 (M + Na)$^+$ (ES$^+$).<br>$^1$H NMR (400 MHz, DMSO-d6) δ 13.12 (br, 1H), 7.54 (t, J = 2.0 Hz, 1H), 7.41 (d, J = 1.6 Hz, 2H), 6.31 (d, J = 0.8 Hz, 1H), 5.96 (d, J = 0.8 Hz, 1H), 5.77 (q, J = 6.4 Hz, 1H), 4.63 (s, 2H), 3.47 (s, 2H), 1.44 (d, J = 6.4 Hz, 3H). |
| 200 | (R)-1-(4-(trifluoromethyl)phenyl)ethan-1-ol)<br>(R)-2-((2-methylene-4-oxo-4-(1-(4-(trifluoromethyl)phenyl)ethoxy)butanoyl)oxy) acetic acid) | LCMS (System 2, Method B) m/z 383.0 (M + Na)$^+$ (ES$^+$).<br>$^1$H NMR (400 MHz, DMSO-d6) δ 13.13 (br, 1H), 7.73 (d, J = 8.4 Hz, 2H), 7.57 (d, J = 8.4 Hz, 2H), 6.30 (d, J = 0.8 Hz, 1H), 5.94 (d, J = 0.8 Hz, 1H), 5.86 (q, J = 6.8 Hz, 1H), 4.62 (s, 2H), 3.46 (s, 2H), 1.47 (d, J = 6.4 Hz, 3H). |
| 201 | (S)-1-(4-(trifluoromethyl)phenyl)ethan-1-ol)<br>(S)-2-((2-methylene-4-oxo-4-(1-(4-(trifluoromethyl)phenyl)ethoxy)butanoyl)oxy) acetic acid) | LCMS (System 2, Method B) m/z 383.0 (M + Na)$^+$ (ES$^+$).<br>$^1$H NMR (400 MHz, DMSO-d6) δ 13.06 (br, 1H), 7.73 (d, J = 8.4 Hz, 2H), 7.57 (d, J = 8.4 Hz, 2H), 6.30 (d, J = 0.8 Hz, 1H), 5.94 (d, J = 0.8 Hz, 1H), 5.86 (q, J = 6.8 Hz, 1H), 4.62 (s, 2H), 3.46 (s, 2H), 1.47 (d, J = 6.4 Hz, 3H). |
| 203 | (S)-1-cyclohexylethan-1-ol<br>(S)-2-((4-(1-cyclohexylethoxy)-2-methylene-4-oxobutanoyl)oxy)acetic acid | LCMS (System 2, Method B) m/z 321.3 (M + Na)$^+$ (ES$^+$).<br>$^1$H NMR (400 MHz, DMSO-d6) δ: 13.14 (br, 1H), 6.28 (s, 1H), 5.92 (s, 1H), 4.62 (s, 2H), 4.66-4.58 (m, 1H), 3.26 (s, 2H), 1.69-1.67 (m, 3H), 1.62-1.53 (m, 2H), 1.42-1.35 (m, 1H), 1.25-1.08 (m, 3H), 1.15 (d, J = 6.4 Hz, 3H), 1.04-0.82 (m, 2H). |

CHIRALPAK AY-3 4.6×100 mm; Flow Rate: 2 mL/min; solvent system: 10% IPA/CO$_2$; collection wavelength: 214 nm). Isomer 1 was the first eluting peak at 1.34 min.

1-(3,5-dichlorophenyl)ethan-1-ol (Isomer 2) was prepared by the following method: Racemic 1-(3,5-dichlorophenyl)ethan-1-ol was resolved using chiral SFC (Column: CHIRALPAK AY-3 4.6×100 mm; Flow Rate: 2 mL/min; solvent system: 10% IPA/CO$_2$; collection wavelength: 214 nm). Isomer 2 was the second eluting peak at 1.53 min.

Example 202—2-((4-(1-cyclohexylcyclopropoxy)-2-methylene-4-oxobutanoyl)oxy)acetic acid

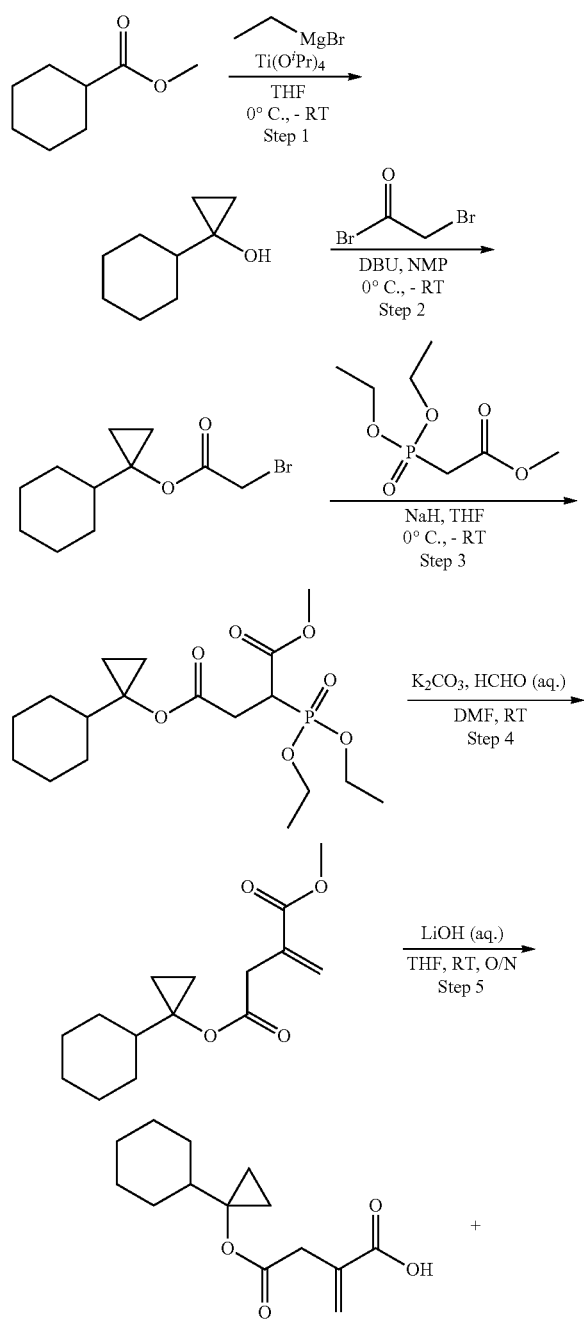

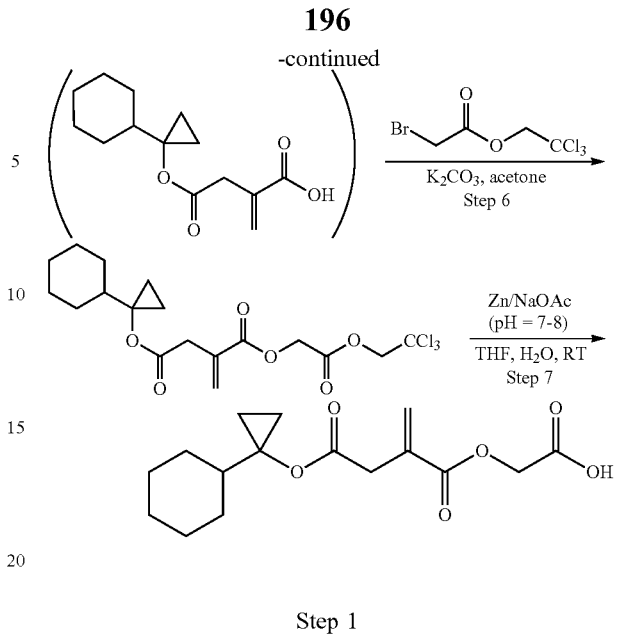

Step 1

To a solution of methyl cyclohexanecarboxylate (4.26 g, 30 mmol) and titanium tetraisopropoxide (11.93 g, 42 mmol) in THF (60 mL) at 0° C. was slowly added a solution of ethyl magnesium bromide in diethyl ether (3M, 30 mL, 90 mmol), and the mixture was stirred at room temperature for 16 h. The reaction mixture was quenched with water (60 mL), and stirred for 1 h until a gray precipitate was formed, and then filtered. The filtrate was extracted with MTBE (3×40 mL), and the combined organic layers were washed with brine, dried over Na$_2$SO$_4$, filtered and concentrated under reduced pressure at 40° C. The residue was purified by flash column chromatography (0-3% EtOAc/petroleum ether) give 1-cyclohexylcyclopropan-1-ol (2.50 g, 17.8 mmol, 60%) as a colourless oil. $^1$H NMR (400 MHz, CDCl$_3$) δ: 1.80-1.75 (m, 4H), 1.69-1.66 (m, 1H), 1.26-1.17 (m, 5H), 0.94-0.92 (m, 1H), 0.70-0.67 (m, 2H), 0.45-0.42 (m, 2H). One exchangeable proton not observed.

Step 2

To a solution of 1-cyclohexylcyclopropan-1-ol (1.50 g, 10.7 mmol) and DBU (2.43 g, 16.05 mmol) in 1-methyl-2-pyrrolidinone (20 mL) was slowly added 2-bromoacetyl bromide (3.24 g, 16.05 mmol) dropwise at 0° C., and the resulting mixture was stirred at room temperature for 1 h. The reaction mixture was diluted with water (20 mL) and MTBE (20 mL), separated and the aqueous layer was extracted with MTBE (2×10 mL). The combined organic layers were washed with brine, dried over Na$_2$SO$_4$, filtered and concentrated under reduced pressure at 40° C. The residue was purified by flash column chromatography (25 g silica, 0-3% MTBE/petroleum ether) to give 1-cyclohexylcyclopropyl 2-bromoacetate (1.70 g, 6.51 mmol, 61%) as a colourless oil. $^1$H NMR (400 MHz, CDCl$_3$) δ: 3.74 (s, 2H), 1.80-1.73 (m, 5H), 1.67-1.64 (m, 1H), 1.24-1.08 (m, 3H), 0.95-0.79 (m, 2H), 0.70-0.67 (m, 4H).

Step 3

To a solution of methyl 2-(diethoxyphosphoryl)acetate (1.36 g, 6.51 mmol) in THF (30 mL) was added NaH suspension in mineral oil (60 wt. %, 261 mg, 6.51 mmol) at 0° C., and the reaction mixture was stirred at 0° C. for 0.5 h. Then 1-cyclohexylcyclopropyl 2-bromoacetate (1.70 g, 6.51 mmol) was added, and the reaction mixture was stirred at room temperature overnight. The reaction mixture was quenched with dilute aqueous HCl (0.5 M) to pH=5, and extracted with EtOAc (2×10 mL). The combined organic layers were washed with brine, dried over $Na_2SO_4$, filtered and concentrated under reduced pressure at 40° C. to give 4-(1-cyclohexylcyclopropyl) 1-methyl 2-(diethoxyphosphoryl)succinate (2.70 g, 6.92 mmol, >100%) as a colourless oil. The crude product was used directly in next step. LCMS (System 2, Method B) m/z 413.2 (M+Na)$^+$ (ES$^+$).

Step 4

To a mixture of 4-(1-cyclohexylcyclopropyl) 1-methyl 2-(diethoxyphosphoryl)succinate (2.70 g, 6.92 mmmol) and potassium carbonate (1.83 g, 13.8 mmol) in THF (20 mL) was added formaldehyde solution in water (37 wt. %, 11.2 mL, 138 mmol) at room temperature, and the reaction mixture was stirred at room temperature for 4 h. The reaction mixture was diluted with $H_2O$ (20 mL) and extracted with MTBE (2×20 mL). The combined organic layers were washed with $H_2O$ (2×15 mL) and brine, dried over $Na_2SO_4$, filtered and concentrated under reduced pressure at 30° C. The residue was purified by flash column chromatography (25 g silica, 0-10% MTBE/petroleum ether) to give 4-(1-cyclohexylcyclopropyl) 1-methyl 2-methylenesuccinate (1.20 g, 4.51 mmol, 65%) as a colourless oil. LCMS (System 2, Method B) m/z 267.3 (M+H)$^+$ (ES$^+$).

Step 5

To a solution of 4-(1-cyclohexylcyclopropyl) 1-methyl 2-methylenesuccinate (600 mg, 2.25 mmol) in THF (8 mL) was added LiOH solution in water (2 M, 3.4 mL, 6.75 mmol), and the reaction mixture was stirred at room temperature for 7 h (about 24% of starting material remained). The reaction mixture was acidified with dilute aqueous HCl (0.5 M) to pH=3 and extracted with EtOAc (2×10 mL). The EtOAc layers were washed with brine, dried over $Na_2SO_4$, filtered and concentrated under reduced pressure at 40° C. to give a 2:1 mixture of 4-(1-cyclohexylcyclopropoxy)-2-methylene-4-oxobutanoic acid and 4-(1-cyclohexylcyclopropoxy)-2-methyl-4-oxobut-2-enoic acid (500 mg, 1.98 mmol, 88%) as a pale yellow oil, which was used directly in the next step. LCMS (System 2, Method C) m/z 253.4 (M+H)$^+$ (ES$^+$).

Step 6

To a solution of a 2:1 mixture of 4-(1-cyclohexylcyclopropoxy)-2-methylene-4-oxobutanoic acid and 4-(1-cyclohexylcyclopropoxy)-2-methyl-4-oxobut-2-enoic acid (500 mg, 1.98 mmol), and potassium carbonate (328 mg, 2.38 mmol) in acetone (10 mL) was added 2,2,2-trichloroethyl 2-bromoacetate (530 mg, 1.98 mmol), and the reaction mixture was stirred at room temperature overnight. The reaction mixture was filtered and the filtrate was concentrated under reduced pressure at 30° C. The residue was purified by flash column chromatography (25 g silica, 0-10% MTBE/petroleum ether) to give 4-(1-cyclohexylcyclopropyl) 1-(2-oxo-2-(2,2,2-trichloroethoxy)ethyl) 2-methylenesuccinate (300 mg, 0.68 mmol, 34%) as a pale yellow oil. LCMS (System 2, Method B) m/z 463.1 (M+Na)$^+$ (ES$^+$).

Step 7

To a solution of 4-(1-cyclohexylcyclopropyl) 1-(2-oxo-2-(2,2,2-trichloroethoxy)ethyl) 2-methylenesuccinate (100 mg, 0.22 mmol) in THF (2 mL) and water (0.5 mL) was added zinc powder (71 mg, 1.10 mmol) and sodium acetate (90 mg, 1.10 mmol), and the reaction mixture was stirred at room temperature overnight. The reaction mixture was filtered and the filtrate was concentrated under reduced pressure at 30° C. The residue was purified by preparative HPLC (Column: Waters X-Bridge C18 OBD 10 μm 19×250 mm; Flow Rate: 20 mL/min; solvent system: MeCN/(0.05% TFA/water) gradient: 30-95% MeCN; collection wavelength: 214 nm). The fractions were concentrated under reduced pressure at 30° C. to remove MeCN, and the residue was lyophilized to give 2-((4-(1-cyclohexylcyclopropoxy)-2-methylene-4-oxobutanoyl)oxy)acetic acid (6 mg, 0.019 mmol, 9%) as a colourless oil. LCMS (System 2, Method B) m/z 311.2 (M+H)$^+$ (ES$^+$). $^1$H NMR (400 MHz, CDCl$_3$) δ: 6.43 (s, 1H), 5.80 (s, 1H), 4.74 (s, 2H), 3.31 (s, 2H), 1.79-1.71 (m, 5H), 1.66-1.63 (m, 1H), 1.25-1.15 (m, 2H), 1.11-1.05 (m, 1H), 0.92-0.83 (m, 2H), 0.74 (d, J=2.0 Hz, 4H). One exchangeable proton not observed.

Example 204—2-((2-methylene-4-oxo-4-((2,2,4,4-tetramethylpentan-3-yl)oxy)butanoyl) oxy)acetic Acid

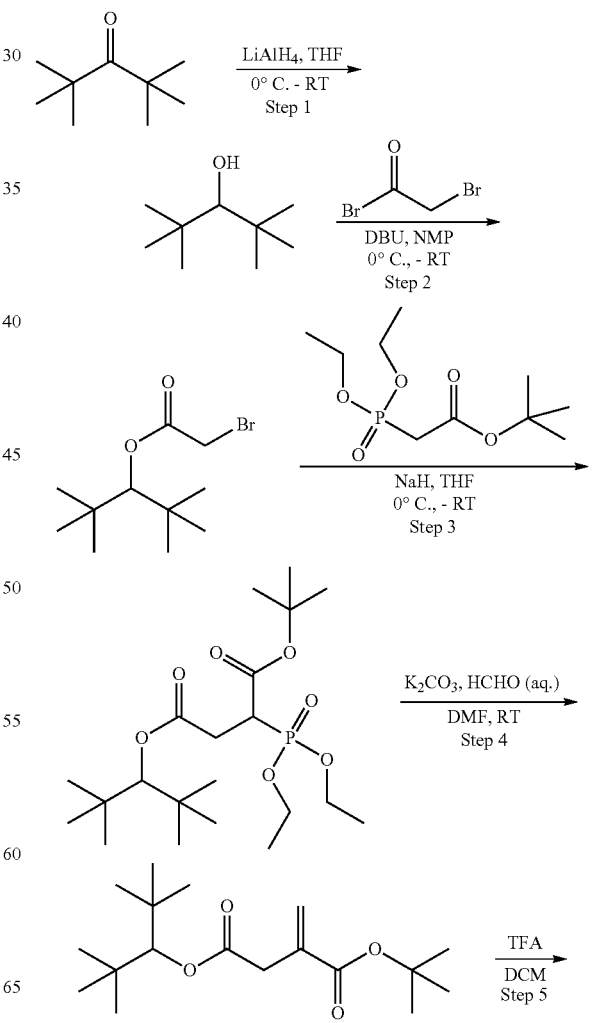

-continued

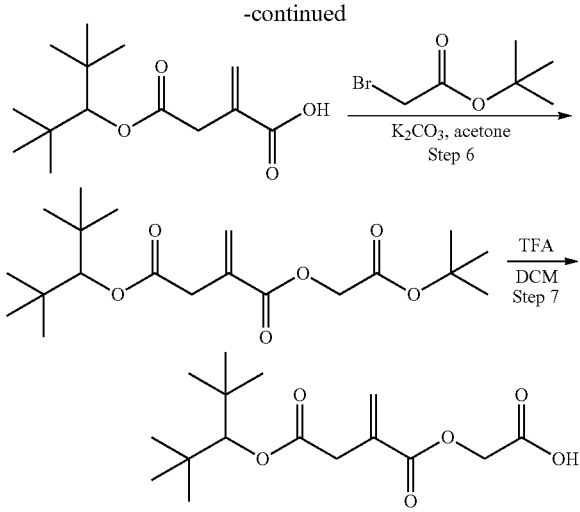

Step 1

To a solution of 2,2,4,4-tetramethylpentan-3-one (1.5 g, 10.6 mmol) in dry THF (40 mL) was added LiAlH$_4$ (802 mg, 21.1 mmol) at 0° C., and the resulting mixture was stirred at room temperature for 1 h. To the reaction mixture was sequentially added water (1 mL), aqueous NaOH (15 wt %, 1 mL), water (2.5 mL) and Na$_2$SO$_4$ (20 g), the mixture was stirred at room temperature for 20 min, filtered, and concentrated under reduced pressure at 35° C. to give 2,2,4,4-tetramethylpentan-3-ol (1.4 g, 9.70 mmol, 90%) as colourless crystals. $^1$H NMR (400 MHz, CDCl$_3$) δ: 3.12 (d, J=2.4 Hz, 1H), 1.23 (s, 18H). One exchangeable proton not observed.

Step 2

To a solution of 2,2,4,4-tetramethylpentan-3-ol (1.3 g, 9.02 mmol) and DBU (2.74 g, 18.0 mmol) in 1-methyl-2-pyrrolidinone (45 mL) was slowly added 2-bromoacetyl bromide (3.64 g, 18.0 mmol) at 0° C. dropwise and the mixture was stirred at room temperature for 1 h. The reaction mixture was diluted with water (10 mL) and MTBE (20 mL), separated and the aqueous layer was extracted with MTBE (2×20 mL). The combined organic layers were washed with brine, dried over Na$_2$SO$_4$, filtered and concentrated under reduced pressure at 40° C. The residue was purified by flash column chromatography (50 g silica, 0-10% EtOAc/petroleum ether) to give 2,2,4,4-tetramethylpentan-3-yl 2-bromoacetate (1.50 g, 5.68 mmol, 62%) as a colorless oil. $^1$H NMR (400 MHz, CDCl$_3$) δ: 4.63 (s, 1H), 3.87 (s, 2H), 1.04 (s, 18H).

Step 3

To a solution of tert-butyl 2-(diethoxyphosphoryl)acetate (1.43 g, 5.68 mmol) in THF (15 mL) was added NaH suspension in mineral oil (60 wt. %, 227 mg, 5.68 mmol) at 0° C., and the reaction mixture was stirred at 0° C. for 0.5 h. 2,2,4,4-Tetramethylpentan-3-yl 2-bromoacetate (1.5 g, 5.68 mmol) was then added and the reaction mixture was stirred at room temperature overnight. The reaction mixture was quenched with dilute aqueous HCl (0.5 M) to pH=5, and extracted with EtOAc (3×20 mL). The combined organic layers were washed with brine, dried over Na$_2$SO$_4$, filtered and concentrated under reduced pressure at 40° C. to give crude 1-(tert-butyl) 4-(2,2,4,4-tetramethylpentan-3-yl) 2-(diethoxyphosphoryl)succinate (3.00 g, 6.87 mmol, >100%) as a colourless oil. The crude product was used directly in next step. LCMS (System 2, Method B) m/z 459.3 (M+Na)$^+$ (ES$^+$).

Step 4

To a solution of 1-(tert-butyl) 4-(2,2,4,4-tetramethylpentan-3-yl) 2-(diethoxyphosphoryl)succinate (3.00 g, ~ 6.87 mmol, crude) and potassium carbonate (1.90 g, 13.8 mmol) in THF (24 mL) and H$_2$O (6 mL) was added formaldehyde solution in water (37 wt. %, 11.15 mL, 138 mmol) at room temperature, and the reaction mixture was stirred at room temperature for 4 h. The reaction mixture was diluted with H$_2$O (15 mL) and extracted with MTBE (3×30 mL). The combined organic layers were washed with H$_2$O (2×10 mL) and brine, dried over Na$_2$SO$_4$, filtered and concentrated under reduced pressure at 40° C. The residue was purified by flash column chromatography (25 g silica, 0-20% MTBE/petroleum ether) to give 1-(tert-butyl) 4-(2,2,4,4-tetramethylpentan-3-yl) 2-methylenesuccinate (1.45 g, 4.64 mmol, 68%) as a colourless oil. LCMS (System 2, Method B) m/z 335.4 (M+Na)$^+$ (ES$^+$). $^1$H NMR (400 MHz, CDCl$_3$) δ: 6.24 (d, J=1.2 Hz, 1H), 5.63 (d, J=1.2 Hz, 1H), 4.57 (s, 1H), 3.35 (d, J=0.8 Hz, 2H), 1.48 (s, 9H), 0.98 (s, 18H).

Step 5

A solution of 1-(tert-butyl) 4-(2,2,4,4-tetramethylpentan-3-yl) 2-methylenesuccinate (450 mg, 1.44 mmol) in TFA/DCM (2:1, 7 mL) was stirred at room temperature for 4 h. The mixture was concentrated under reduced pressure at 40° C. to give 2-methylene-4-oxo-4-((2,2,4,4-tetramethylpentan-3-yl)oxy)butanoic acid (400 mg, 1.56 mmol, >100%) as a colourless oil, which was used directly in the next step. LCMS (System 2, Method C) m/z 279.4 (M+Na)$^+$ (ES$^+$).

Step 6

To a solution of 2-methylene-4-oxo-4-((2,2,4,4-tetramethylpentan-3-yl)oxy)butanoic acid (400 mg, 1.56 mmol), and potassium carbonate (645 mg, 4.68 mmol) in acetone (10 mL) was added tert-butyl 2-bromoacetate (608 mg, 3.12 mmol), and the reaction mixture was stirred at room temperature for 2 days. The reaction mixture was filtered, and the filtrate was concentrated under reduced pressure at 40° C. The residue was purified by flash column chromatography (25 g silica, 0-20% MTBE/petroleum ether) to give 1-(2-(tert-butoxy)-2-oxoethyl) 4-(2,2,4,4-tetramethylpentan-3-yl) 2-methylenesuccinate (430 mg, 1.16 mmol, 81%) as a colourless oil. LCMS (System 2, Method C) m/z 393.4 (M+Na)$^+$ (ES$^+$).

Step 7

A solution of 1-(2-(tert-butoxy)-2-oxoethyl) 4-(2,2,4,4-tetramethylpentan-3-yl) 2-methylenesuccinate (430 mg, 1.16 mmol) in TFA/DCM (2:1, 6 mL) was stirred at room temperature for 1 h. The reaction mixture was filtered and the filtrate was concentrated under reduced pressure at 40° C. The residue was purified by preparative HPLC (Column: Waters X-Bridge C18 OBD 10 μm 19×250 mm; Flow Rate: 20 mL/min; solvent system: MeCN/(0.05% TFA/water) gradient: 50-95% MeCN; collection wavelength: 214 nm). The fractions were concentrated under reduced pressure at 40° C.

to remove MeCN, and the residue was lyophilized to give 2-((2-methylene-4-oxo-4-((2,2,4,4-tetramethylpentan-3-yl)oxy)butanoyl)oxy)acetic acid (302 mg, 0.96 mmol, 83%) as a white solid. LCMS (System 2, Method B) m/z 337.3 (M+Na)+(ES+). $^1$H NMR (400 MHz, CDCl$_3$) δ: 13.01 (br, 1H), 6.30 (d, J=1.2 Hz, 1H), 5.97 (s, J=1.2 Hz, 1H), 4.62 (s, 2H), 4.45 (s, 1H), 3.45 (s, 2H), 0.93 (s, 18H).

Example 207—3-((2-methylene-4-oxo-4-(2,2,4,4-tetramethylcyclobutoxy)butanoyl)oxy) propanoic Acid

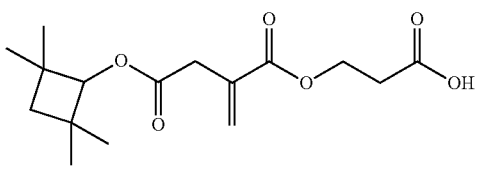 [SMILES: C=C(CC(=O)OC1C(C)(C)CC1(C)C)C(=O)OCCC(=O)O]

Example 207 was prepared according to the procedure of Example 80, but using 2,2,4,4-tetramethylcyclobutan-1-ol instead of 4-octyl itaconate. LCMS (System 2, Method B) m/z 335.2 (M+Na)+ (ES+). $^1$H NMR (400 MHz, DMSO-d6) δ 12.41 (br, 1H), 6.17 (d, J=1.2 Hz, 1H), 5.85 (d, J=0.8 Hz, 1H), 4.36 (s, 1H), 4.25 (t, J=2.0 Hz, 2H), 3.39 (s, 2H), 2.59 (t, J=2.0 Hz, 2H), 1.51 (d, J=11.6 Hz, 1H), 1.41 (d, J=11.6 Hz, 1H), 1.10 (s, 6H), 1.00 (s, 6H).

Biological Example 1—THP-1 AlphaLISA IL-1β and IL-6 Cytokine Assay

Measuring Inhibitory Effects on IL-1β and IL-6 Cytokine Output from THP-1s

The cytokine inhibition profiles of compounds of formula (IW-1) were determined in a differentiated THP-1 cell assay. All assays were performed in RPMI-1640 growth medium (Gibco), supplemented with 10% fetal bovine serum (FBS; Gibco), 1% penicillin-streptomycin and 1% sodium pyruvate unless specified otherwise. The IL-1β and IL-6 cytokine inhibition assays were each run in a background of differentiated THP-1 cells as described below. All reagents described were from Sigma-Aldrich unless specified otherwise. Compounds were prepared as 10 mM DMSO stocks.

Assay Procedure

THP-1 cells were expanded as a suspension up to 80% confluence in appropriate growth medium. Cells were harvested, suspended, and treated with an appropriate concentration of phorbol 12-myristate 13-acetate (PMA) over a 72 hr period (37° C./5% CO$_2$).

Following 72 hrs of THP-1 cell incubation, cellular medium was removed and replaced with fresh growth media containing 1% of FBS. Working concentrations of compounds were prepared separately in 10% FBS treated growth medium and pre-incubated with the cells for 30 minutes (37° C./5% CO$_2$). Following the 30 minute compound pre-incubation, THP-1s were treated with an appropriate concentration of LPS and the THP-1s were subsequently incubated for a 24 hr period (37° C./5% CO$_2$). An appropriate final concentration of Nigericin was then dispensed into the THP-1 plates and incubated for 1 hour (37° C./5% CO$_2$) before THP-1 supernatants were harvested and collected in separate polypropylene 96-well holding plates.

Reagents from each of the IL-1β and IL-6 commercial kits (Perkin Elmer) were prepared and run according to the manufacturer's instructions. Subsequently, fluorescence signal detection in a microplate reader was measured (EnVision® Multilabel Reader, Perkin Elmer).

Percentage inhibition was calculated per cytokine by normalising the sample data to the high and low controls used within each plate (+/−LPS respectively). Percentage inhibition was then plotted against compound concentration and the 50% inhibitory concentration (IC$_{50}$) was determined from the resultant concentration-response curve.

A number of Example compounds of formula (IW-1) were tested and the results are shown in Table 1 below. Dimethyl itaconate and dimethyl fumarate were included as comparator compounds. All compounds of formula (IW-1) shown in Table 1 exhibited comparable or improved cytokine-lowering potencies compared to dimethyl itaconate and/or dimethyl fumarate for IL-1β and/or IL-6. Certain compounds shown in Table 1 exhibited improved cytokine-lowering potencies compared to dimethyl itaconate and/or dimethyl fumarate for IL-1β and/or IL-6.

TABLE 1

THP-1 cell IL-1β and IL-6 IC$_{50}$ values (μM)

| Compound | IL-1β (IC$_{50}$) | IL-6 (IC$_{50}$) |
|---|---|---|
| dimethyl fumarate | 14.4 | 9.3 |
| dimethyl itaconate | >100 | 100.0 |
| Example 1 | 9.3 | 6.0 |
| Example 2 | 5.0 | 2.9 |
| Example 3 | 15.6 | 56.2 |
| Example 4 | 9.3 | 3.6 |
| Example 5 | 6.5 | 2.0 |
| Example 6 | 12.8 | 12.1 |
| Example 7 | 16.7 | 12.0 |
| Example 9 | 4.7 | 2.2 |
| Example 10 | 27.9 | 7.6 |
| Example 11 | 3.7 | NT* |
| Example 12 | 28.2 | 11.3 |
| Example 14 | 1.6 | 2.1 |
| Example 15 | 15.4 | 8.9 |
| Example 16 | 1.7 | 1.1 |
| Example 17 | 1.5 | 1.4 |
| Example 19 | 3.6 | 1.9 |
| Example 20 | 5.6 | 3.4 |
| Example 21 | 2.9 | 2.4 |
| Example 22 | 15.4 | 7.0 |
| Example 23 | 8.2 | 4.5 |
| Example 24 | 15.0 | 4.2 |
| Example 25 | 1.9 | 1.9 |
| Example 26 | 16.1 | NT* |
| Example 27 | 12.2 | 6.4 |
| Example 28 | 5.2 | 2.2 |
| Example 29 | 18.4 | 7.9 |
| Example 30 | 11.3 | 4.8 |
| Example 31 | 12.9 | 15.5 |
| Example 32 | 18.9 | 9.5 |
| Example 33 | 14.1 | 11.7 |
| Example 34 | 31.8 | 16.1 |
| Example 35 | 6.7 | 3.7 |
| dimethyl fumarate | 14.4 | 9.3 |
| dimethyl itaconate | >100 | 100.0 |
| Example 36 | 20.5 | 8.9 |
| Example 38 | 7.4 | 6.8 |
| Example 39 | 5.1 | 7.3 |
| Example 40 | 1.7 | 3.4 |
| Example 46 | 6.7 | 3.0 |
| Example 47 | 3.3 | 3.0 |
| Example 48 | 10.1 | 5.1 |
| Example 49 | 7.2 | 5.5 |
| Example 50 | 2.7 | 1.7 |
| Example 51 | 7.3 | 4 |
| Example 52 | 8.5 | 2.5 |
| Example 53 | 9.3 | 5.4 |
| Example 54 | 3.9 | 1.5 |
| Example 55 | 5.1 | 3.8 |
| Example 56 | 7.9 | 3.5 |

TABLE 1-continued

THP-1 cell IL-1β and IL-6 IC$_{50}$ values (μM)

| Compound | IL-1β (IC$_{50}$) | IL-6 (IC$_{50}$) |
|---|---|---|
| Example 57 | 4.4 | 2.6 |
| Example 58 | 6.5 | 3.8 |
| Example 59 | 13.3 | 8.8 |
| Example 60 | 1.9 | 1.4 |
| Example 61 | 6.1 | 5 |
| Example 62 | 3.5 | 2.8 |
| Example 63 | 1.3 | 2.5 |
| Example 64 | 10.2 | 12.6 |
| Example 65 | 22.6 | 22.4 |
| Example 66 | 2.3 | 2.5 |
| Example 67 | 5.7 | 4.8 |
| Example 68 | 24 | 9.1 |
| Example 69 | 1.7 | 2.2 |
| Example 70 | 6.1 | 9.4 |
| Example 71 | 8.7 | 9.6 |
| Example 72 | 11.4 | 8.2 |
| Example 73 | 24.1 | 23.5 |
| Example 74 | 4.2 | NT* |
| dimethyl fumarate | 14.4 | 9.3 |
| dimethyl itaconate | >100 | 100.0 |
| Example 75 | 11.2 | NT* |
| Example 76 | 4.1 | NT* |
| Example 77 | 14.5 | NT* |
| Example 78 | 4.2 | NT* |
| Example 79 | 11.9 | 13.5 |
| Example 80 | 9.6 | 5.3 |
| Example 81 | 100 | 52.1 |
| Example 82 | 25.7 | 18.9 |
| Example 83 | 34.2 | 96.9 |
| Example 84 | 14.3 | 22 |
| Example 85 | 22.6 | 18.6 |
| Example 86 | 100 | 15.7 |
| Example 87 | 28.1 | 100 |
| Example 88 | 25.2 | 20.4 |
| Example 89 | 17.5 | 12.6 |
| Example 90 | 16.4 | 9.8 |
| Example 91 | 48.1 | 33.8 |
| Example 92 | 75.3 | 21.2 |
| Example 93 | 73.8 | 28.1 |
| Example 94 | 5.3 | NT* |
| Example 95 | 80.6 | NT* |
| Example 96 | 15.7 | 47.1 |
| Example 97 | 29.3 | 30.3 |
| Example 98 | 2.1 | 4.3 |
| Example 99 | 1.9 | 2.5 |
| Example 100 | 11 | 5.1 |
| Example 101 | 15.2 | 4.7 |
| Example 102 | 1.5 | 1.1 |
| Example 103 | 55.5 | NT* |
| Example 104 | 14.4 | NT* |
| Example 105 | 27.9 | NT* |
| Example 106 | 15.6 | NT* |
| Example 107 | 10 | 2.7 |
| dimethyl fumarate | 14.4 | 9.3 |
| dimethyl itaconate | >100 | 100.0 |
| Example 108 | 11.1 | 3.1 |
| Example 109 | 10.6 | 6.8 |
| Example 110 | 8.5 | 4.4 |
| Example 111 | 100 | 70.9 |
| Example 112 | 14.6 | NT* |
| Example 113 | 100 | 48.5 |
| Example 114 | 100 | 56.2 |
| Example 115 | 59.5 | 36.3 |
| Example 116 | 100 | 60.4 |
| Example 117 | 100 | 43.9 |
| Example 118 | 16.2 | 14 |
| Example 119 | 82.4 | 47.5 |
| Example 120 | 26.9 | 7.7 |
| Example 121 | 54.2 | NT* |
| Example 122 | 13 | NT* |
| Example 123 | 19.5 | NT* |
| Example 124 | 52.4 | NT* |
| Example 125 | 17 | NT* |
| Example 126 | 0.7 | NT* |
| Example 127 | 44.9 | NT* |
| Example 128 | 32.7 | NT* |
| Example 129 | 5.5 | NT* |
| Example 130 | 16 | NT* |
| Example 131 | 4.4 | NT* |
| Example 132 | 4.3 | NT* |
| Example 133 | 14.8 | NT* |
| Example 134 | 9.8 | NT* |
| Example 135 | 4.2 | NT* |
| Example 136 | 54.2 | NT* |
| Example 137 | 5.7 | NT* |
| Example 138 | 6.8 | 5.2 |
| Example 139 | 21.7 | 15.1 |
| Example 140 | 7.8 | NT |
| dimethyl fumarate | 14.4 | 9.3 |
| dimethyl itaconate | >100 | 100.0 |
| Example 141 | 6.5 | NT |
| Example 142 | 6.2 | NT |
| Example 143 | 2.0 | NT |
| Example 144 | 1.7 | NT |
| Example 145 | 19.3 | NT |
| Example 146 | 8.5 | NT |
| Example 147 | 13.4 | NT |
| Example 148 | 29.6 | NT |
| Example 149 | 12.1 | NT |
| Example 150 | 11.7 | NT |
| Example 151 | 10.3 | NT |
| Example 152 | 10.3 | NT |
| Example 153 | 7.0 | NT |
| Example 154 | 8.4 | NT |
| Example 155 | 16.5 | NT |
| Example 156 | 27.9 | NT |
| Example 157 | 41.6 | NT |
| Example 158 | 24.2 | NT |
| Example 159 | 31.9 | NT |
| Example 160 | 8.1 | NT |
| Example 161 | 6.8 | NT |
| Example 162 | 14.7 | NT |
| Example 163 | 23.9 | NT |
| Example 164 | 2.0 | NT |
| Example 165 | 15.8 | NT |
| Example 166 | 67.4 | NT |
| Example 167 | 29.1 | NT |
| Example 168 | 49.3 | NT |
| Example 169 | 15.6 | NT |
| Example 170 | 14.7 | NT |
| Example 171 | 21.8 | NT |
| Example 172 | 23.8 | NT |
| Example 173 | 27.6 | NT |
| dimethyl fumarate | 14.4 | 9.3 |
| dimethyl itaconate | >100 | 100.0 |
| Example 174 | 10.9 | NT |
| Example 175 | 7.6 | NT |
| Example 176 | 12.0 | NT |
| Example 177 | 20.5 | NT |
| Example 178 | 24.6 | NT |
| Example 179 | 11.0 | NT |
| Example 180 | 8.2 | NT |
| Example 181 | 32.8 | NT |
| Example 182 | 6.1 | NT |
| Example 183 | 9.6 | NT |
| Example 184 | 33.9 | NT |
| Example 185 | 21.6 | 8.8 |
| Example 186 | 3.5 | NT |
| Example 187 | 2.9 | NT |
| Example 188 | 3.5 | NT |
| Example 189 | 57.9 | NT |
| Example 190 | 58.4 | NT |
| Example 191 | 26.6 | NT |
| Example 192 | 10.6 | NT |
| Example 193 | 17.6 | NT |
| Example 194 | 24.8 | NT |
| Example 195 | 24.3 | NT |
| Example 196 | 18.8 | NT |
| Example 197 | 21.4 | NT |
| Example 198 | 22.0 | NT |
| Example 199 | 18.3 | NT |
| Example 200 | 11.5 | NT |

TABLE 1-continued

THP-1 cell IL-1β and IL-6 IC$_{50}$ values (μM)

| Compound | IL-1β (IC$_{50}$) | IL-6 (IC$_{50}$) |
|---|---|---|
| Example 201 | 24.6 | NT |
| Example 202 | 36.7 | NT |
| Example 203 | 22.0 | NT |
| Example 204 | 41.7 | NT |
| Example 205 | 1.7 | NT |
| Example 206 | 19.1 | NT |
| dimethyl fumarate | 14.4 | 9.3 |
| dimethyl itaconate | >100 | 100.0 |
| Example 207 | 100 | NT |

NT* = not tested

Biological Example 2—NQO1 Enzyme Activation Assay

NQO1 Enzyme Activation Assay as a Readout of NRF2 Activation in THP-1 Cellular Background NAD(P)H dehydrogenase [quinone] 1 (NQO1) is an anti-oxidant target gene upregulated by increased NRF2 activity. Induction of this gene is concomitant with the inhibition of proinflammatory cytokine transcription and suppression of the inflammatory response (Kobayashi E. H. et al., 2016). The NQO1 enzyme activation activities of compounds of formula (IW-1) were determined using a cellular based NQO1 activation assay (Abcam). The NQO1 activation assay was run in differentiated THP-1 cells (a human monocyte-like cell line) as described below. All reagents described are from Sigma-Aldrich unless specified otherwise. Compounds were prepared as 10 mM DMSO stocks.

Assay Procedure

THP-1 cells were expanded as a suspension up to 80% confluence in appropriate growth medium. Cells were harvested, suspended, treated with phorbol 12-myristate 13-acetate (PMA) and plated according to the cell density required for each plate format over a 72 hr period (37° C./5% CO$_2$).

Following 72 hrs of THP-1 cell incubation, cellular medium was removed and replaced with fresh media. Working concentrations of compounds were prepared and pre-incubated for 30 minutes (37° C./5% CO$_2$). Compound treatment was then applied to the PMA treated THP-1 cell plate followed by LPS treatment. A 'low' (DMSO vehicle only) control and 'high' (designated concentration of dimethyl fumarate) was applied to each plate at the point of compound treatment. Cells were subsequently incubated for a 48 hr period (37° C./5% C$_{O2}$) after which all NQO1 assay reagents were prepared according to the manufacturer's instructions. NQO1 extraction buffer was applied to PBS washed THP-1 cells and incubated on ice for 15 minutes to prepare THP-1 lysates for the NQO1 activity assay. THP-1 lysates were diluted 1:5 with PBS and treated with a 1:1 volume of kit prepared NQO1 Reaction Buffer. Absorbance was subsequently measured kinetically on an appropriate reader over a 6 minute period.

For activation determination, the fold change in response per well was determined by first calculating the average NQO1 activation data for the vehicle control and then dividing the individual well response by the averaged NQO1 response for the vehicle control as shown below:

Fold change=(Sample value)/Mean$_{Min}$

Where 'Min'=vehicle control only

The relative 50% activation concentration (EC$_{50}$) was determined from the resulting fold change response curve.

The maximum efficacy (E$_{max}$) was reported as the percentage activation calculated at the top concentration of compound used in the titration applied. If a full curve was unattainable preventing a correct curve fit, the E$_{max}$ value was extrapolated using existing curve data. All percentage activation data were normalised to the DMF and vehicle controls, meaning the E$_{max}$ represents the percentage inhibition achieved by a compound at a particular concentration relative to that achieved by DMF (set as the 'High' control and therefore representative of 100% activation).

A number of compounds of formula (IW-1) were tested, and the results are shown in Table 2 below. Dimethyl itaconate and dimethyl fumarate were included as comparator compounds. All compounds of formula (IW-1) shown in Table 2 (except Example 185) exhibited a lower EC$_{50}$ and/or a higher E$_{max}$ compared with dimethyl itaconate and/or dimethyl fumarate.

TABLE 2

NQO1 enzyme activation

| Compound | EC$_{50}$ (μM) | E$_{max}$ (%) |
|---|---|---|
| dimethyl itaconate | 74.1 | 144 |
| dimethyl fumarate | 12.9 | 126 |
| Example 1 | 6.9 | 167 |
| Example 2 | 4.6 | 213 |
| Example 3 | 14.7 | 91 |
| Example 4 | 13.6 | 171 |
| Example 5 | 5.9 | 81 |
| Example 6 | 30.6 | 154 |
| Example 7 | 7.3 | 78 |
| Example 8 | 35.4 | 152 |
| Example 9 | 9.8 | 98 |
| Example 10 | 15.2 | 107 |
| dimethyl itaconate | 74.1 | 144 |
| dimethyl fumarate | 12.9 | 126 |
| Example 11 | 10.4 | 124 |
| Example 12 | 22.7 | 88 |
| Example 13 | 2.8 | 45 |
| Example 14 | 14.4 | 180 |
| Example 16 | 19.8 | 108 |
| Example 17 | 2.6 | 68 |
| Example 18 | 5.4 | 67 |
| Example 19 | 51.0 | 44 |
| Example 20 | 20.0 | 224 |
| Example 21 | 12.1 | 150 |
| Example 37 | 21.0 | 105 |
| Example 38 | 8.5 | 111 |
| Example 39 | 1.3 | 59 |
| Example 40 | 16.6 | 56 |
| Example 41 | 38.1 | 129 |
| Example 42 | 24.3 | 66 |
| Example 43 | 169.8 | 150 |
| Example 44 | 64.6 | 217 |
| Example 45 | 1.6 | 72 |

Biological Example 3—Primary Human Monocyte AlphaLISA IL-Iβ and IL-6 Cytokine Assay Measuring Inhibitory Effects on IL-1β and IL-6 Cytokine Output from Isolated Primary Human Monocytes The cytokine inhibition profiles of compounds of formula (IW-1) were determined in a CD14$^+$ isolated primary human monocyte cell assay. All assays were performed in RPMI-1640 growth medium (Gibco), supplemented with heat-inactivated fetal bovine serum (FBS) and 1% penicillin-streptomycin unless specified otherwise. The IL-1β and IL-6 cytokine inhibition assays were each run in a background of isolated primary human monocyte cells as described below. All reagents described were from Sigma-Aldrich unless specified otherwise. Compounds were prepared as 100 mM DMSO stocks.

Assay Procedure

Primary peripheral blood mononuclear cells (PBMCs) were isolated from human whole blood. Following PBMC isolation, a CD14$^+$ monocyte isolation step was conducted whereby CD14$^+$ magnetic beads (Miltenyi Biotec) were incubated for 15 minutes with the PBMC suspension that was previously treated with ice cold T-cell isolation buffer (PBS, 0.5% BSA, 2 mM EDTA). Following bead incubation, the treated cell suspension was passed through a magnetic separation column designed to positively select for magnetically labelled cells. The isolated CD14$^+$ monocytes were subsequently plated at the appropriate cell density for the assay, prior to compound treatment on the day of plating. Working concentrations of compounds were prepared separately in RPMI-1640 only growth medium and pre-incubated with the cells for 30 minutes (37° C./5% $CO_2$). Following the 30 minute compound pre-incubation, primary monocytes were treated with an appropriate concentration of LPS and subsequently incubated for a 24 hr period (37° C./5% $CO_2$). An appropriate final concentration of Nigericin was then dispensed into the primary monocyte plates and incubated for 1 hour (37° C./5% $CO_2$) before monocyte supernatants were harvested and collected in separate polypropylene 96-well holding plates prior to commencing the AlphaLISA cytokine assay.

Reagents from each of the IL-1β and IL-6 commercial kits (Perkin Elmer) were prepared and run according to the manufacturer's instructions. Subsequently, fluorescence signal was measured in a microplate reader (EnVision® Multilabel Reader, Perkin Elmer).

Percentage inhibition was calculated per cytokine by normalising the sample data to the high and low controls used within each plate (+/−LPS respectively). Percentage inhibition was then plotted against compound concentration and the 50% inhibitory concentration ($IC_{50}$) was determined from the resultant concentration-response curve.

A number of Example compounds of formula (IW-1) were tested and the results are shown in Table 3 below. Dimethyl fumarate and 4-octyl itaconate were included as comparator compounds. Examples 2, 3 and 9 exhibited lower $IC_{5s}$ than dimethyl fumarate. All compounds which were tested exhibited lower $IC_{50s}$ than 4-octyl itaconate.

TABLE 3 primary monocyte IL-1β and IL-6 $IC_{50}$ values (μM)

| Compound | IL-1β ($IC_{50}$) | IL-6 ($IC_{50}$) |
| --- | --- | --- |
| dimethyl fumarate | 8.5 | 15.7 |
| 4-octyl itaconate | >100 | NT* |
| Example 1 | 8.9 | 26.9 |
| dimethyl fumarate | 8.5 | 15.7 |
| 4-octyl itaconate | >100 | NT* |
| Example 2 | 3.6 | 13.2 |
| Example 3 | 3.9 | NT |
| Example 9 | 3.3 | 10.7 |
| Example 88 | 17.3 | NT |
| Example 90 | 81.3 | NT |
| Example 112 | 13.7 | NT |

NT* = not tested

Biological Example 4—Primary Human Monocyte Derived Macrophages (HMDMs) AlphaLISA IL-1β Cytokine Assay Measuring Inhibitory Effects on IL-1β Cytokine Output from Isolated Primary HMDMs The cytokine inhibition profiles of compounds of formula (IW-1) were determined in a monocyte differentiated macrophage cell assay. All assays were performed in RPMI-1640 growth medium (Gibco), supplemented with heat-inactivated fetal bovine serum (FBS) and 1% penicillin-streptomycin unless specified otherwise. The IL-1β cytokine inhibition assay was run in a background of isolated primary HMDM cells as described below. All reagents described were from Sigma-Aldrich unless specified otherwise. Compounds were prepared as 100 mM DMSO stocks.

Assay Procedure

Primary peripheral blood mononuclear cells (PBMCs) were isolated from human whole blood. Following PBMC isolation, a CD14$^+$ monocyte isolation step was conducted whereby CD14$^+$ magnetic beads (Miltenyi Biotec) were incubated for 15 minutes with the PBMC suspension that was previously treated with ice cold T-cell isolation buffer (PBS, 0.5% BSA, 2 mM EDTA). Following bead incubation, the treated cell suspension was passed through a magnetic separation column designed to positively select for magnetically labelled cells. The isolated CD14$^+$ monocytes were subsequently plated at an appropriate cell density and treated for a 7 day period with M-CSF (BioLegend) to drive macrophage differentiation. Following the differentiation period, working concentrations of compounds were prepared separately in RPMI-1640 only growth medium and pre-incubated with the cells for 30 minutes (37° C./5% $CO_2$). Following the 30 minute compound pre-incubation, primary HMDMs were treated with an appropriate concentration of LPS and subsequently incubated for a 24 hr period (37° C./5% $CO_2$). Nigericin was added and incubated for 1 hour prior to harvesting primary HMDM supernatants and collected in separate polypropylene 96-well holding plates prior to commencing the AlphaLISA cytokine assay.

Reagents from the IL-1β commercial kit (Perkin Elmer) was prepared and run according to the manufacturer's instructions. Subsequently, fluorescence signal was measured in a microplate reader (EnVision® Multilabel Reader, Perkin Elmer).

Percentage inhibition was calculated per cytokine by normalising the sample data to the high and low controls used within each plate (+/−LPS respectively). Percentage inhibition was then plotted against compound concentration and the 50% inhibitory concentration ($IC_{50}$) was determined from the resultant concentration-response curve.

A number of Example compounds of formula (IW-1) were tested and the results are shown in Table 4 below. Dimethyl fumarate was included as a comparator compound. All compounds of formula (IW-1) shown in Table 4 exhibited lower $IC_{50}$ than the comparator compound.

TABLE 4

HMDM IL-1β $IC_{50}$ values (μM)

| Compound | IL-1β ($IC_{50}$) |
| --- | --- |
| dimethyl fumarate | 2.0 |
| Example 1 | 0.4 |
| Example 2 | 0.3 |
| Example 3 | 0.7 |
| Example 4 | 0.4 |
| Example 9 | 1.2 |

Biological Example 5—NRF2+/−GSH Activation Assay

Measuring Compound Activation Effects on the Anti-Inflammatory Transcription Factor NRF2 in DiscoverX PathHunter NRF2 Translocation Kit Potency and efficacy of compounds of formula (IW-1) against the target of interest to activate NRF2 (nuclear factor erythroid 2-related factor 2) were determined using the PathHunter NRF2 translocation kit (DiscoverX). The NRF2 translocation assay was run using an engineered recombinant cell line, utilising enzyme fragment complementation to determine activation of the Keap1-NRF2 protein complex and subsequent translocation of NRF2 into the nucleus. Enzyme activity was quantified using a chemiluminescent substrate consumed following the formation of a functional enzyme upon PK-tagged NRF2 translocation into the nucleus.

The assay was run under either +/−GSH (glutathione) conditions to determine the attenuating activities of GSH against target compounds.

Additionally, a defined concentration of dimethyl fumarate was used as the 'High' control to normalise test compound activation responses to.

Assay Procedure

U2OS PathHunter eXpress cells were thawed from frozen prior to plating. Following plating, U2OS cells were incubated for 24 hrs (37° C./5% $CO_2$) in commercial kit provided cell medium.

Following 24 hrs of U2OS incubation, cells were directly treated with an appropriate final concentration of compound, for −GSH conditions, or for +GSH conditions, an intermediate plate containing 6× working concentrations of compound stocks was prepared in a 6 mM working concentration of GSH solution (solubilised in sterile PBS). Following a 30 minute compound-GSH pre-incubation (37° C./5% $CO_2$) for +GSH treatment, plated U2OS cells were incubated with an appropriate final concentration of compound and GSH.

Following compound (+/−GSH) treatment, the U2OS plates were incubated for a further 6 hours (37° C./5% $CO_2$) before detection reagent from the PathHunter NRF2 commercial kit was prepared and added to test plates according to the manufacturer's instructions. Subsequently, the luminescence signal detection in a microplate reader was measured (PHERAstar®, BMG Labtech).

Percentage activation was calculated by normalising the sample data to the high and low controls used within each plate (+/−DMF). Percentage activation/response was then plotted against compound concentration and the 50% activation concentration ($EC_{50}$) was determined from the plotted concentration-response curve.

A number of compounds of formula (IW-1) were tested, and the results are shown in Table 5 below. Dimethyl itaconate and dimethyl fumarate were included as comparator compounds. Certain compounds of formula (IW-1) shown in Table 5 exhibited a lower or comparable $EC_{50}$ and/or a higher $E_{max}$ compared with dimethyl itaconate and/or dimethyl fumarate.

TABLE 5

| NRF2 activation | | |
|---|---|---|
| Compound | $EC_{50}$ (µM) | $E_{max}$ (%) |
| dimethyl fumarate | 5.6 | 102 |
| dimethyl itaconate | 21.4 | 137 |
| Example 1 | 8.8 | 134 |
| Example 2 | 5.1 | 268 |
| Example 4 | 8.3 | 181 |
| Example 5 | 5.7 | 216 |
| Example 14 | 8.8 | 189 |
| Example 20 | 13.5 | 116 |
| Example 49 | 15.8 | 232 |
| Example 50 | 3.2 | 225 |
| Example 54 | 2.8 | 105 |

TABLE 5-continued

| NRF2 activation | | |
|---|---|---|
| Compound | $EC_{50}$ (µM) | $E_{max}$ (%) |
| Example 69 | 14.7 | 111 |
| Example 75 | 17.5 | 143 |
| Example 78 | 17.7 | 177 |
| Example 80 | 21.5 | 229 |
| Example 81 | 24.9 | 110 |
| Example 82 | 26.5 | 164 |
| Example 84 | 6.3 | 185 |
| Example 85 | 25.0 | 163 |
| Example 86 | 21.0 | 91 |
| Example 87 | 34.2 | 113 |
| Example 88 | 3.2 | 139 |
| Example 89 | 22.4 | 238 |
| Example 90 | 29.4 | 157 |
| Example 91 | 10.1 | 73 |
| Example 92 | 37.8 | 109 |
| Example 93 | 36.0 | 118 |
| Example 94 | 22.2 | 193 |
| Example 95 | 36.5 | 122 |
| Example 96 | 21.2 | 180 |
| Example 98 | 14.7 | 193 |
| Example 99 | 37.6 | 227 |
| Example 100 | 48.7 | 195 |
| Example 101 | 37.9 | 186 |
| dimethyl fumarate | 5.6 | 102 |
| dimethyl itaconate | 21.4 | 137 |
| Example 102 | 6.5 | 191 |
| Example 112 | 8.9 | 173 |
| Example 122 | 17.5 | 178 |
| Example 125 | 38.3 | 116 |
| Example 128 | 38.0 | 104 |
| Example 129 | 5.8 | 178 |
| Example 130 | 29.1 | 164 |
| Example 133 | 33.3 | 227 |
| Example 134 | 20.0 | 183 |
| Example 135 | 11.1 | 157 |
| Example 137 | 4.2 | 96 |
| Example 144 | 2.1 | 176 |
| Example 145 | >100 | 7 |
| Example 156 | 47.9 | 63 |
| Example 157 | >100 | 29 |
| Example 158 | 72.8 | 43 |
| Example 159 | 13.8 | 86 |
| Example 160 | 72.6 | 7 |
| Example 161 | 5.0 | 146 |
| Example 162 | 31.3 | 164 |
| Example 163 | >100 | 0 |
| Example 164 | 4.9 | 168 |
| Example 165 | 10.9 | 191 |
| Example 178 | 14.3 | 188 |
| Example 182 | 5.5 | 188 |
| Example 189 | 18.0 | 137 |
| Example 192 | 11.8 | 194 |

Biological Example 6—Mouse Pharmacokinetic Studies

Pharmacokinetic studies were carried out in 6-8-week-old male C57BL/6 mice having free access to food and water. Intravenous dosing was conducted at 10 mg/kg (5 mL/kg; vehicle: 10% DMSO-90% (25% HP-13-CD in water)) via tail vein injection, with sampling at 3 min, 8 min, 15 min, 30 min, 1, 2, 4, 6 and 8 hours, i.e., 9 time points in total (N=3/time point), using semi-serial bleeding for plasma. Oral compound administration, via gavage, was carried out at 100 mg/kg (10 mL/kg; vehicle: 5% DMSO-95% (0.5% HPMC+0.1% Tween 80 in water)), with sampling at 5 min, 15 min, 30 min, 1, 2, 4, 6, 8 and 24 hours, i.e., 9 time points in total (N=3/time point), using semi-serial bleeding for plasma.

For both intravenous and oral routes, the mice were restrained manually at the designated time points, with ca.

110 µL of blood being taken into K2EDTA tubes via the facial vein. Blood samples were put on ice and centrifuged to obtain plasma samples from which the concentration at each time point was measured by LC-MS/MS.

A number of compounds of formula (IW-1) were tested, and the results are shown in Tables 6 and 7 below. Dimethyl itaconate was included as a comparator compound. All compounds of formula (IW-1) exhibited higher systemic exposures than dimethyl itaconate which was only quantifiable at one timepoint following intravenous dosing and was below the limit of quantification at all timepoints following oral administration.

TABLE 6

Parent compound concentrations (ng/mL) following intravenous administration

| | Time (h) | | | | | | | | |
|---|---|---|---|---|---|---|---|---|---|
| Compound | 0.05 | 0.133 | 0.25 | 0.5 | 1 | 2 | 4 | 6 | 8 |
| dimethyl itaconate | 874 | <24 | <24 | <24 | <24 | <24 | <24 | <24 | <24 |
| Example 82 | 17600 | 8347 | 2783 | 752 | 69 | 2.2 | 1.4 | 1.6 | <0.8 |
| Example 84 | 5575 | —* | 1034 | 217 | 34 | 6.5 | <2.0 | <2.0 | — |
| Example 88 | 42500 | 23533 | 12367 | 6253 | 2513 | 200 | 40 | 11 | 4.2 |
| Example 89 | 27833 | 12377 | 7680 | 2300 | 430 | 65 | 6.8 | <4.0 | <4.0 |
| Example 90 | 19233 | 7160 | 2023 | 1597 | 89 | 3.6 | 2.8 | 1.7 | 1.2 |
| Example 94 | 18000 | 6073 | 2437 | 550 | 42 | 1.9 | 1.4 | <0.8 | <0.8 |
| Example 96 | 15100 | 3587 | 659 | 169 | 6.4 | 3.0 | <0.8 | <0.8 | <0.8 |
| Example 112 | 63467 | 40133 | 36233 | 23533 | 13000 | 3537 | 1513 | 424 | 154 |
| Example 118 | 3053 | 161 | 8.0 | 2.4 | <0.8 | <0.8 | <0.8 | <0.8 | <0.8 |
| Example 125 | 11900 | 3870 | 1068 | 346 | 38 | 3.0 | <0.8 | <0.8 | <0.8 |
| Example 129 | 2920 | 872 | 309 | 96 | 7.7 | <1.6 | <1.6 | <1.6 | <1.6 |
| Example 133 | 11033 | 4573 | 1953 | 315 | 33 | <8.0 | <8.0 | <8.0 | <8.0 |
| Example 134 | 31567 | 7757 | 2890 | 4295 | 74 | 12 | 11 | 1.4 | 1.7 |
| Example 161 | 8887 | 2377 | 846 | 343 | 90 | 5.1 | <4.0 | <4.0 | <4.0 |
| Example 164 | 6690 | 1248 | 534 | 211 | 18 | <4.0 | <4.0 | <4.0 | <4.0 |
| Example 169 | 15600 | 6433 | 2803 | 516 | 8.6 | 2.5 | 1.3 | <0.8 | <0.8 |
| Example 170 | 37167 | 21867 | 8933 | 1663 | 476 | 66 | 12 | <4.0 | <4.0 |
| Example 172 | 23667 | 11300 | 2637 | 1211 | 75 | 9.9 | 6.1 | <4.0 | <4.0 |
| Example 175 | 27467 | 11700 | 6110 | 1193 | 181 | 32 | <4.0 | <4.0 | <4.0 |
| Example 178 | 33367 | 15500 | 5677 | 2850 | 594 | 61 | 8.2 | <4.0 | <4.0 |
| Example 179 | 17867 | 5317 | 1810 | 456 | 13 | <4.0 | <4.0 | <4.0 | <4.0 |
| Example 182 | 40833 | 17933 | 6737 | 2893 | 642 | 88 | 20 | 6.0 | <4.0 |
| Example 192 | 36633 | 21433 | 11273 | 2907 | 400 | 86 | 26 | <4.0 | <4.0 |
| Example 193 | 28833 | 10677 | 4040 | 1450 | 134 | 16 | 4.1 | <4.0 | <4.0 |

*Timepoints where no samples were taken are indicated with a dash, "—".

TABLE 7

Parent compound concentrations (ng/mL) following oral administration

| | Time (h) | | | | | | | | |
|---|---|---|---|---|---|---|---|---|---|
| Compound | 0.083 | 0.25 | 0.5 | 1 | 2 | 4 | 6 | 8 | 24 |
| Dimethyl itaconate | <24 | <24 | <24 | <24 | <24 | <24 | <24 | <24 | <24 |
| Example 49 | —* | 536 | 843 | 344 | 111 | 12 | — | 4.5 | <1.5 |
| Example 80 | — | 850 | 1151 | 715 | 173 | 67 | — | <1.5 | <1.5 |
| Example 82 | 27533 | 18000 | 6447 | 3400 | 1042 | 568 | 112 | 86 | <0.8 |
| Example 84 | — | 9089 | 5116 | 3314 | 1005 | 368 | — | 217 | <31 |
| Example 86 | — | 41 | 943 | 686 | 149 | 19 | — | <3.0 | <3.0 |
| Example 87 | — | 35333 | 15884 | 8515 | 1465 | 198 | — | 31 | <14 |
| Example 88 | 53900 | 43633 | 33767 | 12683 | 10527 | 4105 | 1947 | 72 | 5.5 |
| Example 89 | 43967 | 39133 | 28500 | 13967 | 4737 | 918 | 582 | 16 | 6.8 |
| Example 90 | 22867 | 10637 | 6200 | 3373 | 3473 | 1645 | 1048 | 500 | 1.1 |
| Example 91 | — | 8863 | 6235 | 1920 | 450 | 33 | — | 19 | 13 |
| Example 94 | 27833 | 12563 | 8217 | 3113 | 2137 | 392 | 196 | 90 | <0.8 |
| Example 96 | 15300 | 4773 | 3780 | 1551 | 810 | 856 | 330 | 443 | <0.8 |
| Example 112 | 79833 | 64567 | 72333 | 49500 | 31433 | 21267 | 6783 | 12187 | 25 |
| Example 125 | 9357 | 4360 | 2653 | 1427 | 785 | 427 | 163 | 15 | <0.8 |
| Example 129 | 305 | 1032 | 109 | 255 | 61 | 13 | 16 | 11 | 3.5 |
| Example 133 | 9363 | 9940 | 4267 | 1104 | 527 | 799 | 146 | 101 | <8.0 |
| Example 134 | 17533 | 3500 | 7973 | 1983 | 856 | 636 | 94 | 62 | 7.0 |
| Example 161 | 7023 | 4340 | 1900 | 1265 | 727 | 186 | 108 | 16 | <4.0 |
| Example 164 | 3793 | 2973 | 1859 | 968 | 585 | 381 | 135 | 181 | <4.0 |
| Example 169 | 37800 | 9877 | 4603 | 1750 | 971 | 215 | 57 | 7.7 | <0.8 |
| Example 170 | 55000 | 38367 | 40567 | 10053 | 4420 | 4403 | 441 | 25 | 8.1 |
| Example 175 | 39133 | 19467 | 18233 | 5517 | 1407 | 2000 | 784 | 231 | <4.0 |
| Example 178 | 67067 | 27067 | 27933 | 11050 | 3660 | 1464 | 2245 | 639 | <4.0 |
| Example 182 | 65867 | 46833 | 27867 | 13493 | 5393 | 1372 | 1285 | 417 | 5.9 |

TABLE 7-continued

| | Parent compound concentrations (ng/mL) following oral administration | | | | | | | | |
|---|---|---|---|---|---|---|---|---|---|
| | Time (h) | | | | | | | | |
| Compound | 0.083 | 0.25 | 0.5 | 1 | 2 | 4 | 6 | 8 | 24 |
| Example 192 | 47000 | 60667 | 37900 | 25167 | 8737 | 5440 | 79 | 41 | 6.6 |
| Example 193 | 52900 | 45600 | 31533 | 8927 | 2123 | 920 | 55 | 19 | 5.6 |

*Timepoints where no samples were taken are indicated with a dash, "—".

These results reveal that compounds of the invention display improved systemic exposures, as shown by the plasma concentrations of certain compounds of formula (IW-1) in this assay. All the compounds of formula (IW-1) shown in Table 6 exhibited higher systemic exposures compared with dimethyl itaconate when administered intravenously, and all the compounds of formula (IW-1) shown in Table 7 exhibited higher systemic exposures compared with dimethyl itaconate when administered orally.

Biological Example 7—Hepatocyte Stability Assay

Defrosted cryo-preserved hepatocytes (viability >70%) are used to determine the metabolic stability of a compound via calculation of intrinsic clearance ($Cl_{int}$; a measure of the removal of a compound from the liver in the absence of blood flow and cell binding). Clearance data are particularly important for in vitro work as they can be used in combination with in vivo data to predict the half-life and oral bioavailability of a drug.

The metabolic stability in hepatocytes assay involves a time-dependent reaction using both positive and negative controls. The cells must be pre-incubated at 37° C. then spiked with test compound (and positive control); samples taken at pre-determined time intervals are analysed to monitor the change in concentration of the initial drug compound over 60 minutes. A buffer incubation reaction (with no hepatocytes present) acts as a negative control and two cocktail solutions, containing compounds with known high and low clearance values (verapamil/7-hydroxycoumarin and propranolol/diltiazem), act as positive controls.

1. The assay is run with a cell concentration of 0.5×10⁶ cells/mL in Leibovitz buffer.
2. All compounds and controls are run in duplicate.
3. Compound concentration is 10 μM.
4. All compounds and controls are incubated with both cells and buffer to show turnover is due to hepatic metabolism.
5. All wells on the incubation plate will have 326.7 μL of either cells or buffer added.
6. Prior to assay, cell and buffer-only incubation plates are preincubated for 10 mins at 37° C.
7. The assay is initiated by adding compounds, 3.3 μL of 1 mM in 10% DMSO-90% Buffer; final DMSO concentration is 0.1%.
8. Samples are taken at regular timepoints (0, 5, 10, 20, 40, 60 min) until 60 mins.
9. Sample volume is 40 μL and it is added to 160 μL of crash solvent (acetonitrile with internal standard) and stored on ice.
10. At the end of the assay, the crash plates are centrifuged at 3500 rpm for 20 mins at 4° C.
11. 80 μL of clear supernatant is removed and mixed with 80 μL of deionised water before being analysed by LC-MS/MS.

Raw LC-MS/MS data are exported to, and analysed in, Microsoft Excel for determination of intrinsic clearance. The percentage remaining of a compound is monitored using the peak area of the initial concentration as 100%. Intrinsic clearance and half-life values are calculated using a graph of the natural log of percentage remaining versus the time of reaction in minutes. Half-life (min) and intrinsic clearance ($Cl_{int}$ in μL min⁻¹ 10⁻⁶ cells) values are calculated using the gradient of the graph (the elimination rate constant, k) and Equations 1 and 2.

$$\tau_{\frac{1}{2}} = \frac{\ln 2}{k} \quad \{\text{Equation 1}\}$$

$$Cl_{int} = \left(\frac{\ln 2}{t_{\frac{1}{2}}}\right) \times \left(\frac{350}{0.175}\right) \quad \{\text{Equation 2}\}$$

A number of compounds of formula (IW-1) which were tested in Biological Example 6 were tested in this assay, and the results are shown in Table 8 below. 4-Octyl itaconate was included as a comparator compound.

TABLE 8

| Hepatocyte stability | | | |
|---|---|---|---|
| Compound | Species | $Cl_{int}$ (μL min⁻¹ 10⁻⁶ cells) | T½ (min) |
| 4-octyl itaconate | Human | 401 | 4 |
| | Mouse | 351 | 4 |
| Example 49 | Human | 109 | 13 |
| | Mouse | 138 | 10 |
| Example 80 | Human | 243 | 6 |
| | Mouse | 158 | 9 |
| 4-octyl itaconate | Human | 401 | 4 |
| | Mouse | 351 | 4 |
| Example 82 | Human | 15 | 91 |
| | Mouse | 52 | 27 |
| Example 84 | Human | 86 | 16 |
| | Mouse | 220 | 6 |
| Example 86 | Human | 44 | 31 |
| | Mouse | NT* | NT |
| Example 87 | Human | 11 | 136 |
| | Mouse | 21 | 65 |
| Example 88 | Human | 134 | 13 |
| | Mouse | 297 | 7 |
| Example 89 | Human | 29 | 49 |
| | Mouse | 198 | 13 |
| Example 90 | Human | 8 | 183 |
| | Mouse | 47 | 30 |
| Example 91 | Human | 4 | 352 |
| | Mouse | 29 | 48 |
| Example 94 | Human | 16 | 85 |
| | Mouse | 60 | 23 |
| Example 96 | Human | 11 | 126 |
| | Mouse | 112 | 12 |
| Example 112 | Human | 65 | 25 |
| | Mouse | 255 | 13 |

TABLE 8-continued

Hepatocyte stability

| Compound | Species | $Cl_{int}$ (μL min$^{-1}$ 10$^{-6}$ cells) | T½ (min) |
|---|---|---|---|
| Example 125 | Human | 9 | 198 |
| | Mouse | 101 | 16 |
| Example 129 | Human | 55 | 108 |
| | Mouse | 378 | 4 |
| Example 133 | Human | 48 | 30 |
| | Mouse | 107 | 14 |
| Example 134 | Human | 27 | 53 |
| | Mouse | 256 | 7 |
| Example 161 | Human | 55 | 22 |
| | Mouse | >460 | <3 |
| 4-octyl itaconate | Human | 401 | 4 |
| | Mouse | 351 | 4 |
| Example 164 | Human | 42 | 33 |
| | Mouse | 259 | 5 |
| Example 169 | Human | 5 | 268 |
| | Mouse | 38 | 34 |
| Example 170 | Human | 12 | 120 |
| | Mouse | 64 | 20 |
| Example 179 | Human | 13 | 129 |
| | Mouse | 129 | 13 |
| Example 182 | Human | 60 | 28 |
| | Mouse | 187 | 9 |
| Example 192 | Human | 32 | 54 |
| | Mouse | 350 | 5 |

TABLE 8-continued

Hepatocyte stability

| Compound | Species | $Cl_{int}$ (μL min$^{-1}$ 10$^{-6}$ cells) | T½ (min) |
|---|---|---|---|
| Example 193 | Human | 16 | 109 |
| | Mouse | 79 | 22 |

*NT means not tested int his assay

These results reveal that compounds of the invention, at least those of Table 8, are expected to have acceptable or improved metabolic stabilities, as shown by their intrinsic clearance ($Cl_{int}$) and half-life ($T_{1/2}$) values in this assay. All the compounds of formula (IW-1) shown in Table 8 were more stable, i.e., they exhibited lower intrinsic clearance ($Cl_{int}$) and longer half-life ($T_{1/2}$) values compared with 4-octyl itaconate in at least human or mouse species. Preferred compounds exhibited lower intrinsic clearance ($Cl_{int}$) and longer half-life ($T_{1/2}$) values compared with 4-octyl itaconate in both human and mouse species.

Biological Example 8—Metabolites of Compounds of Formula (IW-1)

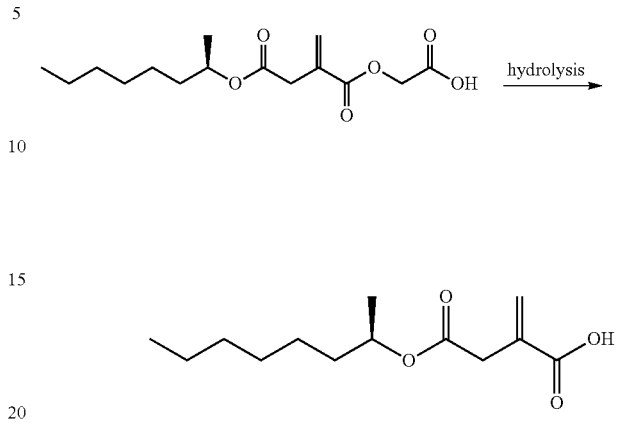

Example 112 undergoes hydrolysis in vivo to form Intermediate 8, as evidenced by a mouse pharmacokinetic study—carried out according to the protocol outlined in Biological Example 6—the data for which are shown in Table 9.

TABLE 9

Example 112 and Intermediate 8 concentrations (ng/mL) following oral administration at 100 mg/kg to the mouse

| | Time (h) | | | | | | | | |
|---|---|---|---|---|---|---|---|---|---|
| Compound | 0.083 | 0.25 | 0.5 | 1 | 2 | 4 | 6 | 8 | 24 |
| Example 112 | 109300 | 115667 | 74200 | 27900 | 14000 | 4883 | 4024 | 867 | <8 |
| Intermediate 8 | 18467 | 19767 | 12767 | 4713 | 2157 | 719 | 614 | 132 | BQL |

Intermediate 8 was tested in the assay described in Biological Examples 1 and 5 and the results are presented in Table 10. Example 112 is also shown as is dimethyl fumarate and dimethyl itaconate which were used as comparator compounds.

TABLE 10

Biological assay data for Intermediate 8

| Compound | IL-1β (IC$_{50}$) | IL-6 (IC$_{50}$) | EC$_{50}$ (μM) | E$_{max}$ (%) |
|---|---|---|---|---|
| dimethyl fumarate | 14.4 | 9.3 | 5.6 | 102 |
| dimethyl itaconate | >100 | 100.0 | 21.4 | 137 |
| Example 112 | 14.6 | NT* | 8.9 | 173 |
| Intermediate 8 | 56.7 | 23.7 | 20.4 | 165 |

As shown in Table 10, Intermediate 8 (which is a metabolite of Example 112) exhibited improved cytokine-lowering potencies compared to dimethyl itaconate for IL-1β and IL-6, and a lower EC$_{50}$ and a higher E$_{max}$ compared with dimethyl itaconate. Intermediate 8 also displayed a higher E$_{max}$ compared to dimethyl fumarate.

REFERENCES

The following publication cited in this specification are herein incorporated by reference in their entirety.
Ackermann et al. *Proc. Soc. Exp. Bio. Med.* 1949, 72(1), 1-9.
Andersen J. L. et al. *Nat. Commun.* 2018, 9, 4344.

Angiari S. and O'Neill L. A. *Cell Res.* 2018, 28, 613-615.
Bagavant G. et al. *Indian J. Pharm. Sci.* 1994, 56, 80-85.
Bambouskova M. et al. *Nature* 2018, 556, 501-504.
Blewett M. M. et al. *Sci. Sign.* 2016, 9 (445), rs10; 6.
Brennan M. S. et al. *PLoS One* 2015, 10, e0120254.
Brück J. et al. *Exp. Dermatol.* 2018, 27, 611-624.
Cocco M. et al. *J. Med. Chem.* 2014, 57, 10366-10382.
Cocco M. et al. *J. Med. Chem.* 2017, 60, 3656-3671.
Cordes T. et al. *J. Biol. Chem.* 2016, 291, 14274-14284.
Cordes T. et al. *Mol. Metab.* 2020, 32, 122-135.
Daly R. et al. *medRxiv* 2019, 19001594; doi: https://doi.org/10.1101/19001594.
Daniels B. P. et al. *Immunity* 2019, 50(1), 64-76.e4.
Dibbert S. et al. *Arch. Dermatol. Res.* 2013, 305, 447-451.
ElAzzouny M. et al. *J. Biol. Chem.* 2017, 292, 4766-4769.
Gillard G. O. et al. *J. Neuroimmunol.* 2015, 283, 74-85.
Gu L. et al. *Immunol. Cell Biol.* 2020 doi:10.1111/imcb.12316.
Hanke T. et al. *Pharmacol. Therapeut.* 2016, 157, 163-187.
Hunt T. et al. *Consortium of Multiple Sclerosis Centers* 2015 Annual Meeting, 27-30 May 2015, Indianapolis, IN., USA: Poster DX37.
Kobayashi E. H. et al. *Nat. Commun.* 2016, 7, 11624.
Kornberg M. D. et al. *Science* 2018, 360, 449-453.
Kulkarni R. A. et al. *Nat. Chem. Biol.* 2019 10.1038/s41589-018-0217-y.
Lampropoulou V. et al. *Cell Metab.* 2016, 24, 158-166.
Lehmann J. C. U. et al. *J. Invest. Dermatol.* 2007, 127, 835-845.
Liao S.-T. et al. *Nat. Commun.* 2019, 10(1), 5091.
Liu H. et al. *Cell Commun. Signal.* 2018, 16, 81.
McGuire V. A. et al. *Sci. Rep.* 2016, 6, 31159.
Michelucci A. et al. *Proc. Natl. Acad. Sci. USA* 2013, 110, 7820-7825.
Mills E. A. et al. *Front. Neurol.* 2018, 9, 5.
Mills E. L. et al. *Cell* 2016, 167, 457-470.
Mills E. L. et al. *Nature* 2018, 556, 113-117.
Mrowietz U. et al. *Trends Pharmacol. Sci.* 2018, 39, 1-12.
Müller S. et al. *J. Dermatol. Sci.* 2017, 87, 246-251.
Murphy M. P. and O'Neill L. A. *J. Cell* 2018, 174, 780-784.
O'Neill L. A. J. and Artyomov M. N. *Nat. Rev. Immunol.* 2019 273-281.
Olagnier D. et al. *Nat. Commun.* 2018, 9, 3506.
Schmidt T. J. et al. *Bioorg. Med. Chem.* 2007, 15, 333-342.
Shan Q. et al. *Biochem. Biophys. Res. Commun.* 2019, 517, 538-544.
Straub R. H. and Schradin C. *Evol. Med. Public Health* 2016, 1, 37-51S.
Straub R. H. and Cutolo M. *Rheumatology* 2016, 55 (Suppl. 2), ii6-ii14.
Sun X. et al., *FASEB J.* 2019, 33, 12929-12940.
Tang C. et al. *Cell Physiol. Biochem.* 2018, 51, 979-990.
Tang C. et al. *Biochem. Biophys. Res. Commun.* 2019, 508, 921-927.
Tang H. et al. *Biochem. Biophys. Res. Commun.* 2008, 375, 562-565.
Tian et al. *Eur. J. Pharmacol.* 2020, 873, 172989.
van der Reest J. et al. *Nat. Commun.* 2018, 9, 1581.
von Glehn F. et al. *Mult. Scler. Relat. Disord.* 2018, 23, 46-50.
Yi F. et al. *Hepatology* 2020, 873, 172989.
Yu X.-H. et al. *Immunol. Cell Biol.* 2019, 97, 134-141.
Zhang S. et al. *Bioorg. Med. Chem.* 2012, 20, 6073-6079.
Zhang D. et al. *Int. Immunopharmacol.* 2019, 77, 105924.
Zhao C. et al. *Microb. Pathogen.* 2019, 133, 103541.
Zhao G. et al. *Biochem. Biophys. Res. Commun.* 2014, 448, 303-307.

MISCELLANEOUS

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of formula (IW-e) or pharmaceutically acceptable salt or solvate thereof:

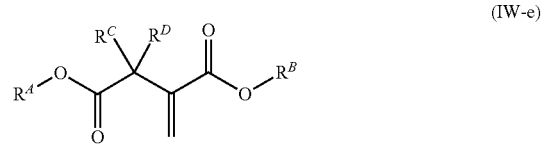

(IW-e)

wherein, $R^A$ is selected from the group consisting of $C_{1-10}$ alkyl, $C_{3-10}$ cycloalkyl and $C_{5-10}$ spirocycloalkyl; wherein $R^A$ is optionally substituted by one or more substituents selected from the group consisting of oxo, $R^{1A}$, $OR^{2A}$, $N^{2A}R^{3A}$, $SR^{2A}$, $SOR^{9A}SO_2R^{9A}$, $SO_2NR^{2A}R^{3A}$, $C(O)R^{2A}$ and $CONR^{2A}R^{3A}$;

$R^{1A}$ is selected from the group consisting of fluoro, methyl, cyano, $SiR^{4A}R^{5A}R^{6A}$, $C_{3-8}$ cycloalkyl and phenyl; wherein methyl, $C_{3-8}$ cycloalkyl and phenyl optionally substituted by $R^{7A}$ and/or $R^{8A}$;

$R^{4A}$, $R^{5A}$ and $R^{6A}$ are independently selected from the group consisting of $C_{1-4}$ alkyl and phenyl;

$R^{7A}$ and $R^{8A}$ are independently selected from the group consisting of oxo, $C_{1-4}$ alkyl, $C_{1-4}$ alkoxy, $C_{1-4}$ haloalkyl, $C_{1-4}$ haloalkoxy, hydroxy, $CO_2H$, cyano, methanesulfonyl and halo;

or, taken together, $R^{7A}$ and $R^{8A}$ form a $C_{3-8}$ cycloalkyl or 4-7 membered heterocyclic ring;

$R^{2A}$ and $R^{3A}$ are independently H, $C_{1-8}$ alkyl, $C_{3-8}$ cycloalkyl or phenyl;

or, taken together, $R^{2A}$ and $R^{3A}$ form a 4-7 membered heterocyclic ring;

$R^{9A}$ is $C_{1-8}$ alkyl, $C_{3-8}$ cycloalkyl or phenyl; and $R^B$ is $C_{1-2}$ alkyl substituted by $CO_2H$ and is optionally further substituted by trifluoromethyl or methyl;

$R^C$ and $R^D$ are independently selected from the group consisting of H, $C_{1-2}$ alkyl, hydroxy, methoxy and fluoro;

or a compound which is selected from the group consisting of:

1-(2-cyanoethyl) 4-octyl 2-methylenesuccinate;
1-(2-(methylsulfonyl)ethyl) 4-octyl 2-methylenesuccinate;
4-octyl 1-(3,3,3-trifluoropropyl) 2-methylenesuccinate;
4-octyl 1-(oxetan-3-yl) 2-methylenesuccinate;

4-octyl 1-(2-(2-oxopyrrolidin-1-yl)ethyl) 2-methylenesuccinate;
1-(3-(dimethylamino)-3-oxopropyl) 4-octyl 2-methylenesuccinate;
4-butyl 1-(2-(methylsulfonyl)ethyl) 2-methylenesuccinate;
1-(2-cyanoethyl) 4-butyl 2-methylenesuccinate;
1-(2-(2,5-dioxopyrrolidin-1-yl)ethyl) 4-octyl 2-methylenesuccinate;
1-(2-cyanoethyl) 4-methyl 2-methylenesuccinate;
1-(2-cyanoethyl) 4-hexyl 2-methylenesuccinate;
4-methyl 1-(2-(methylsulfonyl)ethyl) 2-methylenesuccinate;
4-octyl 1-(2-(trifluoromethoxy)ethyl) 2-methylenesuccinate;
4-hexyl 1-(2-(methylsulfonyl)ethyl) 2-methylenesuccinate;
4-methyl 1-(oxetan-3-yl) 2-methylenesuccinate;
1-(2-(N,N-dimethylsulfamoyl)ethyl) 4-octyl 2-methylenesuccinate;
1-(2-(dimethylamino)ethyl) 4-octyl 2-methylenesuccinate;
1-(3-(methylsulfonyl)propyl) 4-octyl 2-methylenesuccinate;
1-(1-(methylsulfonyl)propan-2-yl) 4-octyl 2-methylenesuccinate;
1-(2-(methylsulfonyl)ethyl) 4-(3-phenoxypropyl) 2-methylenesuccinate;
1-(2-(dimethylamino)-2-oxoethyl) 4-octyl 2-methylenesuccinate;
4-isopropyl 1-(2-(methylsulfonyl)ethyl) 2-methylenesuccinate;
(S)-4-octyl 1-(tetrahydrofuran-3-yl) 2-methylenesuccinate;
(R)-4-octyl 1-(tetrahydrofuran-3-yl) 2-methylenesuccinate;
4-cyclooctyl 1-(2-(methylsulfonyl)ethyl) 2-methylenesuccinate;
4-octyl 1-(tetrahydro-2H-pyran-4-yl) 2-methylenesuccinate;
1-(1-cyanopropan-2-yl) 4-octyl 2-methylenesuccinate;
1-(1-(methylsulfonyl)piperidin-4-yl) 4-octyl 2-methylenesuccinate;
1-(2-methoxyethyl) 4-octyl 2-methylenesuccinate;
1-(2-cyano-2-methylpropyl) 4-octyl 2-methylenesuccinate;
1-(1-methoxypropan-2-yl) 4-octyl 2-methylenesuccinate;
1-((1-cyanocyclopropyl)methyl) 4-octyl 2-methylenesuccinate;
1-(2-methoxypropyl) 4-octyl 2-methylenesuccinate;
1-(2-methoxy-2-methylpropyl) 4-octyl 2-methylenesuccinate;
1-(2-morpholinoethyl) 4-octyl 2-methylenesuccinate;
4-(2-(2-ethoxyethoxy)ethyl) 1-(2-(methylsulfonyl)ethyl) 2-methylenesuccinate;
4-butyl 1-(oxetan-3-yl) 2-methylenesuccinate;
4-hexyl 1-(oxetan-3-yl) 2-methylenesuccinate;
4-butyl 1-(2-tosylethyl) 2-methylenesuccinate;
4-octyl 1-(2-tosylethyl) 2-methylenesuccinate;
4-cyclooctyl 1-methyl 2-methylenesuccinate;
1-methyl 4-octyl 2-methylenesuccinate;
dicyclobutyl 2-methylenesuccinate;
di(oxetan-3-yl) 2-methylenesuccinate;
1-cyclobutyl 4-octyl 2-methylenesuccinate;
1-(1-acetoxyethyl) 4-octyl 2-methylenesuccinate;
1-(1,1-dioxidothietan-3-yl) 4-octyl 2-methylenesuccinate;
1-(2-(tert-butoxy)-2-oxoethyl) 4-octyl 2-methylenesuccinate;
1-(1-acetylazetidin-3-yl) 4-octyl 2-methylenesuccinate;
1-(2-(4-methylpiperazin-1-yl)ethyl) 4-octyl 2-methylenesuccinate;
1-(2-(1,1-dioxidothiomorpholino)ethyl) 4-octyl 2-methylenesuccinate;
1-(2-(methylsulfonamido)ethyl) 4-octyl 2-methylenesuccinate;
4-cyclooctyl 1-(1,1-dioxidothietan-3-yl) 2-methylenesuccinate;
(R)-1-(2-(methylsulfonyl)ethyl) 4-(octan-2-yl) 2-methylenesuccinate;
1-(1-(methylsulfonyl)propan-2-yl) 4-((R)-octan-2-yl) 2-methylenesuccinate;
(R)-1-(1,1-dioxidothietan-3-yl) 4-(octan-2-yl) 2-methylenesuccinate;
(R)-1-(1-acetylazetidin-3-yl) 4-(octan-2-yl) 2-methylenesuccinate;
4-cyclohexyl 1-(1-(methylsulfonyl)propan-2-yl) 2-methylenesuccinate;
4-cyclohexyl 1-(1,1-dioxidothietan-3-yl) 2-methylenesuccinate;
4-cyclohexyl 1-(2-(methylsulfonyl)ethyl) 2-methylenesuccinate;
4-cyclooctyl 1-(1-(methylsulfonyl)propan-2-yl) 2-methylenesuccinate;
1-(1-acetylazetidin-3-yl) 4-cyclooctyl 2-methylenesuccinate;
4-cyclohexyl 1-(tetrahydro-2H-pyran-4-yl) 2-methylenesuccinate;
4-cyclohexyl 1-(2-(2-oxopyrrolidin-1-yl)ethyl) 2-methylenesuccinate;
(S)-1-(1-acetylazetidin-3-yl) 4-(octan-2-yl) 2-methylenesuccinate;
(S)-1-(1,1-dioxidothietan-3-yl) 4-(octan-2-yl) 2-methylenesuccinate;
1-(3-methyloxetan-3-yl) 4-octyl 2-methylenesuccinate;
4-cyclooctyl 1-(1-(methylsulfonyl)piperidin-4-yl) 2-methylenesuccinate;
4-cyclooctyl 1-(tetrahydro-2H-pyran-4-yl) 2-methylenesuccinate;
4-cyclooctyl 1-(2-(2-oxopyrrolidin-1-yl)ethyl) 2-methylenesuccinate;
(R)-4-(octan-2-yl) 1-(2-(2-oxopyrrolidin-1-yl)ethyl) 2-methylenesuccinate;
(R)-4-(octan-2-yl) 1-(tetrahydro-2H-pyran-4-yl) 2-methylenesuccinate;
1-(1-acetylazetidin-3-yl) 4-cyclohexyl 2-methylenesuccinate;
4-cyclohexyl 1-(1-(methylsulfonyl)piperidin-4-yl) 2-methylenesuccinate;
4-hexyl 1-(1-(methylsulfonyl)piperidin-4-yl) 2-methylenesuccinate;
4-hexyl 1-(2-(2-oxopyrrolidin-1-yl)ethyl) 2-methylenesuccinate;
1-(2-(1H-tetrazol-5-yl)ethyl) 4-hexyl 2-methylenesuccinate;
(2-((2-methylene-4-(octyloxy)-4-oxobutanoyl)oxy)acetyl)-L-proline;
N-methyl-N-(2-((2-methylene-4-(octyloxy)-4-oxobutanoyl)oxy)propanoyl)glycine;
(2-((2-methylene-4-(octyloxy)-4-oxobutanoyl)oxy)propanoyl)-L-proline;
(2-((2-methylene-4-(octyloxy)-4-oxobutanoyl)oxy)propanoyl)glycine;

N-(2-((4-(cyclooctyloxy)-2-methylene-4-oxobutanoyl)oxy)acetyl)-N-methylglycine;
(2-((4-(cyclooctyloxy)-2-methylene-4-oxobutanoyl)oxy)acetyl)-L-proline;
(S)—N-methyl-N-(2-((2-methylene-4-(octan-2-yloxy)-4-oxobutanoyl)oxy)acetyl)glycine;
(S)-(2-((2-methylene-4-(octan-2-yloxy)-4-oxobutanoyl)oxy)acetyl)glycine;
1-(2-(4-methylpiperazin-1-yl)-2-oxoethyl) 4-octyl 2-methylenesuccinate;
1-(3-morpholino-3-oxopropyl) 4-octyl 2-methylenesuccinate;
1-(3-(diethylamino)-3-oxopropyl) 4-octyl 2-methylenesuccinate;
1-(3-(methylamino)-3-oxopropyl) 4-octyl 2-methylenesuccinate;
3-((4-(cyclohexyloxy)-2-methylene-4-oxobutanoyl)oxy)-2,2-dimethylpropanoic acid;
1-(2-((N,N-dimethylsulfamoyl)amino)-2-oxoethyl) 4-hexyl 2-methylenesuccinate;
4-hexyl 1-(2-(methylsulfonamido)-2-oxoethyl) 2-methylenesuccinate;
4-hexyl 1-(3-(methylsulfonamido)-2-oxoethyl) 2-methylenesuccinate;
(E)-4-((4-(cyclohexyloxy)-2-methylene-4-oxobutanoyl)oxy)but-2-enoic acid;
3-((2-((4-(cyclohexyloxy)-2-methylene-4-oxobutanoyl)oxy)ethyl)sulfonyl)propanoic acid;
1-((2H-tetrazol-5-yl)methyl) 4-cyclohexyl 2-methylenesuccinate;
2-((3-((2-((3-chlorophenyl)sulfonyl)ethoxy)carbonyl)but-3-enoyl)oxy)acetic acid;
(R)-2-((4-(cyclohexyloxy)-2-methylene-4-oxobutanoyl)oxy)-2-phenylacetic acid;
1-(2-(1H-tetrazol-5-yl)ethyl) 4-cyclohexyl 2-methylenesuccinate;
(S)-1-(2-(1H-tetrazol-5-yl)ethyl) 4-octan-2-yl 2-methylenesuccinate;
1-(2-(1H-tetrazol-5-yl)ethyl) 4-cyclooctyl 2-methylenesuccinate;
1-(2-((3-chlorophenyl)sulfonyl)-2-methylpropyl) 4-cyclooctyl 2-methylenesuccinate;
4-cyclooctyl 1-(2-methyl-2-(methylsulfonyl)propyl) 2-methylenesuccinate;
1-(1-(1H-tetrazol-5-yl)ethyl) 4-cyclooctyl 2-methylenesuccinate;
1-((1H-tetrazol-5-yl)methyl) 4-cyclooctyl 2-methylenesuccinate;
(R)-1-(2-(1H-tetrazol-5-yl)ethyl) 4-octan-2-yl 2-methylenesuccinate;
(2R,3S)-2-acetamido-3-((4-(cyclooctyloxy)-2-methylene-4-oxobutanoyl)oxy)butanoic acid;
4-cyclooctyl 1-(3-(2-ethoxy-2-oxoethyl)oxetan-3-yl) 2-methylenesuccinate;
4-(2-(methylsulfonyl)ethyl) 1-octyl 2-methyl-3-methylenesuccinate;
1-octyl 4-((S)-tetrahydrofuran-3-yl) 2-methyl-3-methylenesuccinate;
1-(1-(1H-tetrazol-5-yl)propan-2-yl) 4-((R)-octan-2-yl) 2-methylenesuccinate;
1-(1-(1H-tetrazol-5-yl)propan-2-yl) 4-((S)-octan-2-yl) 2-methylenesuccinate;
4-cyclohexyl 1-((2-methyl-2H-tetrazol-5-yl)methyl) 2-methylenesuccinate;
4-cyclohexyl 1-((1-methyl-1H-tetrazol-5-yl)methyl) 2-methylenesuccinate;
bis((endo)-3-(methylsulfonyl)-3-azabicyclo[3.2.1]octan-8-yl) 2-methylenesuccinate;
1-((endo)-3-(methylsulfonyl)-3-azabicyclo[3.2.1]octan-8-yl) 4-(2-oxaspiro[3.3]heptan-6-yl) 2-methylenesuccinate;
1-((endo)-3-(methylsulfonyl)-3-azabicyclo[3.2.1]octan-8-yl) 4-(oxepan-4-yl) 2-methylenesuccinate;
4-(1-butoxypropan-2-yl) 1-((endo)-3-(methylsulfonyl)-3-azabicyclo[3.2.1]octan-8-yl) 2-methylenesuccinate;
4-spiro[3.3]heptan-2-yl 1-(3,3,3-trifluoro-2,2-dihydroxypropyl) 2-methylenesuccinate hydrate;
(R)-1-((2H-tetrazol-5-yl)methyl) 4-(octan-2-yl) 2-methylenesuccinate;
1-(2H-tetrazol-5-yl)methyl 4-cycloheptyl 2-methylenesuccinate;
1-(2H-tetrazol-5-yl)methyl 4-spiro[3.3]heptan-2-yl 2-methylenesuccinate;
(S)-1-(2H-tetrazol-5-yl)methyl 4-octan-2-yl 2-methylenesuccinate;
1-(1-(1H-tetrazol-5-yl)ethyl) 4-((S)-octan-2-yl) 2-methylenesuccinate;
1-(cyclopropyl(1H-tetrazol-5-yl)methyl) 4-((S)-octan-2-yl) 2-methylenesuccinate;
dicyclohexyl 2-methylenesuccinate;
1-(3,3-difluorocyclobutyl) 4-octyl 2-methylenesuccinate;
1-((endo)-3-(methylsulfonyl)-3-azabicyclo[3.2.1]octan-8-yl) 4-((R)-octan-2-yl) 2-methylenesuccinate; and
(R)-4-(octan-2-yl) 1-((3-oxo-2,3-dihydroisoxazol-5-yl)methyl) 2-methylenesuccinate;
or a pharmaceutically acceptable salt or solvate thereof.

2. The compound or pharmaceutically acceptable salt or solvate thereof according to claim 1, wherein $R^A$ is $C_{3-10}$ cycloalkyl.

3. The compound or pharmaceutically acceptable salt or solvate thereof according to claim 2, wherein $R^A$ is cyclobutyl.

4. The compound or pharmaceutically acceptable salt or solvate thereof according to claim 1, wherein $R^{1A}$ is substituted by $R^{7A}$ and/or $R^{8A}$ when $R^{1A}$ is methyl, $C_{3-8}$ cycloalkyl or phenyl.

5. The compound or pharmaceutically acceptable salt or solvate thereof according to claim 4, wherein $R^{7A}$ is $C_{1-4}$ haloalkyl.

6. The compound or pharmaceutically acceptable salt or solvate thereof according to claim 1 which is a compound selected from the group consisting of:
2-((2-methylene-4-(octyloxy)-4-oxobutanoyl)oxy)propanoic acid;
3-((2-methylene-4-(octyloxy)-4-oxobutanoyl)oxy)propanoic acid;
3-((4-((4-fluorobenzyl)oxy)-2-methylene-4-oxobutanoyl)oxy)propanoic acid;
3-((4-(cyclooctyloxy)-2-methylene-4-oxobutanoyl)oxy) propanoic acid;
3-((2-methylene-4-(neopentyloxy)-4-oxobutanoyl)oxy) propanoic acid;
(S)-3-((2-methylene-4-(octan-2-yloxy)-4-oxobutanoyl)oxy)propanoic acid;
3-((4-(hexyloxy)-2-methylene-4-oxobutanoyl)oxy)propanoic acid;
3-((2-methylene-4-oxo-4-(3-phenoxypropoxy)butanoyl)oxy)propanoic acid;
3-((4-(cyclohexyloxy)-2-methylene-4-oxobutanoyl)oxy) propanoic acid;
(R)-3-((2-methylene-4-(octan-2-yloxy)-4-oxobutanoyl)oxy)propanoic acid;

(S)-2-((2-methylene-4-(octan-2-yloxy)-4-oxobutanoyl) oxy)acetic acid;
2-((4-(cyclooctyloxy)-2-methylene-4-oxobutanoyl)oxy) acetic acid;
2-((4-(cyclohexyloxy)-2-methylene-4-oxobutanoyl)oxy) acetic acid;
2-((2-methylene-4-(neopentyloxy)-4-oxobutanoyl)oxy) acetic acid;
2-((4-((4-fluorobenzyl)oxy)-2-methylene-4-oxobutanoyl) oxy)acetic acid;
2-((4-(hexyloxy)-2-methylene-4-oxobutanoyl)oxy)acetic acid;
2-((2-methylene-4-oxo-4-(3-phenoxypropoxy)butanoyl) oxy)acetic acid;
2-((2-methylene-4-oxo-4-(spiro[3.3]heptan-2-yloxy)butanoyl)oxy)acetic acid;
2-((2-methylene-4-oxo-4-(2-tosylethoxy)butanoyl)oxy) acetic acid;
2-(N-methyl-2-((2-methylene-4-(octyloxy)-4-oxobutanoyl)oxy)acetamido)acetic acid;
2-((4-(cyclohexyloxy)-2-methylene-4-oxobutanoyl)oxy) propanoic acid;
(R)-2-((2-methylene-4-(octan-2-yloxy)-4-oxobutanoyl) oxy)acetic acid;
2-((4-((4,4-difluorocyclohexyl)methoxy)-2-methylene-4-oxobutanoyl)oxy)acetic acid;
2-((4-(3-ethoxypropoxy)-2-methylene-4-oxobutanoyl) oxy)acetic acid;
2-((4-(bicyclo[2.2.1]heptan-2-yloxy)-2-methylene-4-oxobutanoyl)oxy)acetic acid;
2-((4-cyclobutoxy-2-methylene-4-oxobutanoyl)oxy)acetic acid;
2-((4-(cyclohexyloxy)-2-methylene-4-oxobutanoyl)oxy)-3,3,3-trifluoropropanoic acid;
2-((4-(cyclooctyloxy)-2-methylene-4-oxobutanoyl)oxy)-3,3,3-trifluoropropanoic acid;
3-((4-(cyclooctyloxy)-2-methylene-4-oxobutanoyl)oxy)-4,4,4-trifluorobutanoic acid;
2-(4-(cycloheptyloxy)-2-methylene-4-oxobutanoyloxy) acetic acid;
2-(2-methylene-4-(octan-3-yloxy)-4-oxobutanoyloxy) acetic acid;
2-(2-methylene-4-(octan-4-yloxy)-4-oxobutanoyloxy) acetic acid;
2-((4-(heptan-4-yloxy)-2-methylene-4-oxobutanoyl)oxy) acetic acid;
2-((4-((adamantan-2-yl)oxy)-2-methylene-4-oxobutanoyl)oxy)acetic acid;
2-((4-(1-cyclohexylethoxy)-2-methylene-4-oxobutanoyl) oxy) acetic acid;
2-((4-(1-cycloheptylethoxy)-2-methylene-4-oxobutanoyl)oxy)acetic acid;
2-(2-methylene-4-oxo-4-(spiro[3.4]octan-2-yloxy)butanoyloxy)acetic acid;
2-(2-methylene-4-oxo-4-(spiro[3.5]nonan-2-yloxy)butanoyloxy)acetic acid;
2-(2-methylene-4-oxo-4-(spiro[3.5]nonan-7-yloxy)butanoyloxy)acetic acid;
2-((4-((2,2-dimethylcyclohexyl)oxy)-2-methylene-4-oxobutanoyl)oxy)acetic acid;
4-spiro[3.3]heptan-2-yl 1-(3,3,3-trifluoro-2,2-dihydroxypropyl) 2-methylenesuccinate hydrate;
(R)-1-((2H-tetrazol-5-yl)methyl) 4-(octan-2-yl) 2-methylenesuccinate;
1-(2H-tetrazol-5-yl)methyl 4-cycloheptyl 2-methylenesuccinate;
1-(2H-tetrazol-5-yl)methyl 4-spiro[3.3]heptan-2-yl 2-methylenesuccinate;
(S)-1-(2H-tetrazol-5-yl)methyl 4-octan-2-yl 2-methylenesuccinate;
1-(1-(1H-tetrazol-5-yl)ethyl) 4-((S)-octan-2-yl) 2-methylenesuccinate;
1-(cyclopropyl(1H-tetrazol-5-yl)methyl) 4-((S)-octan-2-yl) 2-methylenesuccinate;
dicyclohexyl 2-methylenesuccinate;
2-((4-(cyclooctyloxy)-3-methyl-2-methylene-4-oxobutanoyl)oxy)acetic acid;
2-((2-methylene-4-oxo-4-(2,2,4,4-tetramethylcyclobutoxy)butanoyl)oxy) acetic acid;
(S)-2-(2-methylene-4-(octan-3-yloxy)-4-oxobutanoyloxy)acetic acid;
2-((4-(cyclooctyloxy)-3-methoxy-2-methylene-4-oxobutanoyl)oxy)acetic acid; and
2-((4-((-adamantan-1-yl)oxy)-2-methylene-4-oxobutanoyl)oxy)acetic acid;
(R)-2-((4-(heptan-2-yloxy)-2-methylene-4-oxobutanoyl) oxy)acetic acid;
2-((2-methylene-4-(nonan-2-yloxy)-4-oxobutanoyl)oxy) acetic acid;
2-((2-methylene-4-(nonan-5-yloxy)-4-oxobutanoyl)oxy) acetic acid;
2-((4-(1-(3,5-dichlorophenyl)ethoxy)-2-methylene-4-oxobutanoyl)oxy)acetic acid;
2-((4-((1-(3,5-dichlorophenyl)propan-2-yl)oxy)-2-methylene-4-oxobutanoyl)oxy)acetic acid;
(R)-2-(2-methylene-4-(octan-3-yloxy)-4-oxobutanoyloxy)acetic acid;
2-((2-methylene-4-oxo-4-(((1R,2S,4R)-1,7,7-trimethylbicyclo[2.2.1]heptan-2-yl)oxy)butanoyl)oxy)acetic acid;
2-((4-(1-cyclohexyl-2,2,2-trifluoroethoxy)-2-methylene-4-oxobutanoyl)oxy)acetic acid;
2-((4-(bicyclo[3.3.1]nonan-9-yloxy)-2-methylene-4-oxobutanoyl)oxy)acetic acid;
(S)-2-((2-methylene-4-oxo-4-((1,1,1-trifluorooctan-2-yl) oxy)butanoyl)oxy)acetic acid;
(R)-2-((2-methylene-4-(nonan-2-yloxy)-4-oxobutanoyl) oxy)acetic acid;
(R)-2-((4-(1-cyclohexylethoxy)-2-methylene-4-oxobutanoyl)oxy)acetic acid;
(R)-4,4,4-trifluoro-3-((2-methylene-4-(((R)-octan-2-yl) oxy)-4-oxobutanoyl)oxy)butanoic acid;
2-((4-(cyclooctyloxy)-3-hydroxy-2-methylene-4-oxobutanoyl)oxy)acetic acid;
2-(3-methylene-5-(4-methylheptan-4-yloxy)-5-oxopent-1-en-2-yloxy)acetic acid;
2-((4-(1-cyclohexylcyclobutoxy)-2-methylene-4-oxobutanoyl)oxy)acetic acid;
2-((2-methylene-4-((2-methyloctan-2-yl)oxy)-4-oxobutanoyl)oxy)acetic acid;
2-((2-methylene-4-((2-methylheptan-2-yl)oxy)-4-oxobutanoyl)oxy)acetic acid;
2-((2-methylene-4-oxo-4-(1-pentylcyclobutoxy)butanoyl)oxy) acetic acid;
2-((2-methylene-4-((2-methylspiro[3.5]nonan-2-yl)oxy)-4-oxobutanoyl)oxy)acetic acid;
2-((2-methylene-4-oxo-4-(((exo)-1,7,7-trimethylbicyclo [2.2.1]heptan-2-yl)oxy)butanoyl)oxy)acetic acid;
2-((2-methylene-4-oxo-4-((2,2,6,6-tetramethylcyclohexyl)oxy) butanoyl)oxy)acetic acid;
2-((4-(1-(3,5-dichlorophenyl)ethoxy)-2-methylene-4-oxobutanoyl)oxy)acetic acid (Isomer 1);
2-((4-(1-(3,5-dichlorophenyl)ethoxy)-2-methylene-4-oxobutanoyl)oxy)acetic acid (Isomer 2);

(R)-2-((2-methylene-4-oxo-4-(1-(4-(trifluoromethyl)phenyl)ethoxy)butanoyl)oxy) acetic acid);
(S)-2-((2-methylene-4-oxo-4-(1-(4-(trifluoromethyl)phenyl)ethoxy)butanoyl)oxy) acetic acid);
2-((4-(1-cyclohexylcyclopropoxy)-2-methylene-4-oxobutanoyl)oxy)acetic acid;
(S)-2-((4-(1-cyclohexylethoxy)-2-methylene-4-oxobutanoyl)oxy)acetic acid;
2-((2-methylene-4-oxo-4-((2,2,4,4-tetramethylpentan-3-yl)oxy)butanoyl)oxy)acetic acid;
(S)-4,4,4-trifluoro-3-((2-methylene-4-(((R)-octan-2-yl)oxy)-4-oxobutanoyl)oxy)butanoic acid;
2-((2-methylene-4-oxo-4-(1-pentylcyclopropoxy)butanoyl)oxy) acetic acid; and
3-((2-methylene-4-oxo-4-(2,2,4,4-tetramethylcyclobutoxy)butanoyl)oxy)propanoic acid;
or a pharmaceutically acceptable salt or solvate of any one thereof.

7. A pharmaceutical composition comprising a compound or a pharmaceutically acceptable salt or solvate thereof according to claim 1 and a pharmaceutically acceptable carrier or excipient.

8. The compound or pharmaceutically acceptable salt or solvate thereof according to claim 1, wherein $R^A$ is substituted by $R^{1A}$ wherein $R^{1A}$ is selected from the group consisting of fluoro, methyl, cyano, $SiR^{4A}R^{5A}R^{6A}$ and phenyl.

9. The compound or pharmaceutically acceptable salt or solvate thereof according to claim 1, wherein $R^C$ is H and $R^D$ is H.

10. The compound or pharmaceutically acceptable salt or solvate thereof according to claim 1, wherein $R^B$ is $C_{1-2}$ alkyl substituted by $CO_2H$.

11. The compound or pharmaceutically acceptable salt or solvate thereof according to claim 1, wherein $R^B$ is $C_{1-2}$ alkyl substituted by $CO_2H$ and is further substituted by trifluoromethyl or methyl.

* * * * *